(12) United States Patent
Shiraishi et al.

(10) Patent No.: US 8,945,870 B2
(45) Date of Patent: *Feb. 3, 2015

(54) DNA ENCODING AN ANTI-SYSTEM ASC AMINO ACID TRANSPORTER 2 (ASCT2) ANTIBODY

(75) Inventors: Norihiko Shiraishi, Tokyo (JP); Akiko Furuya, Tokyo (JP); Hiroe Toki, Tokyo (JP); Hiroshi Ando, Tokyo (JP); Masayo Suzuki, Tokyo (JP); Tsuguo Kubota, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,478

(22) Filed: Aug. 13, 2012

(65) Prior Publication Data

US 2013/0202607 A1 Aug. 8, 2013

Related U.S. Application Data

(62) Division of application No. 12/505,133, filed on Jul. 17, 2009, now Pat. No. 8,268,592.

(60) Provisional application No. 61/081,820, filed on Jul. 18, 2008.

(30) Foreign Application Priority Data

Jul. 17, 2008 (JP) .................................. 2008-185790

(51) Int. Cl.
| | | |
|---|---|---|
| C07H 21/04 | (2006.01) | |
| C12N 15/09 | (2006.01) | |
| C12N 15/12 | (2006.01) | |
| C12N 15/13 | (2006.01) | |
| C12N 15/63 | (2006.01) | |
| C12N 5/07 | (2010.01) | |
| C12N 5/10 | (2006.01) | |
| C12N 5/12 | (2006.01) | |
| C07K 16/28 | (2006.01) | |
| G01N 33/68 | (2006.01) | |
| C07K 16/30 | (2006.01) | |
| G01N 33/574 | (2006.01) | |
| A61K 39/395 | (2006.01) | |
| A61K 39/00 | (2006.01) | |

(52) U.S. Cl.
CPC .................. C07K 16/30 (2013.01); C12N 15/09 (2013.01); C07H 21/04 (2013.01); C12N 5/12 (2013.01); G01N 33/6893 (2013.01); C07K 2317/33 (2013.01); C07K 2317/565 (2013.01); C07K 16/28 (2013.01); C07K 2317/734 (2013.01); C12N 15/63 (2013.01); C07K 2317/56 (2013.01); C07K 2317/732 (2013.01); A61K 39/39533 (2013.01); A61K 2039/505 (2013.01); C07K 2317/73 (2013.01); C12N 2800/10 (2013.01); G01N 33/574 (2013.01); G01N 33/6872 (2013.01)
USPC ..... 435/69.1; 435/70.1; 435/70.2; 435/70.21; 435/326; 435/334; 435/320.1; 435/252.3; 530/387.1; 530/388.1; 530/388.22; 536/23.1; 536/23.5

(58) Field of Classification Search
None
See application file for complete search history.

(56) References Cited

FOREIGN PATENT DOCUMENTS

| WO | 2004/032966 A1 | 4/2004 |
|---|---|---|
| WO | 2004/101772 A2 | 11/2004 |
| WO | 2005/020888 A2 | 3/2005 |
| WO | 2007/109376 A2 | 9/2007 |
| WO | 2010/008075 A1 | 1/2010 |

OTHER PUBLICATIONS

Gregory P. Adams et al., "Monoclonal antibody therapy of cancer," Nature Biotechnology, 2005, 23(9): 1147-1157.
Nelly E. Avissar et al., "$Na^+$-dependent neutral amino acid transporter $ATB^0$ is a rabbit epithelial cell brush-border protein", Am. J. Physiol. Cell Physiol., 2001, 281: 963-971.
Barrie P. Bode, et al., "Molecular and functional analysis of glutamine uptake in human hepatoma and liver-derived cells", Am. J. Physiol. Gastrointest. Liver Physiol., 2002, 283: 1062-1073.
Claire I. Bungard et al., "Glutamine availability up-regulates expression of the amino acid transporter protein ASCT2 in HepG2 cells and stimulates the ASCT2 promoter", Biochem. J., 2004, 382: 27-32.
Florence Casset et al., "A peptide mimetic of an anti-CD4 monoclonal antibody by rational design", Biochemical and Biophysical Research Communications, 2003, 307: 198-205.

(Continued)

Primary Examiner — Bridget E Bunner
(74) Attorney, Agent, or Firm — Sughrue Mion, PLLC

(57) ABSTRACT

An object of the present invention is to provide a monoclonal antibody which is useful for treating or diagnosing a disease relating to system ASC amino acid transporter 2 (hereinafter, referred to as "ASCT2") or a method using the antibody. The present invention provides a monoclonal antibody which specifically recognizes a native three-dimensional structure of an extracellular region of ASCT2 and binds to the extracellular region, or an antibody fragment thereof; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof, and a diagnostic agent using the antibody or the antibody fragment thereof.

10 Claims, 19 Drawing Sheets

(56) References Cited

OTHER PUBLICATIONS

Yvonne Chen et al., "Selection and Analysis of an Optimized Anti-VEGF Antibody: Crystal Structure of an Affinity-matured Fab in Complex with Antigen", J. Mol. Biol., 1999, 293: 865-881.

Man Sung Co et al., "Humanized Anti-Lewis Y Antibodies: In Vitro Properties and Pharmacokinetics in Rhesus Monkeys", Cancer Research, 1996, 56: 1118-1125.

P.M. Colman, "Effects of amino acid sequence changes", Research in Immunology, 1994, 145: 33-36.

Cynthia L. Collins et al., "Determinants of Glutamine Dependence and Utilization by Normal and Tumor-Derived Breast Cell Lines", Journal of Cellular Physiology, 1998, 176: 166-178.

Roberto De Pascalis et al., "Grafting of 'Abbreviated' Complementarity-Determining Regions Containing Specificity-Determining Residues Essential for Ligand Contact to Engineer a Less Immunogenic Humanized Monoclonal Antibody", The Journal of Immunology, 2002, 169: 3076-3084.

Monika Dolinska et al., "Glutamine Transport in C6 Glioma Cells: Substrate Specificity and Modulation in a Glutamine Deprived Culture Medium", Journal of Neuroscience Research, 2001, 66: 959-966.

Bryan C. Fuchs, et al., "Amino acid transporters ASCT2 and LAT1 in cancer: Partners in crime?" Seminars in Cancer Biology, 2005, 15: 254-266.

Bryan C. Fuchs et al., "Stressing Out Over Survival: Glutamine as an Apoptotic Modulator," Journal of Surgical Research, 2006, 131(1): 26-40.

Bronwyn J. Green, et al., "Biodistribution of the $RD_{114}$/mammalian type D retrovirus receptor, RDR", Journal of Gene Medicine, 2004, 6: 249-259.

Philipp Holliger et al., "'Diabodies': Small bivalent and bispecific antibody fragments", Proc. Natl. Acad. Sci., 1993, 90: 6444-6448.

Patrik Holm et al., "Functional mapping and single chain construction of the anti-cytokeratin 8 monoclonal antibody TS1", Molecular Immunology, 2007, 44: 1075-1084.

Ramesh Kekuda et al., "Cloning of the Sodium-dependent, Broad-scope, Neutral Amino Acid Transporter $B^O$ from a Human Placental Choriocarcinoma Cell Line", Journal of Biological Chemistry, 1996, 271(31): 18657-18661.

Rile Li et al., "Expression of Neutral Amino Acid Transporter ASCT2 in Human Prostate", Anticancer Research, 2003, 23(4): 3413-3418.

Robert M. MacCallum et al., Antibody-antigen Interactions: Contact Analysis and Binding Site Topography, J. Mol. Biol., 1996, 262: 732-745.

William E. Paul (Ed.), "Fundamental Immunology: 3rd Edition", Chapter 8, 1993, pp. 242, 292-295, Raven Press, New York.

Timothy M. Pawlik et al., "Phorbol Esters Rapidly Attenuate Glutamine Uptake and Growth in Human Colon Carcinoma Cells", Journal of Surgical Research, 2000, 90: 149-155.

John E. Rasko et al., "The RD114/simian type D retrovirus receptor is a neutral amino acid transporter", Proc. Natl. Acad. Sci., 1999, 96: 2129-2134.

Stuart Rudikoff et al., "Single amino acid substitution altering antigen-binding specificity", Proc. Natl. Acad. Sci., 1982, 79: 1979-1983.

Marta Sidoryk et al., "Increased expression of a glutamine transporter SNAT3 is a marker of malignant gliomas", NeuroReport, 2004, 15(4): 575-578.

Chetankumar S. Tailor et al., "A Sodium-Dependent Neutral-Amino-Acid Transporter Mediates Infections of Feline and Baboon Endogenous Retroviruses and Simian Type D Retroviruses", Journal of Virology, 1999, 73(5): 4470-4474.

Felix F. Vajdos et al., "Comprehensive Functional Maps of Antigen-binding Site of an Anti-ErbB2 Antibody Obtained with Shotgun Scanning Mutagenesis," Journal of Molecular Biology, 2002, 320: 415-428.

Masafumi Wasa et al., "Characterization of l-glutamine transport by a human neuroblastoma cell line", Am. J. Physiol. Cell Physiol., 2002, 282: 1246-1253.

Deborah Witte et al., "Overexpression of the Neutral Amino Acid Transporter ASCT2 in Human Colorectal Adenocarcinoma", Anticancer Research, 2002, 22: 2555-2558.

Herren Wu et al., "Humanization of a Murine Monoclonal Antibody by Simultaneous Optimization of Framework and CDR Residues", J. Mol. Biol., 1999, 294, 151-162.

International Search Report issued Jan. 21, 2010, for PCT/JP2009/062988.

International Search Report issued Apr. 19, 2011, for PCT/JP2011/050556.

Extended European Search Report issued Dec. 30, 2011, in corresponding EP Application No. 09797999.1 (in the name of Kyowa Hakko Kirin Co., Ltd.).

Non-Final Office Action issued Apr. 27, 2012, by the USPTO in counterpart U.S. Appl. No. 13/008,532.

Office Action, dated Aug. 9, 201, issued by the State Intellectual Property Office of the People's Republic of China, in counterpart Application No. 201180006234.1.

Beifen Shen, et al., "Recombinant Antibody," May 31, 2005, pp. 224-225.

Shanqian Yu, et al., "Immunology Information", High Education Press, Nov. 30, 2004, p. 47.

FIG. 1A

```
NM_005628      1:GTAACCGCTACTCCCGGACACCAGACCACCGCCTTCCGTACACAGGGGCCCGCATCCCAC  60
HCHON2001712   0:------------------------------------------------------------  0

NM_005628     61:CCTCCCGGACCTAAGAGCCTGGGTCCCCTGTTTCCGGAGGTCCGCTTCCCGGCCCCCAGA 120
HCHON2001712   0:------------------------------------------------------------  0

NM_005628    121:TTCTGGCATCCCAGCCCTCAGTGTCCAAGACCCAGGCAGCCCGGGTCCCCGCCTCCCGGA 180
HCHON2001712   0:------------------------------------------------------------  0

NM_005628    181:TCCAGGCGTCCGGGATCTGCGCCACCAGAACCTAGCCTCCTGCAGACCTCCGCCATCTGG 240
HCHON2001712   0:------------------------------------------------------------  0

NM_005628    241:GGGCACTCAACCTCCTGGAGCCAAGGGCCCCACGTCCCACCCAGAGAAACTCTCGTATTC 300
HCHON2001712   0:------------------------------------------------------------  0

NM_005628    301:CCAGCTCCTAGGGCCAAGGAACCCGGGCGCTCCGAACTCCCAGCTTTCGGACATCTGGCA 360
HCHON2001712   0:------------------------------------------------------------  0

NM_005628    361:CACGGGGCAGAGCAGAGAAGCTCAGCGCCCAGCCTGGGGAATTTAAACACTCCAGCTTCC 420
HCHON2001712   0:------------------------------------------------------------  0

NM_005628    421:AAGAGCCAAGGAACTTCAGTGCTGTGAACTCACAACTCTAAGGAGCCCTCCAAAGTTCCA 480
HCHON2001712   1:-----------------------------CTCACAACTCTAAGGAGCCCTCCAAAGTTCCA 32
                                                ********************************

NM_005628    481:GTCTCCAGGTGCTGTTACTCAACTCAGTCCTAGGAACGTCGGGTCCTGGGAAGGAGCCCA 540
HCHON2001712  33:GTCTCCAGGTGCTGTTACTCAACTCAGTCCTAGGAACGTCGGGTCCTGGGAAGGAGCCCA  92
                  ************************************************************

NM_005628    541:AGCGCTCCCAGCCAGCTTCCAGGCGCTAAGAAACCCCGGTGCTTCCCATCATGGTGGCCG 600
HCHON2001712  93:AGCGCTCCCAGCCAGCTTCCAGGCGCTAAGAAACCCCGGTGCTTCCCATCATGGTGGCCG 152
                  ************************************************************

NM_005628    601:ATCCTCCTCGAGACTCCAAGGGGCTCGCAGCGGCGGAGCCCACCGCCAACGGGGGCCTGG 660
HCHON2001712 153:ATCCTCCTCGAGACTCCAAGGGGCTCGCAGCGGCGGAGCCCACCGCCAACGGGGGCCTGG 212
                  ************************************************************

NM_005628    661:CGCTGGCCTCCATCGAGGACCAAGGCGCGGCAGCAGGCGGCTACTGCGGTTCCCGGGACC 720
HCHON2001712 213:CGCTGGCCTCCATCGAGGACCAAGGCGCGGCAGCAGGCGGCTACTGCGGTTCCCGGGACC 272
                  ************************************************************
```

FIG. 1 B

```
NM_005628      721: AGGTGCGCCGCTGCCTTCGAGCCAACCTGCTTGTGCTGCTGACAGTGGTGGCCGTGGTGG 780
HCHON2001712   273: AGGTGCGCCGCTGCCTTCGAGCCAACCTGCTTGTGCTGCTGACAGTGGTGG--------- 323
                    ***************************************************

NM_005628      781: CCGGCGTGGCGCTGGGACTGGGGGTGTCGGGGGCCGGGGGTGCGCTGGCGTTGGGCCCGG 840
HCHON2001712   323: ------------------------------------------------------------ 323

NM_005628      841: AGCGCTTGAGCGCCTTCGTCTTCCCGGGCGAGCTGCTGCTGCGTCTGCTGCGGATGATCA 900
HCHON2001712   323: ------------------------------------------------------------ 323

NM_005628      901: TCTTGCCGCTGGTGGTGTGCAGCTTGATCGGCGGCGCCGCCAGCCTGGACCCCGGCGCGC 960
HCHON2001712   324: ---------------TGTGCAGCTTGATCGGCGGCGCCGCCAGCCTGGACCCCGGCGCGC 368
                                   *********************************************

NM_005628      961: TCGGCCGTCTCGGCGCCTGGGCGCTGCTCTTTTTCCTGGTCACCACGCTGCTGGCCGTCGG 1020
HCHON2001712   369: TCGGCCGTCTCGGCGCCTGGGCGCTGCTCTTTTTCCTGGTCACCACGCTGCTGGCCGTCGG 428
                    ***********************************************************

NM_005628     1021: CGCTCGGAGTGGGCTTGGCGCTGGCTCTGCAGCCGGGCGCCGCCTCCGCCGCCATCAACG 1080
HCHON2001712   429: CGCTCGGAGTGGGCTTGGCGCTGGCTCTGCAGCCGGGCGCCGCCTCCGCCGCCATCAACG 488
                    ***********************************************************

NM_005628     1081: CCTCCGTGGGAGCCGCGGGCAGTGCCGAAAATGCCCCCAGCAAGGAGGTGCTCGATTCGT 1140
HCHON2001712   489: CCTCCGTGGGAGCCGCGGGCAGTGCCGAAAATGCCCCCAGCAAGGAGGTGCTCGATTCGT 548
                    ***********************************************************

NM_005628     1141: TCCTGGATCTTGCGAGAAATATCTTCCCTTCCAACCTGGTGTCAGCAGCCTTTCGCTCAT 1200
HCHON2001712   549: TCCTGGATCTTGCGAGAAATATCTTCCCTTCCAACCTGGTGTCAGCAGCCTTTCGCTCAT 608
                    ***********************************************************

NM_005628     1201: ACTCTACCACCTATGAAGAGAGGAATATCACCGGAACCAGGGTGAAGGTGCCCGTGGGGC 1260
HCHON2001712   609: ACTCTACCACCTATGAAGAGAGGAATATCACCGGAACCAGGGTGAAGGTGCCCGTGGGGC 668
                    ***********************************************************

NM_005628     1261: AGGAGGTGGAGGGGATGAACATCCTGGGCTTGGTAGTGTTTGCCATCGTCTTTGGTGTGG 1320
HCHON2001712   669: AGGAGGTGGAGGGGATGAACATCCTGGGCTTGGTAGTGTTTGCCATCGTCTTTGGTGTGG 728
                    ***********************************************************

NM_005628     1321: CGCTGCGGAAGCTGGGGCCTGAAGGGGAGCTGCTTATCCGCTTCTTCAACTCCTTCAATG 1380
HCHON2001712   729: CGCTGCGGAAGCTGGGGCCTGAAGGGGAGCTGCTTATCCGCTTCTTCAACTCCTTCAATG 788
                    ***********************************************************

NM_005628     1381: AGGCCACCATGGTTCTGGTCTCCTGGATCATGTGGTACGCCCCTGTGGGCATCATGTTCC 1440
HCHON2001712   789: AGGCCACCATGGTTCTGGTCTCCTGGATCATGTGGTACGCCCCTGTGGGCATCATGTTCC 848
                    ***********************************************************

NM_005628     1441: TGGTGGCTGGCAAGATCGTGGAGATGGAGGATGTGGGTTTACTCTTTGCCCGCCTTGGCA 1500
HCHON2001712   849: TGGTGGCTGGCAAGATCGTGGAGATGGAGGATGTGGGTTTACTCTTTGCCCGCCTTGGCA 908
                    ***********************************************************
```

FIG. 1C

```
NM_005628    1501: AGTACATTCTGTGCTGCCTGCTGGGTCACGCCATCCATGGGCTCCTGGTACTGCCCCTCA 1560
HCHON2001712  909: AGTACATTCTGTGCTGCCTGCTGGGTCACGCCATCCATGGGCTCCTGGTACTGCCCCTCA  968
                   ************************************************************

NM_005628    1561: TCTACTTCCTCTTCACCCGCAAAAACCCCTACCGCTTCCTGTGGGGCATCGTGACGCCGC 1620
HCHON2001712  969: TCTACTTCCTCTTCACCCGCAAAAACCCCTACCGCTTCCTGTGGGGCATCGTGACGCCGC 1028
                   ************************************************************

NM_005628    1621: TGGCCACTGCCTTTGGGACCTCTTCCAGTTCCGCCACGCTGCCGCTGATGATGAAGTGCG 1680
HCHON2001712 1029: TGGCCACTGCCTTTGGGACCTCTTCCAGTTCCGCCACGCTGCCGCTGATGATGAAGTGCG 1088
                   ************************************************************

NM_005628    1681: TGGAGGAGAATAATGGCGTGGCCAAGCACATCAGCCGTTTCATCCTGCCCATCGGCGCCA 1740
HCHON2001712 1089: TGGAGGAGAATAATGGCGTGGCCAAGCACATCAGCCGTTTCATCCTGCCCATCGGCGCCA 1148
                   ************************************************************

NM_005628    1741: CCGTCAACATGGACGGTGCCGCGCTCTTCCAGTGCGTGGCCGCAGTGTTCATTGCACAGC 1800
HCHON2001712 1149: CCGTCAACATGGACGGTGCCGCGCTCTTCCAGTGCGTGGCCGCAGTGTTCATTGCACAGC 1208
                   ************************************************************

NM_005628    1801: TCAGCCAGCAGTCCTTGGACTTCGTAAAGATCATCACCATCCTGGTCACGGCCACAGCGT 1860
HCHON2001712 1209: TCAGCCAGCAGTCCTTGGACTTCGTAAAGATCATCACCATCCTGGTCACGGCCACAGCGT 1268
                   ************************************************************

NM_005628    1861: CCAGCGTGGGGGCAGCGGGCATCCCTGCTGGAGGTGTCCTCACTCTGGCCATCATCCTCG 1920
HCHON2001712 1269: CCAGCGTGGGGGCAGCGGGCATCCCTGCTGGAGGTGTCCTCACTCTGGCCATCATCCTCG 1328
                   ************************************************************

NM_005628    1921: AAGCAGTCAACCTCCCGGTCGACCATATCTCCTTGATCCTGGCTGTGGACTGGCTAGTCG 1980
HCHON2001712 1329: AAGCAGTCAACCTCCCGGTCGACCATATCTCCTTGATCCTGGCTGTGGACTGGCTAGTCG 1388
                   ************************************************************

NM_005628    1981: ACCCGTCCTGTACCGTCCTCAATGTAGAAGGTGACGCTCTGGGCCCAGGACTCCTCCAAA 2040
HCHON2001712 1389: ACCCGTCCTGTACCGTCCTCAATGTAGAAGGTGACGCTCTGGGGCCAGGACTCCTCCAAA 1448
                   ********************************************* **************

NM_005628    2041: ATTATGTGGACCGTACGGAGTCGAGAAGCACAGAGCCTGAGTTGATACAAGTGAAGAGTG 2100
HCHON2001712 1449: ATTACGTGGACCGTACGGAGTCGAGAAGCACAGAGCCTGAGTTGATACAAGTGAAGAGTG 1508
                   **** *******************************************************

NM_005628    2101: AGCTGCCCCTGGATCCGCTGCCAGTCCCCACTGAGGAAGGAAACCCCCTCCTCAAACACT 2160
HCHON2001712 1509: AGCTGCCCCTGGATCCGCTGCCAGTCCCCACTGAGGAAGGAAACCCCCTCCTCAAACACT 1568
                   ************************************************************

NM_005628    2161: ATCGGGGCCCCGCAGGGGATGCCACGGTCGCCTCTGAGAAGGAATCAGTCATGTAAACCC 2220
HCHON2001712 1569: ATCGGGGCCCCGCAGGGGATGCCACGGTCGCCTCTGAGAAGGAATCAGTCATGTAAACCC 1628
                   ************************************************************

NM_005628    2221: CGGGAGGGACCTTCCCTGCCCTGCTGGGGGTGCTCTTTGGACACTGGATTATGAGGAATG 2280
HCHON2001712 1629: CGGGAGGGACCTTCCCTGCCCTGCTGGGGGTGCTCTTTGGACACTGGATTATGAGGAATG 1688
                   ************************************************************

NM_005628    2281: GATAAATGGATGAGCTAGGGCTCTGGGGGTCTGCCTGCACACTCTGGGGAGCCAGGGGCC 2340
HCHON2001712 1689: GATAAATGGATGAGCTAGGGCTCTGGGGGTCTGCCTGCACACTCTGGGGAGCCAGGGGCC 1748
                   ************************************************************
```

FIG. 1D

```
NM_005628    2341:CCAGCACCCTCCAGGACAGGAGATCTGGGATGCCTGGCTGCTGGAGTACATGTGTTCACA 2400
HCHON2001712 1749:CCAGCACCCTCCAGGACAGGAGATCTGGGATGCCTGGCTGCTGGAGTACATGTGTTCACA 1808
                  ************************************************************

NM_005628    2401:AGGGTTACTCCTCAAAACCCCCAGTTCTCACTCATGTCCCCAACTCAAGGCTAGAAAACA 2460
HCHON2001712 1809:AGGGTTACTCCTCAAAACCCCCAGTTCTCACTCATGTCCCCAACTCAAGGCTAGAAAACA 1868
                  ************************************************************

NM_005628    2461:GCAAGATGGAGAAATAATGTTCTGCTGCGTCCCCACCGTGACCTGCCTGGCCTCCCCTGT 2520
HCHON2001712 1869:GCAAGATGGAGAAATAATGTTCTGCTGCGTCCCCACCGTGACCTGCCTGGCCTCCCCTGT 1928
                  ************************************************************

NM_005628    2521:CTCAGGGAGCAGGTCACAGGTCACCATGGGGAATTCTAGCCCCCACTGGGGGGATGTTAC 2580
HCHON2001712 1929:CTCAGGGAGCAGGTCACAGGTCACCATGGGGAATTCTAGCCCCCACTGGGGGGATGTTAC 1988
                  ************************************************************

NM_005628    2581:AACACCATGCTGGTTATTTTGGCGGCTGTAGTTGTGGGGGGATGTGTGTGTGCACGTGTG 2640
HCHON2001712 1989:AACACCATGCTGGTTATTTTGGCGGCTGTAGTTGTGGGGGGATGTGTGTGTGCAC----- 2043
                  *******************************************************

NM_005628    2641:TGTGTGTGTGTGTGTGTGTGTGTGTGTGTGTGTTCTGTGACCTCCTGTCCCCATGGTACGTC 2700
HCHON2001712 2044:---GTGTGTGTGTGTGTGTGTGTGTGTGTGTGTTCTGTGACCTCCTGTCCCCATGGTACGTC 2100
                     ********************************************************

NM_005628    2701:CCACCCTGTCCCCAGATCCCCTATTCCCTCCACAATAACAGAAACACTCCCAGGGACTCT 2760
HCHON2001712 2101:CCACCCTGTCCCCAGATCCCCTATTCCCTCCACAATAACAGAAACACTCCCAGGGACTCT 2160
                  ************************************************************

NM_005628    2761:GGGGAGAGGCTGAGGACAAATACCTGCTGTCACTCCAGAGGACATTTTTTTTAGCAATAA 2820
HCHON2001712 2161:GGGGAGAGGCTGAGGACAAATACCTGCTGTCACTCCAGAGGACATTTTTTTTAGCAATAA 2220
                  ************************************************************

NM_005628    2821:AATTGAGTGTCAACTATTTAAAAAAAAAAAAAAAA                          2856
HCHON2001712 2221:AATTGAGTGTCAACTATTT----------------                          2239
                  *******************
```

FIG. 2A

| Sample | | | | ASCT2 | |
|---|---|---|---|---|---|
| | | | | Number of Molecule per Poly A(+) RNA 2ng | Ratio to Trachea |
| Blood Cancer | Cell Line | AML | KG-1 | 1.85E+06 | 10.34 |
| | | | THP-1 | 4.23E+05 | 2.36 |
| | | | HL-60 | 3.07E+05 | 1.71 |
| | | ALL | CCRF-CEM | 4.31E+05 | 2.41 |
| | | | CCRF-SB | 9.85E+03 | 0.06 |
| | | | Jurkat | 1.70E+06 | 9.52 |
| | | | HSB-2 | 2.37E+06 | 13.25 |
| | | | HPB-ALL | 1.51E+04 | 0.08 |
| | | CML | K-562 | 2.58E+06 | 14.41 |
| | | | KU812 | 8.54E+05 | 4.77 |
| | | MM | KMS-11 | 3.30E+06 | 18.43 |
| | | | ARH-77 | 1.97E+06 | 10.99 |
| | | | IM-9 | 1.71E+06 | 9.54 |
| | | | RPMI8226 | 9.54E+05 | 5.33 |
| | | | U266B1 | 2.21E+05 | 1.23 |
| | | | MC/CAR | 3.19E+05 | 1.78 |
| | | BL | HS-Sultan | 1.53E+06 | 8.55 |
| | | | Daudi | 1.11E+01 | 0.00 |
| | | | Raji | 4.45E+05 | 2.49 |
| | | | Ramos | 5.14E+04 | 0.29 |
| | | HS | U-937 | 5.76E+05 | 3.22 |
| | | | ML-1 | 1.72E+06 | 9.63 |
| Lung Cancer | Cell Line | Non-Small Cell | PC-14 | 5.80E+04 | 0.32 |
| | | | PC-7 | 6.32E+03 | 0.04 |
| | | | PC-9 | 1.74E+04 | 0.10 |
| | | | PC-1 | 7.33E+03 | 0.04 |
| | | Small Cell | Lu-139 | 4.61E+04 | 0.26 |
| | | | NCI-H69 | 4.08E+03 | 0.02 |
| | | | RERF-LC-MA | 6.58E+04 | 0.37 |
| | | | SBC-5 | 1.03E+04 | 0.06 |
| | Clinical Tumor Tissue | | Lung tumor | 3.57E+05 | 1.99 |
| Stomach Cancer | Cell Line | | Kato III | 6.02E+04 | 0.34 |
| | | | MKN-74 | 2.10E+04 | 0.12 |
| | | | MUGC-4 | 8.73E+03 | 0.05 |
| | | | AZ-521 | 3.32E+04 | 0.19 |
| | Clinical Tumor Tissue | | Stomach | 7.08E+05 | 3.95 |
| Cololectal Cancer | Cell Line | | Colo205 | 2.55E+05 | 1.43 |
| | | | HT-29 | 5.64E+04 | 0.32 |
| | | | LS174T | 3.39E+04 | 0.19 |
| | | | LS180 | 4.89E+04 | 0.27 |
| | | | SW1116 | 6.87E+04 | 0.38 |
| | Cell-Line Xenograft | | xColo205 | 2.30E+04 | 0.13 |
| | | | xHT29 | 1.04E+05 | 0.58 |
| | | | xLS180 | 1.12E+03 | 0.01 |
| | | | xSW116 | 1.16E+03 | 0.01 |
| | | | xWiDr | 3.43E+04 | 0.19 |
| | Clinical Tumor Tissue | | Rectum tumor | 2.64E+04 | 0.15 |

FIG. 2B

| | | | | |
|---|---|---|---|---|
| Pancreatic Cancer | Cell Line | ASPC-1 | 6.76.E+04 | 0.38 |
| | | BXPC-3 | 1.49.E+05 | 0.83 |
| | | CaPan-1 | 4.15.E+04 | 0.23 |
| | Cell-Line Xenograft | xASPC1 | 3.30.E+04 | 0.18 |
| | | xCanopan1 | 2.86.E+04 | 0.16 |
| | | xPANC1 | 3.04.E+04 | 0.17 |
| Melanoma | Cell Line | G-361 | 4.94.E+03 | 0.03 |
| | | HMV-1 | 1.73.E+04 | 0.10 |
| | | SK-MEL-28 | 2.48.E+04 | 0.14 |
| Fibroblast | Cell Line | MRC-5 | 5.96.E+04 | 0.33 |
| Kidney Cancer | Clinical tumor tissue | Kidney tumor | 7.76.E+03 | 0.04 |
| Liver Cancer | | Liver tumor | 2.69.E+04 | 0.15 |
| Uterus Cancer | | Uterus tumor | 1.55.E+03 | 0.01 |
| Breast Cancer | | Breast tumor | 3.83.E+04 | 0.21 |
| Esophagus Cancer | | Esophagus tumor | 8.14.E+05 | 4.55 |
| Fetal Tissue | Brain | fetal brain | 1.16.E+02 | 0.00 |
| | Kidney | fetal kidney | 2.77.E+03 | 0.02 |
| | Liver | fetal liver | 9.12.E+03 | 0.05 |
| | Lung | fetal lung | 3.31.E+03 | 0.02 |
| Normal Tissue | Liver | Liver | 5.59.E+02 | 0.00 |
| | Lung | Lung | 4.38.E+04 | 0.24 |
| | Brain-Whole | Brain-Whole | 1.86.E+03 | 0.01 |
| | Heart | Heart | 5.69.E+02 | 0.00 |
| | Stomach | Stomach | 2.25.E+04 | 0.13 |
| | Spleen | Spleen | 2.15.E+04 | 0.12 |
| | Spinal cord | Spinal cord | 6.18.E+02 | 0.00 |
| | Small Intestine | Small Intestine | 5.13.E+03 | 0.03 |
| | Skeletal muscle | Skeletal muscle | 7.11.E+01 | 0.00 |
| | Uterus tumor | Uterus tumor | 1.43.E+04 | 0.08 |
| | Terachea | Terachea | 1.79.E+05 | 1.00 |
| | Thyroid | Thyroid | 3.19.E+03 | 0.02 |
| | Thymus | Thymus | 3.01.E+04 | 0.17 |
| | Testis | Testis | 6.23.E+04 | 0.35 |
| | Salivery gland | Salivery gland | 4.74.E+04 | 0.26 |
| | Prostate | Prostate | 2.71.E+04 | 0.15 |
| | Placenta | Placenta | 2.18.E+04 | 0.12 |
| | Lymph node | Lymph node | 2.70.E+04 | 0.15 |
| | Pancreas | Pancreas | 4.41.E+03 | 0.02 |
| | Colon | Colon | 1.46.E+04 | 0.08 |
| | Blood | Blood | 2.41.E+03 | 0.01 |
| | Kidney | Kidney | 1.15.E+05 | 0.64 |

FIG. 4

| KM No. | Animal Species | Antibody Class |
|---|---|---|
| KM3842 | Rat | IgG2a |
| KM4000 | Mouse | IgG2b |
| KM4001 | Mouse | IgG1 |
| KM4008 | Mouse | IgG2 |
| KM4012 | Mouse | IgG2b |
| KM4018 | Rat | IgG2a |

FIG. 15

| Antibody | CHO Expressing Cell | | | | | |
|---|---|---|---|---|---|---|
| | Human | Mouse | mEL1 | mEL2 | mEL3 | mEL4 |
| KM4008 | + | - | + | ± | + | + |
| KM4012 | + | - | + | ± | + | + |
| KM4018 | + | - | ± | - | ± | + |

SEQUENCE LISTING

```
<160> NUMBER OF SEQ ID NOS: 87

<210> SEQ ID NO 1
<211> LENGTH: 2856
<212> TYPE: DNA
<213> ORGANISM: Homo sapiens
<220> FEATURE:
<221> NAME/KEY: CDS
<222> LOCATION: (591)..(2216)
<223> OTHER INFORMATION: ASCT2 nucleotide sequence: GenBank Accession
      number NM_005628

<400> SEQUENCE: 1
gtaaccgcta ctcccggaca ccagaccacc gccttccgta cacaggggcc cgcatcccac      60
cctcccggac ctaagagcct gggtcccctg tttccggagg tccgcttccc ggccccaga     120 ttctggcatc ccagccctca gtgtccaaga cccaggcagc ccgggtcccc gcctccgga     180 tccaggcgtc cggatctgc gccaccagaa cctagcctcc tgcagacctc cgccatctgg     240
gggcactcaa cctcctggag ccaagggccc cacgtccac ccagagaaac tctcgtattc     300
ccagctccta gggccaagga acccgggcgc tccgaactcc cagctttcgg acatctggca     360
cacggggcag agcagagaag ctcagcgccc agcctgggga atttaaacac tccagcttcc     420
aagagccaag gaacttcagt gctgtgaact cacaactcta aggagccctc caaagttcca     480
gtctccaggt gctgttactc aactcagtcc taggaacgtc gggtcctggg aaggagccca     540
agcgctccca gccagcttcc aggcgctaag aaacccggt gcttcccatc atg gtg      596
                                                               Met Val
                                                                1 gcc gat cct cct cga gac tcc aag ggg ctc gca gcg gcg gag ccc acc     644
Ala Asp Pro Pro Arg Asp Ser Lys Gly Leu Ala Ala Ala Glu Pro Thr
          5                  10                  15 gcc aac ggg ggc ctg gcg ctg gcc tcc atc gag gac caa ggc gcg gca     692
Ala Asn Gly Gly Leu Ala Leu Ala Ser Ile Glu Asp Gln Gly Ala Ala
     20                  25                  30 gca ggc ggc tac tgc ggt tcc cgg gac cag gtg cgc cgc tgc ctt cga     740
```

| | | | | | | | | | | | | | | |
|---|---|---|---|---|---|---|---|---|---|---|---|---|---|---|
| Ala | Gly | Gly | Tyr | Cys | Gly | Ser | Arg | Asp | Gln | Val | Arg | Arg | Cys | Leu | Arg |
| 35 | | | | 40 | | | | | 45 | | | | | 50 | |

```
gcc aac ctg ctt gtg ctg ctg aca gtg gtg gcc gtg gtg gcc ggc gtg      788
Ala Asn Leu Leu Val Leu Leu Thr Val Val Ala Val Val Ala Gly Val
                55                  60                  65 gcg ctg gga ctg ggg gtg tcg ggg gcc ggg ggt gcg ctg gcg ttg ggc      836
Ala Leu Gly Leu Gly Val Ser Gly Ala Gly Gly Ala Leu Ala Leu Gly
            70                  75                  80 ccg gag cgc ttg agc gcc ttc gtc ttc ccg ggc gag ctg ctg ctg cgt      884
Pro Glu Arg Leu Ser Ala Phe Val Phe Pro Gly Glu Leu Leu Leu Arg
        85                  90                  95 ctg ctg cgg atg atc atc ttg ccg ctg gtg gtg tgc agc ttg atc ggc      932
Leu Leu Arg Met Ile Ile Leu Pro Leu Val Val Cys Ser Leu Ile Gly
    100                 105                 110 ggc gcc gcc agc ctg gac ccc ggc gcg ctc ggc cgt ctg ggc gcc tgg      980
Gly Ala Ala Ser Leu Asp Pro Gly Ala Leu Gly Arg Leu Gly Ala Trp
115                 120                 125                 130 gcg ctg ctc ttt ttc ctg gtc acc acg ctg ctg gcg tcg gcg ctc gga     1028
Ala Leu Leu Phe Phe Leu Val Thr Thr Leu Leu Ala Ser Ala Leu Gly
                135                 140                 145 gtg ggc ttg gcg ctg gct ctg cag ccg ggc gcc gcc tcc gcc gcc atc     1076
Val Gly Leu Ala Leu Ala Leu Gln Pro Gly Ala Ala Ser Ala Ala Ile
            150                 155                 160 aac gcc tcc gtg gga gcc gcg ggc agt gcc gaa aat gcc ccc agc aag     1124
Asn Ala Ser Val Gly Ala Ala Gly Ser Ala Glu Asn Ala Pro Ser Lys
        165                 170                 175 gag gtg ctc gat tcg ttc ctg gat ctt gcg aga aat atc ttc cct tcc     1172
Glu Val Leu Asp Ser Phe Leu Asp Leu Ala Arg Asn Ile Phe Pro Ser
    180                 185                 190 aac ctg gtg tca gca gcc ttt cgc tca tac tct acc acc tat gaa gag     1220
Asn Leu Val Ser Ala Ala Phe Arg Ser Tyr Ser Thr Thr Tyr Glu Glu
195                 200                 205                 210 agg aat atc acc gga acc agg gtg aag gtg ccc gtg ggg cag gag gtg     1268
Arg Asn Ile Thr Gly Thr Arg Val Lys Val Pro Val Gly Gln Glu Val
                215                 220                 225 gag ggg atg aac atc ctg ggc ttg gta gtg ttt gcc atc gtc ttt ggt     1316
Glu Gly Met Asn Ile Leu Gly Leu Val Val Phe Ala Ile Val Phe Gly
            230                 235                 240 gtg gcg ctg cgg aag ctg ggg cct gaa ggg gag ctg ctt atc cgc ttc     1364
Val Ala Leu Arg Lys Leu Gly Pro Glu Gly Glu Leu Leu Ile Arg Phe
        245                 250                 255 ttc aac tcc ttc aat gag gcc acc atg gtt ctg gtc tcc tgg atc atg     1412
Phe Asn Ser Phe Asn Glu Ala Thr Met Val Leu Val Ser Trp Ile Met
    260                 265                 270 tgg tac gcc cct gtg ggc atc atg ttc ctg gtg gct ggc aag atc gtg     1460
Trp Tyr Ala Pro Val Gly Ile Met Phe Leu Val Ala Gly Lys Ile Val
275                 280                 285                 290 gag atg gag gat gtg ggt tta ctc ttt gcc cgc ctt ggc aag tac att     1508
Glu Met Glu Asp Val Gly Leu Leu Phe Ala Arg Leu Gly Lys Tyr Ile
                295                 300                 305 ctg tgc tgc ctg ctg ggt cac gcc atc cat ggg ctg ctg gta ctg ccc     1556
Leu Cys Cys Leu Leu Gly His Ala Ile His Gly Leu Leu Val Leu Pro
            310                 315                 320 ctc atc tac ttc ctc ttc acc cgc aaa aac ccc tac cgc ttc ctg tgg     1604
Leu Ile Tyr Phe Leu Phe Thr Arg Lys Asn Pro Tyr Arg Phe Leu Trp
        325                 330                 335 ggc atc gtg acg ccg ctg gcc act gcc ttt ggg acc tct tcc agt tcc     1652
Gly Ile Val Thr Pro Leu Ala Thr Ala Phe Gly Thr Ser Ser Ser Ser
    340                 345                 350
```

```
gcc acg ctg ccg ctg atg atg aag tgc gtg gag gag aat aat ggc gtg      1700
Ala Thr Leu Pro Leu Met Met Lys Cys Val Glu Glu Asn Asn Gly Val
355                 360                 365                 370 gcc aag cac atc agc cgt ttc atc ctg ccc atc ggc gcc acc gtc aac      1748
Ala Lys His Ile Ser Arg Phe Ile Leu Pro Ile Gly Ala Thr Val Asn
            375                 380                 385 atg gac ggt gcc gcg ctc ttc cag tgc gtg gcc gca gtg ttc att gca      1796
Met Asp Gly Ala Ala Leu Phe Gln Cys Val Ala Ala Val Phe Ile Ala
                390                 395                 400 cag ctc agc cag cag tcc ttg gac ttc gta aag atc atc acc atc ctg      1844
Gln Leu Ser Gln Gln Ser Leu Asp Phe Val Lys Ile Ile Thr Ile Leu
        405                 410                 415 gtc acg gcc aca gcg tcc agc gtg ggg gca gcg ggc atc cct gct gga      1892
Val Thr Ala Thr Ala Ser Ser Val Gly Ala Ala Gly Ile Pro Ala Gly
    420                 425                 430 ggt gtc ctc act ctg gcc atc atc ctc gaa gca gtc aac ctc ccg gtc      1940
Gly Val Leu Thr Leu Ala Ile Ile Leu Glu Ala Val Asn Leu Pro Val
435                 440                 445                 450 gac cat atc tcc ttg atc ctg gct gtg gac tgg cta gtc gac cgg tcc      1988
Asp His Ile Ser Leu Ile Leu Ala Val Asp Trp Leu Val Asp Arg Ser
            455                 460                 465 tgt acc gtc ctc aat gta gaa ggt gac gct ctg ggg gca gga ctc ctc      2036
Cys Thr Val Leu Asn Val Glu Gly Asp Ala Leu Gly Ala Gly Leu Leu
                470                 475                 480 caa aat tat gtg gac cgt acg gag tcg aga agc aca gag cct gag ttg      2084
Gln Asn Tyr Val Asp Arg Thr Glu Ser Arg Ser Thr Glu Pro Glu Leu
        485                 490                 495 ata caa gtg aag agt gag ctg ccc ctg gat ccg ctg cca gtc ccc act      2132
Ile Gln Val Lys Ser Glu Leu Pro Leu Asp Pro Leu Pro Val Pro Thr
    500                 505                 510 gag gaa gga aac ccc ctc ctc aaa cac tat cgg ggg ccc gca ggg gat      2180
Glu Glu Gly Asn Pro Leu Leu Lys His Tyr Arg Gly Pro Ala Gly Asp
515                 520                 525                 530 gcc acg gtc gcc tct gag aag gaa tca gtc atg taa accccgggag           2226
Ala Thr Val Ala Ser Glu Lys Glu Ser Val Met
            535                 540 ggaccttccc tgccctgctg ggggtgctct ttggacactg gattatgagg aatggataaa    2286
tggatgagct agggctctgg gggtctgcct gcacactctg gggagccagg ggccccagca    2346
ccctccagga caggagatct gggatgcctg gctgctggag tacatgtgtt cacaagggtt    2406
actcctcaaa accccagtt ctcactcatg tccccaactc aaggctagaa acagcaaga      2466 tggagaaata atgttctgct gcgtcccac cgtgacctgc ctggcctccc ctgtctcagg     2526
gagcaggtca caggtcacca tggggaattc tagcccccac tgggggatg ttacaacacc     2586 atgctggtta ttttggcggc tgtagttgtg ggggatgtg tgtgtgcacg tgtgtgtgtg     2646
tgtgtgtgtg tgtgtgtgtg tgtgttctgt gacctcctgt ccccatggta cgtcccaccc   2706
tgtccccaga tccctattc cctccacaat aacagaaaca ctcccaggga ctctggggag    2766
aggctgagga caaatacctg ctgtcactcc agaggacatt ttttttagca ataaaattga    2826
gtgtcaacta tttaaaaaaa aaaaaaaaaa                                     2856

<210> SEQ ID NO 2
<211> LENGTH: 541
<212> TYPE: PRT
<213> ORGANISM: Homo sapiens
<220> FEATURE:
<221> NAME/KEY: PEPTIDE
<222> LOCATION: (1)..(541)
<223> OTHER INFORMATION: ASCT2 peptide sequence: GenPept Accession
``` number NP_005619

<400> SEQUENCE: 2

```
Met Val Ala Asp Pro Arg Asp Ser Lys Gly Leu Ala Ala Glu
1               5                   10                  15

Pro Thr Ala Asn Gly Gly Leu Ala Leu Ala Ser Ile Glu Asp Gln Gly
                20                  25                  30

Ala Ala Ala Gly Gly Tyr Cys Gly Ser Arg Asp Gln Val Arg Arg Cys
            35                  40                  45

Leu Arg Ala Asn Leu Leu Val Leu Leu Thr Val Val Ala Val Val Ala
        50                  55                  60

Gly Val Ala Leu Gly Leu Gly Val Ser Gly Ala Gly Gly Ala Leu Ala
65                  70                  75                  80

Leu Gly Pro Glu Arg Leu Ser Ala Phe Val Phe Pro Gly Glu Leu Leu
                85                  90                  95

Leu Arg Leu Leu Arg Met Ile Ile Leu Pro Leu Val Val Cys Ser Leu
            100                 105                 110

Ile Gly Gly Ala Ala Ser Leu Asp Pro Gly Ala Leu Gly Arg Leu Gly
        115                 120                 125

Ala Trp Ala Leu Leu Phe Phe Leu Val Thr Thr Leu Leu Ala Ser Ala
130                 135                 140

Leu Gly Val Gly Leu Ala Leu Ala Leu Gln Pro Gly Ala Ala Ser Ala
145                 150                 155                 160

Ala Ile Asn Ala Ser Val Gly Ala Ala Gly Ser Ala Glu Asn Ala Pro
                165                 170                 175

Ser Lys Glu Val Leu Asp Ser Phe Leu Asp Leu Ala Arg Asn Ile Phe
            180                 185                 190

Pro Ser Asn Leu Val Ser Ala Ala Phe Arg Ser Tyr Ser Thr Thr Tyr
        195                 200                 205

Glu Glu Arg Asn Ile Thr Gly Thr Arg Val Lys Val Pro Val Gly Gln
210                 215                 220

Glu Val Glu Gly Met Asn Ile Leu Gly Leu Val Val Phe Ala Ile Val
225                 230                 235                 240

Phe Gly Val Ala Leu Arg Lys Leu Gly Pro Glu Gly Glu Leu Leu Ile
                245                 250                 255

Arg Phe Phe Asn Ser Phe Asn Glu Ala Thr Met Val Leu Val Ser Trp
            260                 265                 270

Ile Met Trp Tyr Ala Pro Val Gly Ile Met Phe Leu Val Ala Gly Lys
        275                 280                 285

Ile Val Glu Met Glu Asp Val Gly Leu Leu Phe Ala Arg Leu Gly Lys
290                 295                 300

Tyr Ile Leu Cys Cys Leu Leu Gly His Ala Ile His Gly Leu Leu Val
305                 310                 315                 320

Leu Pro Leu Ile Tyr Phe Leu Phe Thr Arg Lys Asn Pro Tyr Arg Phe
                325                 330                 335

Leu Trp Gly Ile Val Thr Pro Leu Ala Thr Ala Phe Gly Thr Ser Ser
            340                 345                 350

Ser Ser Ala Thr Leu Pro Leu Met Met Lys Cys Val Glu Glu Asn Asn
        355                 360                 365

Gly Val Ala Lys His Ile Ser Arg Phe Ile Leu Pro Ile Gly Ala Thr
370                 375                 380

Val Asn Met Asp Gly Ala Ala Leu Phe Gln Cys Val Ala Ala Val Phe
385                 390                 395                 400
```

```
Ile Ala Gln Leu Ser Gln Gln Ser Leu Asp Phe Val Lys Ile Ile Thr
            405                 410                 415

Ile Leu Val Thr Ala Thr Ala Ser Ser Val Gly Ala Ala Gly Ile Pro
        420                 425                 430

Ala Gly Gly Val Leu Thr Leu Ala Ile Ile Leu Glu Ala Val Asn Leu
    435                 440                 445

Pro Val Asp His Ile Ser Leu Ile Leu Ala Val Asp Trp Leu Val Asp
450                 455                 460

Arg Ser Cys Thr Val Leu Asn Val Glu Gly Asp Ala Leu Gly Ala Gly
465                 470                 475                 480

Leu Leu Gln Asn Tyr Val Asp Arg Thr Glu Ser Arg Ser Thr Glu Pro
                485                 490                 495

Glu Leu Ile Gln Val Lys Ser Glu Leu Pro Leu Asp Pro Leu Pro Val
            500                 505                 510

Pro Thr Glu Glu Gly Asn Pro Leu Leu Lys His Tyr Arg Gly Pro Ala
        515                 520                 525

Gly Asp Ala Thr Val Ala Ser Glu Lys Glu Ser Val Met
    530                 535                 540

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
gataaatgga tgagctaggg c                                           21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
gttattgtgg agggaatagg g                                           21

<210> SEQ ID NO 5
<211> LENGTH: 1689
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1689)

<400> SEQUENCE: 5 atg gtg gcc gat cct cct cga gac tcc aag ggg ctc gca gcg gcg gag   48
Met Val Ala Asp Pro Pro Arg Asp Ser Lys Gly Leu Ala Ala Ala Glu
1               5                   10                  15 ccc acc gcc aac ggg ggc ctg gcg ctg gcc tcc atc gag gac caa ggc   96
Pro Thr Ala Asn Gly Gly Leu Ala Leu Ala Ser Ile Glu Asp Gln Gly
            20                  25                  30 gcg gca gca ggc ggc tac tgc ggt tcc cgg gac cag gtg cgc cgc tgc  144
Ala Ala Ala Gly Gly Tyr Cys Gly Ser Arg Asp Gln Val Arg Arg Cys
        35                  40                  45 ctt cga gcc aac ctg ctt gtg ctg ctg aca gtg gtg gcc gtg gtg gcc  192
Leu Arg Ala Asn Leu Leu Val Leu Leu Thr Val Val Ala Val Val Ala
    50                  55                  60
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ggc | gtg | gcg | ctg | gga | ctg | ggg | gtg | tcg | ggg | gcc | ggg | ggt | gcg | ctg | gcg | 240  |
| Gly | Val | Ala | Leu | Gly | Leu | Gly | Val | Ser | Gly | Ala | Gly | Gly | Ala | Leu | Ala |      |
| 65  |     |     |     | 70  |     |     |     | 75  |     |     |     | 80  |     |     |     |      |

|     |     |     |     |     |     |     |     |     |     |     |     |      |
|-----|-----|-----|-----|-----|-----|-----|-----|-----|-----|-----|-----|------|
| ttg | ggc | ccg | gag | cgc | ttg | agc | gcc | ttc | gtc | ttc | ccg | ggc | gag | ctg | ctg | 288  |
| Leu | Gly | Pro | Glu | Arg | Leu | Ser | Ala | Phe | Val | Phe | Pro | Gly | Glu | Leu | Leu |      |
|     |     |     |     | 85  |     |     |     | 90  |     |     |     | 95  |     |     |     |      |

| ctg | cgt | ctg | ctg | cgg | atg | atc | atc | ttg | ccg | ctg | gtg | gtg | tgc | agc | ttg | 336 |
| Leu | Arg | Leu | Leu | Arg | Met | Ile | Ile | Leu | Pro | Leu | Val | Val | Cys | Ser | Leu |     |
|     |     |     | 100 |     |     |     | 105 |     |     |     | 110 |     |     |     |     |     |

| atc | ggc | ggc | gcc | gcc | agc | ctg | gac | ccc | ggc | gcg | ctc | ggc | cgt | ctg | ggc | 384 |
| Ile | Gly | Gly | Ala | Ala | Ser | Leu | Asp | Pro | Gly | Ala | Leu | Gly | Arg | Leu | Gly |     |
|     |     | 115 |     |     |     | 120 |     |     |     | 125 |     |     |     |     |     |     |

| gcc | tgg | gcg | ctg | ctc | ttt | ttc | ctg | gtc | acc | acg | ctg | ctg | gcg | tcg | gcg | 432 |
| Ala | Trp | Ala | Leu | Leu | Phe | Phe | Leu | Val | Thr | Thr | Leu | Leu | Ala | Ser | Ala |     |
|     | 130 |     |     |     | 135 |     |     |     | 140 |     |     |     |     |     |     |     |

| ctc | gga | gtg | ggc | ttg | gcg | ctg | gct | ctg | cag | ccg | ggc | gcc | gcc | tcc | gcc | 480 |
| Leu | Gly | Val | Gly | Leu | Ala | Leu | Ala | Leu | Gln | Pro | Gly | Ala | Ala | Ser | Ala |     |
| 145 |     |     |     | 150 |     |     |     | 155 |     |     |     | 160 |     |     |     |     |

| gcc | atc | aac | gcc | tcc | gtg | gga | gcc | gcg | ggc | agt | gcc | gaa | aat | gcc | ccc | 528 |
| Ala | Ile | Asn | Ala | Ser | Val | Gly | Ala | Ala | Gly | Ser | Ala | Glu | Asn | Ala | Pro |     |
|     |     |     |     | 165 |     |     |     | 170 |     |     |     | 175 |     |     |     |     |

| agc | aag | gag | gtg | ctc | gat | tcg | ttc | ctg | gat | ctt | gcg | aga | aat | atc | ttc | 576 |
| Ser | Lys | Glu | Val | Leu | Asp | Ser | Phe | Leu | Asp | Leu | Ala | Arg | Asn | Ile | Phe |     |
|     |     |     | 180 |     |     |     | 185 |     |     |     | 190 |     |     |     |     |     |

| cct | tcc | aac | ctg | gtg | tca | gca | gcc | ttt | cgc | tca | tac | tct | acc | acc | tat | 624 |
| Pro | Ser | Asn | Leu | Val | Ser | Ala | Ala | Phe | Arg | Ser | Tyr | Ser | Thr | Thr | Tyr |     |
|     |     | 195 |     |     |     | 200 |     |     |     | 205 |     |     |     |     |     |     |

| gaa | gag | agg | aat | atc | acc | gga | acc | agg | gtg | aag | gtg | ccc | gtg | ggg | cag | 672 |
| Glu | Glu | Arg | Asn | Ile | Thr | Gly | Thr | Arg | Val | Lys | Val | Pro | Val | Gly | Gln |     |
|     | 210 |     |     |     | 215 |     |     |     | 220 |     |     |     |     |     |     |     |

| gag | gtg | gag | ggg | atg | aac | atc | ctg | ggc | ttg | gta | gtg | ttt | gcc | atc | gtc | 720 |
| Glu | Val | Glu | Gly | Met | Asn | Ile | Leu | Gly | Leu | Val | Val | Phe | Ala | Ile | Val |     |
| 225 |     |     |     | 230 |     |     |     | 235 |     |     |     | 240 |     |     |     |     |

| ttt | ggt | gtg | gcg | ctg | cgg | aag | ctg | ggg | cct | gaa | ggg | gag | ctg | ctt | atc | 768 |
| Phe | Gly | Val | Ala | Leu | Arg | Lys | Leu | Gly | Pro | Glu | Gly | Glu | Leu | Leu | Ile |     |
|     |     |     |     | 245 |     |     |     | 250 |     |     |     | 255 |     |     |     |     |

| cgc | ttc | ttc | aac | tcc | ttc | aat | gag | gcc | acc | atg | gtt | ctg | gtc | tcc | tgg | 816 |
| Arg | Phe | Phe | Asn | Ser | Phe | Asn | Glu | Ala | Thr | Met | Val | Leu | Val | Ser | Trp |     |
|     |     |     | 260 |     |     |     | 265 |     |     |     | 270 |     |     |     |     |     |

| atc | atg | tgg | tac | gcc | cct | gtg | ggc | atc | atg | ttc | ctg | gtg | gct | ggc | aag | 864 |
| Ile | Met | Trp | Tyr | Ala | Pro | Val | Gly | Ile | Met | Phe | Leu | Val | Ala | Gly | Lys |     |
|     |     | 275 |     |     |     | 280 |     |     |     | 285 |     |     |     |     |     |     |

| atc | gtg | gag | atg | gag | gat | gtg | ggt | tta | ctc | ttt | gcc | cgc | ctt | ggc | aag | 912 |
| Ile | Val | Glu | Met | Glu | Asp | Val | Gly | Leu | Leu | Phe | Ala | Arg | Leu | Gly | Lys |     |
|     | 290 |     |     |     | 295 |     |     |     | 300 |     |     |     |     |     |     |     |

| tac | att | ctg | tgc | tgc | ctg | ctg | ggt | cac | gcc | atc | cat | ggg | ctc | ctg | gta | 960 |
| Tyr | Ile | Leu | Cys | Cys | Leu | Leu | Gly | His | Ala | Ile | His | Gly | Leu | Leu | Val |     |
| 305 |     |     |     | 310 |     |     |     | 315 |     |     |     | 320 |     |     |     |     |

| ctg | ccc | ctc | atc | tac | ttc | ctc | ttc | acc | cgc | aaa | aac | ccc | tac | cgc | ttc | 1008 |
| Leu | Pro | Leu | Ile | Tyr | Phe | Leu | Phe | Thr | Arg | Lys | Asn | Pro | Tyr | Arg | Phe |      |
|     |     |     |     | 325 |     |     |     | 330 |     |     |     | 335 |     |     |     |      |

| ctg | tgg | ggc | atc | gtg | acg | ccg | ctg | gcc | act | gcc | ttt | ggg | acc | tct | tcc | 1056 |
| Leu | Trp | Gly | Ile | Val | Thr | Pro | Leu | Ala | Thr | Ala | Phe | Gly | Thr | Ser | Ser |      |
|     |     |     |     | 340 |     |     |     | 345 |     |     |     | 350 |     |     |     |      |

| agt | tcc | gcc | acg | ctg | ccg | ctg | atg | atg | aag | tgc | gtg | gag | gag | aat | aat | 1104 |
| Ser | Ser | Ala | Thr | Leu | Pro | Leu | Met | Met | Lys | Cys | Val | Glu | Glu | Asn | Asn |      |
|     |     | 355 |     |     |     | 360 |     |     |     | 365 |     |     |     |     |     |      |

| ggc | gtg | gcc | aag | cac | atc | agc | cgt | ttc | atc | ctg | ccc | atc | ggc | gcc | acc | 1152 |
| Gly | Val | Ala | Lys | His | Ile | Ser | Arg | Phe | Ile | Leu | Pro | Ile | Gly | Ala | Thr |      |

-continued

```
                     370                 375                 380
gtc aac atg gac ggt gcc gcg ctc ttc cag tgc gtg gcc gca gtg ttc     1200
Val Asn Met Asp Gly Ala Ala Leu Phe Gln Cys Val Ala Ala Val Phe
385                 390                 395                 400 att gca cag ctc agc cag cag tcc ttg gac ttc gta aag atc atc acc     1248
Ile Ala Gln Leu Ser Gln Gln Ser Leu Asp Phe Val Lys Ile Ile Thr
                405                 410                 415 atc ctg gtc acg gcc aca gcg tcc agc gtg ggg gca gcg ggc atc cct     1296
Ile Leu Val Thr Ala Thr Ala Ser Ser Val Gly Ala Ala Gly Ile Pro
            420                 425                 430 gct gga ggt gtc ctc act ctg gcc atc atc ctc gaa gca gtc aac ctc     1344
Ala Gly Gly Val Leu Thr Leu Ala Ile Ile Leu Glu Ala Val Asn Leu
        435                 440                 445 ccg gtc gac cat atc tcc ttg atc ctg gct gtg gac tgg cta gtc gac     1392
Pro Val Asp His Ile Ser Leu Ile Leu Ala Val Asp Trp Leu Val Asp
    450                 455                 460 cgg tcc tgt acc gtc ctc aat gta gaa ggt gac gct ctg ggg gca gga     1440
Arg Ser Cys Thr Val Leu Asn Val Glu Gly Asp Ala Leu Gly Ala Gly
465                 470                 475                 480 ctc ctc caa aat tac gtg gac cgt acg gag tcg aga agc aca gag cct     1488
Leu Leu Gln Asn Tyr Val Asp Arg Thr Glu Ser Arg Ser Thr Glu Pro
                485                 490                 495 gag ttg ata caa gtg aag agt gag ctg ccc ctg gat ccg ctg cca gtc     1536
Glu Leu Ile Gln Val Lys Ser Glu Leu Pro Leu Asp Pro Leu Pro Val
            500                 505                 510 ccc act gag gaa gga aac ccc ctc ctc aaa cac tat cgg ggg ccc gca     1584
Pro Thr Glu Glu Gly Asn Pro Leu Leu Lys His Tyr Arg Gly Pro Ala
        515                 520                 525 ggg gat gcc acg gtc gcc tct gag aag gaa tca gtc atg gaa caa aaa     1632
Gly Asp Ala Thr Val Ala Ser Glu Lys Glu Ser Val Met Glu Gln Lys
    530                 535                 540 ctc atc tca gaa gag gat ctg aat atg cat acc ggt cat cat cac cat     1680
Leu Ile Ser Glu Glu Asp Leu Asn Met His Thr Gly His His His His
545                 550                 555                 560 cac cat tga                                                         1689
His His
```

```
<210> SEQ ID NO 6
<211> LENGTH: 562
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(562)

<400> SEQUENCE: 6

Met Val Ala Asp Pro Pro Arg Asp Ser Lys Gly Leu Ala Ala Ala Glu
1               5                   10                  15

Pro Thr Ala Asn Gly Gly Leu Ala Leu Ala Ser Ile Glu Asp Gln Gly
            20                  25                  30

Ala Ala Ala Gly Gly Tyr Cys Gly Ser Arg Asp Gln Val Arg Arg Cys
        35                  40                  45

Leu Arg Ala Asn Leu Leu Val Leu Leu Thr Val Ala Val Val Ala
    50                  55                  60

Gly Val Ala Leu Gly Leu Gly Val Ser Gly Ala Gly Gly Ala Leu Ala
65                  70                  75                  80

Leu Gly Pro Glu Arg Leu Ser Ala Phe Val Phe Pro Gly Glu Leu Leu
                85                  90                  95
```

```
Leu Arg Leu Leu Arg Met Ile Ile Leu Pro Leu Val Val Cys Ser Leu
            100                 105                 110

Ile Gly Gly Ala Ala Ser Leu Asp Pro Gly Ala Leu Gly Arg Leu Gly
            115                 120                 125

Ala Trp Ala Leu Leu Phe Phe Leu Val Thr Thr Leu Leu Ala Ser Ala
            130                 135                 140

Leu Gly Val Gly Leu Ala Leu Ala Leu Gln Pro Gly Ala Ala Ser Ala
145                 150                 155                 160

Ala Ile Asn Ala Ser Val Gly Ala Ala Gly Ser Ala Glu Asn Ala Pro
                165                 170                 175

Ser Lys Glu Val Leu Asp Ser Phe Leu Asp Leu Ala Arg Asn Ile Phe
            180                 185                 190

Pro Ser Asn Leu Val Ser Ala Ala Phe Arg Ser Tyr Ser Thr Thr Tyr
            195                 200                 205

Glu Glu Arg Asn Ile Thr Gly Thr Arg Val Lys Val Pro Val Gly Gln
            210                 215                 220

Glu Val Glu Gly Met Asn Ile Leu Gly Leu Val Val Phe Ala Ile Val
225                 230                 235                 240

Phe Gly Val Ala Leu Arg Lys Leu Gly Pro Glu Gly Glu Leu Leu Ile
                245                 250                 255

Arg Phe Phe Asn Ser Phe Asn Glu Ala Thr Met Val Leu Val Ser Trp
            260                 265                 270

Ile Met Trp Tyr Ala Pro Val Gly Ile Met Phe Leu Val Ala Gly Lys
            275                 280                 285

Ile Val Glu Met Glu Asp Val Gly Leu Leu Phe Ala Arg Leu Gly Lys
            290                 295                 300

Tyr Ile Leu Cys Cys Leu Leu Gly His Ala Ile His Gly Leu Leu Val
305                 310                 315                 320

Leu Pro Leu Ile Tyr Phe Leu Phe Thr Arg Lys Asn Pro Tyr Arg Phe
                325                 330                 335

Leu Trp Gly Ile Val Thr Pro Leu Ala Thr Ala Phe Gly Thr Ser Ser
            340                 345                 350

Ser Ser Ala Thr Leu Pro Leu Met Met Lys Cys Val Glu Glu Asn Asn
            355                 360                 365

Gly Val Ala Lys His Ile Ser Arg Phe Ile Leu Pro Ile Gly Ala Thr
            370                 375                 380

Val Asn Met Asp Gly Ala Ala Leu Phe Gln Cys Val Ala Ala Val Phe
385                 390                 395                 400

Ile Ala Gln Leu Ser Gln Gln Ser Leu Asp Phe Val Lys Ile Ile Thr
                405                 410                 415

Ile Leu Val Thr Ala Thr Ala Ser Ser Val Gly Ala Ala Gly Ile Pro
            420                 425                 430

Ala Gly Gly Val Leu Thr Leu Ala Ile Ile Leu Glu Ala Val Asn Leu
            435                 440                 445

Pro Val Asp His Ile Ser Leu Ile Leu Ala Val Asp Trp Leu Val Asp
            450                 455                 460

Arg Ser Cys Thr Val Leu Asn Val Glu Gly Asp Ala Leu Gly Ala Gly
465                 470                 475                 480

Leu Leu Gln Asn Tyr Val Asp Arg Thr Glu Ser Arg Ser Thr Glu Pro
                485                 490                 495

Glu Leu Ile Gln Val Lys Ser Glu Leu Pro Leu Asp Pro Leu Pro Val
            500                 505                 510
```

Pro Thr Glu Glu Gly Asn Pro Leu Leu Lys His Tyr Arg Gly Pro Ala
            515                 520                 525

Gly Asp Ala Thr Val Ala Ser Glu Lys Glu Ser Val Met Glu Gln Lys
        530                 535                 540

Leu Ile Ser Glu Glu Asp Leu Asn Met His Thr Gly His His His His
545                 550                 555                 560

His His

<210> SEQ ID NO 7
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 7
aaggaaaaaa gaattcaaac cccggtgctt cccatcatgg tggccgatcc tcctcgagac      60
tccaaggggc tcgcagcggc ggagcccacc gccaacgggg                           100

<210> SEQ ID NO 8
<211> LENGTH: 140
<212> TYPE: DNA
<213> ORGANISM: Artificial Sequence
<220> FEATURE:
<223> OTHER INFORMATION: Synthetic oligonucleotide

<400> SEQUENCE: 8
cggccaccac tgtcagcagc acaagcaggt tggctcgaag gcagcggcgc acctggtccc      60
gggaaccgca gtagccgcct gctgccgcgc cttggtcctc gatggaggcc agcgccaggc     120
ccccgttggc ggtgggctcc                                                 140

<210> SEQ ID NO 9
<211> LENGTH: 130
<212> TYPE: DNA
<213> ORGANISM: Artificial Sequence
<220> FEATURE:
<223> OTHER INFORMATION: Synthetic oligonucleotide

<400> SEQUENCE: 9
gctgctgaca gtggtggccg tggtggccgg cgtggcgctg gactgggggg tgtcggggc       60 cgggggtgcg ctggcgttgg gcccggagcg cttgagcgcc ttcgtcttcc cgggcgagct    120
gctgctgcgt                                                            130

<210> SEQ ID NO 10
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 10
ccgagcgcgc cggggtccag gctggcggcg ccgccgatca agctgcacac caccagcggc      60
aagatgatca tccgcagcag acgcagcagc agctcgcccg                           100

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 11
ctggaccccg gcgcgctcgg                                                  20

<210> SEQ ID NO 12
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 12
cgatggtacc tcaatggtga tggtgatgat gaccggtatg catattcaga tcctcttctg      60
agatgagttt ttgttccatg actgattcct tctcagaggc gaccgtggca tccctgcgg     120

<210> SEQ ID NO 13
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 13
ggactagtgc ggccgcgatg gtacctcaat ggtgatggtg                            40

<210> SEQ ID NO 14
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 14

Val Ala Asp Pro Pro Arg Asp Ser Lys Gly Leu Ala Ala Ala Glu Cys
1               5                   10                  15

<210> SEQ ID NO 15
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 15
ctggacaggg ctccatagtt ccatt                                            25

<210> SEQ ID NO 16
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 16
ttgaccaggc atcccagagt cacggaggaa                                       30

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
ctaacactca ttcctgttga agctcttgac aa                                    32
```

<210> SEQ ID NO 18
<211> LENGTH: 417
<212> TYPE: DNA
<213> ORGANISM: Mus musculus
<220> FEATURE:
<221> NAME/KEY: CDS
<222> LOCATION: (1)..(417)
<223> OTHER INFORMATION: KM4008VH nucleotide sequence

<400> SEQUENCE: 18

```
atg ggt tgg ctg tgg aac ttg cta ttc ctg atg gca gct gcc caa agt      48
Met Gly Trp Leu Trp Asn Leu Leu Phe Leu Met Ala Ala Ala Gln Ser
1               5                   10                  15 gcc caa gca cag atc cag ttg gta cag tct gga cct gag ctg aag aag      96
Ala Gln Ala Gln Ile Gln Leu Val Gln Ser Gly Pro Glu Leu Lys Lys
                20                  25                  30 cct gga gag aca gtc aag atc tcc tgc aag gct tct ggg tat acc ttc     144
Pro Gly Glu Thr Val Lys Ile Ser Cys Lys Ala Ser Gly Tyr Thr Phe
            35                  40                  45 aca acc ttt gga atg agc tgg gtg aaa cag gtt cca gga aag ggt tta     192
Thr Thr Phe Gly Met Ser Trp Val Lys Gln Val Pro Gly Lys Gly Leu
        50                  55                  60 aag tgg atg ggc tgg ata cac acc tac gct gga gtg cca ata tat ggt     240
Lys Trp Met Gly Trp Ile His Thr Tyr Ala Gly Val Pro Ile Tyr Gly
65                  70                  75                  80 gat gac ttc aag gga cgg ttt gcc ttc tct ttg gaa acc tct gcc agc     288
Asp Asp Phe Lys Gly Arg Phe Ala Phe Ser Leu Glu Thr Ser Ala Ser
                85                  90                  95 act gcc tat ttg cag atc aac aac gtc aaa aat gag gac acg gct aca     336
Thr Ala Tyr Leu Gln Ile Asn Asn Val Lys Asn Glu Asp Thr Ala Thr
                100                 105                 110 tat ttc tgt gca cga cgt tcg gat aat tac cgt tat ttt ttt gac tat     384
Tyr Phe Cys Ala Arg Arg Ser Asp Asn Tyr Arg Tyr Phe Phe Asp Tyr
            115                 120                 125 tgg ggc caa ggc acc act ctc aca gtc tcc tcg                         417
Trp Gly Gln Gly Thr Thr Leu Thr Val Ser Ser
        130                 135
```

<210> SEQ ID NO 19
<211> LENGTH: 139
<212> TYPE: PRT
<213> ORGANISM: Mus musculus
<220> FEATURE:
<221> NAME/KEY: PEPTIDE
<222> LOCATION: (1)..(139)
<223> OTHER INFORMATION: KM4008VH peptide sequence

<400> SEQUENCE: 19

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Thr Phe Gly Met Ser Trp Val Lys Gln Val Pro Gly Lys Gly Leu
        50                  55                  60

Lys Trp Met Gly Trp Ile His Thr Tyr Ala Gly Val Pro Ile Tyr Gly
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Val Lys Asn Glu Asp Thr Ala Thr
```

```
                    100                 105                 110
Tyr Phe Cys Ala Arg Arg Ser Asp Asn Tyr Arg Tyr Phe Phe Asp Tyr
        115                 120                 125

Trp Gly Gln Gly Thr Thr Leu Thr Val Ser Ser
        130                 135

<210> SEQ ID NO 20
<211> LENGTH: 384
<212> TYPE: DNA
<213> ORGANISM: Mus musculus
<220> FEATURE:
<221> NAME/KEY: CDS
<222> LOCATION: (1)..(384)
<223> OTHER INFORMATION: KM4008VL nucleotide sequence

<400> SEQUENCE: 20 atg atg tcc tct gct cgg ttc ctt ggt ctc ctg ttg ctc tgc ttt caa        48
Met Met Ser Ser Ala Arg Phe Leu Gly Leu Leu Leu Leu Cys Phe Gln
1               5                   10                  15 ggt acc aga tgt gat atc cag atg aca cag act aca tcc tcc ctg tct        96
Gly Thr Arg Cys Asp Ile Gln Met Thr Gln Thr Thr Ser Ser Leu Ser
                20                  25                  30 gcc tct ctg gga gac aga gtc acc atc agt tgc agg gca agt cag gac       144
Ala Ser Leu Gly Asp Arg Val Thr Ile Ser Cys Arg Ala Ser Gln Asp
            35                  40                  45 att agg aat tat tta aac tgg tat caa cgt aaa cca cat gga act gtt       192
Ile Arg Asn Tyr Leu Asn Trp Tyr Gln Arg Lys Pro His Gly Thr Val
        50                  55                  60 aaa ctc ctg atc tac tac aca tca aga tta cac tca gga gtc ccg tca       240
Lys Leu Leu Ile Tyr Tyr Thr Ser Arg Leu His Ser Gly Val Pro Ser
65                  70                  75                  80 agg ttc agt ggc agt ggg tct gga aca gat tat tct ctc acc att agc       288
Arg Phe Ser Gly Ser Gly Ser Gly Thr Asp Tyr Ser Leu Thr Ile Ser
                85                  90                  95 aac ctg gaa caa gaa gat att gcc act tac ttt tgc caa cag ggt cat       336
Asn Leu Glu Gln Glu Asp Ile Ala Thr Tyr Phe Cys Gln Gln Gly His
                100                 105                 110 acg ctt cct ccg acg ttc ggt gga ggc acc aag ttg gaa atc aaa cgg       384
Thr Leu Pro Pro Thr Phe Gly Gly Gly Thr Lys Leu Glu Ile Lys Arg
        115                 120                 125

<210> SEQ ID NO 21
<211> LENGTH: 128
<212> TYPE: PRT
<213> ORGANISM: Mus musculus
<220> FEATURE:
<221> NAME/KEY: PEPTIDE
<222> LOCATION: (1)..(128)
<223> OTHER INFORMATION: KM4008VL peptide sequence

<400> SEQUENCE: 21

Met Met Ser Ser Ala Arg Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Arg Asn Tyr Leu Asn Trp Tyr Gln Arg Lys Pro His Gly Thr Val
        50                  55                  60

Lys Leu Leu Ile Tyr Tyr Thr Ser Arg Leu His Ser Gly Val Pro Ser
65                  70                  75                  80
```

```
Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly His
            100                 105                 110

Thr Leu Pro Pro Thr Phe Gly Gly Gly Thr Lys Leu Glu Ile Lys Arg
        115                 120                 125

<210> SEQ ID NO 22
<211> LENGTH: 417
<212> TYPE: DNA
<213> ORGANISM: Mus musculus
<220> FEATURE:
<221> NAME/KEY: CDS
<222> LOCATION: (1)..(417)
<223> OTHER INFORMATION: KM4012VH nucleotide sequence

<400> SEQUENCE: 22 atg ggt tgg ctg tgg aac ttg cta ttc ctg atg gca gct gcc caa agt      48
Met Gly Trp Leu Trp Asn Leu Leu Phe Leu Met Ala Ala Ala Gln Ser
1               5                   10                  15 gcc caa gca cag atc cag ttg gta cag tct gga cct gag ctg aag aag      96
Ala Gln Ala Gln Ile Gln Leu Val Gln Ser Gly Pro Glu Leu Lys Lys
            20                  25                  30 cct gga gag aca gtc aag atc tcc tgc aag gct tct gga tat acc ttc     144
Pro Gly Glu Thr Val Lys Ile Ser Cys Lys Ala Ser Gly Tyr Thr Phe
        35                  40                  45 acg acc tat gga atg agc tgg gtg aaa cag act cca gga aag ggt tta     192
Thr Thr Tyr Gly Met Ser Trp Val Lys Gln Thr Pro Gly Lys Gly Leu
    50                  55                  60 aag tgg atg ggc tgg ata cac acc tac tct gga gtg cca ata tat ggt     240
Lys Trp Met Gly Trp Ile His Thr Tyr Ser Gly Val Pro Ile Tyr Gly
65                  70                  75                  80 gat gac tcc aag gga cgg ttt gcc ttc tct ttg gaa acc tct ggc agc     288
Asp Asp Ser Lys Gly Arg Phe Ala Phe Ser Leu Glu Thr Ser Gly Ser
                85                  90                  95 att gcc tat ttg cag atc aac aac gtc aaa aat gag gac acg gct aca     336
Ile Ala Tyr Leu Gln Ile Asn Asn Val Lys Asn Glu Asp Thr Ala Thr
            100                 105                 110 tat ttc tgt gca aga cgt tcg gat ggt tac cgt tac ttc ttt gac tat     384
Tyr Phe Cys Ala Arg Arg Ser Asp Gly Tyr Arg Tyr Phe Phe Asp Tyr
        115                 120                 125 tgg ggc caa ggc acc act ctc aca gtc tcc tca                         417
Trp Gly Gln Gly Thr Thr Leu Thr Val Ser Ser
    130                 135

<210> SEQ ID NO 23
<211> LENGTH: 139
<212> TYPE: PRT
<213> ORGANISM: Mus musculus
<220> FEATURE:
<221> NAME/KEY: PEPTIDE
<222> LOCATION: (1)..(139)
<223> OTHER INFORMATION: KM4012VH peptide sequence

<400> SEQUENCE: 23

Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Thr Pro Gly Lys Gly Leu
```

```
                   50                  55                  60

Lys Trp Met Gly Trp Ile His Thr Tyr Ser Gly Val Pro Ile Tyr Gly
 65                  70                  75                  80

Asp Asp Ser Lys Gly Arg Phe Ala Phe Ser Leu Glu Thr Ser Gly Ser
                 85                  90                  95

Ile Ala Tyr Leu Gln Ile Asn Asn Val Lys Asn Glu Asp Thr Ala Thr
            100                 105                 110

Tyr Phe Cys Ala Arg Arg Ser Asp Gly Tyr Arg Tyr Phe Phe Asp Tyr
        115                 120                 125

Trp Gly Gln Gly Thr Thr Leu Thr Val Ser Ser
    130                 135

<210> SEQ ID NO 24
<211> LENGTH: 384
<212> TYPE: DNA
<213> ORGANISM: Mus musculus
<220> FEATURE:
<221> NAME/KEY: CDS
<222> LOCATION: (1)..(384)
<223> OTHER INFORMATION: KM4012VL nucleotide sequence

<400> SEQUENCE: 24 atg atg tcc tct gct cag ttc ctt ggt ctc ctg ttg ctc tgc ttt caa     48
Met Met Ser Ser Ala Gln Phe Leu Gly Leu Leu Leu Leu Cys Phe Gln
 1               5                  10                  15 ggt acc aga tgt gat atc cag atg aca cag att aca tcc tcc ctg tct     96
Gly Thr Arg Cys Asp Ile Gln Met Thr Gln Ile Thr Ser Ser Leu Ser
             20                  25                  30 gcc tct ctg gga gac aga gtc acc atc agt tgc agg gca agt cag gac    144
Ala Ser Leu Gly Asp Arg Val Thr Ile Ser Cys Arg Ala Ser Gln Asp
         35                  40                  45 att agg aat tat tta aac tgg tat cag cag aaa cca gat gga act gtt    192
Ile Arg Asn Tyr Leu Asn Trp Tyr Gln Gln Lys Pro Asp Gly Thr Val
     50                  55                  60 aaa ctc ctg atc tac tac aca tca aga tta cac tca gga gtc cca tca    240
Lys Leu Leu Ile Tyr Tyr Thr Ser Arg Leu His Ser Gly Val Pro Ser
 65                  70                  75                  80 agg ttc agt ggc agt ggg tct gga aca gat tat tct ctc acc att agc    288
Arg Phe Ser Gly Ser Gly Ser Gly Thr Asp Tyr Ser Leu Thr Ile Ser
             85                  90                  95 aac ctg gaa caa gaa gat att gcc act tac ttt tgc caa cag ggt aat    336
Asn Leu Glu Gln Glu Asp Ile Ala Thr Tyr Phe Cys Gln Gln Gly Asn
            100                 105                 110 acg ctt cct ccg acg ttc ggt gga ggc acc aag ttg gaa atc aaa cgg    384
Thr Leu Pro Pro Thr Phe Gly Gly Gly Thr Lys Leu Glu Ile Lys Arg
        115                 120                 125

<210> SEQ ID NO 25
<211> LENGTH: 128
<212> TYPE: PRT
<213> ORGANISM: Mus musculus
<220> FEATURE:
<221> NAME/KEY: PEPTIDE
<222> LOCATION: (1)..(128)
<223> OTHER INFORMATION: KM4012VL peptide sequence

<400> SEQUENCE: 25

Met Met Ser Ser Ala Gln Phe Leu Gly Leu Leu Leu Leu Cys Phe Gln
 1               5                  10                  15

Gly Thr Arg Cys Asp Ile Gln Met Thr Gln Ile Thr Ser Ser Leu Ser
             20                  25                  30
```

```
Ala Ser Leu Gly Asp Arg Val Thr Ile Ser Cys Arg Ala Ser Gln Asp
            35                  40                  45

Ile Arg Asn Tyr Leu Asn Trp Tyr Gln Gln Lys Pro Asp Gly Thr Val
 50                  55                  60

Lys Leu Leu Ile Tyr Tyr Thr Ser Arg Leu His Ser Gly Val Pro Ser
 65                  70                  75                  80

Arg Phe Ser Gly Ser Gly Ser Gly Thr Asp Tyr Ser Leu Thr Ile Ser
                 85                  90                  95

Asn Leu Glu Gln Glu Asp Ile Ala Thr Tyr Phe Cys Gln Gln Gly Asn
             100                 105                 110

Thr Leu Pro Pro Thr Phe Gly Gly Thr Lys Leu Glu Ile Lys Arg
         115                 120                 125
```

<210> SEQ ID NO 26
<211> LENGTH: 5
<212> TYPE: PRT
<213> ORGANISM: Mus musculus
<220> FEATURE:
<221> NAME/KEY: PEPTIDE
<222> LOCATION: (1)..(5)
<223> OTHER INFORMATION: KM4008H CDR1 peptide sequence

<400> SEQUENCE: 26

```
Thr Phe Gly Met Ser
 1               5
```

<210> SEQ ID NO 27
<211> LENGTH: 17
<212> TYPE: PRT
<213> ORGANISM: Mus musculus
<220> FEATURE:
<221> NAME/KEY: PEPTIDE
<222> LOCATION: (1)..(17)
<223> OTHER INFORMATION: KM4008 CDR2 peptide sequence

<400> SEQUENCE: 27

```
Trp Ile His Thr Tyr Ala Gly Val Pro Ile Tyr Gly Asp Asp Phe Lys
 1               5                  10                  15

Gly
```

<210> SEQ ID NO 28
<211> LENGTH: 11
<212> TYPE: PRT
<213> ORGANISM: Mus musculus
<220> FEATURE:
<221> NAME/KEY: PEPTIDE
<222> LOCATION: (1)..(11)
<223> OTHER INFORMATION: KM4008H CDR3 peptide sequence

<400> SEQUENCE: 28

```
Arg Ser Asp Asn Tyr Arg Tyr Phe Phe Asp Tyr
 1               5                  10
```

<210> SEQ ID NO 29
<211> LENGTH: 11
<212> TYPE: PRT
<213> ORGANISM: Mus musculus
<220> FEATURE:
<221> NAME/KEY: PEPTIDE
<222> LOCATION: (1)..(11)
<223> OTHER INFORMATION: KM4008L CDR1 peptide sequence

<400> SEQUENCE: 29

```
Arg Ala Ser Gln Asp Ile Arg Asn Tyr Leu Asn
 1               5                  10
```

```
<210> SEQ ID NO 30
<211> LENGTH: 7
<212> TYPE: PRT
<213> ORGANISM: Mus musculus
<220> FEATURE:
<221> NAME/KEY: PEPTIDE
<222> LOCATION: (1)..(7)
<223> OTHER INFORMATION: KM4008L CDR2 peptide sequence

<400> SEQUENCE: 30

Tyr Thr Ser Arg Leu His Ser
1               5

<210> SEQ ID NO 31
<211> LENGTH: 9
<212> TYPE: PRT
<213> ORGANISM: Mus musculus
<220> FEATURE:
<221> NAME/KEY: PEPTIDE
<222> LOCATION: (1)..(9)
<223> OTHER INFORMATION: KM4008L CDR3 peptide sequence

<400> SEQUENCE: 31

Gln Gln Gly His Thr Leu Pro Pro Thr
1               5

<210> SEQ ID NO 32
<211> LENGTH: 5
<212> TYPE: PRT
<213> ORGANISM: Mus musculus
<220> FEATURE:
<221> NAME/KEY: PEPTIDE
<222> LOCATION: (1)..(5)
<223> OTHER INFORMATION: KM4012H CDR1 peptide sequence

<400> SEQUENCE: 32

Thr Tyr Gly Met Ser
1               5

<210> SEQ ID NO 33
<211> LENGTH: 17
<212> TYPE: PRT
<213> ORGANISM: Mus musculus
<220> FEATURE:
<221> NAME/KEY: PEPTIDE
<222> LOCATION: (1)..(17)
<223> OTHER INFORMATION: KM4012H CDR2 peptide sequence

<400> SEQUENCE: 33

Trp Ile His Thr Tyr Ser Gly Val Pro Ile Tyr Gly Asp Asp Ser Lys
1               5                   10                  15

Gly

<210> SEQ ID NO 34
<211> LENGTH: 11
<212> TYPE: PRT
<213> ORGANISM: Mus musculus
<220> FEATURE:
<221> NAME/KEY: PEPTIDE
<222> LOCATION: (1)..(11)
<223> OTHER INFORMATION: KM4012H CDR3 peptide sequence

<400> SEQUENCE: 34

Arg Ser Asp Gly Tyr Arg Tyr Phe Phe Asp Tyr
1               5                   10
```

```
<210> SEQ ID NO 35
<211> LENGTH: 11
<212> TYPE: PRT
<213> ORGANISM: Mus musculus
<220> FEATURE:
<221> NAME/KEY: PEPTIDE
<222> LOCATION: (1)..(11)
<223> OTHER INFORMATION: KM4012L CDR1 peptide sequence

<400> SEQUENCE: 35

Arg Ala Ser Gln Asp Ile Arg Asn Tyr Leu Asn
1               5                   10

<210> SEQ ID NO 36
<211> LENGTH: 7
<212> TYPE: PRT
<213> ORGANISM: Mus musculus
<220> FEATURE:
<221> NAME/KEY: PEPTIDE
<222> LOCATION: (1)..(7)
<223> OTHER INFORMATION: KM4012L CDR2 peptide sequence

<400> SEQUENCE: 36

Tyr Thr Ser Arg Leu His Ser
1               5

<210> SEQ ID NO 37
<211> LENGTH: 9
<212> TYPE: PRT
<213> ORGANISM: Mus musculus
<220> FEATURE:
<221> NAME/KEY: PEPTIDE
<222> LOCATION: (1)..(9)
<223> OTHER INFORMATION: KM4012L CDR3 peptide sequence

<400> SEQUENCE: 37

Gln Gln Gly Asn Thr Leu Pro Pro Thr
1               5

<210> SEQ ID NO 38
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 38
aaaagcggcc gcccactgag cccaagtctt agacatcatg                              40

<210> SEQ ID NO 39
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 39
cgatgggccc ttggtggaag ccgaggagac tgtgagagtg                              40

<210> SEQ ID NO 40
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 40
ccggaattca ttgaagtcaa gactcagcct ggacatgatg                              40
```

<210> SEQ ID NO 41
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 41
ccaccgtacg tttgatttcc aacttggtgc ctccaccgaa          40

<210> SEQ ID NO 42
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 42
cgatgggccc ttggtggagg ctgaggagac tgtgagagtg          40

<210> SEQ ID NO 43
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 43
ccacaaggat tgcattccct tggcac          26

<210> SEQ ID NO 44
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 44
cctgttgaag ctcttgacga cgggtgagg          29

<210> SEQ ID NO 45
<211> LENGTH: 426
<212> TYPE: DNA
<213> ORGANISM: Rattus norvegicus
<220> FEATURE:
<221> NAME/KEY: CDS
<222> LOCATION: (1)..(426)
<223> OTHER INFORMATION: KM4018VH nucleotide sequence

<400> SEQUENCE: 45

```
atg gac atc agg ctc agc ttg gct ttc ctt gtc ctt ttc ata aaa ggt     48
Met Asp Ile Arg Leu Ser Leu Ala Phe Leu Val Leu Phe Ile Lys Gly
 1               5                  10                  15 gtc cag tgt gag gtg cag ctg gtg gag tct ggg gga ggc tta gtg cag     96
Val Gln Cys Glu Val Gln Leu Val Glu Ser Gly Gly Gly Leu Val Gln
             20                  25                  30 tct gga agg tcc ata aga ctc tcc tgt gca gcc tca gga ttc tct ttc    144
Ser Gly Arg Ser Ile Arg Leu Ser Cys Ala Ala Ser Gly Phe Ser Phe
         35                  40                  45 agt aac tat tac atg gcc tgg gtc cgc cag gct cca tcg aag ggt ctg    192
Ser Asn Tyr Tyr Met Ala Trp Val Arg Gln Ala Pro Ser Lys Gly Leu
     50                  55                  60 gag tgg gtc gca tcc att act aaa ggt ggt ggt aat act tac tat cga    240
Glu Trp Val Ala Ser Ile Thr Lys Gly Gly Gly Asn Thr Tyr Tyr Arg
```

```
gac tcc gtg aag ggc cga ttc act ttc tcc aga gat aat gca aaa agc      288
Asp Ser Val Lys Gly Arg Phe Thr Phe Ser Arg Asp Asn Ala Lys Ser
                85                  90                  95 acc cta tat ttg caa atg gac agt ctg agg tct gag gac acg gcc act      336
Thr Leu Tyr Leu Gln Met Asp Ser Leu Arg Ser Glu Asp Thr Ala Thr
            100                 105                 110 tat tac tgt gca aga cag gtt act ata gca gct gta tct acc tcc tac      384
Tyr Tyr Cys Ala Arg Gln Val Thr Ile Ala Ala Val Ser Thr Ser Tyr
        115                 120                 125 ttt gat tcc tgg ggc caa gga gtc atg gtc aca gtc tcc tca              426
Phe Asp Ser Trp Gly Gln Gly Val Met Val Thr Val Ser Ser
130                 135                 140

<210> SEQ ID NO 46
<211> LENGTH: 142
<212> TYPE: PRT
<213> ORGANISM: Rattus norvegicus
<220> FEATURE:
<221> NAME/KEY: PEPTIDE
<222> LOCATION: (1)..(142)
<223> OTHER INFORMATION: KM4018VH peptide sequence

<400> SEQUENCE: 46

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Ser Gly Arg Ser Ile Arg Leu Ser Cys Ala Ala Ser Gly Phe Ser Phe
        35                  40                  45

Ser Asn Tyr Tyr Met Ala Trp Val Arg Gln Ala Pro Ser Lys Gly Leu
    50                  55                  60

Glu Trp Val Ala Ser Ile Thr Lys Gly Gly Gly Asn Thr Tyr Tyr Arg
65              70                  75                  80

Asp Ser Val Lys Gly Arg Phe Thr Phe Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Arg Gln Val Thr Ile Ala Ala Val Ser Thr Ser Tyr
        115                 120                 125

Phe Asp Ser Trp Gly Gln Gly Val Met Val Thr Val Ser Ser
    130                 135                 140

<210> SEQ ID NO 47
<211> LENGTH: 393
<212> TYPE: DNA
<213> ORGANISM: Rattus norvegicus
<220> FEATURE:
<221> NAME/KEY: CDS
<222> LOCATION: (1)..(393)
<223> OTHER INFORMATION: KM4018VL nucleotide sequence

<400> SEQUENCE: 47 atg aag aca gac aca ctc ctg ctg tgg gct ctg ctg ctc tgg gtt cca       48
Met Lys Thr Asp Thr Leu Leu Leu Trp Ala Leu Leu Leu Trp Val Pro
1               5                   10                  15 ggt tgc act ggt gac att gtg ctg acc cag tct cct gct ttg gct gtg       96
Gly Cys Thr Gly Asp Ile Val Leu Thr Gln Ser Pro Ala Leu Ala Val
            20                  25                  30 tct cta ggg cag agg gcc acc atc tcc tgc aag acc aat cag aag gtc      144
Ser Leu Gly Gln Arg Ala Thr Ile Ser Cys Lys Thr Asn Gln Lys Val
```

-continued

```
                   35                  40                  45
gat tat tat ggc aat agt tat gtg tac tgg tac caa cag aaa cca gga      192
Asp Tyr Tyr Gly Asn Ser Tyr Val Tyr Trp Tyr Gln Gln Lys Pro Gly
         50                  55                  60 caa caa ccc aaa ctc ctc atc tat tta gca tcc aac tta gca tct ggg      240
Gln Gln Pro Lys Leu Leu Ile Tyr Leu Ala Ser Asn Leu Ala Ser Gly
 65                  70                  75                  80 atc cct gcc agg ttc agt ggt aga ggg tct ggg aca gac ttc acc ctc      288
Ile Pro Ala Arg Phe Ser Gly Arg Gly Ser Gly Thr Asp Phe Thr Leu
                 85                  90                  95 acc att gat cct gtg gag gct gat gat act gca acc tat tac tgt cag      336
Thr Ile Asp Pro Val Glu Ala Asp Asp Thr Ala Thr Tyr Tyr Cys Gln
             100                 105                 110 cag agt agg aat ctt ccg tac acg ttt gga gct ggg acc aag ctg gaa      384
Gln Ser Arg Asn Leu Pro Tyr Thr Phe Gly Ala Gly Thr Lys Leu Glu
         115                 120                 125 ctg aaa cgg                                                          393
Leu Lys Arg
    130
```

<210> SEQ ID NO 48
<211> LENGTH: 131
<212> TYPE: PRT
<213> ORGANISM: Rattus norvegicus
<220> FEATURE:
<221> NAME/KEY: PEPTIDE
<222> LOCATION: (1)..(131)
<223> OTHER INFORMATION: KM4018VL peptide sequence

<400> SEQUENCE: 48

```
Met Lys Thr Asp Thr Leu Leu Trp Ala Leu Leu Leu Trp Val Pro
 1               5                  10                  15

Gly Cys Thr Gly Asp Ile Val Leu Thr Gln Ser Pro Ala Leu Ala Val
                 20                  25                  30

Ser Leu Gly Gln Arg Ala Thr Ile Ser Cys Lys Thr Asn Gln Lys Val
         35                  40                  45

Asp Tyr Tyr Gly Asn Ser Tyr Val Tyr Trp Tyr Gln Gln Lys Pro Gly
     50                  55                  60

Gln Gln Pro Lys Leu Leu Ile Tyr Leu Ala Ser Asn Leu Ala Ser Gly
 65                  70                  75                  80

Ile Pro Ala Arg Phe Ser Gly Arg Gly Ser Gly Thr Asp Phe Thr Leu
                 85                  90                  95

Thr Ile Asp Pro Val Glu Ala Asp Asp Thr Ala Thr Tyr Tyr Cys Gln
             100                 105                 110

Gln Ser Arg Asn Leu Pro Tyr Thr Phe Gly Ala Gly Thr Lys Leu Glu
         115                 120                 125

Leu Lys Arg
    130
```

<210> SEQ ID NO 49
<211> LENGTH: 5
<212> TYPE: PRT
<213> ORGANISM: Rattus norvegicus
<220> FEATURE:
<221> NAME/KEY: PEPTIDE
<222> LOCATION: (1)..(5)
<223> OTHER INFORMATION: KM4018H CDR1 peptide sequence

<400> SEQUENCE: 49

```
Asn Tyr Tyr Met Ala
 1               5
```

```
<210> SEQ ID NO 50
<211> LENGTH: 17
<212> TYPE: PRT
<213> ORGANISM: Rattus norvegicus
<220> FEATURE:
<221> NAME/KEY: PEPTIDE
<222> LOCATION: (1)..(17)
<223> OTHER INFORMATION: KM4018H CDR2 peptide sequence

<400> SEQUENCE: 50

Ser Ile Thr Lys Gly Gly Gly Asn Thr Tyr Tyr Arg Asp Ser Val Lys
1               5                   10                  15

Gly

<210> SEQ ID NO 51
<211> LENGTH: 14
<212> TYPE: PRT
<213> ORGANISM: Rattus norvegicus
<220> FEATURE:
<221> NAME/KEY: PEPTIDE
<222> LOCATION: (1)..(14)
<223> OTHER INFORMATION: KM4018H CDR3 peptide sequence

<400> SEQUENCE: 51

Gln Val Thr Ile Ala Ala Val Ser Thr Ser Tyr Phe Asp Ser
1               5                   10

<210> SEQ ID NO 52
<211> LENGTH: 15
<212> TYPE: PRT
<213> ORGANISM: Rattus norvegicus
<220> FEATURE:
<221> NAME/KEY: PEPTIDE
<222> LOCATION: (1)..(15)
<223> OTHER INFORMATION: KM4018L CDR1 peptide sequence

<400> SEQUENCE: 52

Lys Thr Asn Gln Lys Val Asp Tyr Tyr Gly Asn Ser Tyr Val Tyr
1               5                   10                  15

<210> SEQ ID NO 53
<211> LENGTH: 7
<212> TYPE: PRT
<213> ORGANISM: Rattus norvegicus
<220> FEATURE:
<221> NAME/KEY: PEPTIDE
<222> LOCATION: (1)..(7)
<223> OTHER INFORMATION: KM4018L CDR2 peptide sequence

<400> SEQUENCE: 53

Leu Ala Ser Asn Leu Ala Ser
1               5

<210> SEQ ID NO 54
<211> LENGTH: 9
<212> TYPE: PRT
<213> ORGANISM: Rattus norvegicus
<220> FEATURE:
<221> NAME/KEY: PEPTIDE
<222> LOCATION: (1)..(9)
<223> OTHER INFORMATION: KM4018L CDR3 peptide sequence

<400> SEQUENCE: 54

Gln Gln Ser Arg Asn Leu Pro Tyr Thr
1               5
```

<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 55
aaaagcggcc gctgcagcac tgcacagact acgcaccatg        40

<210> SEQ ID NO 56
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 56
cgatgggccc ttggtggaag ctgaggagac tgtgaccatg        40

<210> SEQ ID NO 57
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 57
ccggaattcc cagcctctct ttcagctgtc agagatgaag        40

<210> SEQ ID NO 58
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 58
ccaccgtacg tttcagttcc agcttggtcc cagctccaaa        40

<210> SEQ ID NO 59
<211> LENGTH: 1731
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(1731)

<400> SEQUENCE: 59

```
atg gca gtg gat ccc cct aag gct gac ccc aaa ggg gta gta gcg gtg        48
Met Ala Val Asp Pro Pro Lys Ala Asp Pro Lys Gly Val Val Ala Val
1               5                   10                  15 gat tcc acc gcg aac ggt ggc ccc gcg ctg gga tcc aga gag gac cag        96
Asp Ser Thr Ala Asn Gly Gly Pro Ala Leu Gly Ser Arg Glu Asp Gln
            20                  25                  30 agt gcg aaa gca ggt ggt tgc tgc ggt tcc cgt gac cgg gtg cgc cgc       144
Ser Ala Lys Ala Gly Gly Cys Cys Gly Ser Arg Asp Arg Val Arg Arg
        35                  40                  45 tgc att cgc gcc aac ctg ctg gtg ctg ctc acg gtg gct gcg gtg gtg       192
Cys Ile Arg Ala Asn Leu Leu Val Leu Leu Thr Val Ala Ala Val Val
    50                  55                  60 gct ggc gtg ggg ctg ggg ctg ggg gtc tcg gcg gcg ggc ggt gct gac       240
Ala Gly Val Gly Leu Gly Leu Gly Val Ser Ala Ala Gly Gly Ala Asp
65              70                  75                  80
```

```
gcg ctg ggt ccc gcg cgc ttg acc gct ttc gcc ttc ccg gga gag ctg       288
Ala Leu Gly Pro Ala Arg Leu Thr Ala Phe Ala Phe Pro Gly Glu Leu
                 85                  90                  95 ctg ctg cgt ctg ctg aag atg atc atc ctg ccg ctc gtg gtg tgc agc       336
Leu Leu Arg Leu Leu Lys Met Ile Ile Leu Pro Leu Val Val Cys Ser
            100                 105                 110 ctg atc gga ggt gca gcc agc ttg gac cct agc gcg ctc ggt cgt gtg       384
Leu Ile Gly Gly Ala Ala Ser Leu Asp Pro Ser Ala Leu Gly Arg Val
        115                 120                 125 ggc gcc tgg gcg ctg ctc ttt ttc ctg gtc acc aca ctg ctc gcg tcg       432
Gly Ala Trp Ala Leu Leu Phe Phe Leu Val Thr Thr Leu Leu Ala Ser
    130                 135                 140 gcg ctc ggc gtg ggt ttg gcc ctg gcg ctg aag ccg ggc gcc gcc gtt       480
Ala Leu Gly Val Gly Leu Ala Leu Ala Leu Lys Pro Gly Ala Ala Val
145                 150                 155                 160 acc gcc atc acc tcc atc aac gac tct gtt gta gac ccc tgt gcc cgc       528
Thr Ala Ile Thr Ser Ile Asn Asp Ser Val Val Asp Pro Cys Ala Arg
                165                 170                 175 agt gca cca acc aaa gag gtg ctg gat tcc ttt cta gat ctc gtg agg       576
Ser Ala Pro Thr Lys Glu Val Leu Asp Ser Phe Leu Asp Leu Val Arg
            180                 185                 190 aat att ttc ccc tcc aat ctg gtg tct gct gcc ttc cgc tct ttt gct       624
Asn Ile Phe Pro Ser Asn Leu Val Ser Ala Ala Phe Arg Ser Phe Ala
        195                 200                 205 acc tca tat gaa ccc aaa gac aac tca tgt aaa ata ccg caa tcc tgt       672
Thr Ser Tyr Glu Pro Lys Asp Asn Ser Cys Lys Ile Pro Gln Ser Cys
    210                 215                 220 atc cag cgg gag atc aat tca acg atg gtc cag ctt ctc tgt gag gtg       720
Ile Gln Arg Glu Ile Asn Ser Thr Met Val Gln Leu Leu Cys Glu Val
225                 230                 235                 240 gag gga atg aac atc ctg ggc ctg gtg gtc ttc gct atc gtc ttt ggt       768
Glu Gly Met Asn Ile Leu Gly Leu Val Val Phe Ala Ile Val Phe Gly
                245                 250                 255 gtg gct ctg cgg aag ctg ggg ccc gag ggt gag ctg ctc att cgt ttc       816
Val Ala Leu Arg Lys Leu Gly Pro Glu Gly Glu Leu Leu Ile Arg Phe
            260                 265                 270 ttc aac tcc ttc aat gat gcc acc atg gtc ctg gtc tcc tgg att atg       864
Phe Asn Ser Phe Asn Asp Ala Thr Met Val Leu Val Ser Trp Ile Met
        275                 280                 285 tgg tac gca ccc gtt gga atc ctg ttc ctg gtg gcc agc aag att gtg       912
Trp Tyr Ala Pro Val Gly Ile Leu Phe Leu Val Ala Ser Lys Ile Val
    290                 295                 300 gag atg aaa gac gtg cgc cag ctc ttc atc agc ctc ggc aaa tac att       960
Glu Met Lys Asp Val Arg Gln Leu Phe Ile Ser Leu Gly Lys Tyr Ile
305                 310                 315                 320 ctg tgc tgc ctg ctg ggc cac gcc atc cac ggg ctc ctg gtt ctg cct      1008
Leu Cys Cys Leu Leu Gly His Ala Ile His Gly Leu Leu Val Leu Pro
                325                 330                 335 ctc atc tac ttc ctc ttc acc cgc aaa aat ccc tat cga ttc ctg tgg      1056
Leu Ile Tyr Phe Leu Phe Thr Arg Lys Asn Pro Tyr Arg Phe Leu Trp
            340                 345                 350 ggc atc atg aca ccc ctg gcc act gct ttc ggg acc tct tct agc tct      1104
Gly Ile Met Thr Pro Leu Ala Thr Ala Phe Gly Thr Ser Ser Ser Ser
        355                 360                 365 gcc acc ttg cct ctg atg atg aag tgt gta gag gag aag aat ggt gtg      1152
Ala Thr Leu Pro Leu Met Met Lys Cys Val Glu Glu Lys Asn Gly Val
    370                 375                 380 gcc aaa cac atc agc cgg ttc atc cta ccc atc ggc gcc acg gtc aac      1200
Ala Lys His Ile Ser Arg Phe Ile Leu Pro Ile Gly Ala Thr Val Asn
385                 390                 395                 400
```

```
atg gac ggg gcg gcg ctg ttc cag tgt gtg gcg gca gtg ttc atc gca    1248
Met Asp Gly Ala Ala Leu Phe Gln Cys Val Ala Ala Val Phe Ile Ala
            405                 410                 415 caa cta aac ggg gtg tcc ctg gac ttc gtg aag atc atc acc atc ctg    1296
Gln Leu Asn Gly Val Ser Leu Asp Phe Val Lys Ile Ile Thr Ile Leu
        420                 425                 430 gtc aca gcc aca gca tcc agt gtc ggt gcg gca ggg atc cct gca ggg    1344
Val Thr Ala Thr Ala Ser Ser Val Gly Ala Ala Gly Ile Pro Ala Gly
    435                 440                 445 ggc gtc ctc acc ctc gcc atc atc ctg gaa gca gtc agc ctg cct gtg    1392
Gly Val Leu Thr Leu Ala Ile Ile Leu Glu Ala Val Ser Leu Pro Val
450                 455                 460 aag gac atc tcc ttg atc ttg gcc gtg gac tgg cta gtg gac agg tcc    1440
Lys Asp Ile Ser Leu Ile Leu Ala Val Asp Trp Leu Val Asp Arg Ser
465                 470                 475                 480 tgt act gtc ctc aac gtg gaa ggt gat gct ttt ggg gct gga ctg ctt    1488
Cys Thr Val Leu Asn Val Glu Gly Asp Ala Phe Gly Ala Gly Leu Leu
                485                 490                 495 cag agt tac gtg gat cga acc aag atg ccg agc tca gag ccc gaa ttg    1536
Gln Ser Tyr Val Asp Arg Thr Lys Met Pro Ser Ser Glu Pro Glu Leu
            500                 505                 510 atc cag gtg aag aac gag gtg tct ctg aat cca ctg ccc ctc gcc aca    1584
Ile Gln Val Lys Asn Glu Val Ser Leu Asn Pro Leu Pro Leu Ala Thr
        515                 520                 525 gag gag ggg aat ccc ctc ctg aaa cag tac cag gga ccc acc ggg gac    1632
Glu Glu Gly Asn Pro Leu Leu Lys Gln Tyr Gln Gly Pro Thr Gly Asp
    530                 535                 540 tcc agt gcc acg ttc gaa aag gaa tct gtc atg gaa caa aaa ctc atc    1680
Ser Ser Ala Thr Phe Glu Lys Glu Ser Val Met Glu Gln Lys Leu Ile
545                 550                 555                 560 tca gaa gag gat ctg aat atg cat acc ggt cat cat cac cat cac cat    1728
Ser Glu Glu Asp Leu Asn Met His Thr Gly His His His His His His
                565                 570                 575 tga                                                                1731
```

```
<210> SEQ ID NO 60
<211> LENGTH: 576
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(576)

<400> SEQUENCE: 60

Met Ala Val Asp Pro Pro Lys Ala Asp Pro Lys Gly Val Val Ala Val
1               5                   10                  15

Asp Ser Thr Ala Asn Gly Gly Pro Ala Leu Gly Ser Arg Glu Asp Gln
            20                  25                  30

Ser Ala Lys Ala Gly Gly Cys Cys Gly Ser Arg Asp Arg Val Arg Arg
        35                  40                  45

Cys Ile Arg Ala Asn Leu Leu Val Leu Thr Val Ala Ala Val Val
    50                  55                  60

Ala Gly Val Gly Leu Gly Leu Gly Val Ser Ala Ala Gly Gly Ala Asp
65                  70                  75                  80

Ala Leu Gly Pro Ala Arg Leu Thr Ala Phe Ala Phe Pro Gly Glu Leu
                85                  90                  95
```

```
Leu Leu Arg Leu Leu Lys Met Ile Ile Leu Pro Leu Val Val Cys Ser
            100                 105                 110

Leu Ile Gly Gly Ala Ala Ser Leu Asp Pro Ser Ala Leu Gly Arg Val
            115                 120                 125

Gly Ala Trp Ala Leu Leu Phe Phe Leu Val Thr Thr Leu Leu Ala Ser
        130                 135                 140

Ala Leu Gly Val Gly Leu Ala Leu Ala Leu Lys Pro Gly Ala Ala Val
145                 150                 155                 160

Thr Ala Ile Thr Ser Ile Asn Asp Ser Val Asp Pro Cys Ala Arg
                165                 170                 175

Ser Ala Pro Thr Lys Glu Val Leu Asp Ser Phe Leu Asp Leu Val Arg
            180                 185                 190

Asn Ile Phe Pro Ser Asn Leu Val Ser Ala Ala Phe Arg Ser Phe Ala
            195                 200                 205

Thr Ser Tyr Glu Pro Lys Asp Asn Ser Cys Lys Ile Pro Gln Ser Cys
        210                 215                 220

Ile Gln Arg Glu Ile Asn Ser Thr Met Val Gln Leu Leu Cys Glu Val
225                 230                 235                 240

Glu Gly Met Asn Ile Leu Gly Leu Val Val Phe Ala Ile Val Phe Gly
                245                 250                 255

Val Ala Leu Arg Lys Leu Gly Pro Glu Gly Glu Leu Leu Ile Arg Phe
            260                 265                 270

Phe Asn Ser Phe Asn Asp Ala Thr Met Val Leu Val Ser Trp Ile Met
        275                 280                 285

Trp Tyr Ala Pro Val Gly Ile Leu Phe Leu Val Ala Ser Lys Ile Val
        290                 295                 300

Glu Met Lys Asp Val Arg Gln Leu Phe Ile Ser Leu Gly Lys Tyr Ile
305                 310                 315                 320

Leu Cys Cys Leu Leu Gly His Ala Ile His Gly Leu Leu Val Leu Pro
                325                 330                 335

Leu Ile Tyr Phe Leu Phe Thr Arg Lys Asn Pro Tyr Arg Phe Leu Trp
            340                 345                 350

Gly Ile Met Thr Pro Leu Ala Thr Ala Phe Gly Thr Ser Ser Ser Ser
        355                 360                 365

Ala Thr Leu Pro Leu Met Met Lys Cys Val Glu Glu Lys Asn Gly Val
370                 375                 380

Ala Lys His Ile Ser Arg Phe Ile Leu Pro Ile Gly Ala Thr Val Asn
385                 390                 395                 400

Met Asp Gly Ala Ala Leu Phe Gln Cys Val Ala Ala Val Phe Ile Ala
                405                 410                 415

Gln Leu Asn Gly Val Ser Leu Asp Phe Val Lys Ile Ile Thr Ile Leu
            420                 425                 430

Val Thr Ala Thr Ala Ser Ser Val Gly Ala Ala Gly Ile Pro Ala Gly
        435                 440                 445

Gly Val Leu Thr Leu Ala Ile Ile Leu Glu Ala Val Ser Leu Pro Val
        450                 455                 460

Lys Asp Ile Ser Leu Ile Leu Ala Val Asp Trp Leu Val Asp Arg Ser
465                 470                 475                 480

Cys Thr Val Leu Asn Val Glu Gly Asp Ala Phe Gly Ala Gly Leu Leu
                485                 490                 495

Gln Ser Tyr Val Asp Arg Thr Lys Met Pro Ser Ser Glu Pro Glu Leu
            500                 505                 510

Ile Gln Val Lys Asn Glu Val Ser Leu Asn Pro Leu Pro Leu Ala Thr
```

```
            515                 520                 525
Glu Gly Asn Pro Leu Leu Lys Gln Tyr Gln Gly Pro Thr Gly Asp
        530                 535                 540

Ser Ser Ala Thr Phe Glu Lys Glu Ser Val Met Glu Gln Lys Leu Ile
545                 550                 555                 560

Ser Glu Glu Asp Leu Asn Met His Thr Gly His His His His His
                565                 570                 575
```

<210> SEQ ID NO 61
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 61
ccggaattca cggctcagca tggcagtgga tcccctaag gctgacccca aaggggtag      59

<210> SEQ ID NO 62
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 62
cgatggtacc tcaatggtga tgtgatgat gaccggtatg catattcaga tcctcttctg      60
agatgagttt tgttccatg acagattcct tttcgaacgt ggcactggag tccccggtgg    120

<210> SEQ ID NO 63
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 63
tgggtcacgc cattcatggg ctcctggt                                       28

<210> SEQ ID NO 64
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 64
accaggagcc catgaatggc gtgaccca                                       28

<210> SEQ ID NO 65
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 65
cccgcaaaaa ccctatcga ttcctgtggg gcatcg                               36

<210> SEQ ID NO 66
<211> LENGTH: 36
<212> TYPE: DNA
<213> ORGANISM: Artificial Sequence
<220> FEATURE:

<210> SEQ ID NO 66
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 66
cgatgcccca caggaatcga tagggttttt tgcggg    36

<210> SEQ ID NO 67
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 67
cgggagatca attcaacgat ggtccagctt ctctg    35

<210> SEQ ID NO 68
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 68
cagagaagct ggaccatcgt tgaattgatc tcccg    35

<210> SEQ ID NO 69
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 69
gtgcgtggag gagaagaatg gcgtggccaa    30

<210> SEQ ID NO 70
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 70
ttggccacgc cattcttctc ctccacgcac    30

<210> SEQ ID NO 71
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(120)

<400> SEQUENCE: 71

Gln Val Gln Leu Val Gln Ser Gly Ser Glu Leu Lys Lys Pro Gly Ala
1               5                   10                  15

Pro Val Lys Val Ser Cys Lys Ala Ser Gly Tyr Thr Phe Ser Thr Phe
            20                  25                  30

Gly Met Ser Trp Val Arg Gln Ala Pro Gly Gln Gly Leu Glu Trp Met
        35                  40                  45

Gly Trp Ile His Thr Tyr Ala Gly Val Pro Ile Tyr Gly Asp Asp Phe
    50                  55                  60

```
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Arg Ser Asp Asn Tyr Arg Tyr Phe Phe Asp Tyr Trp Gly Gln
            100                 105                 110

Gly Thr Thr Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(107)
<223> OTHER INFORMATION: Description of Artificial sequence: KM4008 LV0
      sequence

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Gly His Thr Leu Pro Pro
                85                  90                  95

Thr Phe Gly Gln Gly Thr Lys Leu Glu Ile Lys
            100                 105

<210> SEQ ID NO 73
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(360)

<400> SEQUENCE: 73 cag gtg cag ttg gtc cag tcc ggc tct gag ctg aag aag cct ggt gcc      48
Gln Val Gln Leu Val Gln Ser Gly Ser Glu Leu Lys Lys Pro Gly Ala
1               5                   10                  15 cct gtg aag gtc tcc tgc aag gct tct ggt tac acc ttc agc acc ttt      96
Pro Val Lys Val Ser Cys Lys Ala Ser Gly Tyr Thr Phe Ser Thr Phe
            20                  25                  30 ggc atg agc tgg gtg cga cag gcc cct ggt caa ggg ctt gag tgg atg     144
Gly Met Ser Trp Val Arg Gln Ala Pro Gly Gln Gly Leu Glu Trp Met
        35                  40                  45 ggt tgg att cac acc tac gct ggt gtg cca atc tat ggt gat gac ttc     192
Gly Trp Ile His Thr Tyr Ala Gly Val Pro Ile Tyr Gly Asp Asp Phe
    50                  55                  60 aag ggt cga ttc gtc ttc agc ctg gac aca tcc gtg agc aca gcc tac     240
Lys Gly Arg Phe Val Phe Ser Leu Asp Thr Ser Val Ser Thr Ala Tyr
```

```
                 65                  70                  75                  80
ttg cag atc agc agc ctg aag gct gag gac acg gcc gtg tat tac tgt          288
Leu Gln Ile Ser Ser Leu Lys Ala Glu Asp Thr Ala Val Tyr Tyr Cys
                     85                  90                  95 gcg cgc cgt tcg gat aat tac cgt tat ttt ttt gac tat tgg ggc cag          336
Ala Arg Arg Ser Asp Asn Tyr Arg Tyr Phe Phe Asp Tyr Trp Gly Gln
                100                 105                 110 ggt acc aca gtc acc gtc tcc tca                                          360
Gly Thr Thr Val Thr Val Ser Ser
            115                 120

<210> SEQ ID NO 74
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(321)

<400> SEQUENCE: 74 gac atc cag atg acc cag tct cct tcc tca ctg tct gca tct gta ggt           48
Asp Ile Gln Met Thr Gln Ser Pro Ser Ser Leu Ser Ala Ser Val Gly
1               5                  10                  15 gac cga gtc acc atc act tgc cgg gca agt cag gac att cgg aat tat           96
Asp Arg Val Thr Ile Thr Cys Arg Ala Ser Gln Asp Ile Arg Asn Tyr
            20                  25                  30 tta aac tgg tat cag cag aaa cca ggg aaa gcc cct aag ctc ctg atc          144
Leu Asn Trp Tyr Gln Gln Lys Pro Gly Lys Ala Pro Lys Leu Leu Ile
        35                  40                  45 tat tac aca tca cga tta cac tca ggg gtc cca tca cgg ttc agc ggc          192
Tyr Tyr Thr Ser Arg Leu His Ser Gly Val Pro Ser Arg Phe Ser Gly
    50                  55                  60 agt ggt tct ggg aca gat ttc act ctc acc atc agc agt ctg cag cct          240
Ser Gly Ser Gly Thr Asp Phe Thr Leu Thr Ile Ser Ser Leu Gln Pro
65                  70                  75                  80 gaa gat ttc gca act tat tac tgc caa cag ggt cat acg ctt cct ccg          288
Glu Asp Phe Ala Thr Tyr Tyr Cys Gln Gln Gly His Thr Leu Pro Pro
                85                  90                  95 acg ttc ggc caa ggg acc aag ctg gag atc aaa                              321
Thr Phe Gly Gln Gly Thr Lys Leu Glu Ile Lys
                100                 105

<210> SEQ ID NO 75
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(360)

<400> SEQUENCE: 75 cag gtg cag ttg gtc cag tcc ggc tct gag ctg aag aag cct ggt gcc           48
Gln Val Gln Leu Val Gln Ser Gly Ser Glu Leu Lys Lys Pro Gly Ala
1               5                  10                  15 cct gtg aag gtc tcc tgc aag gct tct ggt tac acc ttc agc acc ttt           96
Pro Val Lys Val Ser Cys Lys Ala Ser Gly Tyr Thr Phe Ser Thr Phe
            20                  25                  30 ggc atg agc tgg gtg cga cag gcc cct ggt caa ggg ctt aag tgg atg          144
Gly Met Ser Trp Val Arg Gln Ala Pro Gly Gln Gly Leu Lys Trp Met
        35                  40                  45
```

```
ggt tgg att cac acc tac gct ggt gtg cca atc tat ggt gat gac ttc    192
Gly Trp Ile His Thr Tyr Ala Gly Val Pro Ile Tyr Gly Asp Asp Phe
 50                  55                  60 aag ggt cga ttc gtc ttc agc ctg gac aca tcc gtg agc aca gcc tac    240
Lys Gly Arg Phe Val Phe Ser Leu Asp Thr Ser Val Ser Thr Ala Tyr
 65                  70                  75                  80 ttg cag atc agc agc ctg aag gct gag gac acg gcc gtg tat ttc tgt    288
Leu Gln Ile Ser Ser Leu Lys Ala Glu Asp Thr Ala Val Tyr Phe Cys
                 85                  90                  95 gcg cgc cgt tcg gat aat tac cgt tat ttt ttt gac tat tgg ggc cag    336
Ala Arg Arg Ser Asp Asn Tyr Arg Tyr Phe Phe Asp Tyr Trp Gly Gln
            100                 105                 110 ggt acc aca gtc acc gtc tcc tca                                    360
Gly Thr Thr Val Thr Val Ser Ser
        115                 120

<210> SEQ ID NO 76
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(120)

<400> SEQUENCE: 76

Gln Val Gln Leu Val Gln Ser Gly Ser Glu Leu Lys Lys Pro Gly Ala
 1               5                  10                  15

Pro Val Lys Val Ser Cys Lys Ala Ser Gly Tyr Thr Phe Ser Thr Phe
            20                  25                  30

Gly Met Ser Trp Val Arg Gln Ala Pro Gly Gln Gly Leu Lys Trp Met
         35                 40                  45

Gly Trp Ile His Thr Tyr Ala Gly Val Pro Ile Tyr Gly Asp Asp Phe
 50                 55                  60

Lys Gly Arg Phe Val Phe Ser Leu Asp Thr Ser Val Ser Thr Ala Tyr
 65                 70                  75                  80

Leu Gln Ile Ser Ser Leu Lys Ala Glu Asp Thr Ala Val Tyr Phe Cys
                 85                 90                  95

Ala Arg Arg Ser Asp Asn Tyr Arg Tyr Phe Phe Asp Tyr Trp Gly Gln
            100                 105                 110

Gly Thr Thr Val Thr Val Ser Ser
        115                 120

<210> SEQ ID NO 77
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(360)

<400> SEQUENCE: 77 cag gtg cag ttg gtc cag tcc ggc tct gag ctg aag aag cct ggt gcc     48
Gln Val Gln Leu Val Gln Ser Gly Ser Glu Leu Lys Lys Pro Gly Ala
 1               5                  10                  15 cct gtg aag atc tcc tgc aag gct tct ggt tac acc ttc agc acc ttt     96
Pro Val Lys Ile Ser Cys Lys Ala Ser Gly Tyr Thr Phe Ser Thr Phe
            20                  25                  30
```

```
ggc atg agc tgg gtg cga cag gcc cct ggt caa ggg ctt aag tgg atg      144
Gly Met Ser Trp Val Arg Gln Ala Pro Gly Gln Gly Leu Lys Trp Met
        35                  40                  45 ggt tgg att cac acc tac gct ggt gtg cca atc tat ggt gat gac ttc      192
Gly Trp Ile His Thr Tyr Ala Gly Val Pro Ile Tyr Gly Asp Asp Phe
 50                  55                  60 aag ggt cga ttc gtc ttc agc ctg gac aca tcc gtg agc aca gcc tac      240
Lys Gly Arg Phe Val Phe Ser Leu Asp Thr Ser Val Ser Thr Ala Tyr
 65                  70                  75                  80 ttg cag atc agc agc ctg aag gct gag gac acg gcc gtg tat ttc tgt      288
Leu Gln Ile Ser Ser Leu Lys Ala Glu Asp Thr Ala Val Tyr Phe Cys
                 85                  90                  95 gcg cgc cgt tcg gat aat tac cgt tat ttt ttt gac tat tgg ggc cag      336
Ala Arg Arg Ser Asp Asn Tyr Arg Tyr Phe Phe Asp Tyr Trp Gly Gln
            100                 105                 110 ggt acc aca ctc acc gtc tcc tca                                      360
Gly Thr Thr Leu Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(120)

<400> SEQUENCE: 78

Gln Val Gln Leu Val Gln Ser Gly Ser Glu Leu Lys Lys Pro Gly Ala
 1               5                  10                  15

Pro Val Lys Ile Ser Cys Lys Ala Ser Gly Tyr Thr Phe Ser Thr Phe
             20                  25                  30

Gly Met Ser Trp Val Arg Gln Ala Pro Gly Gln Gly Leu Lys Trp Met
        35                  40                  45

Gly Trp Ile His Thr Tyr Ala Gly Val Pro Ile Tyr Gly Asp Asp Phe
 50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Phe Cys
                 85                  90                  95

Ala Arg Arg Ser Asp Asn Tyr Arg Tyr Phe Phe Asp Tyr Trp Gly Gln
            100                 105                 110

Gly Thr Thr Leu Thr Val Ser Ser
        115                 120

<210> SEQ ID NO 79
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(360)

<400> SEQUENCE: 79 cag gtg cag ttg gtc cag tcc ggc cct gag ctg aag aag cct ggt gcc       48
Gln Val Gln Leu Val Gln Ser Gly Pro Glu Leu Lys Lys Pro Gly Ala
 1               5                  10                  15 cct gtg aag atc tcc tgc aag gct tct ggt tac acc ttc agc acc ttt       96
```

|  |  |  |  |  |  |  |  |  |  |  |  |  |
|---|---|---|---|---|---|---|---|---|---|---|---|---|
| Pro | Val | Lys | Ile | Ser | Cys | Lys | Ala | Ser | Gly | Tyr | Thr | Phe | Ser | Thr | Phe |
|  |  |  | 20 |  |  |  |  | 25 |  |  |  |  | 30 |  |  |

```
ggc atg agc tgg gtg aaa cag gcc cct ggt caa ggg ctt aag tgg atg      144
Gly Met Ser Trp Val Lys Gln Ala Pro Gly Gln Gly Leu Lys Trp Met
         35                  40                  45 ggt tgg att cac acc tac gct ggt gtg cca atc tat ggt gat gac ttc      192
Gly Trp Ile His Thr Tyr Ala Gly Val Pro Ile Tyr Gly Asp Asp Phe
 50                  55                  60 aag ggt cga ttc gtc ttc agc ctg gac aca tcc gtg agc aca gcc tac      240
Lys Gly Arg Phe Val Phe Ser Leu Asp Thr Ser Val Ser Thr Ala Tyr
 65                  70                  75                  80 ttg cag atc agc agc ctg aag gct gag gac acg gcc aca tat ttc tgt      288
Leu Gln Ile Ser Ser Leu Lys Ala Glu Asp Thr Ala Thr Tyr Phe Cys
                 85                  90                  95 gcg cgt cgt tcg gat aat tac cgt tat ttt ttt gac tat tgg ggc cag      336
Ala Arg Arg Ser Asp Asn Tyr Arg Tyr Phe Phe Asp Tyr Trp Gly Gln
            100                 105                 110 ggt acc aca ctc acc gtc tcc tca                                      360
Gly Thr Thr Leu Thr Val Ser Ser
        115                 120

<210> SEQ ID NO 80
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(120)

<400> SEQUENCE: 80

Gln Val Gln Leu Val Gln Ser Gly Pro Glu Leu Lys Lys Pro Gly Ala
1               5                   10                  15

Pro Val Lys Ile Ser Cys Lys Ala Ser Gly Tyr Thr Phe Ser Thr Phe
            20                  25                  30

Gly Met Ser Trp Val Lys Gln Ala Pro Gly Gln Gly Leu Lys Trp Met
        35                  40                  45

Gly Trp Ile His Thr Tyr Ala Gly Val Pro Ile Tyr Gly Asp Asp Phe
 50                 55                  60

Lys Gly Arg Phe Val Phe Ser Leu Asp Thr Ser Val Ser Thr Ala Tyr
 65                 70                  75                  80

Leu Gln Ile Ser Ser Leu Lys Ala Glu Asp Thr Ala Thr Tyr Phe Cys
                85                  90                  95

Ala Arg Arg Ser Asp Asn Tyr Arg Tyr Phe Phe Asp Tyr Trp Gly Gln
            100                 105                 110

Gly Thr Thr Leu Thr Val Ser Ser
        115                 120

<210> SEQ ID NO 81
<211> LENGTH: 360
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(360)

<400> SEQUENCE: 81 cag atc cag ttg gtc cag tcc ggc cct gag ctg aag aag cct ggt gcc       48
Gln Ile Gln Leu Val Gln Ser Gly Pro Glu Leu Lys Lys Pro Gly Ala
```

```
                1               5                   10                  15
cct gtg aag atc tcc tgc aag gct tct ggt tac acc ttc aca acc ttt         96
Pro Val Lys Ile Ser Cys Lys Ala Ser Gly Tyr Thr Phe Thr Thr Phe
                20                  25                  30 ggc atg agc tgg gtg aaa cag gcc cct ggt caa ggg ctt aag tgg atg         144
Gly Met Ser Trp Val Lys Gln Ala Pro Gly Gln Gly Leu Lys Trp Met
        35                  40                  45 ggt tgg att cac acc tac gct ggt gtg cca atc tat ggt gat gac ttc         192
Gly Trp Ile His Thr Tyr Ala Gly Val Pro Ile Tyr Gly Asp Asp Phe
    50                  55                  60 aag ggt cga ttc gtc ttc agc ctg gac aca tcc gtg agc aca gcc tac         240
Lys Gly Arg Phe Val Phe Ser Leu Asp Thr Ser Val Ser Thr Ala Tyr
65                  70                  75                  80 ttg cag atc agc agc gtc aag gct gag gac acg gcc aca tat ttc tgt         288
Leu Gln Ile Ser Ser Val Lys Ala Glu Asp Thr Ala Thr Tyr Phe Cys
                85                  90                  95 gcg cgc cgt tcg gat aat tac cgt tat ttt ttt gac tat tgg ggc cag         336
Ala Arg Arg Ser Asp Asn Tyr Arg Tyr Phe Phe Asp Tyr Trp Gly Gln
            100                 105                 110 ggt acc aca ctc acc gtc tcc tca                                         360
Gly Thr Thr Leu Thr Val Ser Ser
        115                 120

<210> SEQ ID NO 82
<211> LENGTH: 120
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(120)

<400> SEQUENCE: 82

Gln Ile Gln Leu Val Gln Ser Gly Pro Glu Leu Lys Lys Pro Gly Ala
1               5                   10                  15

Pro Val Lys Ile Ser Cys Lys Ala Ser Gly Tyr Thr Phe Thr Thr Phe
                20                  25                  30

Gly Met Ser Trp Val Lys Gln Ala Pro Gly Gln Gly Leu Lys Trp Met
        35                  40                  45

Gly Trp Ile His Thr Tyr Ala Gly Val Pro Ile Tyr Gly Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Val Lys Ala Glu Asp Thr Ala Thr Tyr Phe Cys
                85                  90                  95

Ala Arg Arg Ser Asp Asn Tyr Arg Tyr Phe Phe Asp Tyr Trp Gly Gln
            100                 105                 110

Gly Thr Thr Leu Thr Val Ser Ser
        115                 120

<210> SEQ ID NO 83
<211> LENGTH: 321
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (1)..(321)

<400> SEQUENCE: 83
```

```
gac atc cag atg acc cag tct cct tcc tca ctg tct gca tct ctg ggt      48
Asp Ile Gln Met Thr Gln Ser Pro Ser Ser Leu Ser Ala Ser Leu Gly
1               5                   10                  15 gac cga gtc acc atc act tgc cgg gca agt cag gac att cgg aat tat      96
Asp Arg Val Thr Ile Thr Cys Arg Ala Ser Gln Asp Ile Arg Asn Tyr
            20                  25                  30 tta aac tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat tac aca tca cga tta cac tca ggg gtc cca tca cgg ttc agc ggc     192
Tyr Tyr Thr Ser Arg Leu His Ser Gly Val Pro Ser Arg Phe Ser Gly
    50                  55                  60 agt ggt tct ggg aca gat tat act ctc acc atc agc agt ctg cag cct     240
Ser Gly Ser Gly Thr Asp Tyr Thr Leu Thr Ile Ser Ser Leu Gln Pro
65                  70                  75                  80 gaa gat ttc gca act tat ttt tgc caa cag ggt cat acg ctt cct ccg     288
Glu Asp Phe Ala Thr Tyr Phe Cys Gln Gln Gly His Thr Leu Pro Pro
                85                  90                  95 acg ttc ggc caa ggg acc aag ctg gag atc aaa                         321
Thr Phe Gly Gln Gly Thr Lys Leu Glu Ile Lys
                100                 105
```

<210> SEQ ID NO 84
<211> LENGTH: 107
<212> TYPE: PRT
<213> ORGANISM: Artificial Sequence
<220> FEATURE:
<223> OTHER INFORMATION: Synthetic polypeptide
<220> FEATURE:
<221> NAME/KEY: PEPTIDE
<222> LOCATION: (1)..(107)

<400> SEQUENCE: 84

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Leu Glu Ile Lys
                100                 105
```

<210> SEQ ID NO 85
<211> LENGTH: 2758
<212> TYPE: DNA
<213> ORGANISM: Mus musculus
<220> FEATURE:
<221> NAME/KEY: CDS
<222> LOCATION: (556)..(2223)
<223> OTHER INFORMATION: mouse ASCT2 nucleotide sequence: GenBank
      Accession number NM_009201

<400> SEQUENCE: 85

```
ggtcgcttcc gtctagcagc ctcagagaca cgcggcgcgg cctgggaggt ttctccttgg      60
cgccactttc catatccccc gggctgcttc ctatttgcat ctggaaattt gattttctc      120
```

```
tccagagccc gaaacgctcg gtccactcct tctagggctc cagtacccaa gagtccgaga      180
gccaggcgtc ctaatcctgg gatctcggtc tcccggagca aggcatcccg gatctatgcc      240 acttggttg  agcttcctga agacctcagc tacctgagtt tccttactcc ttcagggagt      300
caaagaaccc tctgaagagc tgttccctac tccaacaagg cgctctcaac tcccagtttt      360
cggggattcg acatcaccag gaaaaataaa gggatctccg catacagctc agggagccta      420
ggaccctcca gtttccgaga tccggtggac gcataacttc aaggaccgct gcaaagtttc      480
agcctccatt ctcggtccta aggacgtcac acctagtctc caggctcaca aggaacctcc      540
ctgttacggc tcagc atg gca gtg gat ccc cct aag gct gac ccc aaa ggg      591
             Met Ala Val Asp Pro Pro Lys Ala Asp Pro Lys Gly
              1               5                  10 gta gta gcg gtg gat tcc acc gcg aac ggt ggc ccc gcg ctg gga tcc       639
Val Val Ala Val Asp Ser Thr Ala Asn Gly Gly Pro Ala Leu Gly Ser
         15                  20                  25 aga gag gac cag agt gcg aaa gca ggt ggt tgc tgc ggt tcc cgt gac       687
Arg Glu Asp Gln Ser Ala Lys Ala Gly Gly Cys Cys Gly Ser Arg Asp
 30                  35                  40 cgg gtg cgc cgc tgc att cgc gcc aac ctg ctg gtg ctg ctc acg gtg       735
Arg Val Arg Arg Cys Ile Arg Ala Asn Leu Leu Val Leu Leu Thr Val
45                  50                  55                  60 gct gcg gtg gtg gct ggc gtg ggg ctg ggg ctg ggg gtc tcg gcg gcg       783
Ala Ala Val Val Ala Gly Val Gly Leu Gly Leu Gly Val Ser Ala Ala
                 65                  70                  75 ggc ggt gct gac gcg ctg ggt ccc gcg cgc ttg acc gct ttc gcc ttc       831
Gly Gly Ala Asp Ala Leu Gly Pro Ala Arg Leu Thr Ala Phe Ala Phe
             80                  85                  90 ccg gga gag ctg ctg ctg cgt ctg ctg aag atg atc atc ctg ccg ctc       879
Pro Gly Glu Leu Leu Leu Arg Leu Leu Lys Met Ile Ile Leu Pro Leu
         95                 100                 105 gtg gtg tgc agc ctg atc gga ggt gca gcc agc ttg gac cct agc gcg       927
Val Val Cys Ser Leu Ile Gly Gly Ala Ala Ser Leu Asp Pro Ser Ala
    110                 115                 120 ctc ggt cgt gtg ggc gcc tgg gcg ctg ctc ttt ttc ctg gtc acc aca       975
Leu Gly Arg Val Gly Ala Trp Ala Leu Leu Phe Phe Leu Val Thr Thr
125                 130                 135                 140 ctg ctc gcg tcg gcg ctc ggc gtg ggt ttg gcc ctg gcg ctg aag ccg      1023
Leu Leu Ala Ser Ala Leu Gly Val Gly Leu Ala Leu Ala Leu Lys Pro
                145                 150                 155 ggc gcc gcc gtt acc gcc atc acc tcc atc aac gac tct gtt gta gac      1071
Gly Ala Ala Val Thr Ala Ile Thr Ser Ile Asn Asp Ser Val Val Asp
            160                 165                 170 ccc tgt gcc cgc agt gca cca acc aaa gag gtg ctg gat tcc ttt cta      1119
Pro Cys Ala Arg Ser Ala Pro Thr Lys Glu Val Leu Asp Ser Phe Leu
        175                 180                 185 gat ctc gtg agg aat att ttc ccc tcc aat ctg gtg tct gct gcc ttc      1167
Asp Leu Val Arg Asn Ile Phe Pro Ser Asn Leu Val Ser Ala Ala Phe
    190                 195                 200 cgc tct ttt gct acc tca tat gaa ccc aaa gac aac tca tgt aaa ata      1215
Arg Ser Phe Ala Thr Ser Tyr Glu Pro Lys Asp Asn Ser Cys Lys Ile
205                 210                 215                 220 ccg caa tcc tgt atc cag cgg gag atc aat tca acc atg gtc cag ctt      1263
Pro Gln Ser Cys Ile Gln Arg Glu Ile Asn Ser Thr Met Val Gln Leu
                225                 230                 235 ctc tgt gag gtg gag gga atg aac atc ctg ggc ctg gtg gtc ttc gct      1311
Leu Cys Glu Val Glu Gly Met Asn Ile Leu Gly Leu Val Val Phe Ala
            240                 245                 250
```

```
                                                          -continued atc gtc ttt ggt gtg gct ctg cgg aag ctg ggg ccc gag ggt gag ctg       1359
Ile Val Phe Gly Val Ala Leu Arg Lys Leu Gly Pro Glu Gly Glu Leu
            255                 260                 265 ctc att cgt ttc ttc aac tcc ttc aat gat gcc acc atg gtc ctg gtc       1407
Leu Ile Arg Phe Phe Asn Ser Phe Asn Asp Ala Thr Met Val Leu Val
        270                 275                 280 tcc tgg att atg tgg tac gca ccc gtt gga atc ctg ttc ctg gtg gcc       1455
Ser Trp Ile Met Trp Tyr Ala Pro Val Gly Ile Leu Phe Leu Val Ala
285                 290                 295                 300 agc aag att gtg gag atg aaa gac gtc cgc cag ctc ttc atc agc ctc       1503
Ser Lys Ile Val Glu Met Lys Asp Val Arg Gln Leu Phe Ile Ser Leu
                305                 310                 315 ggc aaa tac att ctg tgc tgc ctg ctg ggc cac gcc atc cac ggg ctc       1551
Gly Lys Tyr Ile Leu Cys Cys Leu Leu Gly His Ala Ile His Gly Leu
            320                 325                 330 ctg gtt ctg cct ctc atc tac ttc ctc ttc acc cgc aaa aat ccc tat       1599
Leu Val Leu Pro Leu Ile Tyr Phe Leu Phe Thr Arg Lys Asn Pro Tyr
        335                 340                 345 cga ttc ctg tgg ggc atc atg aca ccc ctg gcc act gct ttc ggg acc       1647
Arg Phe Leu Trp Gly Ile Met Thr Pro Leu Ala Thr Ala Phe Gly Thr
350                 355                 360 tct tct agc tct gcc acc ttg cct ctg atg atg aag tgt gta gag gag       1695
Ser Ser Ser Ser Ala Thr Leu Pro Leu Met Met Lys Cys Val Glu Glu
365                 370                 375                 380 aag aat ggt gtg gcc aaa cac atc agc cgg ttc atc cta ccc atc ggc       1743
Lys Asn Gly Val Ala Lys His Ile Ser Arg Phe Ile Leu Pro Ile Gly
                385                 390                 395 gcc acg gtc aac atg gac ggg gcg gcg ctg ttc cag tgt gtg gcg gca       1791
Ala Thr Val Asn Met Asp Gly Ala Ala Leu Phe Gln Cys Val Ala Ala
            400                 405                 410 gtg ttc atc gca caa cta aac ggg gtg tcc ctg gac ttc gtg aag atc       1839
Val Phe Ile Ala Gln Leu Asn Gly Val Ser Leu Asp Phe Val Lys Ile
        415                 420                 425 atc acc atc ctg gtc aca gcc aca gca tcc agt gtc ggt gcg gca ggg       1887
Ile Thr Ile Leu Val Thr Ala Thr Ala Ser Ser Val Gly Ala Ala Gly
430                 435                 440 atc cct gca ggg ggc gtc ctc acc ctc gcc atc atc ctg gaa gca gtc       1935
Ile Pro Ala Gly Gly Val Leu Thr Leu Ala Ile Ile Leu Glu Ala Val
445                 450                 455                 460 agc ctg cct gtg aag gac atc tcc ttg atc ttg gcc gtg gac tgg cta       1983
Ser Leu Pro Val Lys Asp Ile Ser Leu Ile Leu Ala Val Asp Trp Leu
                465                 470                 475 gtg gac agg tcc tgt act gtc ctc aac gtg gaa ggt gat gct ttt ggg       2031
Val Asp Arg Ser Cys Thr Val Leu Asn Val Glu Gly Asp Ala Phe Gly
            480                 485                 490 gct gga ctg ctt cag agt tac gtg gat cga acc aag atg ccg agc tca       2079
Ala Gly Leu Leu Gln Ser Tyr Val Asp Arg Thr Lys Met Pro Ser Ser
        495                 500                 505 gag ccc gaa ttg atc cag gtg aag aac gag gtg tct ctg aat cca ctg       2127
Glu Pro Glu Leu Ile Gln Val Lys Asn Glu Val Ser Leu Asn Pro Leu
510                 515                 520 ccc ctc gcc aca gag gag ggg aat ccc ctg ctg aaa cag tac cag gga       2175
Pro Leu Ala Thr Glu Glu Gly Asn Pro Leu Leu Lys Gln Tyr Gln Gly
525                 530                 535                 540 ccc acc ggg gac tcc agt gcc acg ttc gaa aag gaa tct gtc atg tga       2223
Pro Thr Gly Asp Ser Ser Ala Thr Phe Glu Lys Glu Ser Val Met
                545                 550                 555 atatcaggag ggactttcta cgccctggtg acttcacgtt ggaagccggg tcttgcgagc     2283
tggagaaatg gactggatga gggctctagg ggtgggctgt ttacacactc caggaatcta    2343
```

```
ggggtcggtg tctccttcct ggagaggcta ttaggagcct tgttgctggg gtgcatatgc    2403
ttatatgtga atgtgtccac aaatcccacc ccctctccgt tctgtccccc attcaaggaa    2463
tgacattctc agtcacccag agccatctgg cctaccctct caggaaatgg gttgtcctgt    2523
agagttctct acccttttaa aggcaaaagt attgggatgc aatactatct taatgtccct    2583
atctgtggtg tgtgtgcact tgctgtgacc ttcccagtag tccctccatg acagaaaaca    2643
ctcccatgag tctcgaggga aagccaagaa taaatgtcac tccagaacac attttttttt    2703
agcaataaaa tggtgtcaaa tgtattgacc atggccctag agtctgagta ataacc        2758
```

<210> SEQ ID NO 86
<211> LENGTH: 555
<212> TYPE: PRT
<213> ORGANISM: Mus musculus
<220> FEATURE:
<221> NAME/KEY: PEPTIDE
<222> LOCATION: (1)..(555)
<223> OTHER INFORMATION: ASCT2 peptide sequence: GenPept Accession number NP_033227

<400> SEQUENCE: 86

```
Met Ala Val Asp Pro Pro Lys Ala Asp Pro Lys Gly Val Val Ala Val
1               5                   10                  15

Asp Ser Thr Ala Asn Gly Gly Pro Ala Leu Gly Ser Arg Glu Asp Gln
            20                  25                  30

Ser Ala Lys Ala Gly Gly Cys Cys Gly Ser Arg Asp Arg Val Arg Arg
        35                  40                  45

Cys Ile Arg Ala Asn Leu Leu Val Leu Leu Thr Val Ala Ala Val Val
    50                  55                  60

Ala Gly Val Gly Leu Gly Leu Gly Val Ser Ala Ala Gly Gly Ala Asp
65                  70                  75                  80

Ala Leu Gly Pro Ala Arg Leu Thr Ala Phe Ala Phe Pro Gly Glu Leu
                85                  90                  95

Leu Leu Arg Leu Leu Lys Met Ile Ile Leu Pro Leu Val Val Cys Ser
            100                 105                 110

Leu Ile Gly Gly Ala Ala Ser Leu Asp Pro Ser Ala Leu Gly Arg Val
        115                 120                 125

Gly Ala Trp Ala Leu Leu Phe Phe Leu Val Thr Thr Leu Leu Ala Ser
    130                 135                 140

Ala Leu Gly Val Gly Leu Ala Leu Ala Leu Lys Pro Gly Ala Ala Val
145                 150                 155                 160

Thr Ala Ile Thr Ser Ile Asn Asp Ser Val Asp Pro Cys Ala Arg
                165                 170                 175

Ser Ala Pro Thr Lys Glu Val Leu Asp Ser Phe Leu Asp Leu Val Arg
            180                 185                 190

Asn Ile Phe Pro Ser Asn Leu Val Ser Ala Ala Phe Arg Ser Phe Ala
        195                 200                 205

Thr Ser Tyr Glu Pro Lys Asp Asn Ser Cys Lys Ile Pro Gln Ser Cys
    210                 215                 220

Ile Gln Arg Glu Ile Asn Ser Thr Met Val Gln Leu Leu Cys Glu Val
225                 230                 235                 240

Glu Gly Met Asn Ile Leu Gly Leu Val Val Phe Ala Ile Val Phe Gly
                245                 250                 255

Val Ala Leu Arg Lys Leu Gly Pro Glu Gly Glu Leu Leu Ile Arg Phe
            260                 265                 270
```

```
Phe Asn Ser Phe Asn Asp Ala Thr Met Val Leu Val Ser Trp Ile Met
            275                 280                 285
Trp Tyr Ala Pro Val Gly Ile Leu Phe Leu Val Ala Ser Lys Ile Val
290                 295                 300
Glu Met Lys Asp Val Arg Gln Leu Phe Ile Ser Leu Gly Lys Tyr Ile
305                 310                 315                 320
Leu Cys Cys Leu Leu Gly His Ala Ile His Gly Leu Val Leu Pro
                325                 330                 335
Leu Ile Tyr Phe Leu Phe Thr Arg Lys Asn Pro Tyr Arg Phe Leu Trp
            340                 345                 350
Gly Ile Met Thr Pro Leu Ala Thr Ala Phe Gly Thr Ser Ser Ser
            355                 360                 365
Ala Thr Leu Pro Leu Met Met Lys Cys Val Glu Glu Lys Asn Gly Val
370                 375                 380
Ala Lys His Ile Ser Arg Phe Ile Leu Pro Ile Gly Ala Thr Val Asn
385                 390                 395                 400
Met Asp Gly Ala Ala Leu Phe Gln Cys Val Ala Val Phe Ile Ala
                405                 410                 415
Gln Leu Asn Gly Val Ser Leu Asp Phe Val Lys Ile Ile Thr Ile Leu
            420                 425                 430
Val Thr Ala Thr Ala Ser Ser Val Gly Ala Ala Gly Ile Pro Ala Gly
            435                 440                 445
Gly Val Leu Thr Leu Ala Ile Ile Leu Glu Ala Val Ser Leu Pro Val
            450                 455                 460
Lys Asp Ile Ser Leu Ile Leu Ala Val Asp Trp Leu Val Asp Arg Ser
465                 470                 475                 480
Cys Thr Val Leu Asn Val Glu Gly Asp Ala Phe Gly Ala Gly Leu Leu
                485                 490                 495
Gln Ser Tyr Val Asp Arg Thr Lys Met Pro Ser Ser Glu Pro Glu Leu
            500                 505                 510
Ile Gln Val Lys Asn Glu Val Ser Leu Asn Pro Leu Pro Leu Ala Thr
            515                 520                 525
Glu Glu Gly Asn Pro Leu Leu Lys Gln Tyr Gln Gly Pro Thr Gly Asp
530                 535                 540
Ser Ser Ala Thr Phe Glu Lys Glu Ser Val Met
545                 550                 555

<210> SEQ ID NO 87
<211> LENGTH: 2239
<212> TYPE: DNA
<213> ORGANISM: Artificial Sequence
<220> FEATURE:
<223> OTHER INFORMATION: Synthetic oligonucleotide

<400> SEQUENCE: 87
ctcacaactc taaggagccc tccaaagttc cagtctccag gtgctgttac tcaactcagt      60
cctaggaacg tcgggtcctg ggaaggagcc caagcgctcc cagccagctt ccaggcgcta     120
agaaaccccg gtgcttccca tcatggtggc cgatcctcct cgagactcca aggggctcgc     180
agcggcggag cccaccgcca acgggggcct ggcgctggcc tccatcgagg accaaggcgc     240
ggcagcaggc ggctactgcg gttcccggga ccaggtgcgc cgctgccttc gagccaacct     300
gcttgtgctg ctgacagtgg tggtgtgcag cttgatcggc ggcgccgcca gcctggaccc     360
cggcgcgctc ggccgtctgg gcgcctgggc gctgctcttt ttcctggtca ccacgctgct     420
ggcgtcggcg ctcggagtgg gcttggcgct ggctctgcag ccgggcgccg cctccgccgc     480
```

```
catcaacgcc tccgtgggag ccgcgggcag tgccgaaaat gcccccagca aggaggtgct    540
cgattcgttc ctggatcttg cgagaaatat cttcccttcc aacctggtgt cagcagcctt    600
tcgctcatac tctaccacct atgaagagag gaatatcacc ggaaccaggg tgaaggtgcc    660
cgtggggcag gaggtggagg ggatgaacat cctgggcttg gtagtgtttg ccatcgtctt    720
tggtgtggcg ctgcggaagc tggggcctga aggggagctg cttatccgct tcttcaactc    780
cttcaatgag gccaccatgg ttctggtctc ctggatcatg tggtacgccc ctgtgggcat    840
catgttcctg gtggctggca agatcgtgga gatggaggat gtgggtttac tctttgcccg    900
ccttggcaag tacattctgt gctgcctgct gggtcacgcc atccatgggc tcctggtact    960 gccctcatc tacttcctct tcacccgcaa aaacccctac cgcttcctgt ggggcatcgt   1020
gacgccgctg gccactgcct ttgggacctc ttccagttcc gccacgctgc cgctgatgat   1080
gaagtgcgtg gaggagaata atggcgtggc caagcacatc agccgtttca tcctgcccat   1140
cggcgccacc gtcaacatgg acggtgccgc gctcttccag tgcgtggccg cagtgttcat   1200
tgcacagctc agccagcagt ccttggactt cgtaaagatc atcaccatcc tggtcacggc   1260
cacagcgtcc agcgtggggg cagcgggcat ccctgctgga ggtgtcctca ctctggccat   1320
catcctcgaa gcagtcaacc tcccggtcga ccatatctcc ttgatcctgg ctgtggactg   1380
gctagtcgac cggtcctgta ccgtcctcaa tgtagaaggt gacgctctgg gggcaggact   1440
cctccaaaat tacgtggacc gtacggagtc gagaagcaca gagcctgagt tgatacaagt   1500
gaagagtgag ctgcccctgg atccgctgcc agtccccact gaggaaggaa accccctcct   1560
caaacactat cggggggcccg caggggatgc cacggtcgcc tctgagaagg aatcagtcat   1620
gtaaaccccg ggagggacct tccctgccct gctgggggtg ctctttggac actggattat   1680
gaggaatgga taaatggatg agctagggct ctgggggtct gcctgcacac tctggggagc   1740
caggggcccc agcaccctcc aggacaggag atctgggatg cctggctgct ggagtacatg   1800
tgttcacaag ggttactcct caaaaccccc agttctcact catgtcccca actcaaggct   1860
agaaaacagc aagatggaga ataatgttc tgctgcgtcc ccaccgtgac ctgcctggcc   1920
tcccctgtct cagggagcag gtcacaggtc accatgggga attctagccc ccactggggg   1980
gatgttacaa caccatgctg gttattttgg cggctgtagt tgtgggggga tgtgtgtgtg   2040
cacgtgtgtg tgtgtgtgtg tgtgtgtgtg ttctgtgacc tcctgtcccc atggtacgtc   2100
ccaccctgtc cccagatccc ctattccctc cacaataaca gaaacactcc cagggactct   2160
ggggagaggc tgaggacaaa tacctgctgt cactccagag gacatttttt ttagcaataa   2220
aattgagtgt caactattt                                               2239
```

DNA ENCODING AN ANTI-SYSTEM ASC AMINO ACID TRANSPORTER 2 (ASCT2) ANTIBODY

This is a divisional of U.S. patent application Ser. No. 12/505,133, filed Jul. 17, 2009 (now U.S. Pat. No. 8,268,592), which claims priority from Provisional Patent Application No. 61/081,820, filed Jul. 18, 2008, the contents of the prior applications are incorporated herein by reference in their entirety.

BACKGROUND OF ME INVENTION

1. Field of the Invention

The present invention relates to a monoclonal antibody which specifically recognizes a native three-dimensional structure of an extracellular region of system ASC amino acid transporter 2 (hereinafter, referred to as "ASCT2") and binds to the extracellular region, or an antibody fragment thereof; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof, and a diagnostic agent using the antibody or the antibody fragment thereof.

2. Brief Description of the Background Art

An ASCT2 polypeptide is a 10-times transmembrane protein consisting of 541 amino acids in full-length form, and functions as a transporter which transports neutral amino acids through a cell membrane depending on a sodium ion. The amino acid transporter is categorized into several systems, based on functional characteristics including substrate specificity and the like. ASCT2 belongs to System ASC and has functions of intracellular uptake of neutral amino acids such as L-alanine, L-serine, L-threonine, L-cysteine, and L-glutamine depending on a sodium ion (Non-Patent Document 1).

Further, ASCT2 is a viral cell-surface receptor which is shared by type D simian retrovirus and three type C viruses [feline endogenous virus (RD114), baboon endogenous virus, and avian reticuloendotheliosis virus] (Non-Patent Documents 2 and 3).

ASCT2 is also known as sodium-dependent neutral amino acid transporter type 2, adipocyte amino acid transporter, AAAT, neutral amino acid transporter B, MB, amino acid transporter $B^0$, $MB^0$, ATB0, baboon M7 virus receptor, M7V1, M7VS1, insulin-activated amino acid transporter, FLJ31068, RD 114 virus receptor, RD114/simian type D retrovirus receptor, RDR, RDRC, or R16 (Non-patent Documents 1 and 3).

Furthermore, as another name, ASCT2 is known as Solute carrier family 1 (neutral amino acid transport), member 5, Solute carrier family 1 member 5, or SLC1A5 and belongs to SLC1 family.

With respect to the relationship between the development of cancer and the expression of ASCT2 or SLC1A5, it has been found that expression levels of three SLC1A5, SLC7A5 and SLC38A5 are significantly increased in cancerous tissues by studies using expressed sequence tag (EST) database (Non-Patent Document 4). Further, the expression of SLC1A5 is not recognized in a normal liver, but is recognized in clinical tissues of hepatocellular carcinoma or hepatoblastoma (Non-Patent Document 5). In addition, it has been found that the expression of SLC1A5 is higher in clinical tissues of poorly-differenciated astrocytoma or glioblastoma multiforme than that of normal tissues (Non-Patent Document 6).

Further, the expression of ASCT2 is detected in clinical tissues of colorectal cancer and prostate cancer by immunohistological staining or Western blotting, and patients who highly express ASCT2 have a poor outcome (Non-Patent Documents 7 and 8).

Furthermore, ASCT2 is responsible for the uptake of glutamine in several cell lines of colorectal cancer, liver cancer, breast cancer, astrocytoma and neuroblastoma (Non-Patent Documents 9 to 12), and the proliferation of cells is suppressed by competitively inhibiting intracellular uptake of glutamine using an alanine-serine-threonine mixture which is a substrate for ASCT2 (Non-Patent Document 9).

As regards an antibody which binds to ASCT2, a polyclonal antibody against partial peptides of the intracellular N-terminal or C-terminal of human ASCT2 is known (Non-Patent Documents 13, 14 and 15). Since all of these are antibodies which recognize an intracellular portion of ASCT2, they cannot bind to ASCT2 which is expressed on the cell membrane of cells. It is known that when an antibody binds to an antigen protein expressed on the cell membrane, a cellular cytotoxicity due to an effector activity of the antibody, such as antibody-dependent cellular cytotoxicity (hereinafter, referred to as "ADCC activity") or complement-dependent cytotoxicity (hereinafter, referred to as "CDC activity") is induced within the living body (Non-Patent Document 16). However, since these antibodies cannot bind to ASCT2 expressed on the cell membrane of cells, these cellular cytotoxicities due to the effector activity cannot be expected. Further, since all of these antibodies are antibodies which recognize an intracellular portion of ASCT2, they cannot inhibit intracellular uptake of amino acids by ASCT2 which expresses in living cells.

In addition, polyclonal antibodies which recognize human ASCT2 are commercially available from LifeSpan Biosciences (Catalog Numbers: LS-C16840 and LC-C31887), Avia Systems Biology (Catalog Number: ARP42247_T100), Santa Cruz Biotechnology (Catalog Numbers: sc-50698 and sc-50701), or Millipore (Catalog Number: AB5468).

However, it is not known a monoclonal antibody which specifically recognizes a native three-dimensional structure of an extracellular region of ASCT2 and binds to the extracellular region.

[Non-Patent Document 1] J. Biol. Chemistry, 271, 18657 (1996)

[Non-Patent Document 2] Proc. Natl. Acad. Sci. USA, 96, 2129 (1999)

[Non-Patent Document 3] J. Virology, 73, 4470 (1999)

[Non-Patent Document 4] Seminars in Cancer Biology, 15, 254 (2005)

[Non-Patent Document 5] Am. J. Physiol. Gastrointest. Liver Physiol., 283, G1062 (2002)

[Non-Patent Document 6] NeuroReport, 15, 575 (2004)

[Non-Patent Document 7] Anticancer Research, 22, 2555 (2002)

[Non-Patent Document 8] Anticancer Research, 23, 3413 (2003)

[Non-Patent Document 9] J. Surgical Research, 90, 149 (2000)

[Non-Patent Document 10] J. Cellular Physiology, 176, 166 (1998)

[Non-Patent Document 11] J. Neuroscience Research, 66, 959 (2001)

[Non-Patent Document 12] Am. J. Physiol. Cell Physiol., 282, C1246 (2002)

[Non-Patent Document 13] J. Gene Medicine, 6, 249 (2004)

[Non-Patent Document 14] Am. J. Physiol. Cell Physiol., 281, C963 (2001)
[Non-Patent Document 15] Biochem. J., 382, 27 (2004)
[Non-Patent Document 16] Cancer Res., 56, 1118 (1996)

SUMMARY OF THE INVENTION

An object of the present invention is to provide a monoclonal antibody which specifically recognizes a native three-dimensional structure of an extracellular region of ASCT2 and binds to the extracellular region, or an antibody fragment thereof; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof, and a diagnostic agent using the antibody or the antibody fragment thereof.

The present invention can provide a monoclonal antibody which specifically recognizes a native three-dimensional structure of an extracellular region of ASCT2 and binds to the extracellular region, or an antibody fragment thereof; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof, and a diagnostic agent using the antibody or the antibody fragment thereof.

BRIEF DESCRIPTION OF THE DRAWINGS

FIG. 1A shows the alignment of NM_005628 (SEQ ID NO:1) and HCHON2001712 (SEQ ID NO:87). * represents a site where both nucleotide sequences are same.

FIG. 1B shows the alignment of NM_005628 (SEQ ID NO:1) and HCHON2001712 (SEQ ID NO:87). * represents a site where both nucleotide sequences are same.

FIG. 1C shows the alignment of NM_005628 (SEQ ID NO:1) and HCHON2001712 (SEQ ID NO:87). * represents a site where both nucleotide sequences are same. The design positions of amplification primers used in Q-PCR are underlined (Fw#1 corresponds to nucleotides at positions 2281 to 2301 of NM_005628 and nucleotides at positions 1689 to 1709 of HCHON2001712, and Rv#1 corresponds to a reverse chain of nucleotides at positions 2739 to 2719 of NM_005628 and a reverse chain of nucleotides at positions 2139 to 2119 of HCHON2001712).

FIG. 1D shows the alignment of NM_005628 (SEQ ID NO:1) and HCHON2001712 (SEQ ID NO:87). * represents a site where both nucleotide sequences are same. The design positions of amplification primers used in Q-PCR are underlined (Fw#1 corresponds to nucleotides at positions 2281 to 2301 of NM_005628 and nucleotides at positions 1689 to 1709 of HCHON2001712, and Rv#1 corresponds to a reverse chain of nucleotides at positions 2739 to 2719 of NM_005628 and a reverse chain of nucleotides at positions 2139 to 2119 of HCHON2001712).

FIG. 2A shows expression levels of mRNA of ASCT2 gene in cancer cell lines, xenografts, normal tissues and clinical cancer tissues.

FIG. 2B shows expression levels of mRNA of ASCT2 gene in cancer cell lines, xenografts, normal tissues and clinical cancer tissues.

FIG. 4 shows animal species and antibody classes of anti-ASCT2 monoclonal antibodies obtained in Examples.

FIG. 15 shows the reactivity of anti-ASCT2 monoclonal antibodies KM4008, KM4012 and KM4018 with mouse ASCT2-myc/His gene-introduced CHO cells (mouse ASCT2/CHO) and mouse/human chimeric ASCT2/CHO [mouse EL1 type ASCT2-myc/His gene-introduced CHO cell line (mEL1/CHO), mouse EL2 type ASCT2-myc/His gene-introduced CHO cell line (mEL2/CHO), mouse EL3 type ASCT2-myc/His gene-introduced CHO cell line (mEL3/CHO), and mouse EL4 type ASCT2-myc/His gene-introduced CHO cell line (mEL4/CHO)]. The symbols "+", "−", and "±" represent the presence of reactivity, the absence of reactivity, and the decrease in reactivity, respectively.

DETAILED DESCRIPTION OF THE INVENTION

Figure 3:
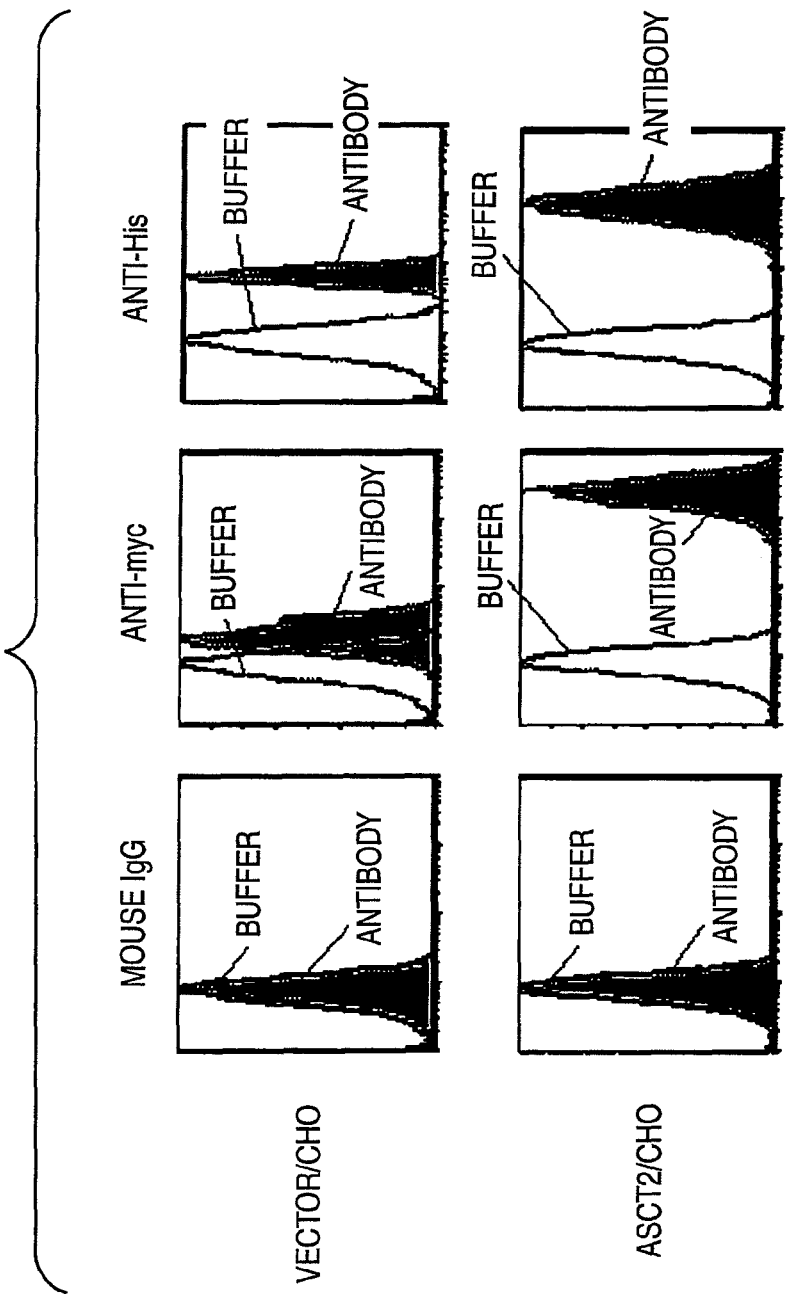
FIG. 3 shows the reactivity of an anti-myc antibody (Anti-Myc) and an anti-His antibody (Anti-His) to immobilized human ASCT2-myc/His gene-introduced CHO cells (ASCT2/CHO) and vector-introduced CHO cells (Vector/CHO), as measured by a flow cytometer. The abscissa represents the fluorescence intensity, and the ordinate represents the cell counts. The antibody is indicated by a black curve, and buffer is indicated by a white curve.

The present invention relates to the following (1) to (44):
[1] A monoclonal antibody which specifically recognizes a native three-dimensional structure of an extracellular region of system ASC amino acid transporter 2 (hereinafter, referred to as "ASCT2") and binds to the extracellular region, or an antibody fragment thereof;
[2] The monoclonal antibody or the antibody fragment thereof described in [1], which inhibits intracellular uptake of an amino acid through ASCT2;
[3] The monoclonal antibody or the antibody fragment thereof described in [1] or [2], which has cellular cytotoxicity;
[4] The monoclonal antibody or the antibody fragment thereof described in [3], in which the cellular cytotoxicity is an antibody-dependent cellular cytotoxicity (ADCC) activity or complement-dependent cytotoxicity (CDC) activity;
[5] The monoclonal antibody or the antibody fragment thereof described in any one of [1] to [4], which binds to human ASCT2 and does not bind to mouse ASCT2;
[6] The monoclonal antibody or the antibody fragment thereof described in [5], which binds to at least EL2 region of human ASCT2;
[7] The monoclonal antibody or the antibody fragment thereof described in [6], which binds to at least any one of amino acids selected from at positions 154, 159 to 160, 163 to 171, 173 to 174, 177, 188, 204 to 205, 207, 210 to 212, and 214 to 223 in the amino acid sequence represented by SEQ ID NO:2;
[8] The antibody or the antibody fragment thereof described in any one of [1] to [7], in which the monoclonal antibody is a monoclonal antibody which binds to an epitope which is recognized by a monoclonal antibody produced from any one of hybridomas selected from a hybridoma KM4008 (FERM BP-10962) and a hybridoma KM4012 (FERM BP-10963);
[9] The antibody or the antibody fragment thereof described in any one of [1] to [8], in which the monoclonal antibody is a monoclonal antibody produced from any one of hybridomas selected from a hybridoma KM4008 (FERM BP-10962) and a hybridoma KM4012 (FERM BP-10963);
[10] The antibody fragment described in any one of [1] to [9], in which the antibody fragment is an antibody fragment selected from Fab, Fab', F(ab')$_2$, a single chain antibody (scFv), a dimerized V region (diabody), a disulfide stabilized V region (dsFv) and a CDR-containing peptide.
[11] The antibody or the antibody fragment thereof described in any one of [1] to [10], in which the monoclonal antibody is a recombinant antibody;
[12] The recombinant antibody or the antibody fragment thereof described in [11], in which the recombinant antibody is a recombinant antibody selected from a human chimeric antibody, a humanized antibody and a human antibody;
[13] The recombinant antibody or the antibody fragment thereof described in [11], which comprises complementarity determining regions (hereinafter, referred to as "CDRs") of a heavy chain variable region (hereinafter, referred to as "VH") and a light chain variable region (hereinafter, referred to as "VL") of the monoclonal antibody described in any one of [1] to [9];
[14] The recombinant antibody or the antibody fragment thereof described in [13], in which CDR1, CDR2 and CDR3 of VH of the antibody comprise the amino acid sequences represented by SEQ ID NOs:26, 27 and 28, respectively;
[15] The recombinant antibody or the antibody fragment thereof described in [13], in which CDR1, CDR2 and CDR3 of VL of the antibody comprise the amino acid sequences represented by SEQ ID NOs:29, 30 and 31, respectively;
[16] The recombinant antibody or the antibody fragment thereof described in [13], in which CDR1, CDR2 and CDR3 of VH of the antibody comprise the amino acid sequences represented by SEQ ID NOs:26, 27 and 28, respectively, and CDR1, CDR2 and CDR3 of VL of the antibody comprise the amino acid sequences represented by SEQ ID NOs:29, 30 and 31, respectively;
[17] The recombinant antibody or the antibody fragment thereof described in [13], in which CDR1, CDR2 and CDR3 of VH of the antibody comprise the amino acid sequences represented by SEQ ID NOs:32, 33 and 34, respectively;
[18] The recombinant antibody or the antibody fragment thereof described in [13], in which CDR1, CDR2 and CDR3 of VL of the antibody comprise the amino acid sequences represented by SEQ ID NOs:35, 36 and 37, respectively;
[19] The recombinant antibody or the antibody fragment thereof described in [13], in which CDR1, CDR2 and CDR3 of VH of the antibody comprise the amino acid sequences represented by SEQ ID NOs:32, 33 and 34, respectively, and CDR1, CDR2 and CDR3 of VL of the antibody comprise the amino acid sequences represented by SEQ ID NOs:35, 36 and 37, respectively;

[20] The recombinant antibody or the antibody fragment thereof described in [13], in which CDR1, CDR2 and CDR3 of VH of the antibody comprise the amino acid sequences represented by SEQ ID NOs:49, 50 and 51, respectively,

[21] The recombinant antibody or the antibody fragment thereof described in [13], in which CDR1, CDR2 and CDR3 of VL of the antibody comprise the amino acid sequences represented by SEQ ID NOs:52, 53 and 54, respectively;

[22] The recombinant antibody or the antibody fragment thereof described in [13], in which CDR1, CDR2 and CDR3 of VH of the antibody comprise the amino acid sequences represented by SEQ ID NOs:49, 50 and 51, respectively, and CDR1, CDR2 and CDR3 of VL of the antibody comprise the amino acid sequences represented by SEQ ID NOs:52, 53 and 54, respectively;

[23] The human chimeric antibody or the antibody fragment thereof described in [12], which comprises VH and VL of the monoclonal antibody described in any one of [1] to [8];

[24] The human chimeric antibody or the antibody fragment thereof described in [23], which is selected from a human chimeric antibody in which VH of the antibody comprises the amino acid sequence represented by SEQ ID NO:19 and VL of the antibody comprises the amino acid sequence represented by SEQ ID NO:21, a human chimeric antibody in which VH of the antibody comprises the amino acid sequence represented by SEQ ID NO:23 and VL of the antibody comprises the amino acid sequence represented by SEQ ID NO:25, and a human chimeric antibody in which VH of the antibody comprises the amino acid sequence represented by SEQ ID NO:46 and VL of the antibody comprises the amino acid sequence represented by SEQ ID NO:48;

[25] The humanized antibody or the antibody fragment thereof described in [12], in which VH of the antibody comprises the amino acid sequence represented by SEQ ID NO:71, or an amino acid sequence in which at least one amino acid residue selected from Val at position 2, Ser at position 9, Val at position 20, Ser at position 30, Arg at position 38, Glu at position 46, Leu at position 86, Val at position 93, Tyr at position 95 and Val at position 116 in the amino acid sequence represented by SEQ ID NO:71 is substituted with other amino acid residue, and/or in which VL of the antibody comprises an amino acid sequence represented by SEQ ID NO:72, or an amino acid sequence in which at least one amino acid residue selected from Pro at position 8, Val at position 15, Gln at position 38, Ala at position 43, Pro at position 44, Phe at position 71 and Tyr at position 87 in the amino acid sequence represented by SEQ ID NO:72 is substituted with other amino acid residue;

[26] The humanized antibody or the antibody fragment thereof described in the above [25], in which VH of the antibody comprises an amino acid sequence in which at least one modification selected from modifications for substituting Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu is introduced in the amino acid sequence represented by SEQ ID NO:71, and VL of the antibody comprises an amino acid sequence in which at least one modification selected from modifications for substituting Pro at position 8 with Thr, Val at position 15 with Leu, Gln at position 38 with Arg, Ala at position 43 with Thr, Pro at position 44 with Val, Phe at position 71 with Tyr, and Tyr at position 87 with Phe is introduced in the amino acid sequence represented by SEQ ID NO:72;

[27] The humanized antibody or the antibody fragment thereof described in [25], in which a humanized antibody is selected from a humanized antibody in which VH of the antibody comprises an amino acid sequence represented by SEQ ID NO:76 and/or VL of the antibody comprises an amino acid sequence represented by SEQ ID NO:72, a humanized antibody in which VH of the antibody comprises an amino acid sequence represented by SEQ ID NO:78 and/or VL of the antibody comprises an amino acid sequence represented by SEQ ID NO:72, a humanized antibody in which VH of the antibody comprises an amino acid sequence represented by SEQ ID NO:80 and/or VL of the antibody comprises an amino acid sequence represented by SEQ ID NO:72, a humanized antibody in which VH of the antibody comprises an amino acid sequence represented by SEQ ID NO:82 and/or VL of the antibody comprises an amino acid sequence represented by SEQ ID NO:72, a humanized antibody in which VH of the antibody comprises an amino acid sequence represented by SEQ ID NO:71 and/or VL of the antibody comprises an amino acid sequence represented by SEQ ID NO:84, a humanized antibody in which VH of the antibody comprises an amino acid sequence represented by SEQ ID NO:76 and/or VL of the antibody comprises an amino acid sequence represented by SEQ ID NO:84, a humanized antibody in which VH of the antibody comprises an amino acid sequence represented by SEQ ID NO:78 and/or VL of the antibody comprises an amino acid sequence represented by SEQ ID NO:84, a humanized antibody in which VH of the antibody comprises an amino acid sequence represented by SEQ ID NO: 80 and/or VL of the antibody comprises an amino acid sequence represented by SEQ ID NO:84, and a humanized antibody in which VH of the antibody comprises an amino acid sequence represented by SEQ ID NO:82 and/or VL of the antibody comprises an amino acid sequence represented by SEQ ID NO:84;

[28] A hybridoma which produces the monoclonal antibody described in any one of [1] to [27];

[29] The hybridoma described in [28], in which the hybridoma is a hybridoma KM4008 (FERM BP-10962) or a hybridoma KM4012 (FERM BP-10963)];

[30] A DNA which encodes the antibody or the antibody fragment thereof described in any one of [1] to [29];

[31] A recombinant vector which comprises the DNA described in [30];

[32] A transformant obtainable by introducing the recombinant vector described in [31] into a host cell;

[33] A process for producing the antibody or the antibody fragment thereof described in any one of [1] to [27], comprising culturing the hybridoma described in [28] or [29] or the transformant described in [32] in a medium to form and accumulate the antibody or the antibody fragment thereof described in any one of [1] to [27] in the culture and collecting the antibody or the antibody fragment thereof from the culture;

[34] A therapeutic agent for ASCT2 related disease comprising the antibody or the antibody fragment thereof described in any one of [1] to [27] as an active ingredient;

[35] The therapeutic agent described in [34], in which the disease relating to ASCT2 is cancer;

[36] The therapeutic agent described in [35], in which the cancer is blood cancer, esophageal cancer, gastric cancer, colorectal cancer, liver cancer or prostate cancer;

[37] A method for immunologically detecting or measuring ASCT2, using the antibody or the antibody fragment thereof described in any one of [1] to [27];
[38] The method described in [37], in which the method for immunologically measuring is an immunoprecipitation method;
[39] A method for immunologically detecting or measuring a cell which expresses ASCT2, using the antibody or the antibody fragment thereof described in any one of [1] to [27];
[40] The method described in [39], in which the method for immunologically detecting is a fluorescent cell staining method;
[41] A reagent for immunologically detecting or measuring ASCT2 using antibody or the antibody fragment thereof described in any one of [1] to [27];
[42] A diagnostic agent for ASCT2 related disease using the antibody or the antibody fragment thereof described in any one of [1] to [27];
[43] The diagnostic agent described in [42], in which the disease relating to ASCT2 is cancer; and
[44] The diagnostic agent described in [43], in which the cancer is blood cancer, esophageal cancer, gastric cancer, colorectal cancer, liver cancer or prostate cancer.

The present invention relates to a monoclonal antibody which specifically recognizes a native three-dimensional structure of an extracellular region of ASCT2 and binds to the extracellular region, or an antibody fragment thereof.

The species of ASCT2 of the present invention is not particularly limited. An example of the species may preferably be a mammal, specifically a human.

The amino acid sequence information of ASCT2 is available from a known database such as NCBI (www.ncbi.nlm.nih.gov/). Examples include human ASCT2 (NCBI Accession No. NP_005619) represented by SEQ ID NO:2, mouse ASCT2 (NCBI Accession No. NP_033227) represented by SEQ ID NO:86, and the like.

ASCT2 of the present invention includes a polypeptide comprising the amino acid sequence represented by SEQ ID NO:2 or an amino acid sequence wherein one or more amino acid residue(s) is/are deleted, substituted and/or added in the amino acid sequence represented by SEQ ID NO:2 and having a function of ASCT2. ASCT2 of the present invention also includes a polypeptide having 60% or more homology, preferably 80% or more homology, more preferably 90% or more homology, further preferably 95% or more homology to the amino acid sequence represented by SEQ ID NO:2 and having a function of ASCT2.

In the present invention, the polypeptide comprising an amino acid sequence wherein one or more amino acid residue(s) is/are deleted, substituted and/or added in the amino acid sequence represented by SEQ ID NO:2 can be obtained by site-specific mutagenesis described in *Molecular Cloning, A Laboratory Manual*, Second Edition, Cold Spring Harbor Laboratory Press (1989), *Current Protocols in Molecular Biology*, John Wiley & Sons (1987-1997), *Nucleic Acids Research*, 10, 6487 (1982), *Proc. Natl. Acad. Sci., USA*, 79, 6409 (1982), *Gene*, 34, 315 (1985), *Nucleic Acids Research*, 13, 4431 (1985), *Proc. Natl. Acad. Sci. USA*, 82, 488 (1985), etc. For example, it can be obtained by introducing a site-specific mutation into DNA having the nucleotide sequence encoding a polypeptide having the amino acid sequence represented by SEQ ID NO:2. The number of amino acid residues which are deleted, substituted and/or added is not specifically limited. The suitable number is 1 to dozens, preferably 1 to 20, more preferably 1 to several, further preferably 1 to 5.

Examples of the gene encoding ASCT2 include the nucleotide sequence represented by SEQ ID NO:1. Examples of the gene encoding ASCT2 also include a gene containing a DNA comprising a nucleotide sequence having deletion, substitution or addition of one or more nucleotides in the nucleotide sequence represented by SEQ ID NO:1 and encoding a polypeptide having the function of ASCT2; a gene containing a DNA comprising a nucleotide sequence having at least 60% or higher homology, preferably 80% or higher homology, and more preferably 95% or higher homology with the nucleotide sequence represented by SEQ ID NO:1 and encoding a polypeptide having the function of ASCT2; a gene comprising a DNA which hybridizes with a DNA having the nucleotide sequence represented by SEQ ID NO:1 under stringent conditions and containing a DNA that encodes a polypeptide having the function of ASCT2, and the like.

In the present invention, the DNA which hybridizes under stringent conditions refers to a DNA which is obtained by colony hybridization, plaque hybridization, Southern hybridization, DNA microarray, or the like using, a DNA having the nucleotide sequence represented by SEQ ID NO:1 as a probe. A specific example of such DNA is a hybridized colony- or plaque derived DNA which can be identified by performing hybridization at 65° C. in the presence of 0.7 to 1.0 mol/l sodium chloride using a filter or slide glass with the PCR product or oligo DNA having immobilized thereon, and then washing the filter or slide glass at 65° C. with a 0.1 to 2-fold concentration SSC solution (1-fold concentration SSC solution: 150 mmol/l sodium chloride and 15 mmol/l sodium citrate). Hybridization can be carried out according to the methods described in *Molecular Cloning, A Laboratory Manual*, Second Edition, Cold Spring Harbor Lab. Press (1989), *Current Protocols in Molecular Biology*, John Wiley & Sons (1987-1997); *DNA Cloning 1: Core Techniques, A Practical Approach*, Second Edition, Oxford University (1995). Specifically, the DNA capable of hybridization includes DNA having at least 60% or more homology, preferably 80% or more homology, more preferably 90% or more homology, and most preferably 95% or more homology to the nucleotide sequence represented by SEQ ID NO:1.

In the nucleotide sequence of the gene encoding a protein of a eukaryote, genetic polymorphism is often recognized. The ASCT2 gene used in the present invention also includes a gene in which small modifications are generated in the nucleotide sequence by such polymorphism.

The number of the homology described in the present invention may be a number calculated by using a homology search program known by the skilled person, unless otherwise indicated. Regarding the nucleotide sequence, the number may be calculated by BLAST [*J. Mol. Biol.*, 215, 403 (1990)] with a default parameter or the like, and regarding the amino acid sequence, the number may be calculated by using BLAST2 [*Nucleic Acids Res.*, 25, 3389 (1997); *Genome Res.*, 7, 649 (1997); www.ncbi.nlm.nih.gov/Education/BLASTinfo/information3.html] with a default parameter or the like.

As the default parameter, G (cost to open gap) is 5 for the nucleotide sequence and 11 for the amino acid sequence; −E (cost to extend gap) is 2 for the nucleotide sequence and 1 for the amino acid sequence; −q (penalty for nucleotide mismatch) is −3; −r (reward for nucleotide match) is 1; −e (expect value) is 10; −W (wordsize) is 11 residues for the nucleotide sequence and 3 residues for the amino acid sequence; −y (dropoff (X) for blast extensions in bits) is 20 for blastn and 7 for a program other than blastn; −X (X dropoff value for gapped alignment in bits) is 15; and −Z (final X dropoff value for gapped alignment in bits) is 50 for blastn and 25 for a program other than blastn (www.ncbi.nlm.nih.gov/blast/html/blastcgihelp.html).

A polypeptide comprising a partial sequence of the amino acid sequence represented by SEQ ID NO:2 can be prepared by methods known to those skilled in the art, for example, by partially deleting a DNA encoding the amino acid sequence represented by SEQ ID NO:2, and culturing a transformant into which an expression vector containing the partially deleted DNA is introduced. Based on the thus constructed polypeptide or DNA, a polypeptide in which one or more amino acids are deleted, substituted and/or added in a partial sequence of the amino acid sequence represented by SEQ ID NO:2 can also be obtained, in accordance with the same method as described above. Further, the polypeptide comprising a partial sequence of the amino acid sequence represented by SEQ ID NO:2, or the polypeptide in which one or more amino acids are deleted, substituted and/or added in a partial sequence of the amino acid sequence represented by SEQ ID NO:2 can also be produced by a chemical synthesis method such as a fluorenylmethyloxycarbonyl (Fmoc) method, a t-butyloxycarbonyl (tBoc) method, or the like.

Examples of the extracellular region of ASCT2 in the present invention include a region predicted by a known transmembrane region prediction programs SOSUI (sos-ui.proteome.bio.tuat.ac.jp/sosuiframe0.html), TMEMM ver. 2 (www.cbs.dtu.dk/services/TMH1VINI-2.0/), ExPAsy Proteomics Server (Ca.expasy.org/), or the like, based on the amino acid sequence of the polypeptide represented by SEQ ID NO:2. Specifically, examples include five regions, at positions 74 to 98, at positions 154 to 224, at positions 287 to 305, at positions 357 to 376 and at positions 420 to 425 which are the extracellular region predicted by ExPASy Proteomics Server. Alternatively, examples include five regions, at positions 65 to 88, at positions 152 to 224, at positions 288 to 306, at positions 361 to 380 and at positions 447 to 451 which are the extracellular regions predicted in the literature [*J. Biol. Chemistry*, 271, 18657 (1996)] or [*J. Virology*, 73, 4470 (1999)]. In the present invention, the five extracellular regions are indicated as an EL1 region, an EL2 region, an EL3 region, an EL4 region and an EL5 region sequentially from the N-terminal side. For example, the EL2 region in an amino acid sequence of the ASCT2 polypeptide represented by SEQ ID NO:2 corresponds to positions 154 to 224 or positions 152 to 224.

The monoclonal antibody of the present invention binds to an extracellular region of ASCT2, preferably any one of the above-mentioned EL1 to EL5 regions, and more preferably the EL2 region.

The native three-dimensional structure of the extracellular region of ASCT2 in the present invention may be any structure, so long as it has a three-dimensional structure equivalent to a three-dimensional structure which can be formed in a native state by the extracellular region of ASCT2 having the amino acid sequence represented by SEQ ID NO:2.

Whether the antibody or the antibody fragment thereof of the present invention specifically recognizes a native three-dimensional structure of an extracellular region of ASCT2 and binds to the extracellular region can be confirmed by radioimmunoassay using a solid-phase sandwich method or the like, or by a known immunological detection method for ASCT2-expressing cells using such as enzyme immunoassay (ELISA) method or the like, preferably a method capable of investigating a binding of an antibody to a particular antigen and a cell expressing the particular antigen, such as a fluorescent cell staining method. For example, specific examples include a fluorescent antibody staining method using an FMAT8100HTS System (manufactured by Applied Biosystems) [*Cancer Immunol. Immunother.*, 36, 373 (1993)] or the like, a fluorescent cell staining method using flow cytometry, surface plasmon resonance using a Biacore System (manufactured by GE Healthcare) or the like, or other methods. Furthermore, a known immunological detection methods [*Monoclonal Antibodies—Principles and practice*, Third edition, Academic Press (1996), *Antibodies—A Laboratory Manual*, Cold Spring Harbor Laboratory (1988), *Monoclonal Antibody Experimental Manual*, Kodan-sha Scientific (1987)] and the like can be combined to confirm the binding.

In the present invention, the cell expressing ASCT2 may be any cell, so long as it expresses ASCT2, and examples include a cell which is naturally present in the human body, a cell line established from the cell which is naturally present in the human body, a cell obtained by gene recombination technique and the like.

The cell which is naturally present in the human body includes a cell expressing the polypeptide in the body of a cancer patient, such as a cell expressing the ASCT2 among tumor cells obtained by biopsy or the like.

Example of a cell line established from the cell which is naturally present in the human body include a cell line expressing ASCT2, among cell lines prepared by establishing the ASCT2-expressing cells obtained from the above cancer patients, and examples include the multiple myeloma cell line KMS-11 [Human Science Research Resources Bank (HSRRB) Accession No. JCRB1179], RPMI 8226 (HSRRB Accession No. JCRB0034) and the like.

Specific examples of the cell obtained by gene recombination techniques may include an ASCT2-expressing cell obtained by introducing an expression vector comprising an ASCT2-encoding cDNA into an insect cell, an animal cell or the like, and others.

The monoclonal antibody of the present invention includes an antibody produced by a hybridoma and a recombinant antibody produced by a transformant transformed with an expression vector containing a gene encoding an antibody.

The hybridoma can be prepared, for example, by preparing the above cell expressing ASCT2 as an antigen, inducing an antibody-producing cell having antigen specificity from an animal immunized with the antigen, and fusing the antigen-producing cell with a myeloma cell. The anti-ASCT2 antibody can be obtained by culturing the hybridoma or administering the hybridoma cell into an animal to cause ascites tumor in the animal and separating and purifying the culture or the ascites.

The animal immunized with an antigen may be any animal, so long as a hybridoma can be prepared, and mouse, rat, hamster, rabbit or the like is suitably used. Also, the antibody of the present invention includes an antibody produced by a hybridoma obtained by fusion of the cell having antibody-producing activity can be obtained from such an animal and immune in vitro with a myeloma cell.

Specific examples of the monoclonal antibody produced by the hybridoma of the present invention may include an antibody KM3998 produced by a hybridoma KM3998, an antibody KM4000 produced by a hybridoma KM4000, an antibody KM4001 produced by a hybridoma KM4001, an antibody KM4008 produced by a hybridoma KM4008, an antibody KM4012 produced by a hybridoma KM4012, an antibody KM4018 produced by a hybridoma KM4018, and the like. The hybridomas KM4008 and KM4012 were deposited with the National Institute of Advanced Industrial Science and Technology (AIST; Tsukuba Central 6, 1-1, Higashi 1-Chome Tsukuba-shi, Ibaraki-ken, Japan) under the Budapest Treaty, on May 1, 2008, as FERM BP-10962 and FERM BP-10963, respectively.

Further, the monoclonal antibody of the present invention also includes a monoclonal antibody that binds to an epitope to which an antibody produced from the above-mentioned hybridomas binds.

The recombinant antibody of the present invention includes an antibody produced by gene recombination, such as a human chimeric antibody, a humanized antibody, a human antibody and an antibody fragment thereof. Among the recombinant antibodies, one having character of a common monoclonal antibody, low immunogenecity and prolonged half-life in blood is preferable as a therapeutic agent.

Examples of the recombinant antibody include a recombinant antibody modified the above mentioned monoclonal antibody by using recombinant technologies.

Examples of the recombinant antibody of the present invention include a recombinant antibody in which Complementarity Determining Region (hereinafter referred to as CDR) 1, CDR2 and CDR3 of a heavy chain variable region (hereinafter, referred to as VH) of the antibody comprise the amino acid sequences represented by SEQ ID NOs:26, 27 and 28, respectively, and/or CDR1, CDR2 and CDR3 of a light chain variable region (hereinafter, referred to as VL) of the antibody comprise the amino acid sequences represented by SEQ ID NOs:29, 30 and 31, respectively; a recombinant antibody in which CDR1, CDR2 and CDR3 of VH of the antibody comprise the amino acid sequences represented by SEQ ID NOs:32, 33 and 34, respectively, and/or CDR1, CDR2 and CDR3 of VL of the antibody comprise the amino acid sequences represented by SEQ ID NOs:35, 36 and 37, respectively; a recombinant antibody in which CDR1, CDR2 and CDR3 of VH of the antibody comprise the amino acid sequences represented by SEQ ID NOs:49, 50 and 51, respectively, and/or CDR1, CDR2 and CDR3 of VL of the antibody comprise the amino acid sequences represented by SEQ ID NOs:52, 53 and 54, respectively; and the like.

The human chimeric antibody is an antibody comprising VH and VL of an antibody of a non-human animal, and a heavy chain constant region (hereinafter referred to as CH) and a light chain constant region (hereinafter referred to as CL) of a human antibody. Specifically, the human chimeric antibody of the present invention can be produced by obtaining cDNAs encoding VH and VL from a hybridoma which produces a monoclonal antibody which specifically recognizes a native three-dimensional structure of an extracellular region of ASCT2 and binds to the extracellular region, inserting each of them into an expression vector for animal cell comprising DNAs encoding CH and CL of human antibody to thereby construct a vector for expression of human chimeric antibody, and then introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human chimeric antibody, any CL can be used, so long as it belongs to the hIg class, and those belonging to κ class or γ class can be used.

Examples of the human chimeric antibody of the present invention include a human chimeric antibody in which VH of the antibody comprises the amino acid sequences represented by SEQ ID NO:19, and VL of the antibody comprises the amino acid sequences represented by SEQ ID NO:21; a human chimeric antibody in which VH of the antibody comprises the amino acid sequence represented by SEQ ID NO:23, and VL of the antibody comprises the amino acid sequence represented by SEQ ID NO:25; a human chimeric antibody in which VH of the antibody comprises the amino acid sequence represented by SEQ ID NO:46, and VL of the antibody comprises the amino acid sequence represented by SEQ ID NO:48; and the like. Specific examples include human chimeric antibodies cKM4008, cKM4012, cKM4018 and the like.

A humanized antibody is an antibody in which amino acid sequences of CDRs of VH and VL of an antibody derived from a non-human animal are grafted into appropriate positions of VH and VL of a human antibody, and is also called a human CDR-grafted antibody, a reshaped-antibody or the like. The humanized antibody of the present invention can be produced by constructing cDNAs encoding an antibody variable region (hereinafter referred to as "V region") in which the amino acid sequences of CDRs of VH and VL of an antibody derived from a non-human animal produced by a hybridoma which produces a monoclonal antibody which specifically recognizes three-dimensional structure of ASCT2 and binds to the extracellular region are grafted into frameworks (hereinafter referred to as "FR") of VH and VL of a suitable human antibody, inserting each of them into a vector for expression of animal cell comprising genes encoding CH and CL of a human antibody to thereby construct a vector for expression of humanized antibody, and introducing it into an animal cell to thereby express and produce the humanized antibody.

As the amino acid sequences of FRs of VH and VL of a humanized antibody, any amino acid sequences can be used, so long as they are amino acid sequences of FRs of VH and VL, respectively, derived from a human antibody. Examples include amino acid sequences of FRs of VH and VL of human antibodies registered in database such as Protein Data Bank, common amino acid sequences of each sub group of FRs of VH and VL of human antibodies described in, for example, *Sequences of Proteins of Immunological Interest*, US Dept. Health and Human Services (1991), and the like.

As the CH of the humanized antibody, any CH can be used, so long as it belongs to the hIg class, and those of the hIgG class are preferred and any one of the subclasses belonging to the hIgG class, such as hIgG1, hIgG2, hIgG3 and hIgG4 can be used. As the CL of the humanized antibody, any CL can be used, so long as it belongs to the hIg class, and those belonging to the κ class or γ class can be used.

Specific examples of the humanized antibody of the present invention include a humanized antibody wherein VH of the antibody comprises the amino acid sequence represented by SEQ ID NO:71, or an amino acid sequence in which at least one amino acid residue selected from Val at position 2, Ser at position 9, Val at position 20, Ser at position 30, Arg at position 38, Glu at position 46, Leu at position 86, Val at position 93, Tyr at position 95 and Val at position 116 in the amino acid sequence represented by SEQ ID NO:71 is substituted with other amino acid residue(s), and/or wherein VL of the antibody comprises the amino acid sequence represented by SEQ ID NO:72, or an amino acid sequence in which at least one amino acid residue selected from Pro at position 8, Val at position 15, Gln at position 38, Ala at position 43, Pro at position 44, Phe at position 71 and Tyr at position 87 in the amino acid sequence represented by SEQ ID NO:72 is substituted with other amino acid residue(s); and the like. In this connection, the number of modifications which are introduced is not limited.

Examples of the amino acid sequence of VH of the antibody include preferably:

a humanized antibody comprising an amino acid sequence in which Ser at position 9, Val at position 20, Arg at position 38, Glu at position 46, Val at position 93, Tyr at position 95 and Val at position 116 in the amino acid sequence represented by SEQ ID NO:71 are substituted with other amino acid residues, a humanized antibody comprising an amino acid sequence in which Val at position 20, Glu at position 46, Tyr at position 95 and Val at position 116 in amino acid sequence represented by SEQ ID NO:71 are substituted with other amino acid residues, or a humanized antibody comprising an amino acid sequence in which Glu at position 46, and Tyr at position 95 in the amino acid sequence represented by SEQ ID NO:71 are substituted with other amino acid residues.

The amino acid sequence of VH of the antibody obtained by the above amino acid modifications may include, for example, an amino acid sequence in which at least one modification selected from amino acid modifications for substituting Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu is introduced in the amino acid sequence represented by SEQ ID NO:71.

Specific example of the amino acid sequence of VH in which ten modifications are introduced include an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced in the amino acid sequence represented by SEQ ID NO:71.

Specific examples of the amino acid sequence of VH in which nine modifications are introduced in the amino acid sequence represented by SEQ ID NO:71 include the following amino acid sequences:

an amino acid sequence in which substitutions of Ser at position 9 with Pro, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, and Val at position 116 with Leu are introduced, and an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, and Tyr at position 95 with Phe are introduced.

Specific examples of the amino acid sequence of VH in which eight modifications are introduced in the amino acid sequence represented by SEQ ID NO:71 include the following amino acid sequences:

an amino acid sequence in which substitutions of Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Val at position 20 with Ile, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Val at position 20 with Ile, Ser at position 30 with Thr, Glu at position 46 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Val at position 20 with Ile, Ser at position 30 with Thr, Arg at position 38 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Val at position 20 with Ile, Ser at position 30 with Thr, Arg at position 38 with Lys, Glu at position 46 with Lys, Val at position 93 with Thr, Tyr at position 95 with Phe, and Val at position 116 with Leu are introduced, an amino acid sequence in which substitutions of Ser at position 9 with Pro, Val at position 20 with Ile, Ser at position 30 with Thr, Arg at position 38 with Lys, Glu at position 46 with Lys, Leu at position 86 with Val, Tyr at position 95 with Phe, and Val at position 116 with Leu are introduced, an amino acid sequence in which substitutions of Ser at position 9 with Pro, Val at position 20 with Ile, Ser at position 30 with Thr, Arg at position 38 with Lys, Glu at position 46 with Lys, Leu at position 86 with Val, Val at position 93 with Thr, and Val at position 116 with Leu are introduced, an amino acid sequence in which substitutions of Ser at position 9 with Pro, Val at position 20 with Ile, Ser at position 30 with Thr, Arg at position 38 with Lys, Glu at position 46 with Lys, Leu at position 86 with Val, Val at position 93 with Thr, and Tyr at position 95 with Phe are introduced, an amino acid sequence in which substitutions of Val at position 2 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Val at position 20 with Ile, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Leu at position 86 with Val, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Glu at position 46 with Lys, Leu at position 86 with Val, Val at position 93 with Thr, and Val at position 116 with Leu are introduced, an amino acid sequence in which substitutions of Val at position 2 with Ile, Val at position 20 Ile, Ser at position 30 with Thr, Arg at position 38 with Lys, Glu at position 46 with Lys, Leu at position 86 with Val, Val at position 93 with Thr, and Tyr at position 95 with Phe are introduced, an amino acid sequence in which substitutions of Val at position 2 with Ile, Ser at position 9 with Pro, Arg at position 38 with Lys, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Ser at position 30 with Thr, Glu at position 46 with Lys, Leu at position 86 with Val, Val at position 93 with Thr, Tyr at position 95 with Phe and Val at position 116 with Leu are introduced, an amino acid sequence in which substitutions of Val at position 2 with Ile, Ser at position 9 with Pro, Ser at position 30 with Thr, Arg at position 38 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Ser at position 30 with Thr, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 2 with Ile, Ser at position 9 with Pro, Ser at position 30 with Thr, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Ser at position 30 with Thr, Arg at position 38 with Lys, Glu at position 46 with Lys, Leu at position 86 with Val, Val at position 93 with Thr, and Val at position 116 with Leu are introduced, an amino acid sequence in which substitutions of Val at position 2 with Ile, Ser at position 9 with Pro, Ser at position 30 with Thr, Arg at position 38 with Lys, Glu at position 46 with Lys, Leu at position 86 with Val, Val at position 93 with Thr, and Tyr at position 95 with Phe are introduced, an amino acid sequence in which substitutions of Val at position 2 with Ile, Ser at position 9 with Pro, Val at position 20 with Ile, Glu at position 46 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Leu at position 86 with Val, Val at position 93 with Thr, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Leu at position 86 with Val, Val at position 93 with Thr, and Tyr at position 95 with Phe are introduced, an amino acid sequence in which substitutions of Val at position 2 with Ile, Ser at position 9 with Pro, Val at position 20 with Ile, Ser at position 30 with Thr, Leu at position 86 with Val, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Glu at position 46 with Lys, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Glu at position 46 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Glu at position 46 with Lys, Leu at position 86 with Val, Val at position 93 with Thr, and Val at position 116 with Leu are introduced, an amino acid sequence in which substitutions of Val at position 2 with Ile, Ser at position 9 with Pro, Val at position 20 with Ile, Ser at position 30 with Thr, Glu at position 46 with Lys, Leu at position 86 with Val, Val at position 93 with Thr, and Tyr at position 95 with Phe are introduced, an amino acid sequence in which substitutions of Val at position 2 with Ile, Ser at position 9 with Pro, Val at position 20 with Ile, Ser at position 30 with Thr, Arg at position 38 with Lys, Val at position 93 with Thr, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Leu at position 86 with Val, Val at position 93 with Thr, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Leu at position 86 with Val, Val at position 93 with Thr, and Tyr at position 95 with Phe are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Tyr at position 95 with Phe, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Val at position 93 with Thr, and Val at position 116 with Leu are introduced, an amino acid sequence in which substitutions of Val at position 2 with Ile, Ser at position 9 with Pro, Val at position 20 Ile, Ser at position 30 with Thr, Arg at position 38 with Lys, Glu at position 46 with Lys, Val at position 93 with Thr, and Tyr at position 95 with Phe are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, and Val at position 116 with Leu are introduced, an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, and Tyr at position 95 with Phe are introduced, and an amino acid sequence in which substitutions of Val at position 2 with Ile, Ser at position 9 with Pro, Val at position 20 with Ile, Ser at position 30 with Thr, Arg at position 38 with Lys, Glu at position 46 with Lys, Leu at position 86 with Val, and Val at position 93 with Thr are introduced.

Specific examples of the amino acid sequence of VH in which seven modifications are introduced in the amino acid sequence represented by SEQ ID NO:71 include the following amino acid sequences:

an amino acid sequence in which substitutions of Val at position 2 with Ile, Ser at position 9 with Pro, Val at position 20 with Ile, Ser at position 30 with Thr, Glu at position 46 with Lys, Tyr at position 95 with Phe, and Val at position 116 with Leu are introduced, an amino acid sequence in which substitutions of Val at position 2 with Ile, Ser at position 9 with Pro, Val at position 20 with Ile, Arg at position 38 with Lys, Glu at position 46 with Lys, Tyr at position 95 with Phe, and Val at position 116 with Leu are introduced, an amino acid sequence in which substitutions of Val at position 2 with Ile, Ser at position 9 with Pro, Val at position 20 with Ile, Glu at position 46 with Lys, Leu at position 86 with Val, Tyr at position 95 with Phe, and Val at position 116 with Leu are introduced, an amino acid sequence in which substitutions of Val at position 2 with Ile, Ser at position 9 with Pro, Val at position 20 with Ile, Glu at position 46 with Lys, Val at position 93 with Thr, Tyr at position 95 with Phe, and Val at position 116 with Leu are introduced, an amino acid sequence in which substitutions of Val at position 2 with Ile, Val at position 20 with Ile, Ser at position 30 with Thr, Arg at position 38 with Lys, Glu at position 46 with Lys, Tyr at position 95 with Phe, and Val at position 116 with Leu are introduced, an amino acid sequence in which substitutions of Val at position 2 with Ile, Val at position 20 with Ile, Ser at position 30 with Thr, Glu at position 46 with Lys, Leu at position 86 with Val, Tyr at position 95 with Phe, and Val at position 116 with Leu are introduced, an amino acid sequence in which substitutions of Val at position 2 with Ile, Val at position 20 with Ile, Ser at position 30 with Thr, Glu at position 46 with Lys, Val at position 93 with Thr, Tyr at position 95 with Phe, and Val at position 116 with Leu are introduced, an amino acid sequence in which substitutions of Val at position 2 with Ile, Val at position 20 with Ile, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 2 with Ile, Val at position 20 with Ile, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 2 with Ile, Val at position 20 with Ile, Glu at position 46 with Lys, Leu at position 86 with Val, Val at position 93 with Thr, Tyr at position 95 with Phe, and Val at position 116 with Leu are introduced, an amino acid sequence in which substitutions of Ser at position 9 with Pro, Val at position 20 with Ile, Ser at position 30 with Thr, Arg at position 38 with Lys, Glu at position 46 with Lys, Tyr at position 95 with Phe, and Val at position 116 with Leu are introduced, an amino acid sequence in which substitutions of Ser at position 9 with Pro, Val at position 20 with Ile, Ser at position 30 with Thr, Glu at position 46 with Lys, Leu at position 86 with Val, Tyr at position 95 with Phe, and Val at position 116 with Leu are introduced, an amino acid sequence in which substitutions of Ser at position 9 with Pro, Val at position 20 with Ile, Ser at position 30 with Thr, Glu at position 46 with Lys, Val at position 93 with Thr, Tyr at position 95 with Phe, and Val at position 116 with Leu are introduced, an amino acid sequence in which substitutions of Ser at position 9 with Pro, Val at position 20 with Ile, Arg at position 38 with Lys, Glu at position 46 with Lys, Leu at position 86 with Val, Tyr at position 95 with Phe, and Val at position 116 with Leu are introduced, an amino acid sequence in which substitutions of Ser at position 9 with Pro, Val at position 20 with Ile, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 20 with Ile, Ser at position 30 with Thr, Arg at position 38 with Lys, Glu at position 46 with Lys, Leu at position 86 with Val, Tyr at position 95 with Phe, and Val at position 116 with Leu are introduced, an amino acid sequence in which substitutions of Val at position 20 with Ile, Ser at position 30 with Thr, Arg at position 38 with Lys, Glu at position 46 with Lys, Val at position 93 with Thr, Tyr at position 95 with Phe, and Val at position 116 with Leu are introduced, an amino acid sequence in which substitutions of Val at position 20 with Ile, Ser at position 30 with Thr, Glu at position 46 with Lys, Leu at position 86 with Val, Val at position 93 with Thr, Tyr at position 95 with Phe, and Val at position 116 with Leu are introduced, an amino acid sequence in which substitutions of Val at position 20 with Ile, Arg at position 38 with Lys, Glu at position 46 with Lys, Leu at position 86 with Val, Val at position 93 with Thr, Tyr at position 95 with Phe, and Val at position 116 with Leu are introduced, and the like.

Specific examples of the amino acid sequence of VH in which six modifications are introduced in the amino acid sequence represented by SEQ ID NO:71 include the following amino acid sequences:

an amino acid sequence in which substitutions of Val at position 20 with Ile, Arg at position 38 with Lys, Glu at position 46 with Lys, Val at position 93 with Thr, Tyr at position 95 with Phe, and Val at position 116 with Leu are introduced, an amino acid sequence in which substitutions of Ser at position 9 with Pro, Arg at position 38 with Lys, Glu at position 46 with Lys, Val at position 93 with Thr, Tyr at position 95 with Phe, and Val at position 116 with Leu are introduced, an amino acid sequence in which substitutions of Ser at position 9 with Pro, Val at position 20 with Ile, Glu at position 46 with Lys, Val at position 93 with Thr, Tyr at position 95 with Phe, and Val at position 116 with Leu are introduced, an amino acid sequence in which substitutions of Ser at position 9 with Pro, Val at position 20 with Ile, Arg at position 38 with Lys, Val at position 93 with Thr, Tyr at position 95 with Phe, and Val at position 116 with Leu are introduced, an amino acid sequence in which substitutions of Ser at position 9 with Pro, Val at position 20 with Ile, Arg at position 38 with Lys, Glu at position 46 with Lys, Tyr at position 95 with Phe, and Val at position 116 with Leu are introduced, an amino acid sequence in which substitutions of Ser at position 9 with Pro, Val at position 20 with Ile, Arg at position 38 with Lys, Glu at position 46 with Lys, Val at position 93 with Thr, and Val at position 116 with Leu are introduced, an amino acid sequence in which substitutions of Ser at position 9 with Pro, Val at position 20 with Ile, Arg at position 38 with Lys, Glu at position 46 with Lys, Val at position 93 with Thr, and Tyr at position 95 with Phe are introduced, and the like.

Specific examples of the amino acid sequence of VH in which five modifications are introduced in the amino acid sequence represented by SEQ ID NO:71 include the following amino acid sequences:

an amino acid sequence in which substitutions of Val at position 2 with Ile, Val at position 20 with Ile, Glu at position 46 with Lys, Tyr at position 95 with Phe, and Val at position 116 with Leu are introduced, an amino acid sequence in which substitutions of Ser at position 9 with Pro, Val at position 20 with Ile, Glu at position 46 with Lys, Tyr at position 95 with Phe, and Val at position 116 with Leu are introduced, an amino acid sequence in which substitutions of Val at position 20 with Ile, Ser at position 30 with Thr, Glu at position 46 with Lys, Tyr at position 95 with Phe, and Val at position 116 with Leu are introduced, an amino acid sequence in which substitutions of Val at position 20 with Ile, Arg at position 38 with Lys, Glu at position 46 with Lys, Tyr at position 95 with Phe, and Val at position 116 with Leu are introduced, an amino acid sequence in which substitutions of Val at position 20 with Ile, Glu at position 46 with Lys, Leu at position 86 with Val, Tyr at position 95 with Phe, and Val at position 116 with Leu are introduced, an amino acid sequence in which substitutions of Val at position 20 with Ile, Glu at position 46 with Lys, Tyr at position 95 with Phe, and Val at position 116 with Leu are introduced, and the like.

Specific examples of the amino acid sequence of VH in which four modifications are introduced in the amino acid sequence represented by SEQ ID NO:71 include the following amino acid sequences:

an amino acid sequence in which substitutions of Ser at position 9 with Pro, Val at position 20 with Ile, Glu at position 46 with Lys, and Tyr at position 95 with Phe are introduced, an amino acid sequence in which substitutions of Ser at position 9 with Pro, Arg at position 38 with Lys, Glu at position 46 with Lys, and Tyr at position 95 with Phe are introduced, an amino acid sequence in which substitutions of Ser at position 9 with Pro, Glu at position 46 with Lys, Val at position 93 with Thr, and Tyr at position 95 with Phe are introduced, an amino acid sequence in which substitutions of Ser at position 9 with Pro, Glu at position 46 with Lys, Tyr at position 95 with Phe, and Val at position 116 with Leu are introduced, an amino acid sequence in which substitutions of Val at position 20 with Ile, Arg at position 38 with Lys, Glu at position 46 with Lys, and Tyr at position 95 with Phe are introduced, an amino acid sequence in which substitutions of Val at position 20 with Ile, Glu at position 46 with Lys, Val at position 93 with Thr, and Tyr at position 95 with Phe are introduced, an amino acid sequence in which substitutions of Val at position 20 with Ile, Glu at position 46 with Lys, Tyr at position 95 with Phe, and Val at position 116 with Leu are introduced, an amino acid sequence in which substitutions of Arg at position 38 with Lys, Glu at position 46 with Lys, Val at position 93 with Thr, and Tyr at position 95 with Phe are introduced, an amino acid sequence in which substitutions of Arg at position 38 with Lys, Glu at position 46 with Lys, Tyr at position 95 with Phe, and Val at position 116 with Leu are introduced, an amino acid sequence in which substitutions of Glu at position 46 with Lys, Val at position 93 with Thr, Tyr at position 95 with Phe, and Val at position 116 with Leu are introduced, and the like.

Specific examples of the amino acid sequence of VH in which three modifications are introduced in the amino acid sequence represented by SEQ ID NO:71 include the following amino acid sequences:

an amino acid sequence in which substitutions of Ser at position 9 with Pro, Val at position 20 with Ile, and Arg at position 38 with Lys are introduced, an amino acid sequence in which substitutions of Ser at position 9 with Pro, Val at position 20 with Ile, and Glu at position 46 with Lys are introduced, an amino acid sequence in which substitutions of Ser at position 9 with Pro, Val at position 20 with Ile, and Val at position 93 with Thr are introduced, an amino acid sequence in which substitutions of Ser at position 9 with Pro, Val at position 20 with Ile, and Tyr at position 95 with Phe are introduced, an amino acid sequence in which substitutions of Ser at position 9 with Pro, Val at position 20 with Ile, and Val at position 116 with Leu are introduced, an amino acid sequence in which substitutions of Ser at position 9 with Pro, Arg at position 38 with Lys, and Glu at position 46 with Lys are introduced, an amino acid sequence in which substitutions of Ser at position 9 with Pro, Arg at position 38 with Lys, and Val at position 93 with Thr are introduced, an amino acid sequence in which substitutions of Ser at position 9 with Pro, Arg at position 38 with Lys, and Tyr at position 95 with Phe are introduced, an amino acid sequence in which substitutions of Ser at position 9 with Pro, Arg at position 38 with Lys, and Val at position 116 with Leu are introduced, an amino acid sequence in which substitutions of Ser at position 9 with Pro, Glu at position 46 with Lys, and Val at position 93 with Thr are introduced, an amino acid sequence in which substitutions of Ser at position 9 with Pro, Glu at position 46 with Lys, and Tyr at position 95 with Phe are introduced, an amino acid sequence in which substitutions of Ser at position 9 with Pro, Glu at position 46 with Lys, and Val at position 116 with Leu are introduced, an amino acid sequence in which substitutions of Ser at position 9 with Pro, Val at position 93 with Thr, and Tyr at position 95 with Phe are introduced, an amino acid sequence in which substitutions of Ser at position 9 with Pro, Val at position 93 with Thr, and Val at position 116 with Leu are introduced, an amino acid sequence in which substitutions of Ser at position 9 with Pro, Tyr at position 95 with Phe, and Val at position 116 with Leu are introduced, an amino acid sequence in which substitutions of Val at position 20 with Ile, Arg at position 38 with Lys, and Glu at position 46 with Lys are introduced, an amino acid sequence in which substitutions of Val at position 20 with Ile, Arg at position 38 with Lys, and Val at position 93 with Thr are introduced, an amino acid sequence in which substitutions of Val at position 20 with Ile, Arg at position 38 with Lys, and Tyr at position 95 with Phe are introduced, an amino acid sequence in which substitutions of Val at position 20 with Ile, Arg at position 38 with Lys, and Val at position 116 with Leu are introduced, an amino acid sequence in which substitutions of Val at position 20 with Ile, Glu at position 46 with Lys, and Val at position 93 with Thr are introduced, an amino acid sequence in which substitutions of Val at position 20 with Ile, Glu at position 46 with Lys, and Tyr at position 95 with Phe are introduced, an amino acid sequence in which substitutions of Val at position 20 with Ile, Glu at position 46 with Lys, and Val at position 116 with Leu are introduced, an amino acid sequence in which substitutions of Val at position 20 with Ile, Val at position 93 with Thr, and Tyr at position 95 with Phe are introduced, an amino acid sequence in which substitutions of Val at position 20 with Ile, Val at position 93 with Thr, and Val at position 116 with Leu are introduced, an amino acid sequence in which substitutions of Val at position 20 with Ile, Tyr at position 95 with Phe, and Val at position 116 with Leu are introduced, an amino acid sequence in which substitutions of Arg at position 38 with Lys, Glu at position 46 with Lys, and Val at position 93 with Thr are introduced, an amino acid sequence in which substitutions of Arg at position 38 with Lys, Glu at position 46 with Lys, and Tyr at position 95 with Phe are introduced, an amino acid sequence in which substitutions of Arg at position 38 with Lys, Glu at position 46 with Lys, and Val at position 116 with Leu are introduced, an amino acid sequence in which substitutions of Arg at position 38 with Lys, Val at position 93 with Thr, and Tyr at position 95 with Phe are introduced, an amino acid sequence in which substitutions of Arg at position 38 with Lys, Val at position 93 with Thr, and Val at position 116 with Leu are introduced, an amino acid sequence in which substitutions of Arg at position 38 with Lys, Tyr at position 95 with Phe, and Val at position 116 with Leu are introduced, an amino acid sequence in which substitutions of Glu at position 46 with Lys, Val at position 93 with Thr, and Tyr at position 95 with Phe are introduced, an amino acid sequence in which substitutions of Glu at position 46 with Lys, Val at position 93 with Thr, and Val at position 116 with Leu are introduced, an amino acid sequence in which substitutions of Glu at position 46 with Lys, Tyr at position 95 with Phe, and Val at position 116 with Leu are introduced, an amino acid sequence in which substitutions of Val at position 93 with Thr, Tyr at position 95 with Phe, and Val at position 116 with Leu are introduced, and the like.

Specific examples of the amino acid sequence of VH in which two modifications are introduced in the amino acid sequence represented by SEQ ID NO:71 include the following amino acid sequences:

an amino acid sequence in which substitutions of Val at position 2 with Ile, and Ser at position 9 with Pro are introduced, an amino acid sequence in which substitutions of Val at position 2 with Ile, and Val at position 20 with Ile are introduced, an amino acid sequence in which substitutions of Val at position 2 with Ile, and Ser at position 30 with Thr are introduced, an amino acid sequence in which substitutions of Val at position 2 with Ile, and Arg at position 38 with Lys are introduced, an amino acid sequence in which substitutions of Val at position 2 with Ile, and Glu at position 46 with Lys are introduced, an amino acid sequence in which substitutions of Val at position 2 with Ile, and Leu at position 86 with Val are introduced, an amino acid sequence in which substitutions of Val at position 2 with Ile, and Val at position 93 with Thr are introduced, an amino acid sequence in which substitutions of Val at position 2 with Ile, and Tyr at position 95 with Phe are introduced, an amino acid sequence in which substitutions of Val at position 2 with Ile, and Val at position 116 with Leu are introduced, an amino acid sequence in which substitutions of Ser at position 9 with Pro, and Val at position 20 with Ile are introduced, an amino acid sequence in which substitutions of Ser at position 9 with Pro, and Ser at position 30 with Thr are introduced, an amino acid sequence in which substitutions of Ser at position 9 with Pro, and Arg at position 38 with Lys are introduced, an amino acid sequence in which substitutions of Ser at position 9 with Pro, and Glu at position 46 with Lys are introduced, an amino acid sequence in which substitutions of Ser at position 9 with Pro, and Leu at position 86 with Val are introduced, an amino acid sequence in which substitutions of Ser at position 9 with Pro, and Val at position 93 with Thr are introduced, an amino acid sequence in which substitutions of Ser at position 9 with Pro, and Tyr at position 95 with Phe are introduced, an amino acid sequence in which substitutions of Ser at position 9 with Pro, and Val at position 116 with Leu are introduced, an amino acid sequence in which substitutions of Val at position 20 with Ile, and Ser at position 30 with Thr are introduced, an amino acid sequence in which substitutions of Val at position 20 with Ile, and Arg at position 38 with Lys are introduced, an amino acid sequence in which substitutions of Val at position 20 with Ile, and Glu at position 46 with Lys are introduced, an amino acid sequence in which substitutions of Val at position 20 with Ile, and Leu at position 86 with Val are introduced, an amino acid sequence in which substitutions of Val at position 20 with Ile, and Val at position 93 with Thr are introduced, an amino acid sequence in which substitutions of Val at position 20 with Ile, and Tyr at position 95 with Phe are introduced, an amino acid sequence in which substitutions of Val at position 20 with Ile, and Val at position 116 with Leu are introduced, an amino acid sequence in which substitutions of Ser at position 30 with Thr, and Arg at position 38 with Lys are introduced, an amino acid sequence in which substitutions of Ser at position 30 with Thr, and Glu at position 46 with Lys are introduced, an amino acid sequence in which substitutions of Ser at position 30 with Thr, and Leu at position 86 with Val are introduced, an amino acid sequence in which substitutions of Ser at position 30 with Thr, and Val at position 93 with Thr are introduced, an amino acid sequence in which substitutions of Ser at position 30 with Thr, and Tyr at position 95 with Phe are introduced, an amino acid sequence in which substitutions of Ser at position 30 with Thr, and Val at position 116 with Leu are introduced, an amino acid sequence in which substitutions of Arg at position 38 with Lys, and Glu at position 46 with Lys are introduced, an amino acid sequence in which substitutions of Arg at position 38 with Lys, and Leu at position 86 with Val are introduced, an amino acid sequence in which substitutions of Arg at position 38 with Lys, and Val at position 93 with Thr are introduced, an amino acid sequence in which substitutions of Arg at position 38 with Lys, and Tyr at position 95 with Phe are introduced, an amino acid sequence in which substitutions of Arg at position 38 with Lys, and Val at position 116 with Leu are introduced, an amino acid sequence in which substitutions of Glu at position 46 with Lys, and Leu at position 86 with Val are introduced, an amino acid sequence in which substitutions of Glu at position 46 with Lys, and Val at position 93 with Thr are introduced, an amino acid sequence in which substitutions of Glu at position 46 with Lys, and Tyr at position 95 with Phe are introduced, an amino acid sequence in which substitutions of Glu at position 46 with Lys, and Val at position 116 with Leu are introduced, an amino acid sequence in which substitutions of Leu at position 86 with Val, and Val at position 93 with Thr are introduced, an amino acid sequence in which substitutions of Leu at position 86 with Val, and Tyr at position 95 with Phe are introduced, an amino acid sequence in which substitutions of Leu at position 86 with Val, and Val at position 116 with Leu are introduced, an amino acid sequence in which substitutions of Val at position 93 with Thr, and Tyr at position 95 with Phe are introduced, an amino acid sequence in which substitutions of Val at position 93 with Thr, and Val at position 116 with Leu are introduced, and an amino acid sequence in which substitutions of Tyr at position 95 with Phe, and Val at position 116 with Leu are introduced.

Specific examples of the amino acid sequence of VH in which one modification is introduced in the amino acid sequence represented by SEQ ID NO:71 include the following amino acid sequences:

an amino acid sequence in which a substitution of Val at position 2 with Ile is introduced, an amino acid sequence in which a substitution of Ser at position 9 with Pro is introduced, an amino acid sequence in which a substitution of Val at position 20 with Ile is introduced, an amino acid sequence in which a substitution of Ser at position 30 with Thr is introduced, an amino acid sequence in which a substitution of Arg at position 38 with Lys is introduced, an amino acid sequence in which a substitution of Glu at position 46 with Lys is introduced, an amino acid sequence in which a substitution of Leu at position 86 with Val is introduced, an amino acid sequence in which a substitution of Val at position 93 with Thr is introduced, an amino acid sequence in which a substitution of Tyr at position 95 with Phe is introduced, and an amino acid sequence in which a substitution of Val at position 116 with Leu is introduced.

With regard to VL of the antibody, preferable examples include a humanized antibody comprising an amino acid sequence in which Val at position 15, Ala at position 43, Pro at position 44, Phe at position 71, and Tyr at position 87 in the amino acid sequence represented by SEQ ID NO:72 are substituted with other amino acid residues, a humanized antibody comprising an amino acid sequence in which Val at position 15, Phe at position 71 and Tyr at position 87 in amino acid sequence represented by SEQ ID NO:72 are substituted with other amino acid residues, and the like.

The amino acid sequence of VL of the antibody obtained by the above amino acid modifications include, for example, an amino acid sequence in which at least one modification selected from amino acid modifications for substituting Pro at position 8 with Thr, Val at position 15 with Leu, Gln at position 38 with Arg, Ala at position 43 with Thr, Pro at position 44 with Val, Phe at position 71 with Tyr, and Tyr at position 87 with Phe is introduced in the amino acid sequence represented by SEQ ID NO:72.

Specific examples of the amino acid sequence of VL in which seven modifications are introduced include an amino acid sequence in which substitutions of Pro at position 8 with Thr, Val at position 15 with Leu, Gln at position 38 with Arg, Ala at position 43 with Thr, Pro at position 44 with Val, Phe at position 71 with Tyr, and Tyr at position 87 with Phe are introduced in the amino acid sequence represented by SEQ ID NO:72.

Specific examples of the amino acid sequence of VL in which six modifications are introduced in the amino acid sequence represented by SEQ ID NO:72 include the following amino acid sequences:

an amino acid sequence in which substitutions of Val at position 15 with Leu, Gln at position 38 with Arg, Ala at position 43 with Thr, Pro at position 44 with Val, Phe at position 71 with Tyr, and Tyr at position 87 with Phe are introduced, an amino acid sequence in which substitutions of Pro at position 8 with Thr, Gln at position 38 with Arg, Ala at position 43 with Thr, Pro at position 44 with Val, Phe at position 71 with Tyr, and Tyr at position 87 with Phe are introduced, an amino acid sequence in which substitutions of Pro at position 8 with Thr, Val at position 15 with Leu, Ala at position 43 with Thr, Pro at position 44 with Val, Phe at position 71 with Tyr, and Tyr at position 87 with Phe are introduced, an amino acid sequence in which substitutions of Pro at position 8 with Thr, Val at position 15 with Leu, Gln at position 38 with Arg, Pro at position 44 with Val, Phe at position 71 with Tyr, and Tyr at position 87 with Phe are introduced, an amino acid sequence in which substitutions of Pro at position 8 with Thr, Val at position 15 with Leu, Gln at position 38 with Arg, Ala at position 43 with Thr, Phe at position 71 with Tyr, and Tyr at position 87 with Phe are introduced, an amino acid sequence in which substitutions of Pro at position 8 with Thr, Val at position 15 with Leu, Gln at position 38 with Arg, Ala at position 43 with Thr, Pro at position 44 with Val, and Tyr at position 87 with Phe are introduced, and an amino acid sequence in which substitutions of Pro at position 8 with Thr, Val at position 15 with Leu, Gln at position 38 with Arg, Ala at position 43 with Thr, Pro at position 44 with Val, and Phe at position 71 with Tyr are introduced.

Specific examples of the amino acid sequence of VL in which five modifications are introduced in the amino acid sequence represented by SEQ ID NO:72 include the following amino acid sequences:

an amino acid sequence in which substitutions of Gln at position 38 with Arg, Ala at position 43 with Thr, Pro at position 44 with Val, Phe at position 71 with Tyr, and Tyr at position 87 with Phe are introduced, an amino acid sequence in which substitutions of Val at position 15 with Leu, Ala at position 43 with Thr, Pro at position 44 with Val, Phe at position 71 with Tyr, and Tyr at position 87 with Phe are introduced, an amino acid sequence in which substitutions of Val at position 15 with Leu, Gln at position 38 with Mg, Pro at position 44 with Val, Phe at position 71 with Tyr, and Tyr at position 87 with Phe are introduced, an amino acid sequence in which substitutions of Val at position 15 with Leu, Gln at position 38 with Mg, Ala at position 43 with Thr, Phe at position 71 with Tyr, and Tyr at position 87 with Phe are introduced, an amino acid sequence in which substitutions of Val at position 15 with Leu, Gln at position 38 with Arg, Ala at position 43 with Thr, Pro at position 44 with Val, and Tyr at position 87 with Phe are introduced, an amino acid sequence in which substitutions of Val at position 15 with Leu, Gin at position 38 with Mg, Ala at position 43 with Thr, Pro at position 44 with Val, and Phe at position 71 with Tyr are introduced, an amino acid sequence in which substitutions of Pro at position 8 with Thr, Ala at position 43 with Thr, Pro at position 44 with Val, Phe at position 71 with Tyr, and Tyr at position 87 with Phe are introduced, an amino acid sequence in which substitutions of Pro at position 8 with Thr, Gln at position 38 with Mg, Pro at position 44 with Val, Phe at position 71 with Tyr, and Tyr at position 87 with Phe are introduced, an amino acid sequence in which substitutions of Pro at position 8 with Thr, Gln at position 38 with Mg, Ala at position 43 with Thr, Phe at position 71 with Tyr, and Tyr at position 87 with Phe are introduced, an amino acid sequence in which substitutions of Pro at position 8 with Thr, Gln at position 38 with Mg, Ala at position 43 with Thr, Pro at position 44 with Val, and Tyr at position 87 with Phe are introduced, an amino acid sequence in which substitutions of Pro at position 8 with Thr, Gln at position 38 with Mg, Ala at position 43 with Thr, Pro at position 44 with Val, and Phe at position 71 with Tyr are introduced, an amino acid sequence in which substitutions of Pro at position 8 with Thr, Val at position 15 with Leu, Pro at position 44 with Val, Phe at position 71 with Tyr, and Tyr at position 87 with Phe are introduced, an amino acid sequence in which substitutions of Pro at position 8 with Thr, Val at position 15 with Leu, Ala at position 43 with Thr, Phe at position 71 with Tyr, and Tyr at position 87 with Phe are introduced, an amino acid sequence in which substitutions of Pro at position 8 with Thr, Val at position 15 with Leu, Ala at position 43 with Thr, Pro at position 44 with Val, and Tyr at position 87 with Phe are introduced, an amino acid sequence in which substitutions of Pro at position 8 with Thr, Val at position 15 with Leu, Ala at position 43 with Thr, Pro at position 44 with Val, and Phe at position 71 with Tyr are introduced, an amino acid sequence in which substitutions of Pro at position 8 with Thr, Val at position 15 with Leu, Gln at position 38 with Arg, Phe at position 71 with Tyr, and Tyr at position 87 with Phe are introduced, an amino acid sequence in which substitutions of Pro at position 8 with Thr, Val at position 15 with Leu, Gln at position 38 with Arg, Pro at position 44 with Val, and Tyr at position 87 with Phe are introduced, an amino acid sequence in which substitutions of Pro at position 8 with Thr, Val at position 15 with Leu, Gln at position 38 with Arg, Pro at position 44 with Val, and Phe at position 71 with Tyr are introduced, an amino acid sequence in which substitutions of Pro at position 8 with Thr, Val at position 15 with Leu, Gln at position 38 with Arg, Ala at position 43 with Thr, and Tyr at position 87 with Phe are introduced, an amino acid sequence in which substitutions of Pro at position 8 with Thr, Val at position 15 with Leu, Gln at position 38 with Arg, Ala at position 43 with Thr, and Phe at position 71 with Tyr are introduced, and an amino acid sequence in which substitutions of Pro at position 8 with Thr, Val at position 15 with Leu, Gln at position 38 with Arg, Ala at position 43 with Thr, and Pro at position 44 with Val are introduced.

Specific examples of the amino acid sequence of VL in which four modifications are introduced in the amino acid sequence represented by SEQ ID NO:72 include the following amino acid sequences:

an amino acid sequence in which substitutions of Val at position 15 with Leu, Pro at position 44 with Val, Phe at position 71 with Tyr, and Tyr at position 87 with Phe are introduced, an amino acid sequence in which substitutions of Val at position 15 with Leu, Ala at position 43 with Thr, Phe at position 71 with Tyr, and Tyr at position 87 with Phe are introduced, an amino acid sequence in which substitutions of Val at position 15 with Leu, Gln at position 38 with Arg, Phe at position 71 with Tyr, and Tyr at position 87 with Phe are introduced, an amino acid sequence in which substitutions of Pro at position 8 with Thr, Val at position 15 with Leu, Phe at position 71 with Tyr, and Tyr at position 87 with Phe are introduced, and the like.

Specific examples of the amino acid sequence of VL in which three modifications are introduced in the amino acid sequence represented by SEQ ID NO:72 may include the following amino acid sequences:

an amino acid sequence in which substitutions of Pro at position 8 with Thr, Val at position 15 with Leu, and Phe at position 71 with Tyr are introduced, an amino acid sequence in which substitutions of Pro at position 8 with Thr, Val at position 15 with Leu, and Tyr at position 87 with Phe are introduced, an amino acid sequence in which substitutions of Pro at position 8 with Thr, Phe at position 71 with Tyr, and Tyr at position 87 with Phe are introduced, an amino acid sequence in which substitutions of Val at position 15 with Leu, Gln at position 38 with Arg, and Phe at position 71 with Tyr are introduced, an amino acid sequence in which substitutions of Val at position 15 with Leu, Gln at position 38 with Arg, and Tyr at position 87 with Phe are introduced, an amino acid sequence in which substitutions of Val at position 15 with Leu, Ala at position 43 with Thr, and Phe at position 71 with Tyr are introduced, an amino acid sequence in which substitutions of Val at position 15 with Leu, Ala at position 43 with Thr, and Tyr at position 87 with Phe are introduced, an amino acid sequence in which substitutions of Val at position 15 with Leu, Pro at position 44 with Val, and Phe at position 71 with Tyr are introduced, an amino acid sequence in which substitutions of Val at position 15 with Leu, Pro at position 44 with Val, and Tyr at position 87 with Phe are introduced, an amino acid sequence in which substitutions of Val at position 15 with Leu, Phe at position 71 with Tyr, and Tyr at position 87 with Phe are introduced, an amino acid sequence in which substitutions of Gln at position 38 with Arg, Phe at position 71 with Tyr, and Tyr at position 87 with Phe are introduced, an amino acid sequence in which substitutions of Ala at position 43 with Thr, Phe at position 71 with Tyr, and Tyr at position 87 with Phe are introduced, an amino acid sequence in which substitutions of Pro at position 44 with Val, Phe at position 71 with Tyr, and Tyr at position 87 with Phe are introduced, and the like.

Specific examples of the amino acid sequence of VL in which two modifications are introduced in the amino acid sequence represented by SEQ ID NO:72 include the following amino acid sequences:

an amino acid sequence in which substitutions of Pro at position 8 with Thr, and Val at position 15 with Leu are introduced, an amino acid sequence in which substitutions of Pro at position 8 with Thr, and Gln at position 38 with Arg are introduced, an amino acid sequence in which substitutions of Pro at position 8 with Thr, and Ala at position 43 with Thr are introduced, an amino acid sequence in which substitutions of Pro at position 8 with Thr, and Pro at position 44 with Val are introduced, an amino acid sequence in which substitutions of Pro at position 8 with Thr, and Phe at position 71 with Tyr are introduced, an amino acid sequence in which substitutions of Pro at position 8 with Thr, and Tyr at position 87 with Phe are introduced, an amino acid sequence in which substitutions of Val at position 15 with Leu, and Gln at position 38 with Arg are introduced, an amino acid sequence in which substitutions of Val at position 15 with Leu, and Ala at position 43 with Thr are introduced, an amino acid sequence in which substitutions of Val at position 15 with Leu, and Pro at position 44 with Val are introduced, an amino acid sequence in which substitutions of Val at position 15 with Leu, and Phe at position 71 with Tyr are introduced, an amino acid sequence in which substitutions of Val at position 15 with Leu, and Tyr at position 87 with Phe are introduced, an amino acid sequence in which substitutions of Gln at position 38 with Arg, and Ala at position 43 with Thr are introduced, an amino acid sequence in which substitutions of Gln at position 38 with Arg, and Pro at position 44 with Val are introduced, an amino acid sequence in which substitutions of Gln at position 38 with Arg, and Phe at position 71 with Tyr are introduced, an amino acid sequence in which substitutions of Gln at position 38 with Arg, and Tyr at position 87 with Phe are introduced, an amino acid sequence in which substitutions of Ala at position 43 with Thr, and Pro at position 44 with Val are introduced, an amino acid sequence in which substitutions of Ala at position 43 with Thr, and Phe at position 71 with Tyr are introduced, an amino acid sequence in which substitutions of Ala at position 43 with Thr, and Tyr at position 87 with Phe are introduced, an amino acid sequence in which substitutions of Pro at position 44 with Val, and Phe at position 71 with Tyr are introduced, an amino acid sequence in which substitutions of Pro at position 44 with Val, and Tyr at position 87 with Phe are introduced, and an amino acid sequence in which substitutions of Phe at position 71 with Tyr, and Tyr at position 87 with Phe are introduced.

Specific examples of the amino acid sequence of VL in which one modification is introduced in the amino acid sequence represented by SEQ ID NO:72 may include the following amino acid sequences:

an amino acid sequence in which a substitution of Pro at position 8 with Thr is introduced, an amino acid sequence in which a substitution of Val at position 15 with Leu is introduced, an amino acid sequence in which a substitution of Gln at position 38 with Arg is introduced, an amino acid sequence in which a substitution of Ala at position 43 with Thr is introduced, an amino acid sequence in which a substitution of Pro at position 44 with Val is introduced, an amino acid sequence in which a substitution of Phe at position 71 with Tyr is introduced, and an amino acid sequence in which a substitution of Tyr at position 87 with Phe is introduced.

In addition, specific examples of the humanized antibody of the present invention include a humanized antibody wherein VH of the antibody comprises the amino acid sequence represented by SEQ ID NO:71 and/or VL of the antibody comprises the amino acid sequence represented by SEQ ID NO:72, a humanized antibody wherein VH of the antibody comprises the amino acid sequence represented by SEQ ID NO:76 and/or VL of the antibody comprises the amino acid sequence represented by SEQ ID NO:72, a humanized antibody wherein VH of the antibody comprises the amino acid sequence represented by SEQ ID NO:78 and/or VL of the antibody comprises the amino acid sequence represented by SEQ ID NO:72, a humanized antibody wherein VH of the antibody comprises the amino acid sequence represented by SEQ ID NO:80 and/or VL of the antibody comprises the amino acid sequence represented by SEQ ID NO:72, a humanized antibody wherein VH of the antibody comprises the amino acid sequence represented by SEQ ID NO:82 and/or VL of the antibody comprises the amino acid sequence represented by SEQ ID NO:72, a humanized antibody wherein VH of the antibody comprises the amino acid sequence represented by SEQ ID NO:71 and/or VL of the antibody comprises the amino acid sequence represented by SEQ ID NO:84, a humanized antibody wherein VH of the antibody comprises the amino acid sequence represented by SEQ ID NO:76 and/or VL of the antibody comprises the amino acid sequence represented by SEQ ID NO:84, a humanized antibody wherein VH of the antibody comprises the amino acid sequence represented by SEQ ID NO:78 and/or VL of the antibody comprises the amino acid sequence represented by SEQ ID NO:84, a humanized antibody wherein VH of the antibody comprises the amino acid sequence represented by SEQ ID NO:80 and/or VL of the antibody comprises the amino acid sequence represented by SEQ ID NO:84, a humanized antibody wherein VH of the antibody comprises the amino acid sequence represented by SEQ ID NO:82 and/or VL of the antibody comprises the amino acid sequence represented by SEQ ID NO:84 and the like.

A human antibody is originally an antibody naturally existing in the human body, and it also includes an antibody obtained from a human antibody phage library or a human antibody-producing transgenic animal, which is prepared based on the recent advanced techniques in genetic engineering, cell engineering and developmental engineering.

The antibody existing in the human body can be prepared, for example by isolating a human peripheral blood lymphocyte, immortalizing it by infecting with EB virus or the like, and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the supernatant of the culture.

In the amino acid sequence constituting the above antibody or antibody fragment, an antibody or antibody fragment thereof in which one or more amino acids are deleted, substituted, inserted or added, having activity similar to the above antibody or antibody fragment is also included in the antibody or antibody fragment of the present invention.

The number of amino acids which are deleted, substituted, inserted and/or added is one or more, and is not specifically limited, but it is within the range where deletion, substitution or addition is possible by known methods such as the site-directed mutagenesis described in *Molecular Cloning*, Second Edition, Cold Spring Harbor Laboratory Press (1989); *Current Protocols in Molecular Biology*, John Wiley & Sons (1987-1997); *Nucleic Acids Research*, 10, 6487 (1982), *Proc. Natl. Acad. Sci. USA*, 79, 6409 (1982); *Gene*, 34, 315 (1985),

*Nucleic Acids Research*, 13, 4431 (1985); *Proc. Natl. Acad Sci. USA*, 82, 488 (1985) or the like. For example, the number is 1 to dozens, preferably 1 to 20, more preferably 1 to 10, and most preferably 1 to 5.

The expression "one or more amino acid residue(s) is/are deleted, substituted, inserted and/or added" in the amino acid sequence of the above antibody means the followings. That is, it means there is deletion, substitution, insertion or addition of one or plural amino acids at optional positions in the same sequence and in one or plural amino acid sequences. Also, the deletion, substitution, insertion or addition may occur at the same time and the amino acid which is substituted, inserted or added may be either a natural type or a non-natural type. The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The antibody fragment of the present invention includes Fab, F(ab')$_2$, Fab', scFv, diabody, dsFv, a peptide comprising CDR and the like.

An Fab is an antibody fragment having a molecular weight of about 50,000 and having antigen binding activity, in which about a half of the N-terminal side of H chain and the entire L chain, among fragments obtained by treating an IgG antibody molecule with a protease, papain (cleaved at an amino acid residue at position 224 of the H chain), are bound together through a disulfide bond. The Fab of the present invention can be produced by treating a monoclonal antibody which specifically recognizes three-dimensional structure of an extracellular region of ASCT2 and binds to the extracellular region with papain. Also, the Fab can be produced by inserting DNA encoding Fab of the antibody into an expression vector for prokaryote or an expression vector for eukaryote, and introducing the vector into a prokaryote or eukaryote to express the Fab.

An F(ab')$_2$ is an antibody fragment having a molecular weight of about 100,000 and having antigen binding activity and comprising two Fab regions which are bound in the hinge position obtained by digesting the lower part of two disulfide bonds in the hinge region of IgG with an enzyme, pepsin. The F(ab')$_2$ of the present invention can be produced by treating a monoclonal antibody which specifically recognizes three-dimensional structure of an extracellular region of ASCT2 and binds to the extracellular region with pepsin. Also, the F(ab')$_2$ can be produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above F(ab')$_2$. The Fab' of the present invention can be produced by F(ab')$_2$ which specifically recognizes three-dimensional structure of an extracellular region of ASCT2 and binds to the extracellular region with a reducing agent, such as dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity. The scFv of the present invention can be produced by obtaining cDNAs encoding VH and VL of a monoclonal antibody which specifically recognizes three-dimensional structure of an extracellular region of ASCT2 and binds to the extracellular region, constructing DNA encoding scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, is an antibody fragment having divalent antigen binding activity. In the divalent antigen binding activity, two antigens may be the same or different. The diabody of the present invention can be produced by obtaining cDNAs encoding VH and VL of a monoclonal antibody which specifically recognizes three-dimensional structure of an extracellular region of ASCT2 and binds to the extracellular region, constructing DNA encoding scFv so that the length of the amino acid sequence of the peptide linker is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with a known methods [*Protein Engineering*, 7, 697 (1994)]. The dsFv of the present invention can be produced by obtaining cDNAs encoding VH and VL of a monoclonal antibody which specifically recognizes three-dimensional structure of an extracellular region of ASCT2 and binds to the extracellular region, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one or more regions of CDRs of VH or VL. Peptide comprising plural CDRs can be bound directly or via an appropriate peptide linker. The peptide comprising CDR of the present invention can be produced by constructing DNA encoding CDRs of VH and VL of a monoclonal antibody which specifically recognizes three-dimensional structure of an extracellular region of ASCT2 and binds to the extracellular region, inserting the DNA into an expression vector for prokaryote or an expression vector for eukaryote, and then introducing the expression vector into a prokaryote or eukaryote to express the peptide. The peptide comprising CDR can also be produced by a chemical synthesis method such as Fmoc method or tBoc method.

The monoclonal antibody of the present invention includes an antibody conjugate in which a monoclonal antibody or an antibody fragment thereof which specifically recognizes a three-dimensional structure of an extracellular region of ASCT2 and binds to the extracellular region is chemically or genetically bound to a radioisotope, an agent having a low molecular weight, an agent having a high molecular weight, a protein, a therapeutic antibody or the like.

The antibody conjugate of the present invention can be produced by chemically conjugating a radioisotope, an agent having a low molecular weight, an agent having a high molecular weight, a protein, a therapeutic antibody or the like to the N-terminal side or C-terminal side of an H chain or an L chain of the monoclonal antibody or the antibody fragment thereof, an appropriate substituent or side chain of the antibody or the antibody fragment, a sugar chain in the antibody or the antibody fragment or the like, which specifically recognizes a three-dimensional structure of an extracellular region of ASCT2 and binds to the extracellular region in the present invention [*Antibody Engineering Handbook*, published by Chijin Shokan (1994)].

Also, the antibody conjugate can be genetically produced by linking a DNA encoding the monoclonal antibody or the antibody fragment thereof which specifically recognizes three-dimensional structure of an extracellular region of ASCT2 and binds to the extracellular region in the present invention to other DNA encoding a protein or a therapeutic antibody to be conjugated, inserting the DNA into a vector for expression, and introducing the expression vector into an appropriate host cell.

The radioisotope includes $^{131}$I, $^{125}$I, $^{90}$Y, $^{64}$Cu, $^{199}$Tc, $^{77}$Lu, $^{211}$At and the like. The radioisotope can directly be conjugated with the antibody by Chloramine-T method or the like. Also, a substance chelating the radioisotope can be conjugated with the antibody. The chelating agent includes 1-isothiocyanatobenzyl-3-methyldiethylene-triaminepentaacetic acid (MX-DTPA) and the like.

The agent having a low molecular weight includes an antitumor agent such as an alkylating agent, a nitrosourea agent, a metabolism antagonist, an antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [*Rinsho Syuyogaku* (Clinical Oncology), Gan to Kagaguryoho-Sha (1996)], a steroid agent such as hydrocortisone and prednisone, a nonsteroidal agent such as aspirin and indomethacin, immune-regulating agent such as aurothiomalate, penicillamine, immuno-suppressing agent such as cyclophosphamide and azathioprine, anti-inflammatory agent such as antihistamine agent, for example, chlorpheniramine maleate and clemastine [*Ensho to Kouensho-Ryoho* (*Inflammation and Anti-inflammation Therapy*), Ishiyaku Shuppann (1982)] and the like. Examples of the antitumor agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), epirubicin, gemcitabine (Gemsal), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, iphosphamide, idarubicin, mesna, irinotecan (CPT-11), nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, FMS-like tyrosine kinase 3 (Flt3) inhibitor, vascular endothelial growth factor receptor (VEGFR) inhibitor, fibroblast growth factor receptor (FGFR) inhibitor, epidermal growth factor receptor (EGFR) inhibitor such as Iressa and Tarceva, radicicol, 17-allylamino-17-demethoxygeldanamycin, rapamycin, amsacrine, all-trans-retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, calicheamicin, ibritumomab tiuxetan, Targretin, ozogamine, clarithromycin, leucovorin, ifosfamide, ketoconazole, aminoglutethimide, suramin, methotrexate, maytansinoid and derivatives thereof.

The method for conjugating the agent having low molecular weight with the antibody includes a method in which the agent and an amino group of the antibody are conjugated through glutaraldehyde, a method in which an amino group of the agent and a carboxyl group of the antibody are conjugated through water-soluble carbodiimide, and the like.

The agent having a high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropyl-methacrylamide, and the like. By binding these compounds having a high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [Bioconjugate Drug, Hirokawa Shoten (1993)]. For example, the method for binding. PEG to an antibody includes a method in which an antibody is allowed to react with a PEG-modifying reagent [*Bioconjugate Drug*, Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The immuno stimulator may be any natural products known as immunoadjuvants. Examples of an agent enhancing immunogen include β(1→3)glucan (lentinan, schizophyllan), α-galactosylceramide (KRN7000) and the like.

The protein includes a cytokine or a growth factor which activates a immunocompetent cell, such as NK cell, macrophage or neutrophil, a toxic protein, and the like.

Examples of the cytokine or the growth factor include interferon (hereinafter referred to as "INF")-α, INF-β, INF-γ, interleukin (hereinafter referred to as "IL")-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like. The toxic protein includes ricin, diphtheria toxin, ONTAK and the like, and also includes a toxic protein wherein mutation is introduced into a protein in order to control the toxicity.

The therapeutic antibody includes an antibody against an antigen in which apoptosis is induced by binding of the antibody, an antibody against an antigen participating in formation of pathologic state of tumor, an antibody which regulates immunological function and an antibody relating to angiogenesis in the pathologic part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, epidermal growth factor receptor (EGFR) and the like.

The antigen participating in formation of pathologic state of tumor or the antigen for the antibody which regulates immunological function includes CD4, CD40, CD40 ligand, B7 family molecule (CD80, CD86, CD274, B7-DC, B7-H2, B7-H3, B7-H4), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B ligand (RANK), RANK ligand, CD25, folic acid receptor 4, cytokine [IL-10, IL-4, IL-5, IL-6, IL-10, IL-13, transforming growth factor (TGF) β, TNFα, etc.], receptors of these cytokines, chemokine (SLC, ELC, I-309, TARC, MDC, CTACK, etc.) and receptors of these chemokines.

The antigen for the antibody which inhibits angiogenesis in the pathologic part includes vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, Ephilin, SDF-1, receptors thereof and the like.

A fusion antibody with a protein or therapeutic antibody can be produced by linking a cDNA encoding a monoclonal antibody or antibody fragment to a cDNA encoding the protein, constructing a DNA encoding the fusion antibody, inserting the DNA into an expression vector for prokaryote or eukaryote, and then introducing the expression vector into a prokaryote or eukaryote to express the fusion antibody.

In the case where the above antibody conjugate is used for the detection method, method for quantitative determination, detection reagent, reagent for quantitative determination or diagnostic agent in the present invention, examples of the agent to which a monoclonal antibody or an antibody fragment thereof which specifically recognizes a three-dimensional structure of an extracellular region of ASCT2 and binds to the extracellular region is bound includes a label used in routine immunological detecting or measuring method. The label includes enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC), and the like.

Furthermore, the present invention includes a monoclonal antibody which inhibits intracellular uptake of amino acids by ASCT2, and an antibody fragment thereof.

Examples of the method of evaluating an inhibitory activity of the antibody or antibody fragment thereof of the present invention on intracellular uptake of amino acids by ASCT2, include a method in which an antibody or an antibody fragment thereof is allowed to react with a normal or cancer cell expressing ASCT2, and then is evaluated the inhibition of glutamine-dependent proliferation using a viable cell counting reagent, or the like [*J. Surgical Research,* 90, 149 (2000)], a method in which an antibody or an antibody fragment thereof is allowed to react with a normal or cancer cell expressing ASCT2, and then is evaluated the inhibition of uptake of amino acids such as radioactive material-labeled alanine using appropriate equipment such as scintillation counter [*J. Biol. Chem.,* 271, 14883 (1996)], or the like.

In addition, the present invention includes a monoclonal antibody and an antibody fragment thereof having a cellular cytotoxicity such as a complement-dependent cytotoxicity (CDC) activity, or an antibody-dependent cellular cytotoxicity (ADCC) activity.

The CDC activity or ADCC activity of the antibody or the antibody fragment thereof of the present invention against the antigen-positive cell line can be evaluated by known assay methods [*Cancer Immunol. Immunother,* 36, 373 (1993)].

Furthermore, the present invention includes a monoclonal antibody having an apoptosis-inducing activity, and an antibody fragment thereof.

Moreover, the present invention includes a monoclonal antibody which does not bind to mouse ASCT2, but also binds to human ASCT2, and an antibody fragment thereof.

Further, the present invention includes a monoclonal antibody which binds to at least the EL2 region of human ASCT2, and an antibody fragment thereof, for example, a monoclonal antibody which binds to at least any one of amino acids at positions 154, 159 to 160, 163 to 171, 173 to 174, 177, 188, 204 to 205, 207, 210 to 212, and 214 to 223, in the amino acid sequence represented by SEQ ID NO:2, and an antibody fragment thereof.

The binding specificity of the antibody or antibody fragment thereof of the present invention can be evaluated by a known epitope analysis method, for example by measuring the binding activity to human/mouse chimeric ASCT2 in which an appropriate site is replaced with a sequence of mouse ASCT2, based on the amino acid sequence information.

Also, the present invention relates to a therapeutic agent for a disease relating to ASCT2 comprising the monoclonal antibody or antibody fragment which specifically recognizes three-dimensional structure of an extracellular region of ASCT2 and binds to the extracellular region as an active ingredient.

The disease relating to ASCT2 is not limited, so long as it is a disease relating to a cell expressing ASCT2, such as cancer.

The cancer includes blood cancer, breast cancer, uterine cancer, colorectal cancer, esophageal cancer, stomach cancer, ovarian cancer, lung cancer, renal cancer, rectal cancer, thyroid cancer, uterine cervix cancer, small intestinal cancer, prostate cancer and pancreatic cancer. Preferable examples of the cancer include blood cancer, esophageal cancer, stomach cancer, colorectal cancer, liver cancer and prostate cancer. Examples of blood cancer include myeloid leukemia, lymphoid leukemia, multiple myeloma, Hodgkin's lymphoma and non-Hodgkin's lymphoma.

The therapeutic agent in the present invention includes a therapeutic agent comprising the above monoclonal antibody or antibody fragment of the present invention as an active ingredient.

The therapeutic agent comprising the antibody or antibody fragment thereof, or conjugate thereof of the present invention may comprise only the antibody or antibody fragment thereof, or conjugate thereof as an active ingredient. It is generally preferred that the therapeutic agent is prepared as a pharmaceutical preparation produced by an appropriate method well known in the technical field of pharmaceutics, and by mixing it with one or more pharmaceutically acceptable carriers.

It is preferred to administer the therapeutic agent by the route that is most effective for the treatment. Examples include oral administration and parenteral administration, such as buccal, tracheal, rectal, subcutaneous, intramuscular or intravenous administration and intravenous administration is preferred.

The therapeutic agent may be in the form of spray, capsules, tablets, powder, granules, syrup, emulsion, suppository, injection, ointment, tape, and the like.

Although the dose or the frequency of administration varies depending on the objective therapeutic effect, administration method, treating period, age, body weight and the like, it is usually 10 µg/kg to 8 mg/kg per day and per adult.

Further, the present invention relates to a method for immunologically detecting or measuring ASCT2, a reagent for immunologically detecting or measuring ASCT2, a method for immunologically detecting or measuring a cell expressing ASCT2, and a diagnostic agent for diagnosing a disease relating to ASCT2, comprising a monoclonal antibody which specifically recognizes a native three-dimensional structure of an extracellular region of ASCT2 and binds to the extracellular region, or an antibody fragment thereof as an active ingredient.

In the present invention, the method for detecting or measuring the amount of ASCT2 may be any known method. For example, it includes an immunological detecting or measuring method.

The immunological detecting or measuring method is a method in which an antibody amount or an antigen amount is detected or determined using a labeled antigen or antibody. Examples of the immunological detecting or measuring method include radioactive substance-labeled immunoantibody method (RIA), enzyme immunoassay (EIA or ELISA), fluorescent immunoassay (FIA), luminescent immunoassay, Western blotting method, physico-chemical method and the like.

The above disease relating to ASCT2 can be diagnosed by detecting or measuring a cell expressing ASCT2 by using the monoclonal antibody or antibody fragment of the present invention.

For the detection of the cell expressing ASCT2, known immunological detection methods can be used, and an immunoprecipitation method, a fluorescent cell staining method, an immune tissue staining method and the like are preferably used. Also, a fluorescent antibody staining method using FMAT 8100 HTS system (Applied Biosystem) and the like can be used.

In the present invention, the living body sample to be used for detecting or measuring ASCT2 is not particularly limited, so long as it has a possibility of containing a cell expressing ASCT2, such as tissue cells, blood, blood plasma, serum, pancreatic fluid, urine, fecal matter, tissue fluid or culture fluid.

The diagnostic agent containing the monoclonal antibody or antibody fragment thereof, or conjugate thereof may further contain a reagent for carrying out an antigen-antibody reaction or a reagent for detection of the reaction depending on the desired diagnostic method. The reagent for carrying out the antigen-antibody reaction includes a buffer, a salt, and the like. The reagent for detection includes a reagent generally used for the immunological detecting or measuring method, such as labeled secondary antibody which recognizes the monoclonal antibody, antibody fragment thereof or conjugates thereof and substrate corresponding to the labeling.

The present invention can provide a monoclonal antibody which specifically recognizes a native three-dimensional structure of an extracellular region of system ASC amino acid transporter 2 (hereinafter referred to as ASCT2) and binds to the extracellular region, or an antibody fragment thereof; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof, and a diagnostic agent using the antibody or the antibody fragment thereof.

A process for producing the antibody of the present invention, a method for treating the disease and a method for diagnosing the disease are specifically described below.

1. Preparation Method of Monoclonal Antibody (1) Preparation of Antigen

ASCT2 or a cell expressing ASCT2 as an antigen can be obtained by introducing an expression vector comprising cDNA encoding a full length of ASCT2 or a partial length thereof is introduced into *Escherichia coli*, yeast, an insect cell, an animal cell or the like. In addition, ASCT2 can be purified from various human tumor cell lines, human tissue and the like which express a large amount of ASCT2. The tumor cell line and the tissue can be allowed to use as antigens. Furthermore, a synthetic peptide having a partial sequence of the ASCT2 can be prepared by a chemical synthesis method such as Fmoc method or tBoc method and used as an antigen.

ASCT2 used in the present invention can be produced, for example, by expressing a DNA encoding ASCT2 in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like according to the following method.

Firstly, a recombinant vector is prepared by inserting a full length cDNA comprising the region encoding ASCT2 into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing ASCT2 can be obtained by introducing the recombinant vector into a host cell suitable for the expression vector.

The expression vector may be any one, so long as it can replicate autonomously in the host cell to be used or it can be integrated into a chromosome comprising an appropriate promoter at such a position that the DNA encoding the polypeptide can be transcribed.

The host cell may be any one, so long as it can express the objective gene. Examples include a microorganism which belongs to the genera *Escherichia*, such as *Escherichia coli*, yeast, an insect cell, an animal cell and the like.

When a prokaryote such as *Escherichia coli* is used as the host cell, it is preferred that the recombinant vector used in the present invention is autonomously replicable in the prokaryote and comprising a promoter, a ribosome binding sequence, the DNA encoding ASCT2 and a transcription termination sequence. The recombinant vector is not necessary to have a transcription termination sequence, but a transcription termination sequence is preferably set just below the structural gene. The recombinant vector may further comprise a gene regulating the promoter.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides).

Furthermore, the nucleotide sequence of the DNA encoding ASCT2 can be substituted with another base so as to be a suitable codon for expressing in a host cell, thereby improve the productivity of the objective ASCT2.

Any expression vector can be used, so long as it can perform in the host cell to be used. Examples of the expression vector includes pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Examples of host cell include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* BB101, *Escherichia coli* No. 49, *Escherichia coli* W3110, *Escherichia coli* NY49, *Escherichia coli* DH5α and the like.

Any introduction method of the recombinant vector can be used, so long as it is a method for introducing DNA into the host cell, and examples include a method using a calcium ion described in *Proc. Natl. Acad. Sci. USA*, 69, 2110 (1972), *Gene*, 17, 107 (1982) and *Molecular & General Genetics*, 168, 111 (1979) and the like.

When an animal cell is used as the host cell, any expression vector can be used, so long as it can function in the animal cell. Examples include pcDNAl, pcDM8 (manufactured by Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840, (1987)], pcDNAI/Amp (manufactured by Invitrogen), pcDNA3.1 (manufactured by Invitrogen), pREP4 (manufactured by Invitrogen), pAGE103 *Biochemistry*, 101, 1307 (1987)1 pAGE210, pME18SFL3, pKANTEX93 (WO 97/10354) and the like.

Any promoter can be used, so long as it can function in an animal cell. Examples include a promoter of immediate early (IE) gene of cytomegalovirus (CMV), SV40 early promoter, a promoter of retrovirus, a metallothionein promoter, a heat shock promoter, SRα promoter, Molony murine leukemia virus promoter or enhancer, and the like. Also, the enhancer of the IE gene of human CMV can be used together with the promoter.

The host cell includes human Namalwa cell, monkey COS cell, Chinese hamster ovary (CHO) cell, HST5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

ASCT2 can be produced by culturing the transformant derived from a microorganism, an animal cell or the like having a recombinant vector comprising the DNA encoding ASCT2 in a medium to form and accumulate ASCT2 in the culture, and recovering it from the culture. The method for culturing the transformant in the medium is carried out according to the usual method used in culturing of hosts.

When ASCT2 is expressed in a cell derived from eukaryote, ASCT2 to which sugars or sugar chains bind can be obtained.

When a microorganism transformed with a recombinant vector containing an inducible promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for the Biological Medicine*, 73, 1 (1950)], Iscoove's modified Dulbecco's medium (IMDM), the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Regarding the expression method of the gene encoding ASCT2, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing ASCT2 includes a method of intracellular expression in a host cell, a method of extracellular secretion from a host cell, a method of producing on a host cell membrane outer envelope, and the like. The appropriate method can be selected by changing the host cell used and the structure of the ASCT2 produced.

When the ASCT2 is produced in a host cell or on a host cell membrane outer envelope, ASCT2 can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO 94/23021, and the like.

Also, the production amount of ASCT2 can be increased in accordance with the method described in Japanese Published Unexamined Patent Application No. 227075/90 utilizing a gene amplification system using a dihydrofolate reductase gene.

The resulting ASCT2 can be isolated and purified, for example, as follows.

When ASCT2 is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general protein isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When ASCT2 is expressed intracellularly by forming an inclusion body, the cells are recovered, disrupted and centrifuged in the same manner, and the inclusion body of ASCT2 are recovered as a precipitation fraction. The recovered inclusion body of the protein is solubilized with a protein denaturing agent. The protein is made into a normal three-dimensional structure by diluting or dialyzing the solubilized solution, and then a purified preparation of ASCT2 is obtained by the same isolation purification method as above.

When ASCT2 or the derivative such as a glycosylated product is secreted extracellularly, ASCT2 or the derivative such as a glycosylated product can be recovered from the culture supernatant. That is, the culture is treated by a method such as centrifugation in the same manner as above to obtain a culture supernatant, a purified preparation of ASCT2 can be obtained from the culture supernatant by the same isolation purification method as above.

Also, ASCT2 used in the present invention can be produced by a chemical synthesis method, such as Fmoc method or tBoc method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat or hamster 3 to 20 weeks old is immunized with the antigen prepared in the above (1), and antibody-producing cells are collected from the spleen, lymph node or peripheral blood of the animal. Also, when the increase of a sufficient titer in the above animal is recognized due to low immunogenecity, a ASCT2 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual*, Cold Spring Harbor Laboratory (1988)] or the like. An animal showing a sufficient antibody titer in their sera against the antigen used for the immunization is used as the supply source of antibody-producing cells for fusion.

Three to seven days after final administration of the antigen, tissue containing the antibody-producing cells such as the spleen from the immunized animal is excised to collect the antibody-producing cells. When the spleen cells are used, the spleen is cut out and loosened, followed by centrifuged. Then, antibody-producing cells for fusion are obtained by removing erythrocytes.

(3) Preparation of Myeloma Cell

An established cell line obtained from mouse is used as myeloma cells. Examples include 8-azaguanine-resistant mouse (derived from BALB/c) myeloma cell line P3-X63Ag8-U1 (P3-U1) [*Current Topics in Microbiology and Immunology*, 18, 1 (1978)], P3-NS1/1-Ag41 (NS-1) [*European J. Immunology*, 6, 511 (1976)], SP2/0-Ag14 (SP-2) [*Nature*, 276, 269 (1978)], P3-X63-Ag8653 (653) [*J. Immunology*, 123, 1548 (1979)], P3-X63-Ag8 (X63) [*Nature*, 256, 495 (1975)] and the like.

The myeloma cells are subcultured in a normal medium [a medium in which glutamine, 2-mercaptoethanol, gentamicin, FBS and 8-azaguanine are added to RPMI-1640 medium] and they are subcultured in the normal medium 3 or 4 days before cell fusion to ensure the cell number of $2\times10^7$ or more on the day for fusion.

(4) Cell Fusion and Preparation of Hybridoma for Producing Monoclonal Antibody

The antibody-producing cells for fusion obtained by the above (2) and myeloma cells obtained by the above (3) were sufficiently washed with a minimum essential medium (MEM) or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells: the myeloma cells=5 to 10:1, followed by centrifugation. Then, the supernatant is discarded. The precipitated cell group is sufficiently loosened. After loosening the precipitated cell, the mixture of polyethylene glycol-1000 (PEG-1000), MEM and dimethylsulfoxide is added to the cell under stirring at 37° C. In addition, 1 to 2 mL of MEM medium is added several times every one or two minutes, and MEM is added to give a total amount of 50 mL. After centrifugation, the supernatant is discarded. After the cells are gently loosen, the cells are gently suspended in HAT medium [a medium in which hypoxanthine, thymidine and aminopterin is added to the normal medium]. The suspension is cultured in a 5% $CO_2$ incubator for 7 to 14 days at 37° C.

After the culturing, a portion of the culture supernatant is sampled and a hybridoma which is reactive to an antigen containing ASCT2 and is not reactive to an antigen not containing ASCT2 is selected by binding assay as described below. Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Purified Monoclonal Antibody

The hybridoma cells producing a monoclonal antibody obtained by the above (4) are administered by intraperitoneal injection into 8- to 10-week-old mice or nude mice treated with 0.5 mL of pristane (2,6,10,14-tetramethylpentadecane (pristane) is intraperitoneally administered, followed by feeding for 2 weeks). The hybridoma develops ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained by the above (4) is cultured in RPMI1640 medium containing 10% FBS or the like and the supernatant is removed by centrifugation. The precipitated cells are suspended in Hybridoma SFM medium containing 5% DIGO GF21 and cultured for 3 to 7 days. The purified monoclonal antibody can be obtained by centrifusing the obtained cell suspension, followed by purifying the resulting supernatant with Protein A column or Protein G column to collect the IgG fractions.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using an enzyme immunoassay method and inhibition assay of intracellular uptake of amino acids.

(6-a) Binding Assay

As the antigen, a gene-introduced cell or a recombinant protein obtained by introducing an expression vector containing a cDNA encoding ASCT2 obtained in (1) into *Escherichia coli*, yeast, an insect cell, an animal cell or the like, or a purified polypeptide or partial peptide obtained from a human tissue is used. When the antigen is a partial peptide, a conjugate is prepared with a carrier protein such as BSA or KLH and is used.

After making these antigens into a solid layer by dispensing in a 96-well plate, a substance to be tested such as serum, a culture supernatant of a hybridoma or a purified monoclonal antibody is dispensed therein as the primary antibody and allowed to react. After thoroughly washing with PBS, PBS-Tween, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction is carried out in response to the label of the secondary antibody to select a monoclonal antibody which specifically reacts with the antigen.

(6-b) Inhibition Assay of Intracellular Uptake of Amino Acids

As an assay cell, a gene-introduced cell in which the expression vector comprising cDNA encoding ASCT2 is introduced into a cell such as an animal cell obtained in the above (1), or a normal or cancer cell expressing ASCT2 can be used.

The activity of the monoclonal antibody or antibody fragment thereof of the present invention to inhibit intracellular uptake of amino acids through ASCT2 is evaluated using a method comprising reacting a monoclonal antibody or an antibody fragment thereof with a normal or cancer cell expressing ASCT2, and then evaluating the inhibition of glutamine-dependent proliferation using a viable cell counting reagent, or the like [*J. Surgical Research*, 90, 149 (2000)], a method comprising reacting a monoclonal antibody or an antibody fragment thereof with a normal or cancer cell expressing ASCT2 and then evaluating the inhibition of uptake of amino acids such as radioactive material-labeled alanine using appropriate equipment such as scintillation counter [*J. Biol. Chem.*, 271, 14883 (1996)] or the like.

2. Preparation of Recombinant Antibody

As production examples of recombinant antibodies, processes for producing a human chimeric antibody and a humanized antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to x class, and the like. As the DNAs encoding CH and CL of a human antibody, the cDNA may be generally used and a chromosomal DNA comprising an exon and an intron can be also used. As the expression vector for animal cell, any expression vector can be used, so long as a gene encoding the C region of a human antibody can be inserted thereinto and expressed therein. Examples include pAGE107 [*Cytotechnol.*, 3, 133 (1990)], pAGE103 [*J. Biochem.*, 101, 1307 (1987)], pHSG274 [Gene, 27, 223 (1984)], pKCR [*Proc. Natl. Acad Sci. USA*, 78, 1527 (1981)], pSG1bd2-4 [*Cytotechnol.*, 4, 173 (1990)], pSE1UK1Sed1-3 [*Cytotechnol.*, 13, 79 (1993)] and the like. Examples of a promoter and enhancer used for an expression vector for animal cell include an SV40 early promoter [*J. Biochem.*, 101, 1307 (1987)], a Moloney mouse leukemia virus LTR [*Biochem. Biophys. Res. Commun.*, 149, 960 (1987)], an immunoglobulin H chain promoter [*Cell*, 41, 479 (1985)] and enhancer [*Cell*, 33, 717 (1983)] and the like.

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods*, 167, 271 (1994)]. Examples of the tandem type of the vector for expression of recombinant antibody include pKANTEX93 (WO 97/10354), pEE18 [Hybridoma, 17, 559 (1998)], and the like.

(2) Obtaining of cDNA Encoding V Region of Antibody Derived from Non-Human Animal and Analysis of Amino Acid Sequence cDNAs encoding VH and VL of non-human antibody and analysis of amino acid sequence are obtained as follows.

mRNA is extracted from hybridoma cells producing an antibody derived from a non-human animal to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of an mouse antibody as the probe. The full length of the nucleotide sequences of VH and VL of mouse antibody of interest on the recombinant phage or recombinant plasmid are determined, and the full length of the amino acid sequences of VH and VL are deduced from the nucleotide sequences, respectively.

Examples of the non-human animal for preparing a hybridoma cell which produces a non-human antibody include mouse, rat, hamster, rabbit, or the like. Any animals can be used so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)] using a kit such as RNA easy kit (manufactured by Qiagen) and the like.

Examples of the method for preparing mRNA from total RNA include an oligo (dT) immobilized cellulose column method [*Molecular Cloning, A Laboratory Manual*, Second Edition, Cold Spring Harbor Laboratory Press (1989)], a method using a kit such as Oligo-dT30<Super> mRNA Purification Kit (manufactured by Takara Bio) and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Cold Spring Harbor Lab. Press (1989); Current Protocols in Molecular Biology, Supplement 1, John Wiley & Sons (1987-1997)]; a method using a kit such as Super Script Plasmid System for cDNA Synthesis and Plasmid Cloning (manufactured by GIBCO BRL), ZAP-cDNA Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λExCell and pT7T3 18U (manufactured by Pharmacia), pcD2 [*Mol. Cell. Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include KL1-Blue MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH and VL of a non-human antibody or the like 1 from the cDNA library [*Molecular Cloning, A Laboratory Manual*, Second Edition, Cold Spring Harbor Laboratory Press (1989)]. Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1, John Wiley & Sons (1987-1997)) by preparing primers and using cDNA prepared from mRNA or a cDNA library as the template.

The nucleotide sequence of the cDNA can be determined by digesting the cDNA selected with appropriate restriction enzymes and the like, cloning the fragments into a plasmid such as pBluescript SK(−) (manufactured by Stratagene), carrying out the reaction by a usually used nucleotide analyzing method such as analyzing the sequence using an automatic nucleotide sequence analyzer such as A.L.F. DNA sequencer (manufactured by Pharmacia) after the dideoxy method [Proc. Natl. Acad. Sci. USA, 74, 5463 (1977)].

Whether the obtained cDNAs encode the full amino acid sequences of VL and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the full length of the amino acid sequence of VH and VL can be examined by carrying out a homology search with sequences in any database, for example, SWISS-PROT, PIR-Protein or the like using the obtained full length of the amino acid sequences of VH and VL, for example, according to the BLAST method [*J. Mol. Biol.*, 215, 403 (1990)] or the like.

(3) Construction of Vector for Expression of Human Chimeric Antibody cDNAs encoding VH and \TL of antibody of non-human animal are respectively cloned in the upstream of genes encoding CH or CL of human antibody of vector for expression of recombinant antibody mentioned in the above (1) to thereby construct a vector for expression of human chimeric antibody. For example, in order to ligate cDNA comprising a nucleotide sequence of 3'-terminal of VH or VL of antibody of non-human animal and a nucleotide sequence of 5'-terminal of CH or CL of human antibody, each cDNA encoding VH and VL of antibody of non-human animal is prepared so as to encodes appropriate amino acids encoded by a nucleotide sequence of a linkage portion and designed to have an appropriate recognition sequence of a restriction enzyme. The obtained cDNAs encoding VH and VL of antibody are respectively cloned so that each of them is expressed in an appropriate form in the upstream of gene encoding CH or CL of human antibody of the vector for expression of humanized antibody mentioned in the above (1) to construct a vector for expression of human chimeric antibody.

In addition, cDNA encoding VH or VL of non-human animal is amplified by PCR using a synthetic DNA having a recognition sequence of an appropriate restriction enzyme at both ends and each of them is cloned to the vector for expression of recombinant antibody obtained in the above (1).

(4) Construction of cDNA Encoding V Region of Humanized Antibody cDNAs encoding VH or VL of a humanized antibody can be obtained as follows. First, amino acid sequences of framework region (hereinafter referred to as "FR") in VH or VL of a human antibody to which amino acid sequences of CDRs in VH or VL of an antibody derived from a non-human animal antibody are transplanted are respectively selected. Any amino acid sequences of FR of a human antibody can be used, so long as they are derived from human. Examples include amino acid sequences of FRs of human antibodies registered in database such as Protein Data Bank or the like, and amino acid sequences common to subgroups of FRs of human antibodies [*Sequences of Proteins of Immunological Interest*, US Dept. Health and Human Services (1991)], and the like. In order to inhibit the decrease in the binding activity of the antibody, amino acid sequences having high homology (at least 60% or more) with the amino acid sequence of FR in VH or VL of the original antibody is selected.

Then, amino acid sequences of CDRs of the original antibody are grafted to the selected amino acid sequence of FR in VH or VL of the human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed.

Based on the designed nucleotide sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR and the lengths of DNAs which can be synthesized.

Furthermore, the cDNA encoding VH or VL of a humanized antibody can be easily cloned into the vector for expression of humanized antibody constructed in (1) by introducing the recognition sequence of an appropriate restriction enzyme to the 5' terminal of the synthetic DNAs existing on the both ends.

After the PCR, an amplified product is cloned into a plasmid such as pBluescript SK (−) (manufactured by Stratagene) or the like, and the nucleotide sequence is determined according to a method similar to the method described in (2) to obtain a plasmid having a DNA sequence encoding the amino acid sequence of VH or VL of a desired humanized antibody.

(5) Modification of Amino Acid Sequence of V Region of Humanized Antibody

It is known that when a humanized antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)]. In humanized antibodies, among the amino acid sequences of FRs in VH and VL of a human antibody, an amino acid residue which directly relates to binding to an antigen, an amino acid residue which interacts with an amino acid residue in CDR, and an amino acid residue which maintains the three-dimensional structure of an antibody and indirectly relates to binding to an antigen is identified and modified to an amino acid residue which is found in the original non-humanized antibody to thereby increase the antigen binding activity which has been decreased.

In order to identify the amino acid residues relating to the antigen binding activity in FR, the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. In addition, various attempts must be currently be necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (4). With regard to the amplified product obtained by the PCR, the nucleotide sequence is determined according to the method as described in (2) so that whether the objective modification has been carried out is confirmed.

(6) Construction of Vector for Expression of Humanized Antibody

A vector for expression of humanized antibody can be constructed by cloning each cDNA encoding VH or VL of a constructed recombinant antibody into upstream of each gene encoding CH or CL of the human antibody in the vector for expression of recombinant antibody as described in (1).

For example, when recognizing sequences of an appropriate restriction enzymes are introduced to the 5'-terminal of synthetic DNAs positioned at both ends among synthetic DNAs used in the construction of VH or VL of the humanized antibody in (4) and (5), cloning can be carried out so that they are expressed in an appropriate form in the upstream of each gene encoding CH or CL of the human antibody in the vector for expression of humanized antibody as described in the above (1).

(7) Transient Expression of Recombinant Antibody

In order to efficiently evaluate the antigen binding activity of various humanized antibodies produced, the recombinant antibodies can be expressed transiently using the vector for expression of recombinant antibody as described in (3) and (6) or the modified expression vector thereof.

Any cell can be used as a host cell, so long as the host cell can express a recombinant antibody. Generally, COS-7 cell (ATCC CRL1651) is used [*Methods in Nucleic Acids Res.*, CRC Press, 283 (1991)]. Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme immunoassay [*Monoclonal Antibodies Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(8) Obtaining Transformant which Stably Expresses Recombinant Antibody and Preparation of Recombinant Antibody A transformant which stably expresses a recombinant antibody can be obtained by introducing the vector for expression of recombinant antibody described in (3) and (6) into an appropriate host cell.

Examples of the method for introducing the expression vector into a host cell include electroporation [Japanese Published Unexamined Patent Application No. 257891/90, *Cytotechnology*, 3, 133 (1990)] and the like.

As the host cell into which a vector for expression of a recombinant antibody is introduced, any cell can be used, so long as it is a host cell which can produce the recombinant antibody. Examples include mouse SP2/0-Ag14 cell (ATCC CRL1581), mouse P3×63-Ag8.653 cell (ATCC CRL1580), CHO cell in which a dihydrofolate reductase gene (hereinafter referred to as "dhfr") is defective [*Proc. Natl. Acad. Sci. U.S.A.*, 77, 4216 (1980)], lection resistance-acquired Lec13 [*Somatic Cell and Molecular genetics*, 12, 55 (1986)], CHO cell in which α1,6-fucosyltransaferse gene is defected (WO 2005/35586, WO 02/31140), rat YB2/3HL.P2.G11.16Ag.20 cell (ATCC CRL1662), and the like.

In addition, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetylglucosamine in the reducing end through α-bond in a complex type N-glycoside-linked sugar chain, or a protein relating to transport of an intracellular sugar nucleotide, GDP-fucose, to the Golgi body are introduced is decreased or deleted, preferably CHO cell in which α1,6-fucosyltransferase gene is defected as described in WO05/35586, WO02/31140 or the like, can also be used.

After introduction of the expression vector, transformants which express a recombinant antibody stably are selected by culturing in a medium for animal cell culture containing an agent such as G418 sulfate (hereinafter referred to as "G418") or the like (Japanese Published Unexamined Patent Application No. 257891/90).

Examples of the medium for animal cell culture include RPM:11640 medium (manufactured by Invitrogen), GIT medium (manufactured by Nihon Pharmaceutical), EX-CELL301 medium (manufactured by JRH), IMDM medium (manufactured by Invitrogen), Hybridoma-SFM medium (manufactured by Invitrogen), media obtained by adding various additives such as fetal calf serum (hereinafter referred to as "FCS") to these media, and the like. The recombinant antibody can be produced and accumulated in a culture supernatant by culturing the selected transformants in a medium. The expression amount and antigen binding activity of the recombinant antibody in the culture supernatant can be measured by ELISA or the like. Also, in the transformant, the expression amount of the recombinant antibody can be increased by using DHFR amplification system or the like according to the method disclosed in Japanese Published Unexamined Patent Application No. 257891/90.

The recombinant antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. For example, the recombinant antibody can be purified by a combination of gel filtration, ion-exchange chromatography, ultrafiltration and the like. The molecular weight of the H chain or the L chain of the purified recombinant antibody or the antibody molecule as a whole is determined by polyacrylamide gel electrophoresis (hereinafter referred to as "SDS-PAGE") [*Nature*, 227, 680 (1970)], Western blotting [*Monoclonal Antibodies—Principles and practice*, Third edition, Academic Press (1996), *Antibodies—A Laboratory Manual*, Cold Spring Harbor Laboratory (1988)], and the like.

3. Activity Evaluation of the Monoclonal Antibody or Antibody Fragment

The activity of the purified monoclonal antibody or antibody fragment of the present invention can be evaluated in the following manner.

The binding activity to ASCT2-expressing cell is evaluated by the binding assay described in the above 1 (6a). Furthermore, it can be measured by fluorescent antibody technique [*Cancer Immunol. Immunother.*, 36, 373 (1993)], a surface plasmon resonance method using such as BIAcore system or the like.

The inhibitory activity on intracellular uptake of amino acids by ASCT2 can be evaluated by the method described in the above 1-(6b).

In addition, CDC activity or ADCC activity against an antigen positive cell line is evaluated by a known method [*Cancer Immunol. Immunother.*, 36, 373 (1993)].

4. Method for Treating Disease Using the Anti-ASCT2 Monoclonal Antibody or Antibody Fragment of the Present Invention A monoclonal antibody which specifically recognizes a native three-dimensional structure of ASCT2 and binds to the extracellular region, or an antibody fragment thereof, of the present invention can be used for treating a disease relating to ASCT2.

The therapeutic agent comprising the monoclonal antibody or antibody fragment of the present invention or derivatives thereof may be only the antibody or antibody fragment or derivatives thereof as an active ingredient, and is preferably supplied as a pharmaceutical preparation produced by an appropriate method well known in the technical field of pharmaceutics, by mixing it with one or more pharmaceutically acceptable carriers.

Examples of a route of administration include oral administration and parenteral administration, such as buccal, tracheal, rectal, subcutaneous, intramuscular or intravenous administration. Examples of the dosage form includes sprays, capsules, tablets, powder, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution or a mixture of both thereof.

Suppositories can be prepared using a carrier such as cacao butter, hydrogenated fat or carboxylic acid.

Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. It is possible to produce pharmaceutical preparations such as aerosols and dry powders.

In addition, the components exemplified as additives for oral preparations can also be added to the parenteral preparations.

5. Method for Diagonosing Disease Using the Anti-ASCT2 Monoclonal Antibody or Antibody Fragment of the Present Invention A disease relating to ASCT2 can be diagnosed by detecting or determining ASCT2 or a cell expressing ASCT2 using the monoclonal antibody or antibody fragment of the present invention.

A diagnosis of cancer, one of the diseases relating to ASCT2, can be carried out by, for example, the detection or measurement of ASCT2 as follows.

Firstly, on the living body samples collected from two or more of the living bodies of healthy persons, the expressed amount of ASCT2 in the living body samples of healthy persons is confirmed by carrying out detection or measurement of ASCT2 by the following immunological means using the monoclonal antibody or antibody fragment of the present invention or derivatives thereof. By examining the amount of ASCT2 also in the living body samples of the person to be tested in the same manner, the amount is compared with the amount in healthy persons. When the amount of the polypeptide in the person to be tested is increased in comparison with the healthy persons, it can be diagnosed that cancer is positive.

An immunological method is a method in which an antibody amount or an antigen amount is detected or determined using a labeled antigen or antibody. Examples of the immunological method include radioactive substance-labeled immunoantibody method, enzyme immunoassay, fluorescent immunoassay, luminescent immunoassay, Western blotting method, physico-chemical means and the like.

Examples of the radioactive substance-labeled immunoantibody method include a method, in which the antibody or antibody fragment of the present invention is allowed to react with an antigen or a cell expressing an antigen, then anti-immunoglobulin antibody subjected to radioactive labeling, a binding fragment thereof or the like is allowed to react therewith, followed by determination using a scintillation counter or the like.

Examples of the enzyme immunoassay include a method, in which the antibody or antibody fragment of the present invention is allowed to react with an antigen or a cell expressing an antigen or the like, then an anti-immunoglobulin antibody or an binding fragment thereof subjected to antibody labeling is allowed to react therewith and the colored pigment is measured by a spectrophotometer, and, for example, sandwich ELISA may be used. As a label used in the enzyme immunoassay, any known enzyme label [*Enzyme Immunoassay*, published by Igaku Shoin (1987)] can be used. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, two kinds of antibody which recognizes the antigen to be detected or measured or the antibody fragment thereof in which antigen recognizing site is different are prepared and one antibody or antibody fragments is previously adsorbed on a plate (such as a 96-well plate) and another antibody or antibody fragment is labeled with a fluorescent substance such as FITC, an enzyme such as peroxidase, or biotin. The plate to which the above antibody is adsorbed is allowed to react with the cell separated from living body or disrupted cell suspension thereof, tissue or disintegrated solution thereof, cultured cells, serum, pleural effusion, ascites, eye solution or the like, then allowed to react with labeled monoclonal antibody or antibody fragment and a detection reaction corresponding to the labeled substance is carried out. When an antigen concentration in the sample to be tested is measured by the method, antigen concentration in the sample to be tested can be calculated from a calibration curve prepared by a stepwise dilution of antigen of known concentration. As an antibody used for sandwich ELISA, any of a polyclonal antibody and a monoclonal antibody may be used or antibody fragments such as Fab, Fab' and F(ab)$_2$ may be used. As a combination of two kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay includes a method described in the literatures [*Monoclonal Antibodies—Principles and practice*, Third Edition, Academic Press (1996); *Manual for Monoclonal Antibody Experiments*, Kodansha Scientific (1987)] and the like. As a label for the fluorescent immunoassay, any of known fluorescent labels (*Fluorescent Immunoassay*, Soft Science, (1983)) may be used as described already. Examples include FITC, RITC and the like.

The luminescent immunoassay can be carried out using the methods described in the literature [*Bioluminescence and Chemical Luminescence, Rinsho Kensa,* 42, Hirokawa Shoten (1998)] and the like. As a label used for luminescent immunoassay, any of known luminescent labels can be included. Examples include acridinium ester, lophine or the like may be used.

Western blotting is a method in which an antigen or a cell expressing an antigen is fractionated by SDS-polyacrylamide gel electrophoresis [*Antibodies—A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example thereof is described below. Cells or tissues in which a polypeptide having the amino acid sequence represented by SEQ ID NO:2 is expressed are dissolved in a solution and, under reducing conditions, 0.1 to 30 μg as a protein amount per lane is electrophoresed by an SDS-PAGE method. The electrophoresed protein is transferred to a PVDF membrane and allowed to react with PBS containing 1 to 10% of BSA (hereinafter referred to as "BSA-PBS") at room temperature for 30 minutes for blocking. Here, the monoclonal antibody of the present invention is allowed to react therewith, washed with PBS containing 0.05 to 0.1% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL Western Blotting Detection Reagents (manufactured by Amersham) or the like to thereby detect a polypeptide having the amino acid sequence represented by SEQ ID NO:2. As an antibody used for the detection in Western blotting, an antibody which can be bound to a polypeptide having no three-dimensional structure of a natural type is used.

The physicochemical method is specifically carried out by reacting ASCT2 as the antigen with the antibody or antibody fragment of the present invention to form an aggregate, and detecting this aggregate. Other examples of the physico-chemical methods include a capillary method, a one-dimensional immunodiffusion method, an immunoturbidimetry, a latex immunoturbidimetry [*Handbook of Clinical Test Methods*, Kanehara Shuppan, (1988)] and the like. For example, in a latex immunodiffusion method, a carrier such as polystyrene latex having a particle size of about of 0.1 to 1 μm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

On the other hand, for the detection or measurement of the cell expressing ASCT2, known immunological detection methods can be used, and an immunoprecipitation method, a immuno cell staining method, an immune tissue staining method, a fluorescent antibody staining method and the like are preferably used.

An immunoprecipitation method is a method in which a cell expressing ASCT2 is allowed to react with the monoclonal antibody or antibody fragment of the present invention and then a carrier having specific binding ability to immunoglobulin such as protein G-Sepharose is added so that an antigen-antibody complex is precipitated. Also, the following method can be carried out. The monoclonal antibody or antibody fragment of the present invention is solid-phased on a 96-well plate for ELISA and then blocked with BSA-PBS. When the antibody is in a non-purified state such as a culture supernatant of hybridoma cell, anti-mouse immunoglobulin or rat immunoglobulin or protein A or G or the like is previously adsorbed on a 96-well plate for ELISA and blocked with BSA-PBS and a culture supernatant of hybridoma cell is dispensed thereto for binding. After BSA-PBS is discarded and the residue is sufficiently washed with PBS, reaction is carried out with a dissolved solution of cells or tissues expressing ASCT2. An immune precipitate is extracted from the well-washed plate with a sample buffer for SDS-PAGE and detected by the above-described Western blotting.

An immune cell staining method and an immune tissue staining method are methods where cells or tissues in which antigen is expressed are treated, if necessary, with a surfactant, methanol or the like to make an antibody easily permeate to the cells or tissues, then the monoclonal antibody of the present invention is allowed to react therewith, then further allowed to react with an anti-immunoglobulin antibody or binding fragment thereof subjected to fluorescent labeling such as FITC, enzyme labeling such as peroxidase or biotin labeling and the label is visualized and observed under a microscope Also, the detection can be carried out by a fluorescent antibody staining method [*Monoclonal Antibodies—Principles and practice*, Third Edition, Academic Press (1996), *Manual for Experiments of Monoclonal Antibodies*, Kodansha Scientific (1987)] in which cells are allowed to react with a fluorescence-labeled antibody and analyzed by a flow cytometer. Particularly, since the monoclonal antibody or antibody fragment of the present invention binds to an extracellular region of ASCT2, it can be preferably used for detection of a cell expressing the polypeptide maintaining a natural type three-dimensional structure by a fluorescent antibody staining method.

In addition, in the case of using FMAT8100HTS system (manufactured by Applied Biosystems) and the like among fluorescent antibody staining methods, the antigen quantity or antibody quantity can be measured without separating the formed antibody-antigen complex and the free antibody or antigen which is not concerned in the formation of the antibody-antigen complex.

The present invention is described below by Examples; however, the present invention is not limited to the following Examples.

Example 1

Analysis of ASCT2 Gene Expression in Various Cell Lines, Xenografts, and Normal Tissues (1) Construction of Xenografts with Subcutaneous Transplantation of a Cancer Cell Line into SCID Mice and Preparation of Tumor Mass In accordance with the following procedure, human cancer cell lines were subcutaneously transplanted into SCID mice to thereby construct xenografts. A tumor mass was extracted and prepared from the resulting xenografts.

Cells derived from human pancreatic cancer cell lines [ASPC-1 (ATCC Accession No. CRL-1682), CaPan-1 (ATCC Accession No. HTB-79), PANC-1 (ATCC Accession No. CRL-1469)], and human colorectal cancer cell lines [Colo205 (Riken (Physicochemical Research Institute) Cell Bank No. RCB2127), HT-29 (ATCC Accession No. HTB-38), LS180 (ATCC Accession No. CCL-187), SW1116 (ATCC Accession No. CCL-233), and WiDr (ATCC Accession No. CCL-218)] were suspended in PBS to give a cell density of about $1 \times 10^8$ cells/mL. Into the ventral hypodermis of 4 Fox CHASE C.B-17/Icr-scidJcl mice per group (male, 5 weeks old, purchased from CLEA Japan), 100 μL/animal of each cell suspension was transplanted.

Each of the cells were suspended and subcultured in an RPM 1640 medium (manufactured by Invitrogen) containing 10% inactivated fetal bovine serum (manufactured by Invitrogen), in a $CO_2$ incubator at 37° C. to use for transplantation.

The resulting xenografts were named as xASPC1, xCaPan1, xPANC1, xColo205, xHT29, xLS180, xSW1116, and xWiDr, respectively.

After tumor transplantation, the diameter of tumor mass was measured day by day using vernier calipers. The animals in which the major axis of the tumor became about 1 cm were sequentially sacrificed by bleeding under anesthesia and then each tumor mass was excised. Each tumor mass was cut into 4 portions and quickly frozen using liquid nitrogen, followed by storage in a freezer at −80° C.

(2) Extraction of Total RNA and Purification of Poly A(+) RNA

From cell lines and tumor mass of xenografts prepared in the above (1), total RNA was extracted and poly A(+) RNA was purified in accordance with the following procedure.

As a cell line, blood cancer-derived cell line {KG-1 (ATCC Accession No. CCL-246), THP-1 (ATCC Accession No. TIB-202), HL-60 (ATCC Accession No. CCL-240) [all, acute myeloid leukemia (AML) derived cell line], CCRF-CEM (ATCC Accession No. CCL-119), CCRF-SB (ATCC Accession No. CCL-120), Jurkat (ATCC Accession No. TIB-152), HSB-2 (ATCC Accession No. CCL-120), HPB-ALL (Riken Cell Bank No.:RCB1935) [all, acute lymphatic leukemia (ALL) derived cell line], K-562 (ATCC Accession No. CCL-243), KU812 (ATCC Accession No. CRL-2099) [all, chronic myelocytic leukemia (CML) derived cell line], KMS-11 (HSRRB No. JCRB 1179), ARH-77 (ATCC Accession No. CRL-1621), IM-9 (ATCC Accession No. CCL-159), RPMI18226 (HSRRB No. JCRB0034), U266B1 (ATCC Accession No. T1E-196), MC/CAR (ATCC Accession No. CRL-8083) [all, multiple myeloma (MM) derived cell line], HS-Sultan (ATCC Accession No. CRL-1484), Daudi (ATCC Accession No. CCL-213), Raji (ATCC Accession No. CCL-86), Ramos (ATCC Accession No. CRL-1596) [all, Burkitt's lymphoma (BL) derived cell line], U-937 (ATCC Accession No. CRL-1593.2), ML-1 (DSMZ No. ACC464) [all, histiocytic lymphoma (HS) derived cell line]}, lung cancer derived cell line [PC-14 (Riken Cell Bank No.:RCB0446), PC-7 (Immuno-Biological Laboratories Co., Ltd.; Product No.: 37011), PC-9 (Immuno-Biological Laboratories Co., Ltd.; Product No. 37012), PC-1 (Immuno-Biological Laboratories Co., Ltd.; Product No. 37008) (all, non-small cell lung cancer), Lu-139 (Riken Cell Bank No.:RCB0469), NCI-H69 (ATCC Accession No. HTB-119), RERF-LC-MA (HSRRB No. JCR130812), SBC-5 (HSRRB No. JCRB0819) (all, small-cell lung cancer)], gastric cancer derived cell line [Kato III (Riken Cell Bank No. RCB2088), MKN-74 (HSRRB No. JCRB0255), NUGC-4 (Riken Cell Bank No. RCB 1939), AZ-521 (HSRRB No. JCRB0061)], colorectal cancer derived cell line {Colo205 (Riken Cell Bank No. RCB2127), HT-29 (ATCC Accession No. HTB-38), LS174T[European Collection of Cell Cultures (ECACC) No. 87060401], LS180 (ATCC Accession No. CCL187), SW1116 (ATCC Accession No. CCL-233)}, pancreatic cancer derived cell line [ASPC-1 (ATCC Accession No. CRL-1682), BXPC-3 (ATCC Accession No. CRL-1687), CaPan-1 (ATCC Accession No. HTB-79)], malignant melanoma (melanoma) derived cell line [G-361 (ATCC Accession No. CRL-1424), HMV-1 (Riken Cell Bank No. RCB0004), SK-MEL-28 (ATCC Accession No. HTB-72)], and normal human lung fibroblast [MRC-5 (ATCC Accession No. CCL-171)] were used.

The extraction of total RNA from the cell lines was carried out as follows. In the case of adhesive cell lines, the medium was removed using an aspirator after culturing, washing with an appropriate volume of PBS was carried out and cells were recovered using a spatula made of silicone. They were sufficiently suspended and lysed by adding 1 mL of a TRIzol Reagent (manufactured by Invitrogen) per the cells corresponding to 10 $cm^2$ of cultured area. In addition, the resulting cell lysate was passed through an 18-gauge injection needle 10 times to cleave the genomic DNA into pieces. In the case of floating cell lines, the cell culture was centrifuged at 1,500 rpm for 5 minutes using a refrigerated centrifuge (manufactured by Hitachi Koki, Himac CF15R, rotor: T11A21), the medium was removed by decantation and the cells were suspended in PBS. The cell suspension was centrifuged again at 1,500 rpm for 5 minutes using a refrigerated centrifuge (manufactured by Hitachi Koki, Himac CF15R, rotor: T11A21) and the cells were recovered. To $1 \times 10^7$ recovered cells, 1 mL of a TRIzol Reagent (manufactured by Invitrogen) was added and suspended sufficiently so as to lyse cells. The cell lysate was passed through an 18-gauge injection needle 10 times to cleave the genomic DNA into pieces.

Lysis of tumor mass of the xenografts prepared in (1) and extraction of total RNA were carried out as follows. Frozen tumor mass was poured into 10 mL of a TRIzol Reagent (manufactured by Invitrogen) and immediately lysed using a Polytron homogenizer (PT 2100, manufactured by Kinematica) at 30,000 rpm for 15 seconds to give cell lysates. Each of the cell lysates was centrifuged at 11,000 rpm for 10 minutes using a refrigerated centrifuge (manufactured by Hitachi Koki, Himac CF15R, rotor: T11A21) and each of the supernatants was transferred to a fresh tube carefully so as not to carry over the precipitate. To the supernatant, 2 mL of chloroform was added and vigorously stirred for 15 seconds and the mixture was allowed to stand at room temperature for 2 to 3 minutes and centrifuged at 3,000 rpm for 90 minutes at 4° C. using a refrigerated centrifuge (manufactured by Hitachi Koki, Himac CF7D2, rotor: RT3S3). Each of the supernatants was transferred to a fresh tube, and 5 mL of isopropanol was added thereto, followed by gentle mixing. The mixture was allowed to stand at room temperature for 10 minutes and centrifuged at 11,000 rpm for 10 minutes using a refrigerated centrifuge (manufactured by Hitachi Koki, Himac CF15R, rotor: T11A21) and, after removing the supernatant, 10 mL of a 75% aqueous ethanol solution was added thereto, followed by mixing and centrifugation at 11,000 rpm for 5 minutes using a refrigerated centrifuge (manufactured by Hitachi Koki, Himac CF15R, rotor: T11A21) to give a precipitate. The precipitate was dissolved in an appropriate volume of RNase-free water to prepare a total RNA sample. The concentration of the total RNA sample was measured by an absorption spectrophotometer and it was confirmed that the ratio of A260/A280 was 1.7 or more. When the ratio of A260/A280 was less than 1.7, further purification was carried out using an RNeasy kit (manufactured by Qiagen).

From 400 µg of the total RNA sample prepared as above, poly A(+) RNA was purified using a Micro Poly(A) Pure Kit (manufactured by Ambion) in accordance with the instructions attached thereto.

(3) Synthesis of cDNA cDNA was synthesized from the poly A(+) RNA obtained in (2) or commercially available tissue-derived mRNA using a SuperScript First-Strand Synthesis System for RT-PCR (manufactured by Invitrogen).

As mRNA derived from human normal tissues (liver, lung, whole brain, heart, stomach, spleen, spinal cord, small intestine, skeletal muscle, uterus, respiratory tract, thyroid gland, thymus gland, testis, salivary gland, prostate gland, placenta, lymph node, pancreas, large intestine, blood, or kidney), commercially available mRNA (manufactured by Clontech) was used. As mRNA derived from the human clinical cancer tissues (lung cancer, gastric cancer, colorectal cancer, kidney cancer, liver cancer, uterine cancer, breast cancer, or esophageal cancer), commercially available RNA (manufactured by BioChain) was also used.

To 1 µg of poly A(+) RNA obtained in (2) or commercially available tissue-derived mRNA, 1 µL of 10 mmol/L dNTPs and 1 µL of a 0.5 µg/µL Oligo $(dT)_{12-18}$ were added, and then DEPC water was added thereto to give a total volume of 7 µL. The reaction solution was heated to denaturation at 65° C. for 5 minutes, quenched on ice and allowed to stand for 1 minute or longer. To the mRNA solution, 10×RT buffer (2 µL), magnesium chloride (4 µL, 25 mmol/L), 0.1 mol/L DTT (2 µL) and RNase OUT Recombinant Ribonuclease Inhibitor (1 µL) were added and the temperature was kept at 42° C. for 2 minutes. SuperscriptII RT (14) was further added thereto to carry out reverse transcription reaction at 42° C. for 50 minutes. The enzyme was inactivated by heating at 70° C. for 15 minutes. Then, 1 µL of E. coli RNase H was added to reaction solution and reacted at 37° C. for 20 minutes. DEPC water was added to the resulting solution to give a total volume of 1 mL.

Hereinafter, the reaction system of real-time PCR employed 10 µL of a five-fold dilution of the above-prepared solution.

(4) Quantitative Determination of Expression Levels of mRNA of the ASCT2 Gene in Cell Lines, Tumor Mass of Xenografts, and Normal Tissues by Real-Time PCR Method (Quantitative PCR Method, or Q-PCR Method)

To 10 µL of each cDNA prepared in (3) (corresponding to 2 ng of poly A(+) RNA), a forward primer (Fw#1) for detecting a cDNA of the ASCT2 gene comprising the nucleotide sequence represented by SEQ ID NO:3 which was designed from SEQ ID NO:1, and a reverse primer (Rv#1) for detecting a cDNA of the ASCT2 gene comprising the nucleotide sequence represented by SEQ ID NO:4 (all manufactured by Proligo) were added to give a final concentration of 300 nmol/L for each of them. Furthermore, to the resulting solution, 10×R-PCR buffer ($Mg^{2+}$-free, manufactured by Takara Bio, 2 µL), 250 mmol/L $Mg^{2+}$ solution (0.2 µL), dNTPs (10 mmol/L, 0.6 µL), Ex Taq R-PCR (manufactured by Takara Bio, 0.2 µL) and SYBR Green I (manufactured by BMA; original solution product was diluted 2,500-fold, 1 µL) were added. DEPC water was added thereto to give a total volume of 20 µL.

PCR was carried out under the following reaction conditions: initially activation of Taq DNA polymerase and denaturation of a template DNA at 94° C. for 5 minutes, and then 45 cycles each consisting of three processes, denaturation at 94° C. for 30 seconds, annealing at 65° C. for 30 seconds, and DNA elongation at 72° C. for 30 seconds. The fluorescence intensity generated by SYBR Green I intercalated to the amplified product was measured by PRISM 7700 (manufactured by Applied Biosystems) and data were analyzed according to the software, Sequence Detector ver. 1.7a, attached to the instrument PRISM 7700. Whether the signal obtained by the above real-time PCR was the desired amplified fragment was judged by the size of the major amplified fragment obtained by subjecting the reaction solution after completion of the reaction to agarose gel electrophoresis. The above real-time PCR was carried out using a 96-well PCR plate. Besides the above cDNA-containing reaction solution, a negative control (sterile water) and a sample for the preparation of a calibration curve (1×10 to 1×10$^6$ copies/well) prepared using a plasmid HCHON2001712 (*Homo sapiens* cDNA FLJ43232 fis, The DNA Data Bank of Japan (DDBJ) Accession No. AK125222) encoding a partial fragment of ASCT2 purified by a Qiagen Plasmid Midi Kit (manufactured by Qiagen) were arranged as a sample in each well of the PCR plate and PCR was then carried out.

FIGS. 1(1) to (4) show the alignment of a full-length sequence of NM_005628 (SEQ ID NO:1, GenBank Accession No. NM_005628) which is a standard sequence of ASCT2 and the alignment of a full-length sequence of plasmid HCHON2001712 which is used as a template for the preparation of a calibration curve. There are different sites between full-length sequences of NM_005628 and HCHON2001712. Therefore, both of the forward primer (Fw#1) for detecting a cDNA comprising the nucleotide sequence represented by SEQ ID NO:3 and the reverse primer (Rv#1) for detecting a cDNA comprising the nucleotide sequence represented by SEQ ID NO:4 which were used for the measurement of an ASCT2 expression level were designed using the region in which sequences of NM_005628 and HCHON2001712 were completely identical therebetween.

Results of the expression level of mRNA of the ASCT2 gene in each of the thus obtained cell lines, xenograft tumor mass and normal tissues were shown in FIGS. 2(1) to (2). The mRNA expression level was shown as a relative ratio in terms of numbers of expressed ASCT2 molecules per 2 ng of poly A(+) RNA and the ASCT2 gene-expression level in the airway showing the highest expression in normal tissues was defined as 1. As compared with a normal airway, enhanced expression levels were recognized, that is, 10-fold or higher enhanced expression for blood cancer-derived cell lines KG-1 (AML-derived cell line), HSB-2 (ALL-derived cell line), K-562 (CML-derived cell line), and KMS-11 and ARH-77 (both are MM-derived cell lines), 5-fold or higher enhanced expression for Jurkat (ALL-derived cell line), IM-9, RPMI 8226 (both are MM-derived cell lines), HS-Sultan (BL-derived cell line), and ML-1 (HL-derived cell line), and 2-fold or higher enhanced expression for THP-1 (AML-derived cell line), CCRF-CEM (ALL-derived cell line), KU812 (CML-derived cell line), Raji (BL-derived cell line), U-937 (HS-derived cell line), gastric cancer tissues, and esophageal cancer tissues.

Example 2

Construction of CHO Cell Line Introducing Human ASCT2-myc/His Gene

In accordance with the following procedure, a plasmid pCR4-SLC 1 A5-myc/His was obtained comprising the nucleotide sequence represented by SEQ ID NO:5 and the amino acid sequence represented by SEQ ID NO:6. Using this plasmid, a CHO cell line into which the human ASCT2-myc/His gene was introduced was obtained.

To the respective primers (10 μmol/L, each 1 μL) comprising each of the nucleotide sequences of SEQ ID NOs:7 to 10, 10×Ex Taq buffer (10 μL), dNTPs (2 mmol/L, 10 μL), and Ex Taq polymerase (1 μL, all manufactured by Takara Bio) were added, and sterile water was further added thereto to give a total volume of 100 μL. In a manner similar to the procedure described in Example 1(3), PCR was carried out under the following reaction conditions: reaction at 96° C. for 2 minutes, and then 35 cycles each consisting of three processes, reaction at 96° C. for 1 minute, reaction at 60° C. for 1 minute, and reaction at 72° C. for 1 minute. As a result, the nucleotide sequence (hereinafter, referred to as "N-SLC1A5") was synthesized corresponding to the nucleotide sequence at positions 1 to 370 when the nucleotide at a translation initiation point of the human ASCT2 gene was defined as position 1. The reaction product was separated by agarose gel electrophoresis. The resulting about 0.4-kb amplified fragment was extracted using a QIAquick Gel Extraction Kit (manufactured by Qiagen), and then cloned into a pCR4TOPO vector using a TOPO TA cloning kit (manufactured by Invitrogen) (hereinafter, the resulting plasmid is referred to as "pCR4-N-SLC1A5").

Next, to 10 ng of the plasmid HCHON2001712 (DDBJ Accession No. AK125222) comprising the human ASCT2 gene as a template, the respective primers (10 μmol/L, each 1 μL) comprising the nucleotide sequences represented by SEQ ID NOs:11 and 12, 10×Ex Taq buffer (10 μL), dNTPs (2 mmol/L, 10 μL), and Ex Taq polymerase (1 all manufactured by Takara Bio) were added, and sterile water was further added thereto to give a total volume of 100 μL. Under the same reaction conditions as described above, PCR was carried out to synthesize a nucleotide sequence (hereinafter, referred to as "C-SLC1A5-myc/His") encoding a fusion protein having an addition of myc/His to the C-terminal of a nucleotide sequence corresponding to the nucleotide sequence of the human ASCT2 gene at positions 365 to 1623. The reaction product was separated by agarose gel electrophoresis. The resulting about 1.2-kb amplified fragment was extracted using a QIAquick Gel Extraction Kit (manufactured by Qiagen). To the resulting extraction fragment as a template, the primers (10 μmol/L, each 1 μL) comprising the nucleotide sequences represented by SEQ ID NOs: 11 and 13, 10×Ex Taq buffer (10 μL), dNTPs (2 mmol/L, 10 μL), and Ex Taq polymerase (1 μL, all manufactured by Takara Bio) were added, and sterile water was further added thereto to give a total volume of 100 μL. Under the same reaction conditions as described above, PCR was carried out to add NotI and SpeI restriction enzyme sites to the C-terminal of C-SLC1A5-myc/His. The resulting reaction product was separated by agarose gel electrophoresis. The resulting about 1.2-kb amplified fragment was extracted using a QIAquick Gel Extraction Kit (manufactured by Qiagen), and then cloned into a pCR4TOPO vector using a TOPO TA cloning kit (manufactured by Invitrogen) (hereinafter, the resulting plasmid is referred to as "pCR4-C-SLC1A5-myc/His"). The resulting gene sequence exhibited no amino acid variation even though there was a substitution of T at position 1455 with C when a nucleotide at which a translation initiation point of the sequence represented by SEQ ID NO:1 was defined as position 1.

The resulting pCR4-N-SLC1A5 was digested with BssHII (manufactured by Takara Bio) and SpeI (manufactured by Takara Bio) and separated by agarose gel electrophoresis. The resulting about 4.4-kb gene fragment was extracted using a QIAquick Gel Extraction Kit (manufactured by Qiagen).

Similarly, the resulting pCR4-C-SLC1A5-myc/His was digested with BssHII (manufactured by Takara Bio) and SpeI (manufactured by Takara Bio), and an about 1.4-kb gene fragment was extracted. Each extraction fragments were ligated using a Ligation high (manufactured by Toyobo), and then *Escherichia coli* DH5α (manufactured by Toyobo) was transformed with the resulting vector, in accordance with the method of Cohen et al [*Proc, Natl, Acad-Sci. USA.* 69 2110 (1972)]. A plasmid was extracted from the resulting transformant using an automated plasmid isolation system PI-50 (manufactured by Kurabo), and a plasmid pCR4-SLC1A5 myc/His comprising the nucleotide sequence represented by SEQ ID NO:5 and the amino acid sequence represented by SEQ ID NO:6 was obtained.

The resulting pCR4-SLC1A5 myc/His was digested with EcoRI (manufactured by Takara Bio) and KpnI (manufactured by Takara Bio), and in a manner similar to the above, a gene fragment was extracted to obtain a fragment comprising a nucleotide sequence (hereinafter, referred to as "SLC1A5-myc/His") encoding a fusion protein in which myc/His was added to the C-terminal of the human ASCT2 gene.

The resulting fragment containing SLC 1 A5-myc/His was ligated into a pKANTEX93 vector (WO97/10354) which had been previously digested with EcoRI (manufactured by Takara Bio) and KpnI (manufactured by Takara Bio). In a manner similar to the above, *Escherichia coli* DH5α (manufactured by Toyobo) was transformed with the ligation product. After obtaining a transformant, an expression plasmid pKANTEX-SLC1A5-myc/His was obtained using a plasmid isolation kit (manufactured by Qiagen).

In accordance with electroporation [*Cytotechnology*, 3, 133 (1990)], introduction of pKANTEX-SLC1A5-myc/His into a CHO/DG44 cell [*Somatic Cell and Molecular Genetics*. 12, 555 (1986)] was carried out in the following manner. The cells used herein were those subcultured in a medium where 1×HT supplement (manufactured by Invitrogen) was added to IMDM (manufactured by Invitrogen) containing 10% FBS (manufactured by Life Technologies) and gentamicin (50 μg/mL, manufactured by Nacalai Tesque) (hereinafter, referred to as "A3 medium"). CHO/DG44 cells were suspended in buffer containing potassium chloride (137 nmol/L), sodium chloride (2.7 nmol/L), disodium hydrogen phosphate (8.1 mmol/L), sodium dihydrogen phosphate (1.5 nmol/L) and magnesium chloride (4 mmol/L) (hereinafter, referred to as "K-PBS") to give a cell density of $8\times10^6$ cells/mL, and the resulting cell suspension (200 μL, $1.6\times10^6$ cells in terms of cell count) was mixed with an expression plasmid pKANTEX-SLC1A5-myc/His (10 μg). The mixture was transferred into a cuvette (interelectrode distance: 2 mm), and gene introduction was carried out using a GenePulser II (manufactured by Bio-Rad) at a pulse voltage of 0.35 kV and an electric capacity of 250 μF. The cuvette was allowed to stand on ice, and a cell suspension in the cuvette was suspended in a cell culture vessel containing an A3 medium and cultured in a 5% $CO_2$ incubator at 37° C. Four days after the culturing, the culture medium was exchanged with an A3 medium containing G418 (manufactured by Nacalai Tesque; 0.5 mg/mL), followed by cell culture. With medium exchange and subculturing during the cell culture, a transformed cell resistant to G418 was obtained about two weeks after the gene introduction.

The resulting G418-resistant transformed cells were diluted to give a cell density of 5 cells/10 mL in an A3 medium containing 0.5 mg/L of G418 (manufactured by Nacalai Tesque), and 100 μL/well of the diluted cell suspension was dispensed into a 96-well plate, followed by growing in stepwise increasing concentrations of methotrexate. In this manner, a clone showing a high expression level of ASCT2-myc/His was selected, from which a CHO cell line with the introduction of human ASCT2-myc/His gene was then obtained.

The resulting human ASCT2-myc/His gene-introduced CHO cells ($1\times10^5$ to $5\times10^5$ cells) were suspended in 70% ethanol-PBS (1 mL) and fixed at ice temperature for 30 minutes. After dispensing at $1\times10^6$ to $5\times10^6$ cells/well into a 96-well U-bottom plate and subsequent centrifugation at 1,500 rpm for 5 minutes, the supernatant was discarded, followed by blocking with 1% BSA-PBS at ice temperature for 30 minutes. After removing the supernatant by centrifugation, an anti-myc antibody PL14 (manufactured by Medical & Biological Laboratories), an anti-His antibody (manufactured by Qiagen) and a mouse IgG1 isotype control (manufactured by Dako), as the primary antibodies, were diluted with 1% BSA-PBS to give final concentrations of 1.0, 0.1 and 0.1 μg/mL, respectively, and dispensed at 100 μL/well to react at ice temperature for 60 minutes. After the plate was washed once with 1% BSA-PBS, 100 μL/well of an FITC-labeled anti-mouse immunoglobulin G (H+L) (manufactured by DAKO) diluted 50-fold with 1% BSA-PBS, as the secondary antibody, was added and react at ice temperature for 30 minutes under shading. After washing once again with 1% BSA-PBS, the cells were suspended in PBS and the fluorescence intensity was measured by a flow cytometer (Cytomics FC500MPL, manufactured by Beckman Coulter). The results were shown in FIG. 3. From the fact that a high reactivity was detected in the anti-myc antibody and the anti-His antibody, it was confirmed that a desired CHO cell line with the introduction of the human ASCT2-myc/His gene was constructed.

Example 3

Construction of Monoclonal Antibody Against N-Terminal Partial Peptide of ASCT2

(1) Preparation of Immunogen

For binding to a carrier protein, an N-terminal partial peptide of the human ASCT2 gene represented by SEQ ID NO:14 (amino acid residues at positions 2 to 16 from the N-terminal) in which Cys was added to the C-terminal was synthesized using an automated synthesizer (PSSM-8, manufactured by Shimadzu).

In order to enhance the immunogenity, a conjugate with KLH (manufactured by Wako Pure Chemical) was prepared as follows and used as an immunogen. That is, KLH was dissolved in PBS to give a concentration of 10 mg/mL and a 1/10 volume of N-(m-maleimide benzoyloxy)succinimide (MBS, manufactured by Nacalai Tesque, 25 mg/mL) was then added thereto dropwise, followed by reaction under stirring for 30 minutes. The reaction solution was passed through a gel filtration column (Sephadex G-25 column, manufactured by GE Healthcare) which had been previously equilibrated with PBS, and non-reacted MBS was removed to obtain KLH-MBS. The N-terminal partial peptide of human ASCT2 to which Cys was added (1 mg) was dissolved in sodium phosphate buffer (0.1 mol/L, pH 7.0) and 2.5 mg of KLH-MBS was added thereto, followed by reaction under stirring at room temperature for 3 hours. After the reaction was complete, the reaction solution was dialyzed against PBS, thereby obtaining a human ASCT2 N-terminal peptide-KLH conjugate as an immunogen.

(2) Immunization of Animals and Preparation of Antibody-Producing Cell

The human ASCT2 N-terminal peptide-KLH conjugate (100 μg) obtained in the above (1) together with 2 mg of aluminum gel and 1×10⁹ cells of a pertussis vaccine (manufactured by Chiba Serum Institute) was administered to 4-week old female SD rats (manufactured by Japan SLC). Two weeks after the first administration, the conjugate (100 μg) was additionally administered to the rats once a week, four times in total. Blood was collected from caudal veins of the rats, and the reactivity thereof with the human ASCT2 partial peptide was investigated by the following enzyme immunoassay. Three days after the final immunization, the spleen was excised from the rat which showed sufficient antibody titer.

The spleen was minced into small pieces in MEM (manufactured by Nissui Pharmaceutical), loosened with forceps, and centrifuged at 1,200 rpm for 5 minutes (CR5B, manufactured by Hitachi). To the obtained precipitated fraction, Tris-ammonium chloride buffer (pH 7.65) was added and reacted for 1 to 2 minutes, whereby red blood cells were removed. The cell fraction obtained as a precipitation fraction was washed three times with MEM, thereby preparing antibody-producing cells.

(3) Enzyme Immunoassay

As an assay antigen, the Cys-added N-terminal partial peptide of human ASCT2 presented by SEQ ID NO:14 was prepared in the form of a conjugate with thyroglobulin (hereinafter, referred to as "THY"), according to the following procedure. The construction method of the conjugate was the same as in (1), but succinimidyl 4-[N-maleimide methyl]-cyclohexane-1-carboxylate (SMCC, manufactured by Sigma) was used instead of MBS.

The resulting human ASCT2 N-terminal peptide-THY conjugate (10 μg/mL, at 50 μL/well) was dispensed into a 96-well EIA plate (manufactured by Greiner), and allowed to stand at 4° C. overnight for adsorption. After the non-adsorbed conjugate was washed, 1% BSA-PBS (100 μL/well) was added to the plate, followed by reaction at room temperature for 1 hour, and the remaining active groups were blocked. After the non-reacted BSA-PBS was washed, 50 μL/well of the test material such as antiserum or culture supernatant, as the primary antibody, was dispensed to the plate, followed by reaction for 2 hours. The plate was washed with 0.05% Tween-PBS and 50 μL/well of a diluted peroxidase-labeled anti-rat immunoglobulin (manufactured by Dako) as the secondary antibody was added to the plate, followed by reaction at room temperature for 1 hour. After the plate was washed with 0.05% Tween-PBS, a 2,2-azinobis(3-ethylbenzothiazoline-6-sulfonic acid)ammonium (ABTS) substrate solution [ABTS (manufactured by Wako Pure Chemical, 1 mmol/L), citrate buffer (0.1 mol/L, pH 4.2), and $H_2O_2$ (0.1%)] was added to the well and then color-developed. An absorbance (OD415-OD490) at a sample wavelength of 415 nm and then a reference wavelength of 490 nm was measured using a plate reader (Emax microplate reader, Molecular Devices).

(4) Preparation of Mouse Myeloma Cell

The 8-azaguanine-resistant mouse myeloma cell line P3-U1 [P3X63Ag8U.1, ATCC Accession No. CRL-1597, European Journal of Immunology, 6, 511 (1976)] was cultured in a medium (hereinafter referred to as "normal medium") where glutamine (1.5 mmol/L), 2-mercaptoethanol ($5\times10^{-5}$ mol/L), gentamicin (10 μg/mL) and FBS (10%) were added to an RPMI 1640 medium (manufactured by Invitrogen) to ensure the cell count of $2\times10^7$ or more necessary for cell fusion, and was provided as parent cells in the cell fusion.

(5) Preparation of Hybridoma

The antibody-producing cells obtained in (2) and the myeloma cells obtained in (4) were mixed at a ratio of 10:1 and the obtained cells were centrifuged at 1,200 rpm for 5 minutes (CR5B, manufactured by Hitachi). The supernatant was discarded and the precipitated cells were well loosened. A mixture of PEG 1000 (1 g), MEM (manufactured by Invitrogen, 1 mL) and dimethyl sulfoxide (0.35 mL) was added thereto at 0.5 mL/1×10⁸ antibody-producing cells and at 37° C. under stirring, and MEM (1 mL) was added several times to the suspension every 1 to 2 minutes and then MEM was added to give a total volume of 50 mL. After centrifugation at 900 rpm for 5 minutes (CR5B, manufactured by Hitachi), the supernatant was discarded and the precipitated cells were slowly loosened. Then, the cells were suspended in 100 mL of a normal medium to which HAT Media Supplement (manufactured by Invitrogen) was added (hereinafter, referred to as "HAT medium") by gently pipetting up and down.

Into a 96-well culture plate, 200 μL/well of the obtained suspension was dispensed and cultured in a 5% $CO_2$ incubator for 10 to 14 days at 37° C.

After culturing, the culture supernatant was examined by the enzyme immunoassay described in (3), the wells which specifically reacted to the N-terminal partial peptide of human ASCT2 were selected. The cells contained in the selected wells were subjected to cloning by a limiting dilution method twice to give a hybridoma KM3842 which produces a monoclonal antibody against the N-terminal partial peptide of ASCT2. The antibody subclass of KM3842 was determined to be rat IgG2a by using a subclass typing kit (manufactured by ABT Sarotech) (FIG. 4).

(6) Obtaining of Purified Monoclonal Antibody

The hybridoma (5×10⁶ to 20×10⁶ cells/animal) obtained in (5) was intraperitoneally injected into pristane-treated 8-week-old female nude mice (Balb/c, manufactured by Japan SLC). After 10 to 21 days, the hybridoma became to ascites carcinoma. The ascitic fluid (1 to 8 mL/animal) was collected from the mice which had produced ascites. Then, the ascites was centrifuged at 3,000 rpm for 5 minutes (CR5B, manufactured by Hitachi) to remove solids. The resulting solution was purified by the caprylic acid precipitation method [Antibodies-A Laboratory Manual, Cold Spring Harbor Laboratory (1988)] to obtain a purified KM3842 antibody.

Example 4

Figure 5:
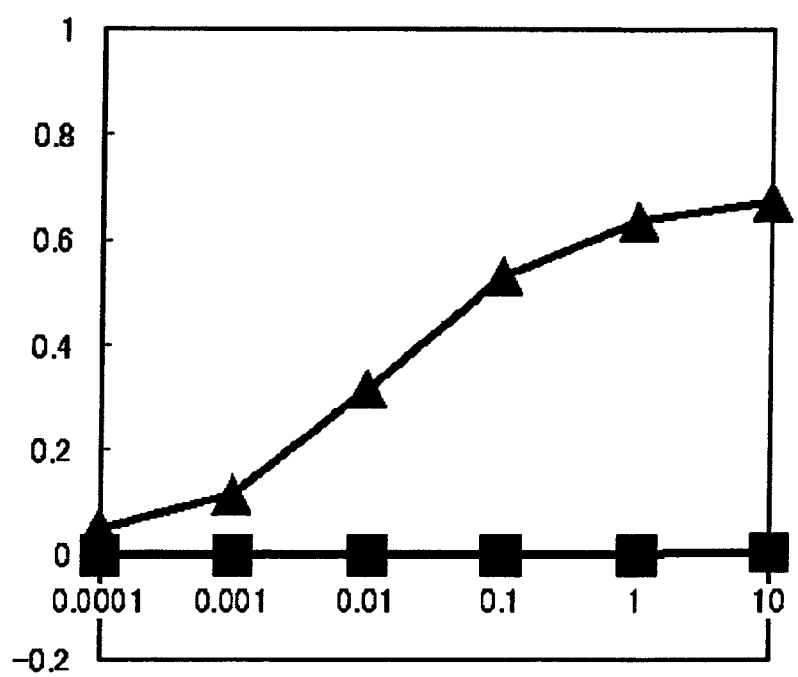
FIG. 5 shows the reactivity of a monoclonal antibody KM43842 against the N-terminal peptide of ASCT2 to an N-terminal peptide of ASCT2, in binding ELISA. The abscissa represents an antibody concentration (μg/mL), and the ordinate represents an absorbance ratio (OD415/490). ▲ represents an absorbance ratio in the case of using a human ASCT2 N-terminal peptide-THY conjugate and ■ represents an absorbance ratio in the case of using a control peptide-THY conjugate.

Investigation of Reactivity of N-Terminal Partial Peptide of ASCT2 with Purified Monoclonal Antibody The reactivity of a monoclonal antibody KM3842 with the N-terminal partial peptide of ASCT2 was examined in accordance with the enzyme immunoassay described in Example 3(3). The purified antibody KM3842 obtained in Example 3(6) was diluted with 1% BSA-PBS to give concentrations of 10, 1, 0.1, 0.01, 0.001, and 0.0001 μg/mL, respectively, and used as a primary antibody. As a result of the measurement, as shown in FIG. 5, the antibody KM3842 exhibited a specific reactivity with the N-terminal partial peptide of ASCT2.

Example 5

Construction of Monoclonal Antibody Against Extracellular Region of ASCT2

(1) Preparation of Immunogen

The human ASCT2-myc/His gene-introduced CHO cell line obtained in Example 2 was cultured in IMDM (manufactured by Invitrogen) containing 10% FBS for 2 to 3 days and was peeled off using a 0.02% ethylenediaminetetraacetic acid (EDTA) solution (manufactured by Nacalai Tesque). The cells were suspended in PBS to give a cell count of $6\times10^6$ to $1\times10^7$ cells per one immunized animal.

(2) Immunization of Animal and Preparation of Antibody-Producing Cell

The cell suspension obtained in (1) was administered to 6-week old male BXSB mice (n=3/group, manufactured by Japan SLC) or 4-week old female SD rats (n=3/group, manufactured by Japan SLC) together with $1\times10^9$ cells of a pertussis vaccine (manufactured by Chiba Serum Institute). One week after the administration, the cell suspension was administered to the animals once a week, four times in total. Thereafter, blood was collected from the fundus oculi of mice or caudal veins of rats. The antibody titer thereof in the blood was measured by a fluorescent cell staining method using the following cell-based assay system (ABI 8200 Cellular Detection System, manufactured by Applied Biosystems) or flow cytometer (Cytomics FC500 MPL, manufactured by Beckman Coulter). Three days after the final immunization, the spleen was excised from a mouse or rat which showed sufficient antibody titer.

In the same manner as Example 3(2), the antibody-producing cells were prepared from the obtained spleen.

(3) Fluorescent Cell Staining Method—1 (Cell-Based Assay System)

The ASCT2-myc/His gene-introduced CHO cell line obtained in Example 2 and the vector-introduced CHO cells were used as assay cells. Each cell were cultured in IMDM (manufactured by Invitrogen) containing 10% FBS for 2 to 3 days and peeled off with a trypsin-EDTA solution (manufactured by Invitrogen) was suspended in the same medium, seeded into an ABI8200 black 96-well plate at a cell density of $1\times10^4$ cells/100 μL medium/well, and cultured overnight. The test substance such as antiserum or culture supernatant (10 μL/well) was dispensed to the plate as the primary antibody, 100 μL/well of ALEXA647-labeled anti-mouse immunoglobulin G (H+L) or ALEXA647-labeled anti-rat immunoglobulin G (H+L) (all manufactured by Invitrogen) was then added as the secondary antibody, followed by allowing to stand for 4 hours under shading. Fluorescence of 650 to 685 nm excited with a laser (633 nm He/Ne) was measured by the ABI 8200 Cellular Detection System (manufactured by Applied Biosystems).

(4) Fluorescent Cell Staining Method—2 (Flow Cytometer)

The human ASCT2-myc/His gene-introduced CHO cell line obtained in Example 2 and vector-introduced CHO cells were used as assay cells. Each cells which were cultured in IMDM (manufactured by Invitrogen) containing 10% FBS for 2 to 3 days and peeled off with a 0.02% EDTA solution (manufactured by Nacalai Tesque) were washed with PBS and were blocked for 20 minutes at ice temperature using 1% BSA-PBS in order to avoid the non-specific adsorption of antibodies. The resulting cells were seeded into a 96-well U-bottom plate at cell density of $5\times10^5$ cells/50 μL/well, followed by centrifugation at 1,800 rpm for 2 minutes (05PR-22, manufactured by Hitachi Koki), and then the supernatant was removed. The test substance (50 μL/well) such as antiserum or culture supernatant was dispensed as the primary antibody, followed by reaction at ice temperature for 30 minutes. Washing was carried out 3 times by a centrifugation method using PBS and 50 μL/well of ALEXA 488-labeled anti-mouse immunoglobulin G (G+L) or ALEXA488-labeled anti-rat immunoglobulin G (G+L) (all manufactured by Invitrogen) was added as the secondary antibody, followed by reaction at ice temperature for 30 minutes under shading. After the cells were washed again using PBS three times by centrifugation, the cells were suspended in PBS, and the fluorescence of 510 to 530 nm excited with a 488 nm Ar laser was measured by a flow cytometer (Cytomics FC500MPL, manufactured by Beckman Coulter).

(5) Construction of Hybridoma

In the Same Manner as Example 3(5), the Cell Fusion was Carried Out between the antibody-producing cell obtained in (2) and the myeloma cell obtained in Example 3(4).

Next, the cells obtained from the cell fusion were suspended in an HAT medium. Into a 96-well culture plate, 200 μL/well of the suspension of the resulting cell was dispensed and the cells were cultured in a 5% $CO_2$ incubator for 8 to 10 days at 37° C.

The reactivity of the post-culture supernatant was confirmed by the fluorescent cell staining method described in the above (3) and (4) and the well which reacts with the human ASCT2-myc/His gene-introduced CHO cell line and does not react with the vector-introduced CHO cells was selected. Then, the cells contained in the selected wells were subjected to cloning by a limiting dilution method twice to give hybridomas KM3998, KM4000, KM4001, KM4008, KM4012, and KM4018 which produce monoclonal antibodies against the extracellular region of ASCT2.

The determination of the subclass of a mouse monoclonal antibody among the obtained hybridomas was carried out in accordance with the following procedure.

Anti-mouse immunoglobulin rabbit polyclonal antibodies (manufactured by Dako, 10 μg/mL, 50 μL/well) was dispensed into a 96-well EIA plate (manufactured by Greiner) and allowed to stand at 4° C. overnight for adsorption. After the non-absorbed conjugate was washed, 100 μL/well of 1% BSA-PBS was added to the plate, followed by reaction at room temperature for 1 hour in order to block the remaining active groups. After the non-reacted BSA-PBS was washed, 50 pt/well of the test material was dispensed to the plate, followed by reaction for 2 hours. The plate was washed with 0.05% Tween-PBS and a diluted subclass-specific peroxidase-labeled anti-mouse immunoglobulin (manufactured by Invitrogen; 50 μL/well) was added to the plate as the secondary antibody, followed by reaction at room temperature for 1 hour. The plate was washed with 0.05% Tween-PBS and color-developed by adding the ABTS substrate solution used in Example 3(3). Then, an absorbance (OD415-OD490) at a sample wavelength of 415 nm and a reference wavelength of 490 nm was measured using a plate reader (Emax microplate reader, Molecular Devices). The subclass of the mouse monoclonal antibody whose subclass could not be determined by the above-mentioned method was determined using a mouse rat monoclonal isotyping kit (manufactured by Dainippon Sumitomo Pharma). Further, the subclass of the rat monoclonal antibody was determined using a rat monoclonal isotyping kit (manufactured by Dainippon Sumitomo Pharma).

FIG. 4 shows the list of the subclass of the antibody derived from individual hybridomas.

(6) Obtaining of Purified Monoclonal Antibodies—1

Purified antibodies of KM3998 were obtained in accordance with the following procedure.

The hybridoma ($5\times10^6$ to $20\times10^6$ cells/animal) obtained in (5) was intraperitoneally injected into pristane-treated 8-week-old female nude mice (Balb/c, manufactured by Japan SLC). The ascitic fluid (1 to 8 mL/animal) was collected from the mice when the hybridoma developed ascites tumor in 10 to 21 days. Then, the ascites was subjected to filtration [5 μm, polyethersulfone (PES) membrane, manufactured by Pall] to remove solids, followed by purification with the caprylic acid precipitation method [Antibodies—A Laboratory Manual, Cold Spring Harbor Laboratory (1988)].

(7) Obtaining of Purified Monoclonal Antibodies—2

Each of the purified antibodies of KM4000, KM4001, KM4008, KM4012 and KM4018 were obtained in accordance with the following procedure.

The individual hybridomas obtained in the above (5) were cultured in RPMI 1640 containing 10% FBS in a 5% $CO_2$ incubator at 37° C. At the point of the cell count of $5\times10^7$ cells, the supernatant was discarded by centrifugation at 1,200 rpm for 5 minutes (CR5B, manufactured by Hitachi). The resulting cells were suspended at a cell density of $1\times10^5$ cells/mL in a Hybridoma-SFM (manufactured by Gibco) comprising 5% Daigo's GF21 (manufactured by Wako Pure Chemical) to give a volume of 500 mL and then cultured in a 5% $CO_2$ incubator for three days at 37° C. The resulting cell suspension was centrifuged at 1,500 rpm for 5 minutes and the resulting supernatant was filtered through a bottle top filter (0.2 μm, PES membrane, manufactured by Corning).

Purification was carried out using a Protein A-conjugated resin (manufactured by Millipore) for KM4000, KM4001, KM4008 and KM4012 and using a Protein G-conjugated resin (manufactured by Millipore) for KM4018. Each resin was packed into a 1 mL mini-column and 10 mL of equilibration buffer was passed through it to achieve equilibration. The equilibration buffer to be used was glycine (1 mol/L)-sodium chloride (0.15 mol/L) (pH 8.6) for the Protein A-conjugated resin and glycine (0.5 mol/L)-PBS (pH 7.4) for the Protein G-conjugated resin. The culture supernatant which was obtained by the filtration treatment was passed through the column at a flow rate of about 100 mL/h and then the column was washed with 10 mL of the equilibration buffer. Thereafter, the antibodies adsorbed to the column were eluted with citrate buffer (0.1 mol/L, pH 3.0). Into tubes in which 80 μL of Tris (2 mol/L, pH 8.0) had been previously filled, and then 500 μL/tube of the eluted antibodies were aliquoted. Then, an absorbance (OD280 nm) of each tube was measured using a UV-V spectrophotometer (UV-1600, manufactured by Shimadzu) and the fraction in which the protein was detected was recovered. After overnight dialysis in PBS at 4° C., the fraction was filtrated (0.2 μm, PES membrane, manufactured by Pall) and the antibody concentration was calculated from the absorbance at 280 nm (OD280 nm) [OD280 nm measurement value (A)/1.4=protein concentration (mg/mL)].

Example 6

Evaluation of Reactivity of Monoclonal Purified Antibodies with Extracellular Region of ASCT2

(1) Fluorescent Cell Staining Method (Flow Cytometer)

The human ASCT2-myc/His gene-introduced CHO cell obtained in Example 2, the vector-introduced CHO cell and the multiple myeloma cell line KMS-11 (HSRRB No. JCRB1179) were respectively cultured in a 5% $CO_2$ incubator for 3 to 4 days at 37° C. The human ASCT2-myc/His gene-introduced CHO cells and the vector-introduced CHO cells were peeled off with a 0.02% EDTA solution (manufactured by Nacalai Tesque) and washed with a mixed solution of PBS, 0.02% EDTA and 0.05% sodium azide. Additionally, in order to avoid the non-specific adsorption of antibodies, the cells were blocked for 30 minutes at ice temperature using 1% BSA-PBS for the human ASCT2-myc/His gene-introduced CHO cells and the vector-introduced CHO cells, and using 100 μg/mL of human IgG (manufactured by Sigma) for KMS-11. The cells were seeded into a 96-well U-bottom plate so as to give a density of $1\times10^5$ to $5\times10^5$ cells/100 μL/well and centrifuged at 1,500 rpm for 5 minutes (05PR-22, manufactured by Hitachi Koki) and then the supernatant was removed. The test substances as the primary antibody, i.e., the purified antibodies and rat IgG2a-UNLB (negative control, manufactured by Beckman Coulter) or KM511 {negative control, anti-G-CSF derivative antibody, [*Agric. Biol. Chem.*, 53, 1095 (1989)], mouse IgG1} were diluted to give a final concentration of 10 μg/mL in a mixed solution (hereinafter, referred to as "Dilution Solution A") of 1% BSA-PBS, 0.02% EDTA and 0.05% sodium azide and the resulting solution was added at the volume of 100 μL/well, followed by reaction for 60 minutes at ice temperature. After washing twice with the Dilution Solution A, 100 μL/well of ALEXA488-labeled anti-mouse immunoglobulin G (G+L) (manufactured by Invitrogen) or 100 μL/well of ALEXA488-labeled anti-rat immunoglobulin G (G+L) (manufactured by Invitrogen) or 100 μL/well of an FITC-labeled anti-mouse kappa-chain antibody (manufactured by Southern Biotech) or an FITC-labeled anti-rat kappa-chain antibody (manufactured by Southern Biotech), diluted with Dilution Solution A, was added as the secondary antibody, followed by reaction for 30 minutes at ice temperature under shading. Washing with Dilution Solution A was carried out three times again, the cells were suspended in PBS and the fluorescence intensity was measured by a flow cytometer (Cytomics FC500MPL, manufactured by Beckman Coulter).

Figure 6:
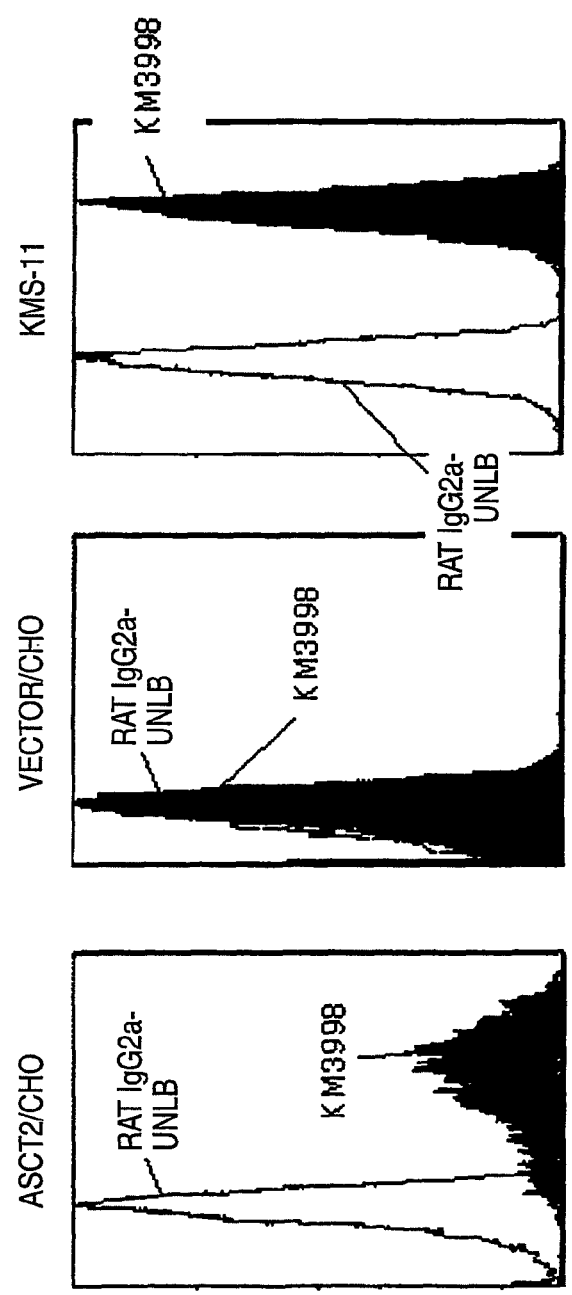
FIG. 6 shows the reactivity of an anti-ASCT2 monoclonal antibody KM3998 to ASCT2-myc/His gene-introduced CHO cells (ASCT2/CHO), vector-introduced CHO cells (Vector/CHO), and KMS-11 by means of fluorescent cell staining (flow cytometer). The abscissa represents the fluorescence intensity, and the ordinate represents the cell counts. KM3998 is indicated by a black curve, and rat IgG2a-UNLB is indicated by a white curve.
Figure 7:
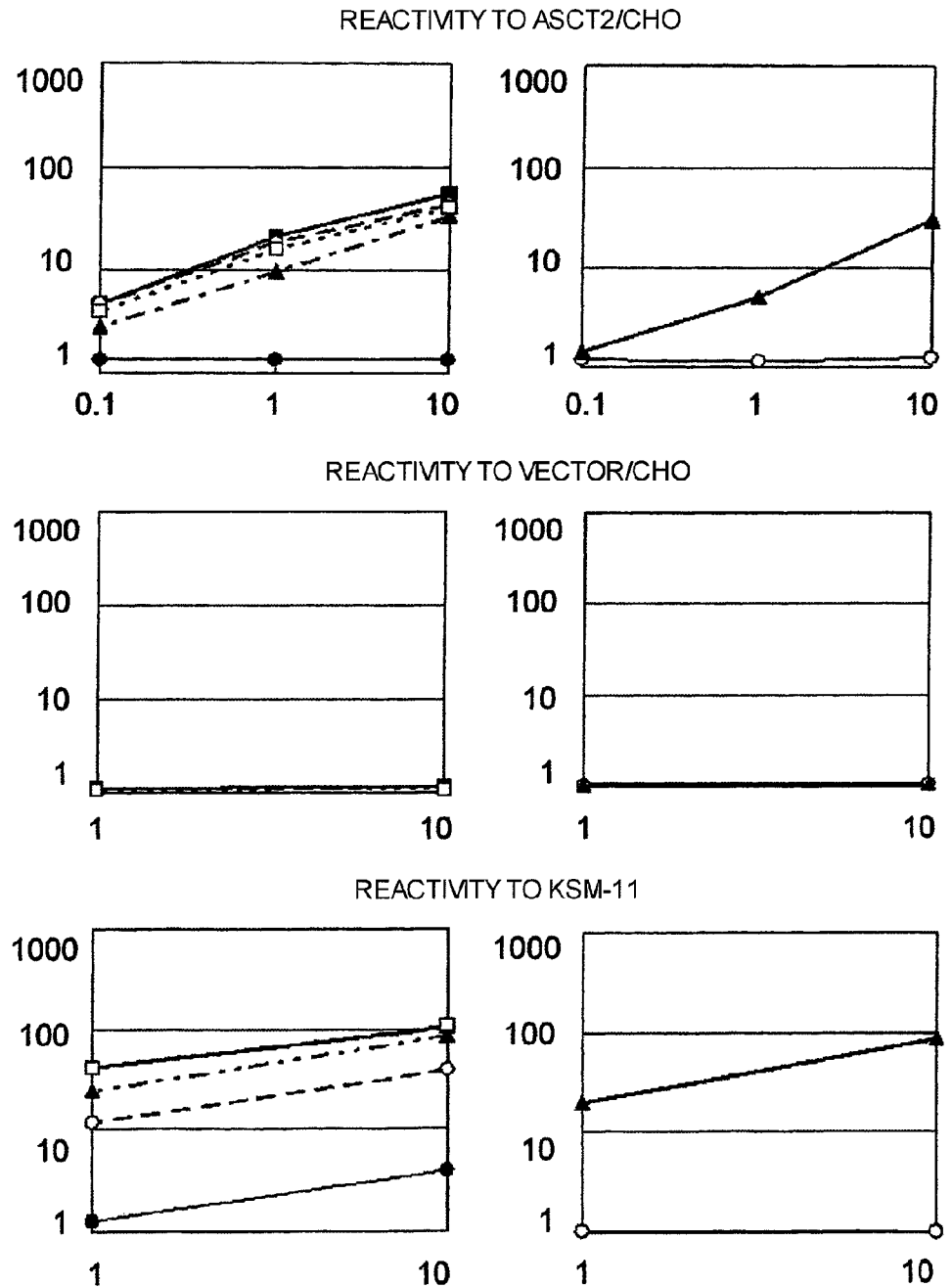
FIG. 7 shows the reactivity of anti-ASCT2 monoclonal antibodies KM4000, KM4001, KM4008, KM4012 and KM4018 to human ASCT2-myc/His gene-introduced CHO cells (ASCT2/CHO), vector-introduced CHO cells (Vector/CHO) and KMS-11 by means of fluorescent cell staining (flow cytometer). The abscissa represents an antibody concentration (μg/mL), and the ordinate represents a mean fluorescence intensity. The mean fluorescence intensity is indicated by ● and solid line for KM511, by ■ and thick solid line for KM4000, by ▲ and dotted line for KM4001, by ○ and dotted line for KM4008, by □ and dotted line for KM4012, by the symbol □ and solid line for rat IgG2a-UNLB, and by ▲ and thick solid line for KM4018.

The measurement results are shown in FIGS. 6 and 7.

As shown in FIG. 6, KM13998 exhibited a high binding activity to the human ASCT2-myc/His gene-introduced CHO cells and KMS-11 expressing ASCT2mRNA, but no binding activity to the vector-introduced CHO cells. The negative control antibody rat IgG2a-UNLB exhibited no binding activity for any type of cell. From these results, it was demonstrated that KM3998 has a specific binding activity for ASCT2-expressing cells.

Further, as shown in FIG. 7, KM4000, KM4001, KM4008, KM4012 and KM4018 exhibited a potent binding activity (mean fluorescence intensity) to the human ASCT2-myc/His gene-introduced CHO cells and the ASCT2-mRNA-expressing KMS-11, but exhibited no binding activity to the vector-introduced CHO cells. In addition, the negative control antibodies, i.e., rat IgG2a-UNLB and KM511 exhibited no binding activity for any type of cells. From these results, it was demonstrated that KM4000, KM4001, KM4008, KM4012, and KM4018 has a specific binding activity to ASCT2-expressing cells.

(2) Western Blotting

To each of the human ASCT2-myc/His gene-introduced CHO cell obtained in Example 2, the vector-introduced CHO cell, the multiple myeloma cell line KMS-11 (HSRRB No. JCRB1179) and the colorectal cancer cell line WiDr (ATCC Accession No. CCL-218), a mixed solution (hereinafter, referred to as "cell lysis buffer A") of Tris-HCl (50 mmol/L, pH 7.2), 1% Triton X-100, sodium chloride (150 mmol/L), magnesium chloride (2 mmol/L), calcium chloride (2 mmol/L), 0.1% sodium azide, phenylmethanesulfonyl fluoride (PMSF, 5 μmol/L), N-ethyl maleimide (50 mmol/L), leupeptin (1 mg/mL) and dithiothreitol (0.1 mmol/L) was added at a volume of 1 mL per $5\times10^7$ cells, and the resulting solution was allowed to stand at 4° C. for 2 hours. The solution was centrifuged to obtain the supernatant which was used as a cell lysate. Each of cell lysates of $5\times10^4$ cells/lane was fractionated using SDS-polyacrylamide electrophoresis (PAGEL, manufactured by Atto) and transferred to a PVDF membrane (manufactured by Millipore). After the transferred PVDF membrane was blocked with 10% BSA-PBS, each of the test substances as the primary antibody, i.e., the purified antibodies, KM3842 (positive control) obtained in Example 3, rat IgG2a-UNLB (negative control, manufactured by Beckman Coulter) and KM511 (negative control) was diluted to give a concentration of 10 μg/mL in 1% BSA-PBS, followed by reaction at 4° C. overnight. The resulting PVDF membrane was thoroughly washed with 0.1% Tween-PBS (hereinafter, referred to as "PBST"), followed by reaction with the secondary antibody, i.e., peroxidase-labeled anti-mouse immunoglobulin G (H+L) (manufactured by Zymed) or peroxidase-labeled anti-rat immunoglobulin G (H+L) (manufactured by Dako) for 1 hour at room temperature. The PVDF membrane was thoroughly washed again with PBST and the antibody-bound band was detected using ECL Western Blotting Detection Reagents (manufactured by Amersham Pharmacia).

KM3842 could detect a band around a molecular weight of 75 kDa corresponding to a molecular weight of ASCT2 in the human ASCT2-myc/His gene-introduced CHO cells, ASCT2 mRNA-expressing KMS-11 cells and WiDr cells, but KM3998, KM4000, KM4001, KM4008, KM4012 and KM4018 could not detect ASCT2. Further, the reactivity of any antibody was not recognized against the vector-introduced CHO cells.

From the results of the above flow cytometry and Western blotting, it is considered that the each of binding activity of KM3998, KM4000, KM4001, KM4008, KM4012 and KM4018 to ASCT2 was lost by SDS denaturation of ASCT2 and it was demonstrated that KM3998, KM4000, KM4001, KM4008, KM4012 and KM4018 were the antibodies which recognize and bind to the native three-dimensional structure of ASCT2.

(3) Immunoprecipitation Method

To each of the human ASCT2-myc/His gene-introduced CHO cell obtained in Example 2 and the vector-introduced CHO cells, a mixed solution (hereinafter, referred to as "cell lysis buffer B") of Tris-HCl (50 mmol/L, pH 7.5), 1% Triton X-100, sodium chloride (150 mmol/L), EDTA (5 mmol/L), 0.1% SDS, 0.5% sodium deoxycholate, Protease inhibitor cocktail (manufactured by Roche Diagnostics) and Phosphatase inhibitor cocktail (manufactured by Roche Diagnostics) was added at a volume of 1 mL per $2 \times 10^7$ cells and the resulting solution was stirred at 4° C. for 30 minutes, followed by centrifugation (CF15D, manufactured by Hitachi Koki). A protein concentration of the resulting supernatant was measured using a protein assay reagent (manufactured by Bio-Rad) and adjusted to 5 mg/mL by cell lysis buffer B to be used as a cell lysate.

Then, 2 μg of each test substance, i.e., the purified antibody, KM3842 (positive control) obtained in Example 3, rat IgG2a-UNLB (negative control, manufactured by Beckman Coulter) and KM511 (negative control), was mixed with 1 mg of the resulting cell lysate at 4° C. for 1 hour.

With 0.1% BSA-PBST (300 μL), Protein G-Sepharose beads (manufactured by Amersham; 30 μL) or Protein A-Sepharose beads (manufactured by Amersham; 30 μL) was pre-treated for 30 minutes or more, followed by centrifugation to remove the supernatant and the beads were suspended in a mixed solution (hereinafter, referred to as "bead wash buffer") (90 μL) of Tris-HCl (50 mmol/L, pH 7.5), 1% Triton X-100, sodium chloride (150 mmol/L), EDTA (5 mmol/L) and Protease inhibitor cocktail (manufactured by Roche Diagnostics).

To the bead suspension, a mixed solution (100 μL) of antibodies and cell lysate was added and mixed at 4° C. for 2 hours and then the beads were recovered by centrifugation. The recovered beads were washed three to five times with the bead wash buffer and dissolved in a mixed solution (hereinafter, referred to as "SDS-PAGE sample buffer") of 2% SDS, Tris-HCl (62 mmol/L, pH 6.8) and 10% glycerol. The resulting solution was analyzed by the following immunoblotting.

The obtained solution was fractionated by SDS-polyacrylamide electrophoresis and transferred to a PVDF membrane (manufactured by Millipore).

The resulting PVDF membrane was blocked with 5% skim milk-PBST and allowed to react with 3.5 μg/mL of KM3842 (positive control) obtained in Example 3 as a primary antibody for 2 hours at room temperature. The resulting PVDF membrane was thoroughly washed with PBST and allowed to react with peroxidase-labeled anti-rat immunoglobulin G (H+L) (manufactured by Dako) at room temperature for 1 hour. The PVDF membrane was thoroughly washed again with PBST and the antibody-bound band was detected using ECL Western Blotting Detection Reagents (manufactured by Amersham Pharmacia).

KM4000, KM4001, KM4008, KM4012, KM4018 and positive control antibody KM3842 could detect a band around a molecular weight of 75 kDa. As a result, it was demonstrated that KM4000, KM4001, KM4008, KM4012 and KM4018 are antibodies which can detect ASCT2 by the immunoprecipitation reaction and recognize the three-dimensional structure of ASCT2.

(4) Inhibitory Activity on Intracellular Uptake of Amino Acids by ASCT2

The human colorectal cancer cell line WiDr (ATCC Accession No. CCL-218) was adjusted to give a cell density of $2 \times 10^4$ cells/mL in a Dulbecco's modified Eagle's medium (DMEM, manufactured by Invitrogen) containing 10% inactivated dialyzed fetal bovine serum (hereinafter, referred to as dFBS, manufactured by Invitrogen) (hereinafter, referred to as "glutamine-free medium") and 100 μL/well of the resulting suspension was seeded into a 96-well plate, followed by culturing in a 5% $CO_2$ incubator at 37° C. for 24 hours.

Each test substance, i.e., purified antibody, rat IgG2a-UNLB (negative control, manufactured by Beckman Coulter), KM511 (negative control) or a glutamine-competitive amino acid mixture [AST mixture, a mixture of alanine, serine and threonine (all manufactured by Sigma), 3.3 mmol/L for each)], was diluted with PBS to give a final concentration of 31.6 to 0.03 μg/mL. After, 20 μL/well of the resulting solution was added to the well, 20 μL/well of a glutamine solution (manufactured by Invitrogen) which was prepared to have a final concentration of 0.2 mmol/L in a glutamine-free medium was added. To the wells of the control and the wells of the blank plate, PBS (20 μL/well) and the above glutamine solution (20 μL/well) were added. After addition of antibodies, the plates except for the blank plate were incubated in a 5% $CO_2$ incubator at 37° C. for 72 hours.

Furthermore, 20 μL/well of {4-[3-(4-iodophenyl)-2-(4-nitrophenyl)-2H-5-tetrazolio]-1,3-benzenedisulfonate} diluted to 50% in a glutamine-free medium (hereinafter, referred to as "WST-1 reagent", manufactured by Roche Diagnostics) was added thereto, followed by further incubation at 37° C. for 2 hours.

An absorbance at 450 nm (control wavelength 650 nm) was measured using a microplate spectrophotometer (Emax microplate reader, manufactured by Molecular Devices). A relative proliferation rate (%) of the antibody-added well was calculated by regading an absorbance of the non-antibody added control well as 100% and an absorbance of the blank plate well as 0%.

Figure 8:
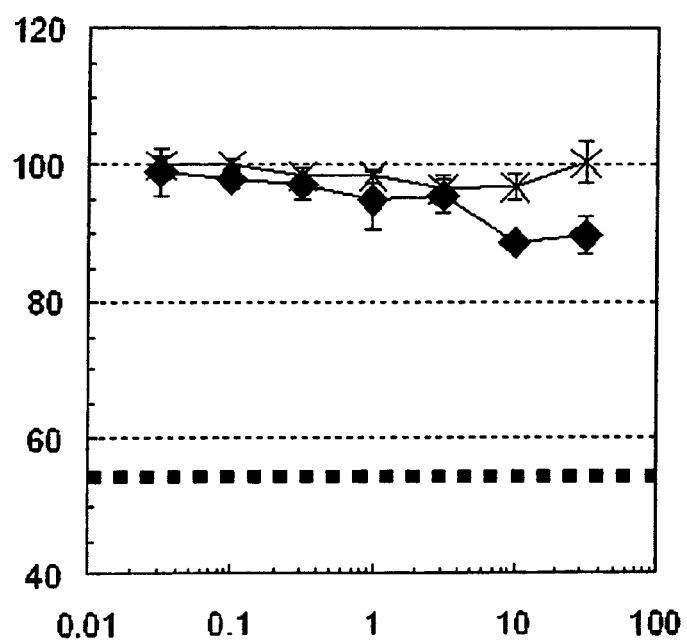
FIG. 8 shows the inhibitory activity of an anti-ASCT2 monoclonal antibody KM3998 on glutamine-dependent proliferation of the human colorectal cancer cell line WiDr. The abscissa represents a final concentration (μg/mL) of KM3998, and the ordinate represents a relative value (%) obtained by taking proliferation of non-antibody treated cells to be 100%. The relative proliferation rate is indicated by ♦ and solid line for KM3998, by x and solid line for rat IgG2a-UNLB, and by dotted line for AST mixture.
Figure 9:
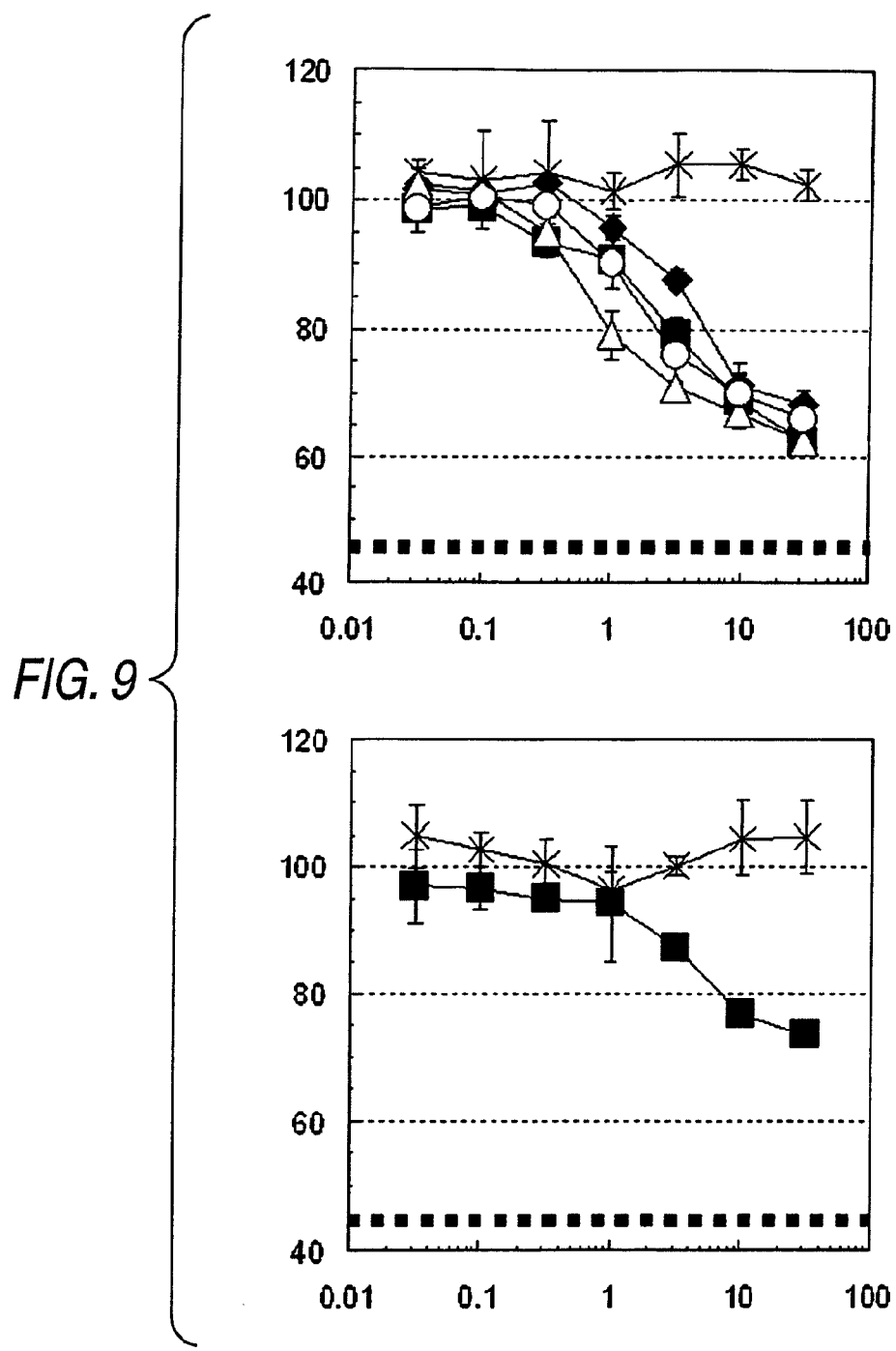
FIG. 9 shows the inhibitory activities of anti-ASCT2 monoclonal antibodies KM4000, KM4001, KM4008, KM4012 and KM4018 on glutamine-dependent proliferation of the human colorectal cancer cell line WiDr. The abscissa represents a final concentration (μg/mL) of individual antibodies, and the ordinate represents a relative value (%) obtained by taking proliferation of non-antibody treated cells to be 100%. The relative proliferation rate is indicated by ♦ and solid line for KM4000, by ■ and solid line for KM4001, by Δ and solid line for KM4008, by ○ and solid line for KM4012, by x and solid line for KM511, by ■ and solid line for KM4018, by x and solid line for rat IgG2a-UNLB, and by dotted line for AST mixture.

The measurement results were shown in FIGS. 8 and 9.

As shown in FIG. 8, KM3998 exhibited slight inhibition of cell proliferation at a high concentration, but its inhibitory effect was lower than that of the glutamine-competitive amino acid mixture. Therefore, it was found that a neutralizing activity of KM3998 on ASCT2 was low.

Further, as shown in FIG. 9, all of KM4000, KM4001, KM4008, KM4012 and KM4018 strongly inhibited the cell proliferation depending on an antibody concentration. As a result, it was demonstrated that KM4000, KM4001, KM4008, KM4012 and KM4018 strongly neutralize the function of ASCT2 for intracellular uptake of glutamine and consequently exhibit a significant inhibitory activity against the proliferation of cancer cells.

Example 7

Isolation and Analysis of cDNA Encoding Variable Regions of Anti-ASCT2 Monoclonal Antibody (1) Preparation of mRNA from Anti-ASCT2 Monoclonal Antibody-Producing Hybridoma Cell From $5 \times 10^7$ cells of the respective hybridomas KW4008, KM4012 and KM4018 obtained in Example 5(5), about 6 µg of mRNA was prepared using an RNeasy Maxi Kit (manufactured by Qiagen) and an Oligotex-dT30<Super>mRNA Purification Kit (manufactured by Takara Bio) in accordance with the instructions attached thereto.

(2) Gene Cloning of H Chain and L Chain Variable Regions of Anti-ASCT2 Monoclonal Antibody Using a BD SMART RACE cDNA Amplification Kit (manufactured by BD Biosciences) in accordance with the instructions attached thereto, cDNAs each comprising the nucleotide sequence of BD SMART II A Oligonucleotide attached to the kit at the 5'-terminal were obtained from 0.6 µg of mRNA of KM4008, KM4012 and KM4018 obtained in (1).

The resulting cDNA was used as a template and PCR was carried out using the universal primer A mix attached to the kit and the mouse Ig(γ)-specific primer (mG3a2 or mG2ba1) represented by SEQ ID NOs:15 and 16 or the rat Ig(γ)-specific primer (rG2a) represented by SEQ ID NO:43 so that the cDNA fragment of VH was amplified. Another PCR was carried out using the mouse Ig(κ)-specific primer (mKa1) represented by SEQ ID NO:17 or the rat Ig(κ)-specific primer (rKa2) represented by SEQ ID NO:44 in place of the Ig(γ)-specific primer to amplify the cDNA fragment of VL.

PCR for the rat Ig(κ)-specific primer (rKa2) was carried out by heating at 94° C. for 5 minutes; 40 cycles each consisting of reaction at 94° C. for 15 seconds, reaction at 68° C. for 30 seconds and reaction at 72° C. for 3 minutes; and then reaction at 72° C. for 10 minutes. Other PCR was carried out by heating at 94° C. for 5 minutes; 5 cycles each consisting of reaction at 94° C. for 15 seconds and reaction at 72° C. for 3 minutes; 5 cycles each consisting of reaction at 94° C. for 15 seconds and reaction at 72° C. for 3 minutes and 30 seconds; and 30 cycles each consisting of reaction at 94° C. for 15 seconds, reaction at 68° C. for 30 seconds and reaction at 72° C. for 3 minutes, followed by reaction at 72° C. for 10 minutes. The PCR was carried out using a PTC-200 DNA Engine (manufactured by Bio-Rad). The resulting PCR product of H chain and L chain had a size of about 700 bp and about 800 bp in the H chain and the L chain, respectively.

In order to determine the nucleotide sequence of the resulting PCR product, the PCR product was separated by agarose gel electrophoresis and extracted using a Gel Extraction Kit (manufactured by Qiagen). The resulting extraction fragment was ligated into a pCR4TOPO vector using a TOPO TA cloning kit (manufactured by Invitrogen), and *Escherichia coli* DH5α (manufactured by Toyobo) was transformed with the resulting vector, using a method of Cohen et al [*Proc. Natl. Acad. Sci. USA,* 69, 2110 (1972)]. A plasmid was extracted from the resulting transformant using an automated plasmid isolation system PI-50 (manufactured by Kurabo) to obtain a plasmid, followed by reaction using a Big Dye Terminator Cycle Sequencing FS Ready Reaction Kit (manufactured by PE Biosystems) in accordance with the instructions attached thereto and then the nucleotide sequence was analyzed using a DNA sequencer ABI PRISM 3700 (manufactured by PE Biosystems).

As a result, a plasmid 08H2b10 comprising the full-length H chain cDNA of KM4008, a plasmid 08La4 comprising the full-length L chain cDNA of KM4008, a plasmid 12Ha5 comprising the full-length H chain cDNA of KM4012, a plasmid 12La4 comprising the full-length L chain cDNA of KM4012, a plasmid 18rHa1 comprising the full-length H chain cDNA of KM4018 and a plasmid 18Lb3 comprising the full-length L chain cDNA of KM14018 in which an ATG sequence presumed to be an initiation codon was present at the 5' terminal of cDNA were prepared.

A full-length nucleotide sequence of VH contained in the plasmid 08H2b10 comprising the H chain cDNA of KM4008 was represented by SEQ ID NO:18, a full-length amino acid sequence of secretory VH comprising a signal sequence deduced from the full-length nucleotide sequence of VH contained in the plasmid 08H2b10 was represented by SEQ ID NO:19, a full-length nucleotide sequence of VL contained in the plasmid 08La4 comprising the L chain cDNA of KM4008 was represented by SEQ ID NO:20, a full-length amino acid sequence of secretory VL comprising a signal sequence deduced from the full-length nucleotide sequence of VL contained in the plasmid 08La4 was represented by SEQ ID NO:21, a full-length nucleotide sequence of VH contained in the plasmid 12Ha5 comprising the H chain cDNA of KM4012 was represented by SEQ ID NO:22, a full-length amino acid sequence of secretory VH comprising a signal sequence deduced from the full-length nucleotide sequence of VH contained in the plasmid 12Ha5 was represented by SEQ ID NO:23, a full-length nucleotide sequence of VL contained in the plasmid 12La4 comprising the L chain cDNA of KM4012 was represented by SEQ ID NO:24, a full-length amino acid sequence of secretory VL comprising a signal sequence deduced from the full-length nucleotide sequence of VL contained in the plasmid 12La4 was represented by SEQ ID NO:25, a full-length nucleotide sequence of VH contained in the plasmid 18rHa1 comprising the H chain cDNA of KM4018 was represented by SEQ ID NO:45, a full-length amino acid sequence of secretory VH comprising a signal sequence deduced from the full-length nucleotide sequence of VH contained in the plasmid 18rHa1 was represented by SEQ ID NO:46, a full-length nucleotide sequence of VL contained in the plasmid 18Lb3 comprising the L chain cDNA of KM4018 was represented by SEQ ID NO:47, and a full-length amino acid sequence of secretory VL comprising a signal sequence deduced from the full-length nucleotide sequence of VL contained in the plasmid 18Lb3 was represented by SEQ ID NO:48, respectively.

(3) Analysis of Amino Acid Sequence of V Region of Anti-ASCT2 Monoclonal Antibody The N-terminal amino acid sequences of the H chain and L chain in the purified monoclonal antibodies of KM4008, KM4012 and KM4018 obtained in Example 5(7) were analyzed using a protein sequencer (PPSQ-10, manufactured by Shimadzu) and about 20 residues were determined. From the comparison of the obtained analysis results with the amino acid sequences deduced from the nucleotide sequences of individual antibodies obtained in (2), it was found that the individual sequences were identical to the corresponding sequence and thus confirmed that the nucleotide sequences obtained in the (2) were nucleotide sequences of the desired antibodies. Further, from the comparison with amino acid sequence data of known mouse antibodies or rat antibodies [*SEQUENCES of Proteins of Immunological Interest*, US Dept. Health and Human Services (1991)], it became clear that each of the isolated cDNAs was a full-length cDNA encoding the anti-ASCT2 monoclonal antibody KM4008, KM4012 or KM4018 comprising a secretory signal sequence; the secretory signal sequence of the H chain and L chain of KM4008 were the amino acid sequence from positions 1 to 19 in the amino acid sequence represented by SEQ ID NO:19 and the amino acid sequence from positions 1 to 20 in the amino acid sequence represented by SEQ ID NO:21, respectively; the secretory signal sequence of the H chain and L chain of KM4012 were the amino acid sequence from positions 1 to 19 in the amino acid sequence represented by SEQ ID NO:23 and the amino acid sequence from positions 1 to 20 in the amino acid sequence represented by SEQ ID NO:25, respectively; the secretory signal sequence of the H chain and L chain of KM4018 were the amino acid sequence from positions 1 to 19 in the amino acid sequence represented by SEQ ID NO:46 and the amino acid sequence from positions 1 to 20 in the amino acid sequence represented by SEQ ID NO:48, respectively.

Then, using the amino acid sequences of VH and VL of the anti-ASCT2 monoclonal antibodies KM4008, KM4012 and KM4018, amino acid sequence database of known proteins were searched by the BLASTP method [*Nucleic Acid Res.* 25, 3389 (1997)]. As a result, no completely identical amino acid sequence was found for both VH and VL and it was confirmed that VH and VL of the anti-ASCT2 monoclonal antibodies KM4008, KM4012, and KM4018 had novel amino acid sequences.

Further, the CDR sequences of VH and VL of the anti-ASCT2 monoclonal antibodies KM4008, KM4012, and KM4018 were identified by comparing them with the amino acid sequences of known antibodies. Amino acid sequences of CDR1, CDR2 and CDR3 of VH of the anti-ASCT2 monoclonal antibody KM4008 were represented by SEQ ID NOs: 26, 27 and 28, respectively and amino acid sequences of CDR1, CDR2 and CDR3 of VL thereof were represented by SEQ ID NOs:29, 30 and 31, respectively; amino acid sequences of CDR1, CDR2 and CDR3 of VH of the anti-ASCT2 monoclonal antibody KM4012 were represented by SEQ ID NOs:32, 33 and 34, respectively, and amino acid sequences of CDR1, CDR2 and CDR3 of VL thereof were represented by SEQ ID NOs:35, 36 and 37, respectively; and amino acid sequences of CDR1, CDR2 and CDR3 of VH of the anti-ASCT2 monoclonal antibody KM4018 were represented by SEQ ID NOs:49, 50 and 51, respectively, and amino acid sequences of CDR1, CDR2 and CDR3 of VL thereof were represented by SEQ ID NOs:52, 53 and 54, respectively.

Example 8

Construction of Anti-ASCT2 Human Chimeric Antibody (1) Construction of Anti-ASCT2 Human Chimeric Antibody-Expressing Vector cKM4008_93

Using a vector pKANTEX93 (WO97/10354) for the expression of a humanized antibody and a plasmid 08H2b 10 comprising an H chain cDNA of KM4008 and a plasmid 08La4 comprising an L chain cDNA of KM4008 each of which obtained in Example 7(2), an anti-ASCT2 human chimeric antibody-expressing vector cKM4008_93 was constructed as follows.

The PCR was carried out in the same manner as in Example 2. To the plasmid 08H2b10 (100 ng) as a template, primers (10 µmol/L, each of 1 µL) having the nucleotide sequences represented by SEQ ID NOs:38 and 39, 10×Ex Taq buffer (5 µL), dNTPs (2.5 mmol/L, 4 µL), and Ex Taq polymerase (1 µL, all manufactured by Takara Bio) were added, followed by adding sterile water to give a total volume of 50 µL. The PCR was carried out by denaturation at 96° C. for 2 minutes; 30 cycles each consisting of reaction at 94° C. for 1 minute, reaction at 55° C. for 1 minute, and reaction at 72° C. for 1 minute; and then reaction at 72° C. for 5 minutes. As a result, a gene fragment encoding VH of KM4008 was amplified in which a restriction enzyme recognizing sequence for insertion into pKANTEX93 was added.

In addition, using the plasmid 08La4 (100 ng) as a template, primers (10 µmol/L, each of 1 µL) having the nucleotide sequences represented by SEQ ID NOs:40 and 41, 10×Ex Taq buffer (5 µL), dNTPs (2.5 mmol/L, 4 µL) and Ex Taq polymerase (1 µL, all manufactured by Takara Bio), the PCR was carried out in the same manner as above to amplify a gene fragment encoding VL of KM4008 in which a restriction enzyme recognizing sequence for insertion into pKANTEX93 was added.

Each of the resulting reaction products was separated by agarose gel electrophoresis and the about 0.5-kbp amplified fragment was extracted using a Gel Extraction Kit (manufactured by Qiagen). The obtained gene fragment was ligated into a pCR4TOPO vector using a TOPO TA cloning kit (manufactured by Invitrogen), and *Escherichia coli* DH5α (manufactured by Toyobo) was transformed with the ligation product, as a same manner in Example 7(2), thereby obtaining a plasmid 08VH3 comprising a nucleotide sequence encoding VH of KM4008 and a plasmid 08VL6 comprising a nucleotide sequence encoding VL of KM4008.

The resulting plasmid 08VH3 was digested with restriction enzymes ApaI (manufactured by Takara Bio) and NoI (manufactured by Takara Bio), and the plasmid 08VL6 was digested with restriction enzymes EcoRI (manufactured by Takara Bio) and BsiWI (manufactured by Takara Bio) and separated by agarose gel electrophoresis separation of the plasmids. The resulting about 0.5-kbp gene fragment was extracted using a Gel Extraction Kit (manufactured by Qiagen).

The resulting digested fragment of the plasmid 08VL6 was ligated into the pKANTEX93 vector digested with the same restriction enzymes EcoRI (manufactured by Takara Bio) and BsiWJ (manufactured by Takara Bio). *Escherichia coli* DH5α (manufactured by Toyobo) was transformed with the ligation product, in the same manner as Example 7(2), and the pKANTEX93 vector in which VL of KM4008 were inserted was obtained using a plasmid isolation kit (manufactured by Qiagen).

The pKANTEX93 vector with insertion of VL of KM4008 was digested with ApaI (manufactured by Takara Bio) and NotI (manufactured by Takara Bio) and then ligated into the above plasmid 08VH3-digested fragment. Then, *Escherichia coli DH5α* (manufactured by Toyobo) was transformed with the ligation product, as a same manner in Example 7(2), and an anti-ASCT2 human chimeric antibody expression vector cKM4008_93 in which VH and VL of KM4008 were inserted was obtained using a plasmid isolation kit (manufactured by Qiagen).

(2) Construction of Anti-ASCT2 Human Chimeric Antibody-Expressing Vector cKM4012_93

In the same manner as (1), an anti-ASCT2 human chimeric antibody-expressing vector cKM4012_93 was constructed from the vector pKANTEX93 for the expression of a humanized antibody (WO97/10354), and the plasmid 12Ha5 comprising the H chain cDNA of KM4012 and the plasmid 12La4 comprising the L chain cDNA of KM4012 obtained in Example 7(2).

Using plasmids 12Ha5 and 12La4 as templates, the primers for the amplification of VH having the nucleotide sequences represented by SEQ ID NOs:38 and 42 and the primers for amplification of VL having the nucleotide sequences represented by SEQ ID NOs:40 and 41, the PCR was carried out to amplify a gene fragment. Each of the resulting reaction products was separated, extracted and ligated into a pCR4TOPO vector. *Escherichia coli* DH5α (manufactured by Toyobo) was transformed with the ligation product, thereby obtaining a plasmid 12VH1 comprising the nucleotide sequence encoding VH of KM4012, and a plasmid 12VL11 comprising the nucleotide sequence encoding VL of KM4012.

The resulting plasmids 12VH1 and 12VL11 were digested with restriction enzymes, respectively, separated and extracted to obtain fragments of the plasmid 12VH1 and the plasmid 12VL11. Each of the resulting fragments was ligated into the restriction enzyme-digested pKANTEX93 vector. Then, *Escherichia coli* DH5α (manufactured by Toyobo) was transformed with the ligation product and an anti-ASCT2 human chimeric antibody expression vector cKM4012_93 in which VH and VL of KM4012 were inserted was obtained.

(3) Construction of Anti-ASCT2 Human Chimeric Antibody-Expressing Vector cKM4018_93

In a same manner as the (1), an anti-ASCT2 human chimeric antibody expression vector cKM4018_93 was constructed from the vector pKANTEX93 for the expression of a humanized antibody (WO97/10354), and the plasmid 18rHa1 comprising the H chain cDNA of KM4018 and the plasmid 18Lb3 comprising the L chain cDNA of KM4018 obtained in Example 7(2).

Using the plasmids 18rHa1 and 18Lb3 as templates, the primers for the amplification of VH having the nucleotide sequences represented by SEQ ID NOs:55 and 56 and primers for the amplification of VL having the nucleotide sequences represented by SEQ ID NOs:57 and 58, PCR was carried out to amplify the gene fragment. Each of the resulting reaction products was separated, extracted, and ligated into a pCR4TOPO vector, and *Escherichia coli* DH5α (manufactured by Toyobo) was transformed with the ligation product, thereby obtaining a plasmid 18VH5 comprising a nucleotide sequence encoding VH of KM4018, and a plasmid 18V2L1 comprising a nucleotide sequence encoding VL of KM4018.

The resulting plasmids 18VH5 and 18V2L1 were digested with restriction enzymes, respectively, separated, and extracted to obtain fragments of the plasmid 18VH5 and the plasmid 18V2L1. Each of the resulting fragments was ligated into the restriction enzyme-digested pKANTEX93 vector. Then, *Escherichia coli.* DH5α (manufactured by Toyobo) was transformed with the ligation product and an anti-ASCT2 human chimeric antibody expression vector cKM4018_93 was obtained in which VH and VL of KM4018 were instructed.

(4) Expression of Anti-ASCT2 Human Chimeric Antibody in Animal Cell

Using the anti-ASCT2 human chimeric antibody-expressing vector cKM4008_93 obtained in the above (1), expression of the anti-ASCT2 human chimeric antibody in an animal cell was carried out by a conventional method [*Antibody Engineering, A Practical Guide*, W.H. Freeman and Company (1992)]. Similarly, using the anti-ASCT2 human chimeric antibody-expressing vector cKM4012_93, or the anti-ASCT2 human chimeric antibody-expressing vector cKM4018_93, expression of individual anti-ASCT2 human chimeric antibodies in an animal cell was carried out. In this manner, transformants were obtained which produce an anti-ASCT2 human chimeric antibodies.

(5) Obtaining of Purified Antibody

After each of transformants obtained in the above (4) was cultured by a conventional culturing method, the cell suspensions were collected and centrifuged at 3,000 rpm and 4° C. for 15 minutes to recover the supernatants. The culture supernatants were subjected to sterile filtration using a 0.22-1 μm Millex GV filter (manufactured by Millipore). The anti-ASCT2 human chimeric antibodies cKM4008, cKM4012 and cKM4018 (hereinafter referred to as cKM4008, cKM4012, and cKM4018, respectively) were purified from the resulting culture supernatants, using a Protein A High-capacity resin (manufactured by Millipore) column in accordance with the instructions attached thereto.

The degree of purification and expressed molecular size of purified preparations of the resulting cKM4008, cKM4012, cKM4018 were confirmed by SDS-PAGE using a gradient gel (Catalog Number: E-T520L, manufactured by Atto) in accordance with the instructions attached thereto. With regard to phoretic patterns of the purified anti-ASCT2 human chimeric antibodies, one band was found around a molecular weight of 150 to 200 kilodaltons (hereinafter, referred to as "kDa") under non-reducing conditions, and two bands of about 50 kDa and about 25 kDa were found under reducing conditions [*Antibodies—A Laboratory Manual, Cold Spring Harbor Laboratory, Chapter* 14 (1988), *Monoclonal Antibodies Principles and Practice*, Academic Press Limited (1996)]. Those phoretic patterns were consistent with the results for antibodies of the IgG class, obtained by SDS-PAGE under the same conditions. Thus, it was confirmed that the anti-ASCT2 human chimeric antibodies cKM4008, cKM4012 and cKM4018 were expressed as antibody molecules having a correct structure.

Example 9

Investigation of Reactivity of Anti-ASCT2 Human Chimeric Antibody (1) Fluorescent Cell Staining Method (Flow Cytometer)

Each of the human ASCT2-myc/His gene-introduced CHO cell obtained in Example 2, and the multiple myeloma cell line OPM-2 (DSMZ Accession No. ACC50) was cultured in a 5% $CO_2$ incubator for 3 to 4 days at 37° C. The human ASCT2-myc/His gene-introduced CHO cells were peeled off with a 0.02% EDTA solution (manufactured by Nacalai Tesque), and in order to avoid the non-specific adsorption of antibodies, the cells were blocked for 30 minutes at ice temperature using 1% BSA-PBS. The cells were seeded into a 96-well U-bottom plate so as to give a density of $1\times10^5$ to $5\times10^5$ cells/100 μL/well. The plates were centrifugation at 1,500 rpm for 5 minutes (05PR-22, manufactured by Hitachi Koki), and then the supernatant was removed. As the primary antibody, the purified antibody which was a test substance was diluted to give a final concentration of 0.01 μg/mL to 10 μg/mL in 1% BSA-PBS, and dispensed to the plate at 100 μL/well, followed by reaction at ice temperature for 60 minutes. After washing the cells with 1% BSA-PBS, FITC-labeled anti-human immunoglobulin G (H+L) (manufactured by Jackson Laboratories) diluted with 1% BSA-PBS was added as the secondary antibody, followed by reaction at ice temperature for 30 minutes under shading. The cells were washed with 1% BSA-PBS and then suspended in PBS. The fluorescence intensity of the cells was measured by a flow cytometer (Cytomics FC500MPL, manufactured by Beckman Coulter).

Figure 10:
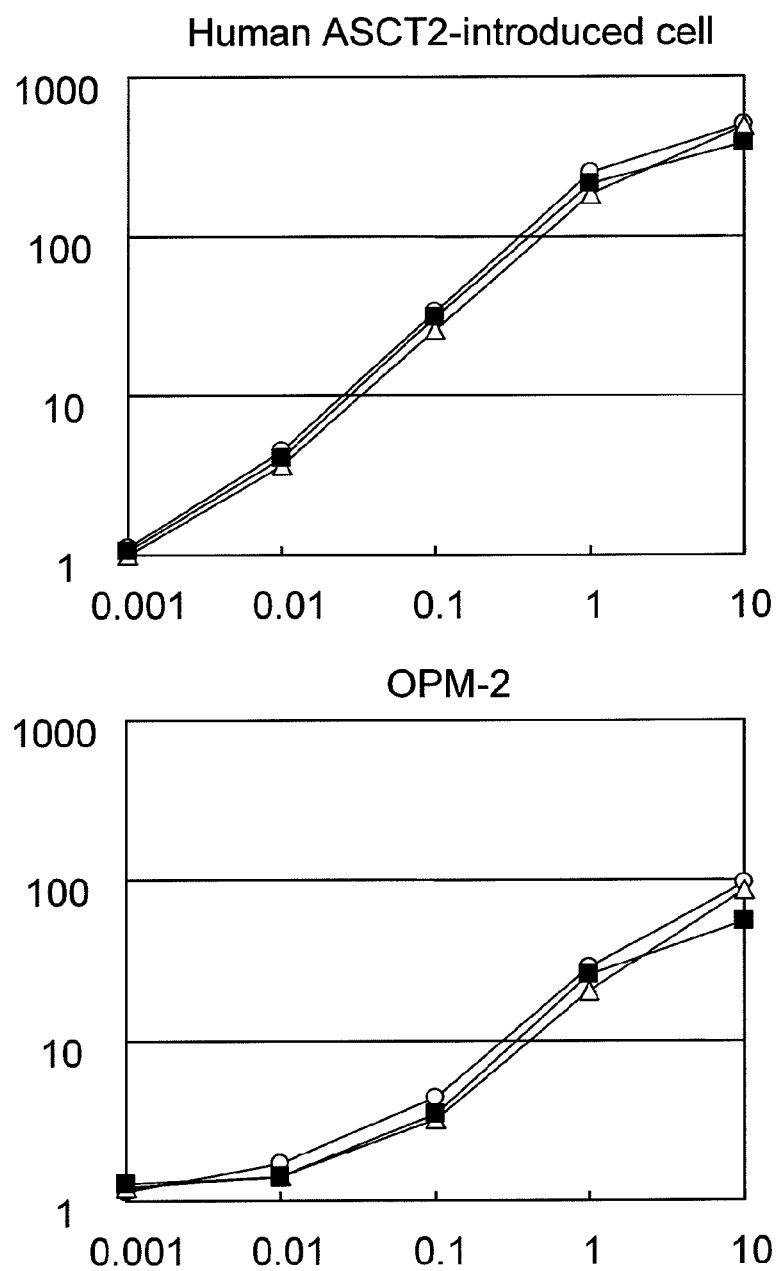
FIG. 10 shows the reactivity of an anti-ASCT2 human chimeric antibody to human ASCT2-myc/His gene-introduced CHO cells (ASCT2/CHO) and human multiple myeloma cell line OPM-2 by means of fluorescent cell staining (flow cytometer). The abscissa represents an antibody concentration (μg/mL), and the ordinate represents a mean fluorescence intensity. The mean fluorescence intensity is indicated by ○ and solid line for cKM4008, by Δ and solid line for cKM4012, and by ■ and solid line for cKM4018.

The measurement results are given in FIG. 10. As shown in FIG. 10, each of anti-ASCT2 human chimeric antibodies cKM4008, cKM4012 and cKM4018 exhibited a potent binding activity for the human ASCT2-myc/His gene-introduced CHO cells. In addition, it was found that the chimeric antibodies cKM4008, cKM4012 and cKM4018 exhibit a potent reactivity with the multiple myeloma cell line OPM-2.

(2) ADCC Activity

The multiple myeloma cell line KMS-11 (HSRRB No. JCRB 1179) was used as a target cell. The cell was adjusted to give a cell density of $2 \times 10^5$ cells/mL using RPMI 1640 medium (manufactured by Invitrogen) containing 5% FBS (manufactured by Invitrogen) and containing no Phenol Red (hereinafter, referred to as "ADCC activity assay medium") and was used as a target cell solution. Lymphoprep (manufactured by Nycomed) was used for the preparation of an effector cell solution, and, a peripheral blood mononuclear cell (PBMC) fraction was separated from healthy human peripheral blood in accordance with the instructions attached thereto. The separated PBMC fraction was washed in an ADCC activity assay medium by centrifugation twice, was adjusted to give a cell density of $2 \times 10^6$ cells/mL and then used as an effector cell solution.

Into a 96-well U-bottom plate (manufactured by Falcon), 50 μl, ($1 \times 10^4$ cells/well) of the target cell solution was dispensed and then 50 μL of the effector cell solution (ratio of effector cells: target cells=10:1) was added. In addition, the anti-ASCT2 human chimeric antibody cKM4008, cKM4012 or cKM4018 was diluted in an ADCC activity assay medium. The diluted antibody was added to the plate to give a total volume of 150 μL at a final concentration of 0.01 ng/mL to 1000 ng/mL, followed by reaction at 37° C. for 4 hours. After the reaction was complete, the plate was centrifuged and a lactic acid dehydrogenase (LDH) activity in the supernatant was detected by measuring the absorbance using an LDH-Cytotoxic Test (manufactured by Wako Pure Chemical) in accordance with the instructions attached thereto. The absorbance of spontaneous release of the target cells was obtained using an ADCC activity assay medium in place of the effector cells solution and the antibody solution, and the absorbance data of spontaneous release of the effector cells was obtained using an ADCC activity assay medium in place of the target cell solution and the antibody solution, followed by carrying out the same operation as above. The absorbance of total release of the target cells was obtained using an ADCC activity assay medium in place of the antibody solution and the effector cell solution, by adding 20 μL of a 9% Triton X-100 solution at 45 minutes before completion of the reaction and carrying out the same operation as above. The ADCC activity was calculated by the following formula.

ADCC activity (%)=[(absorbance of sample)−(absorbance of spontaneous release of effector cells/target cells)]/(absorbance of total release of target cells)−(absorbance of spontaneous release of target cells)]×100 (Formula)

Figure 11:
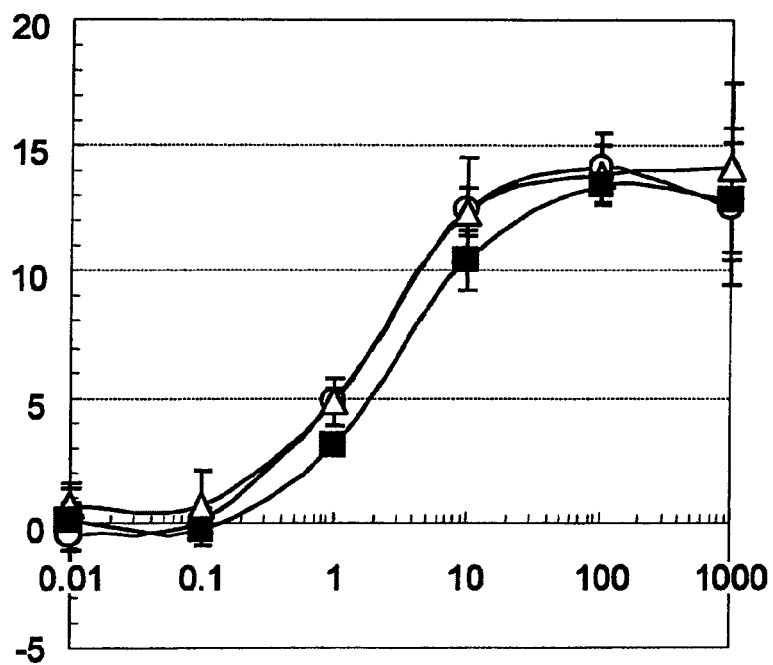
FIG. 11 shows the ADCC activity of an anti-ASCT2 human chimeric antibody on the human multiple myeloma cell line KMS-11. The abscissa represents an antibody concentration (ng/mL), and the ordinate represents an ADCC activity. The ADCC activity is indicated by ○ and solid line for cKM4008, by Δ and solid line for cKM4012, and by ■ and solid line for cKM4018.

The measurement results are shown in FIG. 11. As shown in FIG. 11, it was demonstrated that the anti-ASCT2 human chimeric antibodies cKM4008, cKM4012 and cKM4018 exhibited an ADCC activity against the cells which expressed ASCT2 depending on an antibody concentration.

(3) CDC Activity

As target cells, the human ASCT2-myc/His gene-introduced CHO cell obtained in Example 2 and the colorectal cancer cell line Colo205 (ATCC Accession No. CCL-222) were peeled off using a 0.02%-EDTA Solution (manufactured by Nacalai Tesque), washed in RPMI 1640 medium (manufactured by Invitrogen) containing 1.4% BSA (manufactured by Invitrogen) and 50 μg/mL gentamicin (manufactured by Nacalai Tesque), which was prepared as a CDC assay medium and then suspended in the same medium at a cell density of $2 \times 10^5$ cells/mL. The resulting suspension was used as a target cell solution.

The human complement serum (S2257-5ML, manufactured by Sigma) was dissolved in 5 mL of deionized water and was two-fold diluted by adding an equal volume of a CDC assay medium. The resulting dilution was used as a human complement solution.

Into a 96-well flat-bottom plate (manufactured by Sumitomo Bakelite), 50 μL/well of the complement solution was dispensed. Then, to the well, 50 μL of the target cell solution was added. Then, 50 μL of each of antibody solutions diluted with a CDC assay medium was additionally added to give a total volume of 150 μL and reacted at 37° C. for 2 hours in the presence of 5% $CO_2$. To the well, 15 μL/well of a WST-1 reagent (manufactured by Roche Diagnostics) was added. The resulting solution was stirred with a plate mixer, followed by at 37° C. for 2 hours in the presence of 5% $CO_2$. The absorbance at 450 nm (control wavelength 650 nm) was measured using a microplate spectrophotometer (Emax microplate reader, manufactured by Molecular Devices). The absorbance of a well to which 50 μl, of the complement solution and 100 μL of the CDC medium were added, was measured as blank. The absorbance of a well to which 50 μL of the target cells, 50 μL of the complement solution and 50 μL of the CDC assay medium were added (antibody not added) were measured. The CDC activity was calculated by the following formula.

CDC activity (%)={1−[(absorbance of antibody-added sample)−(absorbance of blank)]/[(absorbance of non-antibody added sample)−(absorbance of blank)]×100} (Formula)

Figure 12:
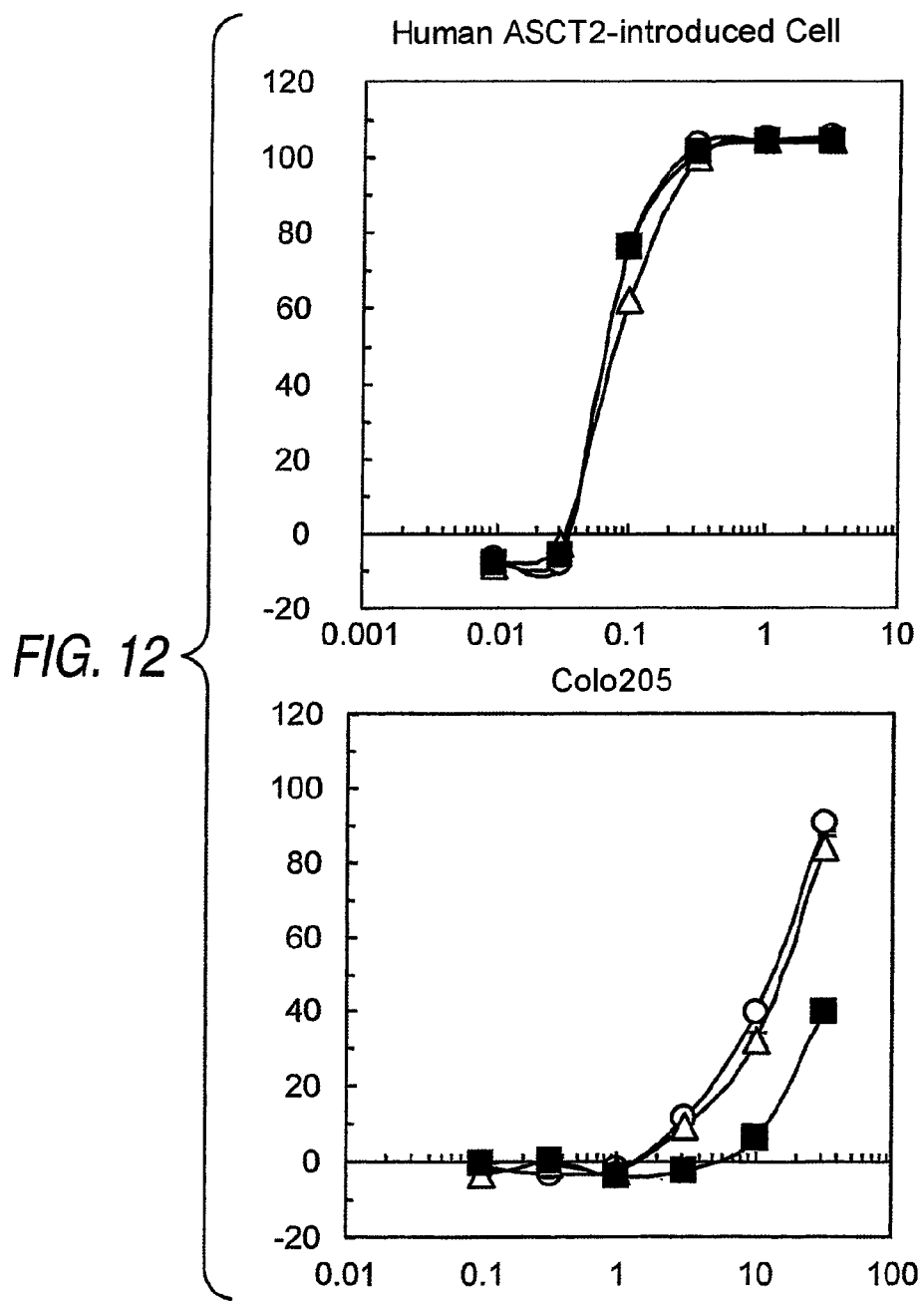
FIG. 12 shows the CDC activity of an anti-ASCT2 human chimeric antibody on human ASCT2-myc/His gene-introduced CHO cells (ASCT2/CHO) and human colorectal cancer cell line Colo205. The abscissa represents an antibody concentration (μg/mL), and the ordinate represents a CDC activity. The CDC activity is indicated by ○ and solid line for cKM4008, by Δ and solid line for cKM4012, and by ■ and solid line for cKM4018.

The measurement results are shown in FIG. 12. As shown in FIG. 12, it was found that the anti-ASCT2 human chimeric antibodies cKM4008, cKM4012 and cKM4018 exhibit a CDC activity against the cells which express ASCT2 depending on the antibody concentration. In addition, it was also found that the anti-ASCT2 human chimeric antibodies cKM4008, cKM4012 and cKM4018 have a CDC activity against the colorectal cancer cell line Colo205.

(4) Inhibitory Activity on Intracellular Uptake of Amino Acids by ASCT2

Into a 96-well plate, 100 μL/well of the human colorectal cancer cell line WiDr (ATCC Accession No. CCL-218), which was adjusted to give a cell density of $1 \times 10^4$ cells/mL in a DMEM (manufactured by Invitrogen) containing 10% dFBS (manufactured by Invitrogen) (hereinafter, referred to as "glutamine-free medium"), was seeded and cultured in a 5% $CO_2$ incubator at 37° C. for 24 hours.

To the well, 20 μL/well of each test substance, i.e., the anti-ASCT2 human chimeric antibody, KM511 (negative control) or a glutamine-competitive amino acid mixture [AST mixture, a mixture of alanine, serine and threonine (all manufactured by Sigma), 3.3 mmol/L for each)], which was diluted with PBS to give a final concentration of 10 to 0.01 μg/mL, was added, followed by further addition of 20 μL/well of a glutamine solution (manufactured by Invitrogen) which was prepared to give a final concentration of 0.2 mmol/L in a glutamine-free medium. To the wells of the control and the wells of the blank plate, 20 μL/well of PBS and 20 μL/well of the above glutamine solution were added. After addition of antibodies, the plates except for the blank plate were incubated in a 5% $CO_2$ incubator at 37° C. for 72 hours.

Then, 20 μL/well of a WST-1 reagent (manufactured by Roche Diagnostics) diluted to 50% in the glutamine-free medium was added thereto and further incubated at 37° C. for 2 hours.

The absorbance at 450 nm (control wavelength 650 nm) was measured using a microplate spectrophotometer (Emax microplate reader, manufactured by Molecular Devices). A relative proliferation rate (%) of the well with adding the antibody was calculated by regarding the absorbance of the well of the control without adding the antibody as 100% and regarding an absorbance of the well of the blank plate as 0%.

Figure 13:
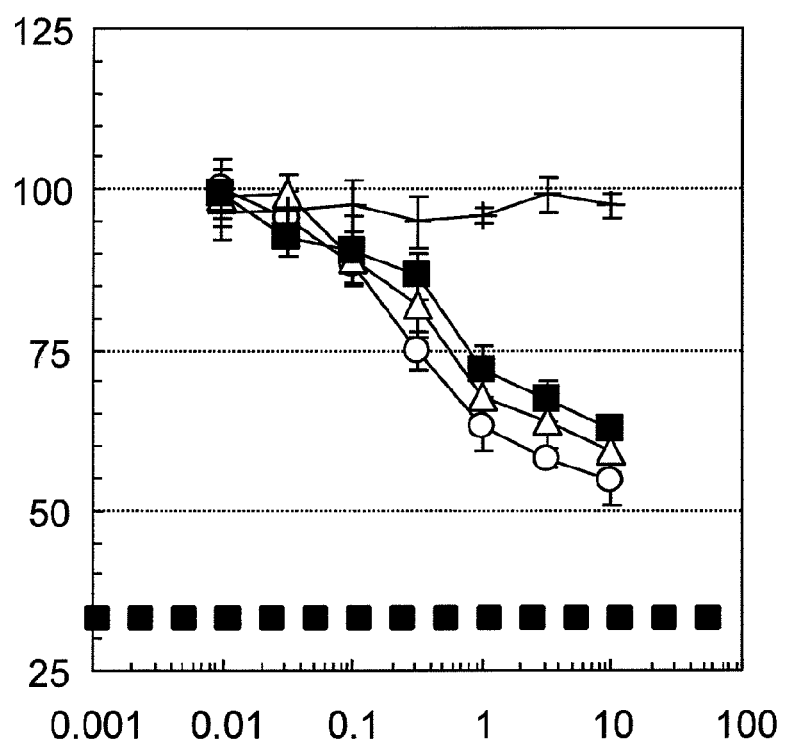
FIG. 13 shows the inhibitory activity of anti-ASCT2 human chimeric antibodies on glutamine-dependent proliferation of the human colorectal cancer cell line WiDr. The abscissa represents a final concentration (μg/mL) of individual antibodies, and the ordinate represents a relative value (%) obtained by taking proliferation of non-antibody treated cells to be 100%. The relative proliferation rate is indicated by ○ and solid line for cKM4008, by Δ and solid line for KM4012, by ■ and solid line for KM4018, by + and solid line for KM511 and by dotted line for AST mixture.

The measurement results are shown in FIG. 13. As shown in FIG. 13, all of the anti-ASCT2 human chimeric antibodies cKM4008, cKM4012 and cKM4018 remarkably inhibited cell proliferation depending on the antibody concentration. As a result, it was demonstrated that cKM4008, cKM4012 and cKM4018 strongly neutralized the function of ASCT2 for intracellular uptake of glutamine, and consequently exhibited a significant inhibitory activity against the proliferation of cancer cells.

Example 10

Construction of Mouse ASCT2-Myc/his Gene-Introduced Cell Line (Hereinafter, Referred to as "Mouse ASCT2/CHO")

In accordance with the following procedure, the plasmid pBluescript II SK (−)-Mouse_ASCT2-myc/His comprising the nucleotide sequence represented by SEQ ID NO:59 and the amino acid sequence represented by SEQ ID NO:60 was obtained, and a mouse ASCT2-myc/His gene-introduced CHO cell line was obtained using this plasmid.

Into 50 mL of an ampicillin-containing LB medium, 10 μL of the solution of an *E. coli* comprising a mouse ASCT2 gene clone (Clone ID: 4192790, manufactured by Open Biosystems) was seeded, cultured under stirring overnight and then centrifuged (CR2DGII, manufactured by Hitachi Koki, 6,000 rpm, 10 minutes) to recover bacteria. A plasmid comprising mouse ASCT2 gene was prepared from the obtained bacteria using a plasmid isolation kit (manufactured by Qiagen). Total 100 μL of a solution containing 100 ng of the obtained plasmid as a template, 10×KOD buffer I (10 μL), dNTPs (2 mmol/L, 5 μL), $MgCl_2$ (25 mmol/L, 4 μL), primers (10 μmol/L, each of 1 μL) having the nucleotide sequences represented by SEQ ID NOs:61 and 62, KOD polymerase (1 μL, manufactured by Toyobo), and dimethyl sulfoxide (5 μL) was prepared, and the PCR was carried out by reaction at 96° C. for 3 minutes; 35 cycles each consisting of reaction at 95° C. for 1 minute, reaction at 50° C. for 1 minute, and reaction at 72° C. for 1.5 minutes; and then reaction at 72° C. for 7 minutes. The reaction product was separated by agarose gel electrophoresis, and the resulting about 1.7-kb amplified fragment was extracted using a QIAquick Gel Extraction Kit (manufactured by Qiagen). The resulting extraction fragment was digested with EcoRI (manufactured by Takara Bio) and KpnI (manufactured by Takara Bio) and then re-extracted using a QIAquick Gel Extraction Kit. The extraction fragment was ligated into a pBluescript II SK (−) vector digested with EcoRI (manufactured by Takara Bio) and KpnI (manufactured by Takara Bio) using a Ligation high (manufactured by Toyobo), and then *Escherichia coli* DH5α (manufactured by Toyobo) was transformed with the ligation product in accordance with the method of Cohen et al [*Proc, Natl, Acad-Sci. USA*. 69 2110 (1972)]. A plasmid was extracted from the resulting transformant using an automated plasmid isolation system PI-50 (manufactured by Kurabo), and a plasmid pBluescript II SK (−)-Mouse_ASCT2-myc/His comprising the nucleotide sequence represented by SEQ ID NO:59 and the amino acid sequence represented by SEQ ID NO:60 was obtained.

The resulting pBluescript II SK (−)-Mouse_ASCT2-myc/His was digested with EcoRI (manufactured by Takara Bio) and KpnI (manufactured by Takara Bio), and a gene fragment was extracted in the same manner as in the above and ligated into a pKANTEX93 vector (WO97/10354) which had been previously digested with EcoRI and KpnI. Then, *Escherichia coli* DH5α (manufactured by Toyobo) was transformed with the ligation product in the same manner as in the above, thereby obtaining a transformant. The plasmid pKANTEx-Mouse_ASCT2-myc/His was obtained from the transformant using a plasmid isolation kit (manufactured by Qiagen).

In accordance with the following procedure, the pKAN-TEX-Mouse ASCT2-myc/His was introduced into CHO/DG44 cells [*Somatic cell and Molecular Genetics*, 12, 555 (1986)] by an electroporation method [*Cytotechnology*, 3, 133 (1990)]. The cells used herein are those subcultured in a medium where 1×HT supplement (manufactured by Invitrogen) was added to IMDM (manufactured by Invitrogen) containing 10% dFBS (manufactured by Invitrogen) and gentamicin (manufactured by Nacalai Tesque, 50 μg/mL) (hereinafter, referred to as "A4 medium"). The CHO/DG44 cells were suspended in buffer containing potassium chloride (137 nmol/L), sodium chloride (2.7 nmol/L), disodium hydrogen phosphate (8.1 mmol/L), sodium dihydrogen phosphate (1.5 nmol/L) and magnesium chloride (4 mmol/L) (hereinafter, referred to as "K-PBS") to give a density of $8×10^6$ cells/mL, and the resulting cell suspension (200 μL, $1.6×10^6$ cells in terms of cell count) was mixed with an expression plasmid pKANTEX-Mouse_ASCT2-myc/His (10 μg). The mixture was transferred into a cuvette (interelectrode distance: 2 mm), and the gene introduction was carried out using a GenePulser II (manufactured by Bio-Rad) at a pulse voltage of 0.35 kV and an electric capacity of 250 μF. The cuvette was allowed to stand on ice, and a cell suspension in the cuvette was suspended in a cell culture vessel containing an A4 medium and cultured in a 5% $CO_2$ incubator at 37° C. After four day culturing, the culture medium was exchanged with an A4 medium containing 0.5 mg/mL of G418 (manufactured by Nacalai Tesque) and continued to culture the cells. With medium exchange and subculturing during the cell culture, a transformed cell line resistant to G418 was obtained about two weeks after the gene introduction.

The resulting G418-resistant transformant cells were diluted to give a cell density of 5 cells/mL in an A4 medium containing 0.5 mg/mL of G418 (manufactured by Nacalai Tesque), and 100 μL/well of the diluted cell suspension was dispensed into a 96-well plate, and treated with a stepwise increasing concentration of methotrexate. In this manner, a clone which highly expresses mouse ASCT2-myc/His was selected, thereby obtaining mouse ASCT2/CHO.

Example 11

Construction of Mouse/Human Chimeric ASCT2-Myc/his Gene-Introduced Cell Line (Hereinafter, Referred to as "Mouse/Human Chimeric ASCT2/CHO")

Figure 14:
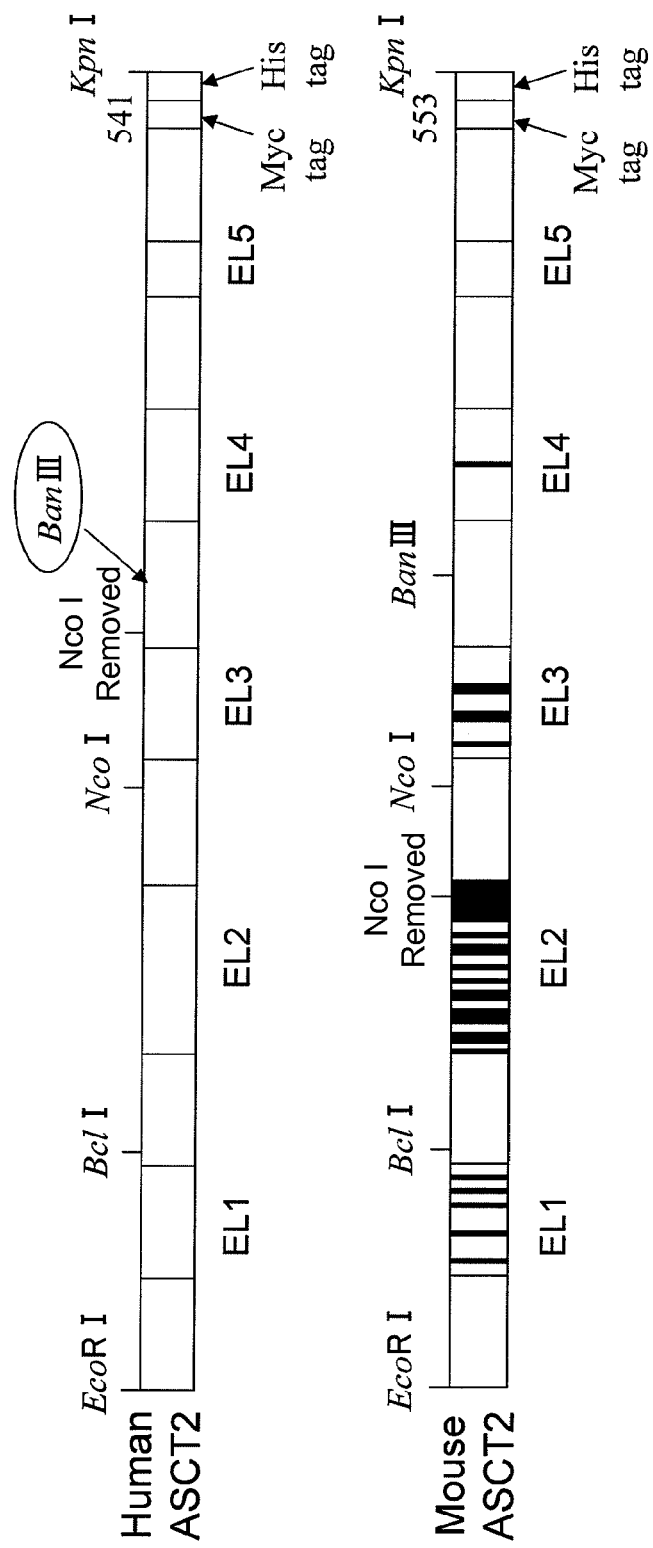
FIG. 14 shows a schematic illustration of a human ASCT2 protein and a mouse ASCT2 protein. Black color represents amino acids which are different between the human and mouse proteins in putative extracellular regions (EL1, EL2, EL3, EL4 and EL5).

FIG. 14 shows a diagram of human and mouse ASCT2 proteins. In the diagram of the mouse ASCT2 protein in FIG.

14, the black portion (in an extracellular region of mouse ASCT2, amino acids corresponding to positions 74, 79, 84, 87, 90, 154, 159, 160, 163 to 171, 173, 174, 177, 188, 204, 205, 207, 210 to 212, 214 to 223, 287, 293, 296, 297, 300, 301 and 367 of human ASCT2) represents different amino acids between human and mouse ASCT2. In the extracellular region of ASCT2, the number of different amino acids between human and mouse ASCT2 is 5 in EL1, so many in EL2, 6 in EL3, and 1 in EL4. With regard to EL1, EL2 and EL3, in order to cleave a domain containing each region at restriction enzyme sites located near the domain and then obtain a mouse replacement form by recombination, the silent mutations were introduced using a QuickChange Site-Directed Mutagenesis Kit (manufactured by Stratagene) and thereby obtained a human ASCT2 gene in which an NcoI site was lost and a Ban/III site was introduced in a late region of EL3, and a mouse ASCT2 gene in which an NcoI site in EL2 was lost. With regard to EL4 which has one difference in the amino acid sequence, a human ASCT2 gene was converted into a mouse type by introducing mutation. A nucleotide sequence of the protein in which a myc/His tag was fused to the C-terminal side of each variant was constructed as follows, and then introduced into a CHO cell.

(1) Construction of Variant Human ASCT2 Gene

PfuTubo DNA polymerase (1 μL) was added to total 50 μL of a solution containing pCR4-SLC1A5-myc/His constructed in Example 2 as a template, the primers (0.1 μg/mL, 2.5 μL) comprising the nucleotide sequence represented by SEQ ID NOs:63 and 64, 10× reaction buffer (5 μL) attached to QuikChange Site-Directed Mutagenesis Kit and dNTPs (1 μL), and PCR was carried out by reaction at 95° C. for 30 seconds; 18 cycles each consisting of three processes, reaction at 95° C. for 30 seconds, reaction at 55° C. for 1 minute, and reaction at 68° C. for 5 minute; and then reaction at 37° C. for 1 hour with addition of 1 μL of DnpI after completion of the reaction. *Escherichia coli* XL 1-Blue (manufactured by Stratagene) attached to a QuickChange Site-Directed Mutagenesis Kit was transformed with 2 μL of the reaction product. A plasmid was extracted from the resulting transformant using an automated plasmid isolation system PI-50 (manufactured by Kurabo) and a plasmid pCR4-hNco1KO_ASCT2-myc/His was obtained. Using this plasmid as a template, and the primers (0.1 μg/mL, 2.5 μL) comprising the nucleotide sequences represented by SEQ ID NOs:65 and 66, respectively, a plasmid pCR4-hBam3KI_ASCT2-myc/His was obtained in the same manner as in the above. The obtained plasmid was digested with EcoRI (manufactured by Takara Bio) and KpnI (manufactured by Takara Bio), extracted using a QIAquick Gel Extraction Kit, and was ligated into a pBluescript II SK (−) vector (manufactured by Stratagene) which had been previously digested with EcoRI and KpnI, using a Ligation high (manufactured by Toyobo). Then, *Escherichia coli*t DH5α (manufactured by Toyobo) was transformed with the ligation product, in accordance with the method of Cohen et al [*Proc. Natl. Acad. Sci. USA,* 69, 2110 (1972)], and a plasmid pBluescript II SK (−) hBam3KI_ASCT2-myc/His was obtained in the same manner as above.

(2) Construction of Variant Mouse ASCT2 Gene

Using pBluescript II SK (−)-Mouse-ASCT2-myc/His constructed in Example 10 as a template, and primers comprising the nucleotide sequences represented by SEQ ID NOs:67 and 68, respectively, a plasmid pBluescript II SK (−)-mNcoKO_ASCT2-myc/His was obtained in the same manner as in Example 11(1).

(3) Construction of Mouse/Human Chimeric ASCT2/CHO

A plasmid, which was obtained by re-transforming dam-*Escherichia coli* (Catalog Number: C2925, manufactured by New England Biolabs) with the plasmids obtained in (1) and (2), was digested with EcoRI (manufactured by Takara Bio) and BclI (equivalent to FbaI, manufactured by Takara Bio), and ligated into a plasmid comprising a human ASCT2 gene as a vector, using a mouse ASCT2 gene as an insert. Then, *Escherichia coli* DH5α (manufactured by Toyobo) was transformed with the ligation product to obtain a plasmid pBluescript II SK (−)-mEL1 ASCT2-myc/His in which EL1 was replaced with a mouse type of ELL Similarly, a plasmid pBluescript II SK (−)-mEL2 ASCT2-myc/His and a plasmid pBluescript II SK (−)-mEL3 ASCT2-myc/His were obtained by replacing EL2 with a mouse type of EL2 at BclI and NcoI sites and replacing EL3 with a mouse type of EL3 at NcoI and BamIII sites, respectively.

Using the pBluescript II SK (−)hBam3KI_ASCT2-myc/His obtained in (1) as a template, and the primers having the nucleotide sequences represented by SEQ ID NOs:69 and 70, the plasmid pBluescript II SK (−)-mEL4_ASCT2-myc/His in which EL4 was replaced with a mouse type of EL4 was obtained in the same manner as in Example 11(1).

The resulting pBluescript II SK (−)-mEL1_ASCT2-myc/His, pBluescript II SK (−)-mEL2_ASCT2-myc/His, pBluescript II SK (−)-mEL3_ASCT2-myc/His and pBluescript II SK (−)-mEL4-ASCT2-myc/His were digested with EcoRI (manufactured by Takara Bio) and KpnI (manufactured by Takara Bio) and each of gene fragments was extracted in the same manner as above, and ligated into a pKANTEX93 vector (WO97/10354) which had been previously digested with EcoRI and KpnI. Then, *Escherichia coli* DH5α (manufactured by Toyobo) was transformed with the ligation product to obtain transformants. Then, the expression plasmids pKANTEX-mEL1_ASCT2-myc/His, pKANTEX-mEL2_ASCT2-myc/His, pKANTEX-mEL3_ASCT2-myc/His and pKANTEX-mEL4_ASCT2-myc/His were obtained from the respective transformants using a plasmid isolation kit (manufactured by Qiagen).

In accordance with the electroporation method, pKANTEX-mEL1-ASCT2-myc/His, pKANTEX-mEL2_ASCT2-myc/His, pKANTEX-mEL3_ASCT2_myc/His and pKANTEX-mEL4_ASCT2-myc/His were introduced into CHO/DG44 cells respectively in the same manner as in Example 10, and thereby obtained a mouse EL1 type ASCT2-myc/His gene-introduced CHO cell line (hereinafter, referred to as "mEL1/CHO"), a mouse EL2 type ASCT2-myc/His gene-introduced CHO cell line (hereinafter, referred to as "mEL2/CHO"), a mouse EL3 type ASCT2-myc/His gene-introduced CHO cell line (hereinafter, referred to as "mEL3/CHO") and a mouse EL4 type ASCT2-myc/His gene-introduced CHO cell line (hereinafter, referred to as "mEL4/CHO"), respectively.

Example 12

Reactivity of Anti-ASCT2 Monoclonal Antibody with Mouse ASCT2/CHO and Mouse/Human Chimeric ASCT2/CHO Using the mouse ASCT2/CHO and mouse/human chimeric ASCT2/CHO cells constructed in Examples 10 and 11 and FITC-labeled anti-mouse immunoglobulin G (H+L) (manufactured by Dako) or ALEXA488-labeled anti-rat immunoglobulin G (G+L) (manufactured by Invitrogen) as the secondary antibody, the reactivity of anti-ASCT2 monoclonal antibodies KM4008, KM4012 and KM4018 was measured in the same manner as in Example 9(1).

The measurement results are shown in FIG. 15. As shown in FIG. 15, all of the anti-ASCT2 monoclonal antibodies KM4008, KM4012 and KM4018 exhibited no reactivity with mouse ASCT2. In addition, KM4008 and KM4012 exhibited a decreased reactivity with mEL2/CHO. On the other hand, KM4018 exhibited no reactivity with mEL2/CHO, and a decreased reactivity with mEL1/CHO and mEL3/CHO.

From these results, it was demonstrated that the anti-ASCT2 monoclonal antibodies KM4008 and KM4012 recognize and bind to EL2, and the anti-ASCT2 monoclonal antibody KM4018 recognizes and binds to a three-dimensional structure comprising EL1, EL2 and EL3.

Example 13

Preparation of Anti-ASCT2 Humanized Antibody (1) Design of Amino Acid Sequences of VH and VL of Anti-ASCT2 Humanized Antibody An amino acid sequence of VH of an anti-ASCT2 humanized antibody was designed as follows.

Firstly, the amino acid sequence of FR of VH of a human antibody was selected in order to graft amino acid sequences of CDR1 to CDR3 of KM4008VH represented by SEQ ID NOs:26 to 28, respectively, obtained in Example 7(3). Using a GCG Package (manufactured by Genetics Computer Group) as a sequence analysis system, based on the amino acid sequence database of conventional proteins by the BLASTP method [*Nucleic Acids Res.*, 25, 3389 (1997)], a human antibody having a high homology with KM4008 was searched. When the homology score was compared with the homology of an actual amino acid sequence, SWISSPROT database accession no. BAC01342, the immunoglobulin heavy chain VHDJ region (hereinafter, referred to as "BAC01342") exhibited a homology of 77.0%, and it was a human antibody which had the highest homology, so the amino acid sequence of FR of this antibody was selected.

Amino acid sequences of CDRs of VH of KM4008 represented by SEQ ID NOs:26 to 28 were grafted into an appropriate position of the thus determined amino acid sequence of FR of the human antibody. In this manner, an amino acid sequence HV0 of VH of the anti-ASCT2 humanized antibody represented by SEQ ID NO:71 was designed.

Next, an amino acid sequence of VL of the anti-ASCT2 humanized antibody was designed as follows.

An amino acid sequence of FR of VL of a human antibody was selected in order to graft amino acid sequences of CDR1 to CDR3 of KM4008VL represented by SEQ ID NOs:29 to 31, respectively, obtained in Example 7(3). Kabat et al. have classified VL of conventionally known various human antibodies into four subgroups (HSG I to IV) based on the homology of their amino acid sequences and reported on the consensus sequences for each of the subgroups [*Sequences of Proteins of Immunological Interest*, US Dept. Health and Human Services (1991)]. Accordingly, the homology was examined between the amino acid sequences of FR of consensus sequences of subgroups I to IV of VL of the human antibody and the amino acid sequence of FR of VL of KM4008.

As a result of the homology analysis, the homology of HSG I, HSG II, HSG III, and HSG IV was 77.5%, 60.0%, 63.8%, and 68.8%, respectively. Therefore, the amino acid sequence of FR of KM4008VL had the highest homology with the subgroup I.

Based on these results, the amino acid sequence of CDR of VL of KM4008 was grafted into an appropriate position of an amino acid sequence of FR of the consensus sequence of subgroup I of VL of the human antibody. However, since Leu at position 124 in the amino acid sequence of VL of KM4008 represented by SEQ ID NO:21 was not the amino acid residue having the highest use frequency in the region which corresponded to the amino acid sequence of the human antibody FR cited by Kabat, but is an amino acid residue which was used at a relatively high frequency, the above amino acid residue recognized in the amino acid sequence of KM4008 was used. In this manner, the amino acid sequence LV0 of VL of an anti-ASCT2 humanized antibody represented by SEQ ID NO:72 was designed.

The amino acid sequence HV0 of VH and amino acid sequence LV0 of VL of the anti-ASCT2 humanized antibody designed in the above are sequences in which the amino acid sequence of CDR of the anti-ASCT2 mouse monoclonal antibody KM4008 alone was grafted into the selected amino acid sequence of FR of the human antibody. However, it is known that when a humanized antibody is produced by simply grafting only CDRs of a mouse antibody into FRs of a human antibody, its antigen-binding activity is lower than that of the original mouse antibody. For these reasons, in order to avoid lowering of the binding activity, the amino acid residues which are considered to have an influence on the binding activity, among the amino acid residues of FRs which are different between human antibodies and mouse antibodies, are usually modified together with the grafting of the amino acid sequence of CDRs. Thus, in this Example, the amino acid residues of FRs which is considered to influence on the binding activity were identified as follows.

Firstly, a three-dimensional structure of V region of the antibody (hereinafter, referred to as "HV0LV0") comprising the amino acid sequence of HV0 of VH and amino acid sequence of LV0 of VL of anti-ASCT2 humanized antibody designed in the above was constructed using a computer modeling technique. The three dimensional structure was prepared and displayed using Discovery Studio (manufactured by Accelrys) in accordance with instructions attached thereto. In addition, a computer model of the three-dimensional structure of the V region of the anti-ASCT2 mouse monoclonal antibody KM4008 was also constructed in the same manner. Further, in the amino acid sequence of FRs of VH and VL of HV0LV0, amino acid residues which were different from those of KM4008 were selected and replaced with the corresponding amino acid residues of KM4008, and the three-dimensional structure model was constructed based on the resulting amino acid sequence in the same manner. The amino acid residues predicted to influence on the binding activity of the antibody were identified by comparing three-dimensional structures of the V regions of the constructed KM4008, HV0LV0 and modified product.

As a result, as the amino acid residues among amino acid residues of FR of HV0LV0, which are considered to change a three-dimensional structure of the antigen binding region and therefore influence on the binding activity of the antibody, Val at position 2, Ser at position 9, Val at position 20, Ser at position 30, Arg at position 38, Glu at position 46, Leu at position 86, Val at position 93, Tyr at position 95 and Val at position 116 in the HV0 sequence, and Pro at position 8, Val at position 15, Gln at position 38, Ala at position 43, Pro at position 44, Phe at position 71, and Tyr at position 87 in the LV0 sequence were respectively selected.

By modifying at least one or more amino acid sequences of these selected amino acid residues into the amino acid residues which are present at the same positions of KM4008, VH and VL of a humanized antibody having various modifications were designed.

Specifically, regarding VH, at least one modification among the amino acid modifications for substituting Val at position 2 with Ile, Ser at position 9 with Pro, Val at position 20 with Ile, Ser at position 30 with Thr, Arg at position 38 with Lys, Glu at position 46 with Lys, Leu at position 86 with Val, Val at position 93 with Thr, Tyr at position 95 with Phe, and Val at position 116 with Leu was introduced in the amino acid sequence represented by SEQ ID NO:71. Further, regarding VL, at least one modification among the amino acid modifications for substituting Pro at position 8 with Thr, Val at position 15 with Leu, Gln at position 38 with Arg, Ala at position 43 with Thr, Pro at position 44 with Val, Phe at position 71 with Tyr, and Tyr at position 87 with Phe was introduced in the amino acid sequence represented by SEQ ID NO:72.

As a result, HV0LV3, HV2LV0, HV2LV3, HV4LV0, HV4LV3, HV7LV0, HV7LV3, HV10LV0, and HV10LV3 were respectively designed as antibody V regions of the anti-ASCT2 humanized antibody with modifications of at least one of amino acid residues present in FR of HV0LV0. The amino acid sequences of H chain variable regions HV2, HV4, HV7 and HV10, and L chain variable region LV3 were represented by SEQ ID NOs:76, 78, 80, 82 and 84, respectively.

(2) Preparation of Anti-ASCT2 Humanized Antibody

A DNA encoding the amino acid sequence of the variable region of the anti-ASCT2 humanized antibody was prepared in mammalian cells using a codon which was used at a high frequency, when amino acid modification(s) were carried out using a codon which is used as a DNA encoding the amino acid sequence of VH or VL of KM4008. The nucleotide sequences encoding the amino acid sequence of HV0 and LV0 of the anti-ASCT2 humanized antibody were represented by SEQ ID NOs:73 and 74, respectively, whereas the nucleotide sequences encoding the amino acid sequences of variable regions HV2, HV4, HV7, HV10 and LV3 on which amino acid modification(s) were made were represented by SEQ ID NOs:75, 77, 79, 81 and 83, respectively.

Using these nucleotide sequences, humanized antibody-expressing vectors were constructed and humanized antibodies were respectively expressed in the same manner as in Example 8.

While the invention has been described in detail and with reference to specific embodiments thereof, it will be apparent to one skill in the art that various changes and modifications can be made therein without departing from the spirit and scope thereof.

This application is based on Japanese application No. 2008-185790, filed on Jul. 17, 2008, and U.S. provisional application No. 61/081,820, filed on Jul. 18, 2008, the entire contents of which are incorporated hereinto by reference. All references cited herein are incorporated in their entirety.

What is claimed is:

1. A DNA encoding a monoclonal antibody or an antigen-binding fragment thereof, wherein said monoclonal antibody or antigen-binding fragment thereof specifically binds to a native three-dimensional structure of an extracellular region of human system ASC amino acid transporter 2 (ASCT2), and does not bind to mouse ASCT2.

2. The DNA of claim 1, wherein said monoclonal antibody or antigen-binding fragment thereof binds to at least the EL2 region of human ASCT2.

3. The DNA of claim 1, wherein said monoclonal antibody or antigen-binding fragment thereof comprises complementarity determining regions (CDRs) of a heavy chain variable region (VH) and a light chain variable region (VL), and wherein (A) CDR1, CDR2 and CDR3 of VH of the antibody comprise the amino acid sequences of SEQ ID NOs: 26, 27 and 28, respectively, and CDR1, CDR2 and CDR3 of VL of the antibody comprise the amino acid sequences of SEQ ID NOs: 29, 30 and 31, respectively; (B) CDR1, CDR2 and CDR3 of VH of the antibody comprise the amino acid sequences of SEQ ID NOs: 32, 33 and 34, respectively, and CDR1, CDR2 and CDR3 of VL of the antibody comprise the amino acid sequences of SEQ ID NOs: 35, 36 and 37, respectively; or (C) CDR1, CDR2 and CDR3 of VH of the antibody comprise the amino acid sequences of SEQ ID NOs: 49, 50 and 51, respectively, and CDR1, CDR2 and CDR3 of VL of the antibody comprise the amino acid sequences of SEQ ID NOs: 52, 53 and 54, respectively.

4. The DNA of claim 1, wherein said monoclonal antibody or antigen-binding fragment thereof binds to at least one amino acid residue in SEQ ID NO: 2, wherein said at least one amino acid residue is at a position in SEQ ID NO: 2 selected from the group consisting of positions 154; 159 to 160; 163 to 171; 173 to 174; 177; 188; 204 to 205; 207; 210 to 212; and 214 to 223.

5. The DNA of claim 1, wherein said monoclonal antibody or antigen-binding fragment thereof is (A) a monoclonal antibody which binds to an epitope which is recognized by a monoclonal antibody produced from any one of hybridomas selected from a hybridoma KM4008 (FERM BP-10962) and a hybridoma KM4012 (FERM BP-10963); or (B) a monoclonal antibody produced from any one of hybridomas selected from a hybridoma KM4008 (FERM BP-10962) and a hybridoma KM4012 (FERM BP-10963).

6. The DNA of claim 1, wherein said antigen-binding fragment is selected from the group consisting of a Fab, a Fab', a F(ab')$_2$, a single chain antibody (scFv), a diabody, and a disulfide stabilized Fv region (dsFv).

7. The DNA of claim 1, wherein said monoclonal antibody or antigen-binding fragment thereof is a recombinant antibody or antigen-binding fragment thereof.

8. The DNA of claim 7, wherein said recombinant antibody or antigen-binding fragment thereof is a human chimeric antibody or human antibody, or an antigen-binding fragment thereof.

9. A recombinant vector comprising the DNA of claim 1.

10. A transformant obtained by introducing the recombinant vector of claim 9 into a host cell.

* * * * *